(12) United States Patent
Barsanti et al.

(10) Patent No.: US 9,242,969 B2
(45) Date of Patent: Jan. 26, 2016

(54) BIARYL AMIDE COMPOUNDS AS KINASE INHIBITORS

(71) Applicant: Novartis AG, Basel (CH)

(72) Inventors: Paul A. Barsanti, Pleasant Hill, CA (US); Matthew Burger, Albany, CA (US); Yan Lou, Pleasanton, CA (US); Gisele Nishiguchi, Albany, CA (US); Valery Polyakov, Moraga, CA (US); Savithri Ramurthy, Walnut Creek, CA (US); Alice Rico, Castro Valley, CA (US); Lina Setti, Fremont, CA (US); Aaron Smith, Fremont, CA (US); Benjamin Taft, Oakland, CA (US); Huw Tanner, Alameda, CA (US); Alan DiPesa, Roslindale, MA (US); Naeem Yusuff, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/204,823

(22) Filed: Mar. 11, 2014

(65) Prior Publication Data

US 2014/0275003 A1 Sep. 18, 2014

Related U.S. Application Data

(60) Provisional application No. 61/783,558, filed on Mar. 14, 2013.

(51) Int. Cl.

| *C07D 401/04* | (2006.01) |
|---|---|
| *C07D 403/04* | (2006.01) |
| *A61K 31/5377* | (2006.01) |
| *A61K 31/541* | (2006.01) |
| *C07D 413/04* | (2006.01) |
| *A61K 45/06* | (2006.01) |
| *C07D 213/74* | (2006.01) |
| *C07D 237/20* | (2006.01) |
| *C07D 239/42* | (2006.01) |
| *C07D 239/47* | (2006.01) |
| *C07D 239/48* | (2006.01) |
| *C07D 277/42* | (2006.01) |
| *C07D 401/12* | (2006.01) |
| *C07D 413/12* | (2006.01) |

(Continued)

(52) U.S. Cl.
CPC .......... *C07D 413/04* (2013.01); *A61K 31/5377* (2013.01); *A61K 31/541* (2013.01); *A61K 45/06* (2013.01); *C07D 213/74* (2013.01); *C07D 213/75* (2013.01); *C07D 233/88* (2013.01); *C07D 237/20* (2013.01); *C07D 239/42* (2013.01); *C07D 239/47* (2013.01); *C07D 239/48* (2013.01); *C07D 241/20* (2013.01); *C07D 263/58* (2013.01); *C07D 277/42* (2013.01); *C07D 401/04* (2013.01); *C07D 401/12* (2013.01); *C07D 401/14* (2013.01); *C07D 403/04* (2013.01); *C07D 403/12* (2013.01); *C07D 405/04* (2013.01); *C07D 405/12* (2013.01); *C07D 405/14* (2013.01); *C07D 413/12* (2013.01); *C07D 413/14* (2013.01); *C07D 417/12* (2013.01); *C07D 471/04* (2013.01); *C07D 487/04* (2013.01); *C07D 491/107* (2013.01); *C07D 493/04* (2013.01); *C07D 493/10* (2013.01); *C07D 495/04* (2013.01); *C07D 498/08* (2013.01); *C07D 513/04* (2013.01)

(58) Field of Classification Search
CPC .. C07D 401/04; C07D 401/12; C07D 401/14; C07D 403/04; C07D 403/12; C07D 403/14; A61K 31/5377; A61K 31/541
USPC ................ 544/60, 72, 122; 514/227.8, 230.8, 514/231.8, 232.2, 235.8
See application file for complete search history.

(56) References Cited

U.S. PATENT DOCUMENTS

| 3,707,475 A | 12/1972 | Lombardino et al. |
| 5,717,100 A | 2/1998 | Selnick et al. |

(Continued)

FOREIGN PATENT DOCUMENTS

| DE | 21 55 558 A1 | 6/1972 |
| DE | 30 29 376 A1 | 3/1982 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao
(74) *Attorney, Agent, or Firm* — Scott W. Reid

(57) ABSTRACT

The present invention provides compounds of Formula (I)

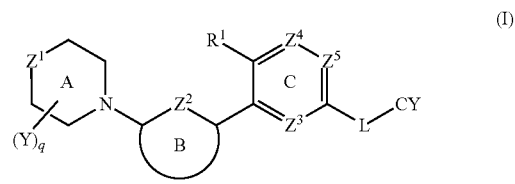

as described herein, and salts thereof, and therapeutic uses of these compounds for treatment of disorders associated with Raf kinase activity. The invention further provides pharmaceutical compositions comprising these compounds, and compositions comprising these compounds and a therapeutic co-agent.

17 Claims, No Drawings

(51) Int. Cl.

| | | |
|---|---|---|
| C07D 413/14 | (2006.01) | |
| C07D 417/12 | (2006.01) | |
| C07D 493/10 | (2006.01) | |
| C07D 403/12 | (2006.01) | |
| C07D 401/14 | (2006.01) | |
| C07D 405/14 | (2006.01) | |
| C07D 213/75 | (2006.01) | |
| C07D 233/88 | (2006.01) | |
| C07D 405/04 | (2006.01) | |
| C07D 405/12 | (2006.01) | |
| C07D 241/20 | (2006.01) | |
| C07D 471/04 | (2006.01) | |
| C07D 487/04 | (2006.01) | |
| C07D 263/58 | (2006.01) | |
| C07D 491/107 | (2006.01) | |
| C07D 493/04 | (2006.01) | |
| C07D 495/04 | (2006.01) | |
| C07D 498/08 | (2006.01) | |
| C07D 513/04 | (2006.01) | |

(56) References Cited

U.S. PATENT DOCUMENTS

| | | | |
|---|---|---|---|
| 6,211,177 B1 | 4/2001 | Sperl et al. | |
| 6,248,771 B1 | 6/2001 | Shenoy et al. | |
| 6,268,391 B1 | 7/2001 | Dickerson et al. | |
| 6,358,932 B1 | 3/2002 | Monia | |
| 6,399,603 B1 | 6/2002 | Jacobs et al. | |
| 6,417,194 B1 | 7/2002 | Fox et al. | |
| 6,458,813 B1 | 10/2002 | Mantlo et al. | |
| 6,465,493 B1 | 10/2002 | Burgess et al. | |
| 6,608,053 B2 * | 8/2003 | Hayakawa et al. | 514/227.8 |
| 7,071,216 B2 | 7/2006 | Renhowe et al. | |
| 7,423,150 B2 | 9/2008 | Costales et al. | |
| 7,531,553 B2 | 5/2009 | Di Pietro et al. | |
| 8,129,394 B2 | 3/2012 | Hunag et al. | |
| 8,242,260 B2 | 8/2012 | Costales et al. | |
| 8,299,108 B2 | 10/2012 | Amiri et al. | |
| 8,415,382 B2 | 4/2013 | Costales et al. | |
| 8,563,553 B2 | 10/2013 | Costales et al. | |
| 2001/0014679 A1 | 8/2001 | Tang et al. | |
| 2003/0166633 A1 | 9/2003 | Gaster et al. | |
| 2004/0053973 A1 | 3/2004 | Ohkawa et al. | |
| 2004/0063946 A1 | 4/2004 | Ohkawa et al. | |
| 2004/0087626 A1 | 5/2004 | Renhowe et al. | |
| 2004/0122237 A1 | 6/2004 | Amiri et al. | |
| 2005/0192287 A1 | 9/2005 | Costales et al. | |
| 2005/0282805 A1 | 12/2005 | Hangeland et al. | |
| 2009/0005359 A1 | 1/2009 | Cossrow et al. | |
| 2009/0298815 A1 | 12/2009 | Adams et al. | |
| 2013/0096149 A1 | 4/2013 | Madera et al. | |
| 2013/0210818 A1 | 8/2013 | Huang et al. | |
| 2013/0224195 A1 | 8/2013 | Costales et al. | |
| 2014/0011825 A1 | 1/2014 | Costales et al. | |
| 2014/0178360 A1 | 6/2014 | Kuo et al. | |

FOREIGN PATENT DOCUMENTS

| | | |
|---|---|---|
| EP | 0 149 884 B1 | 12/1992 |
| EP | 1 232 153 B1 | 11/2004 |
| EP | 1 721 905 A1 | 11/2006 |
| GB | 2 306 108 A | 4/1997 |
| JP | 02-188579 A | 7/1990 |
| JP | 03-157383 A | 7/1991 |
| JP | 2000-302680 A2 | 1/2000 |
| JP | 2007-246520 A | 9/2007 |
| WO | 98/08845 A1 | 3/1998 |
| WO | 00/42012 A1 | 7/2000 |
| WO | 00/59506 A1 | 10/2000 |
| WO | 00/62778 A1 | 10/2000 |
| WO | 01/38324 A2 | 5/2001 |
| WO | 01/52845 A1 | 7/2001 |
| WO | 01/52846 A1 | 7/2001 |
| WO | 01/62756 A1 | 8/2001 |
| WO | 01/66539 A1 | 9/2001 |
| WO | 01/66540 A1 | 9/2001 |
| WO | 01/72737 A1 | 10/2001 |
| WO | 01/96308 A1 | 12/2001 |
| WO | 02/39954 A2 | 5/2002 |
| WO | 02/42273 A2 | 5/2002 |
| WO | 02/44156 A2 | 6/2002 |
| WO | 02/064136 A2 | 8/2002 |
| WO | 02/076960 A1 | 10/2002 |
| WO | 02/094808 A1 | 11/2002 |
| WO | 03/047577 A2 | 6/2003 |
| WO | 03/082272 A1 | 10/2003 |
| WO | 03/087304 A2 | 10/2003 |
| WO | 2004/002948 A1 | 1/2004 |
| WO | 2004/026859 A1 | 4/2004 |
| WO | 2004/026863 A1 | 4/2004 |
| WO | 2004/085425 A1 | 10/2004 |
| WO | 2005/034869 A2 | 4/2005 |
| WO | 2005/047266 A1 | 5/2005 |
| WO | 2005/103028 A1 | 11/2005 |
| WO | 2005/105814 A1 | 11/2005 |
| WO | 2005/116000 A1 | 12/2005 |
| WO | 2005/123050 A1 | 12/2005 |
| WO | 2006/005914 A1 | 1/2006 |
| WO | 2006/005915 A1 | 1/2006 |
| WO | 2006/005918 A1 | 1/2006 |
| WO | 2006/026306 A1 | 3/2006 |
| WO | 2006/038734 A1 | 4/2006 |
| WO | 2006/044509 A2 | 4/2006 |
| WO | 2007/118149 A2 | 10/2007 |
| WO | 2008/071605 A2 | 6/2008 |
| WO | 2009/001132 A1 | 12/2008 |
| WO | 2009/003998 A2 | 1/2009 |
| WO | 2009/006389 A2 | 1/2009 |
| WO | 2009/007749 A2 | 1/2009 |
| WO | 2009/012283 A1 | 1/2009 |
| WO | 2009/014637 A2 | 1/2009 |
| WO | 2009/030952 A2 | 3/2009 |
| WO | 2009/032667 A1 | 3/2009 |
| WO | 2009/047163 A1 | 4/2009 |
| WO | 2009/106885 A1 | 9/2009 |
| WO | 2009/115572 A2 | 9/2009 |
| WO | 2009/137391 A2 | 11/2009 |
| WO | 2009/152356 A2 | 12/2009 |
| WO | 2010/010154 A1 | 1/2010 |
| WO | 2010/048149 A2 | 4/2010 |
| WO | 2010/071837 A1 | 6/2010 |
| WO | 2011/026911 A1 | 3/2011 |
| WO | 2011/059610 A1 | 5/2011 |
| WO | 2011/081205 A1 | 7/2011 |
| WO | 2011/139107 A2 | 11/2011 |
| WO | 2012/034363 A1 | 3/2012 |
| WO | 2012/109075 A1 | 8/2012 |
| WO | 2013/022766 A1 | 2/2013 |
| WO | 2013/033167 A1 | 3/2013 |
| WO | 2013/041652 A1 | 3/2013 |
| WO | 2013/164769 A1 | 11/2013 |
| WO | 2013/171640 A1 | 11/2013 |
| WO | 2014/008214 A1 | 1/2014 |
| WO | 2014/058691 A1 | 4/2014 |

OTHER PUBLICATIONS

Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
CAS Registry No. 730972-83-5, STN Entry Date Aug. 23, 2004.
CAS Registry No. 867157-50-4, STN Entry Date Nov. 10, 2005.
Deng et al., Knowledge-based design of target-focused libraries using protein-ligand interaction constraints. J Med Chem. Jan. 26, 2006;49(2):490-500.
Jensen, A note on the term "Chalcogen." Journal of Chemical Education, Sep. 1997;74(9):1063-4.

(56) References Cited

OTHER PUBLICATIONS

Kim et al., Synthesis and biological evaluation of 4(5)-(6-alkylpyridin-2-yl)imidazoles as transforming growth factor-beta type 1 receptor kinase inhibitors. J Med Chem. Jun. 28, 2007;50(13):3143-7. Epub Jun. 7, 2007.

Kim et al., Synthesis of heteroaryl substituted imidazole derivatives. Bull Korean Chem Soc. 2000;21(3):345-7.

Krayushkin et al., Photochromic dihetarylethenes 7, synthesis . . . Russian Chemical Bulletin. International Edition. Jan. 2001;50(1):116-21.

Revesz et al., SAR of 2,6-diamino-3,5-difluoropyridinyl substituted heterocycles as novel p38MAP kinase inhibitors. Bioorg Med Chem Lett. Aug. 19, 2002;12(16):2109-12. PubMEd PMID: 12127515.

Tsai et al., Discovery of a selective inhibitor of oncogenic B-Raf kinase with potent antimelanoma activity. Proc Natl Acad Sci U S A. Feb. 26, 2008;105(8):3041-6.

White et al., Chemiluminescence in liquid solutions: The chemiluminescence of lophine and its derivatives. Photochemistry and Photobioloby. 1965;4:1129-55.

Wolin et al., Dual binding site inhibitors of B-RAF kinase. Bioorganic & Medicinal Chemistry Letters. Apr. 2008;18:2825-9.

Al-Ali et al., Chemical interrogation of the neuronal kinome using a primary cell-based screening assay. ACS Chem Biol. May 17, 2003;8(5)1027-36.

Andreyev et al., Kirsten ras mutations in patients with colorectal cancer: the multicenter "RASCAL" study. J Natl Cancer Inst. May 6, 1998;90(9):675-84.

Babchia et al., The PI3K/Akt and mTOR/P70S6K signaling pathways in human uveal melanoma cells: interaction with B-Raf/ERK. Invest Ophthalmol Vis Sci. Jan. 2010;51(1):421-9.

Banker, Modern Pharmaceutics. Marcel Dekker. New York. 1996. 3 pages.

Bos, Ras oncogenes in human cancer: a review. Cancer Res. Sep. 1, 1989;49(17):4682-9.

Brose et al., BRAF and RAS mutations in human lung cancer and melanoma. Cancer Res. Dec. 1, 2002;62(23):6997-7000.

Davies et al., Mutations of the BRAF gene in human cancer. Nature. Jun. 27, 2002;417(6892):949-54.

De Bono et al., Therapeutics targeting signal transduction for patients with colorectal carcinoma. Br Med Bull. 2002;64:227-54.

Gopalsamy et al., Hit to lead optimization of pyrazolo[1,5-a]pyrimidines as B-Raf kinase inhibitors. Bioorg & Med Chem Lett. Oct. 2009;19(24):6890-2.

Hatzivassiliou et al., RAF inhibitors prime wild-type RAF to activate the MAPK pathway and enhance growth. Nature. Mar. 18, 2010;464:431-5. (Includes Methods page and Supplementary Information).

Hoshino et al., Constitutive activation of the 41-/43-kDa mitogen-activated protein kinase signaling pathway in human tumors. Oncogene. Jan. 21, 1999;18(3):813-22.

Kawasaki et al., The second messenger phosphatidylinositol-5-phosphate facilitates antiviral innate immune signaling. Cell Host & Microbe. Aug. 14, 2013;14(2):148-58.

Lambert et al., Targeting the PI3K and MAPK pathways to treat Kaposi's-sarcoma-associated herpes virus infection and pathogenesis. Expert Opin Ther Targets. May 2007;11(5):589-99.

Martin et al., Inhibition of PIKfyve by YM-201636 dysregulates autophagy and leads to apoptosis-independent neuronal cell death. PLoS One. Mar. 2013;8(3):1-14.

Moore et al., Phase !study of the raf-1 kinase inhibitor BAY 43/9006 in patients with advanced refractory solid tumors. Proceedings of the American Society of Clinical Oncology. 2002;21. Abstract 1816. <http://www.asco.org/portal/site/ASCO/template.RAW/menuitem.34d60f5624ba07fd506fe . . .> Last accessed Dec. 3, 2008. 2 pages.

Patani et al., Bioisosterism: A Rational Approach in Drug Design. Chem Rev. Dec. 19, 1996;96(8):3147-3176.

Pollock et al., High frequency of BRAF mutations in nevi. Nat Genet. Jan. 2003;33(1):19-20.

Rowinsky et al., Ras protein farnesyltransferase: A strategic target for anticancer therapeutic development. J Clin Oncol. Nov. 1999;17(11):3631-52.

Scharovsky et al., Inhibition of ras oncogene: a novel approach to antineoplastic therapy. J Biomed Sci. Jul.-Aug. 2000;7(4):292-8.

Strumberg et al., Final results of a phase I pharmacokinetic and pharmacodynamic study of the raf kinase inhibitor BAY 43/9006 in patients with solid tumors. Proceedings of the American Society of Clinical Oncology. 2002;21. Abstract 121. <http://www.asco.oreportal/site/ASCO/template.RAW/menuitem.34d60f5624ba07fd506fe . . .> Last accessed Dec. 3, 2008. 2 pages.

Wenglowsky et al., Pyrazolopyridine inhibitors of B-RafV600E. Part 4: Rational design and kinase selectivity profile of cell potent type II inhibitors. Bioorg Med Chem Lett. Oct. 1, 2012;22(19):6237-41.

Wolff, Burger's Medicinal Chemistry and Drug Discovery. 5th Edition. Volume 1: Principles and Practice. John Wiley & Sons. 1995:975.

Yuen et al., Similarity of the phenotypic patterns associated with BRAF and KRAS mutations in colorectal neoplasia. Cancer Res. Nov. 15, 2002;62(22):6451-5.

Zuccotto et al., Through the "Gatekeeper Door": Exploring the active kinase conformation. J Med Chem. Apr. 8, 2010;53(7):2681-94.

\* cited by examiner

BIARYL AMIDE COMPOUNDS AS KINASE INHIBITORS

CROSS-REFERENCE TO RELATED APPLICATION

This application claims the benefit of priority to U.S. Provisional Application No. 61/783,558, filed Mar. 14, 2013, the content of which is incorporated herein by reference.

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. Because they function collectively as a signal transduction cascade, the number of distinct kinases and their varying substrate specificities create a complex and highly branched pathway. Roskoski, *Biochem. Biophys. Res. Comm.*, 399, 313-17 (2010). Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, and each of these has a number of sites where phosphorylation at serine, threonine or tyrosine can cause either activation or inhibition. Matallanas, et al., *Genes and Cancer* 2:232 (2011, published online 10 May 2011). Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. Hatzivassiliou, et al., *Nature*, vol. 464, 431-36 (18 Mar. 2010). In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations. Id.

SUMMARY OF THE INVENTION

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds are thus suited for treatment of BRaf wild-type and KRas mutant tumors, as well as B-Raf V600E mutant tumors.

In one aspect, the invention provides compounds of the formula (I):

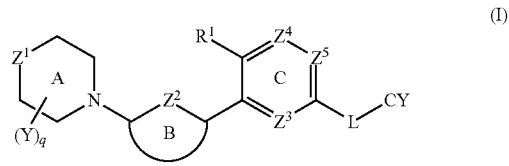

as further described herein, including the pharmaceutically acceptable salts of these compounds. The compounds of Formula (I) are inhibitors of Raf kinases as shown by data herein, and are accordingly useful to treat conditions such as melanoma, breast cancer, sarcoma, GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compounds of the invention exhibit low levels of paradoxical activation of the Raf pathway.

In another aspect, the invention provides pharmaceutical compositions comprising a compound of Formula (I) admixed with at least one pharmaceutically acceptable carrier or excipient, optionally admixed with two or more pharmaceutically acceptable carriers or excipients. In addition, the invention includes combinations of a compound of Formula (I) with a co-therapeutic agent, optionally including one or more pharmaceutically acceptable carriers, and methods of treatment using a compound of Formula (I) in combination with a co-therapeutic agent. Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of a compound of Formula (I) or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes compounds of Formula (I) and the subgenera thereof that are disclosed herein, including each species disclosed herein, for use in therapy, particularly for use to treat cancers such as melanoma, breast cancer, lung cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes compounds of Formula (I) and the subgenera of Formula (I) described herein, and all stereoisomers (including diastereoisomers and enantiomers), tautomers and isotopically enriched versions thereof (including deuterium substitutions), as well as pharmaceutically acceptable salts of these compounds. In particular, where a heteroaryl ring containing N as a ring atom is optionally substituted with hydroxyl, e.g., a 2-hydroxypyridine ring, tautomers where the hydroxyl is depicted as a carbonyl (e.g., 2-pyridone) are included. Compounds of the present invention also comprise polymorphs of compounds of formula I (or sub-formulae thereof) and salts thereof.

DETAILED DESCRIPTION

The following definitions apply unless otherwise expressly provided.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to alkyl groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, or 1-4 substituents, up to the number of hydrogens present on the unsubstituted alkyl group. Suitable substituents for alkyl groups, if not otherwise specified, may be selected from halogen, CN, oxo, hydroxy, substituted or unsubstituted $C_{1-4}$ alkoxy, substituted or unsubstituted $C_{3-6}$ cycloalkyl, substituted or unsubstituted $C_{3-6}$ heterocycloalkyl, substituted or unsubstituted phenyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, COO($C_{1-4}$alkyl), —O(C=O)—$C_{1-4}$ alkyl, —NHC(=O)$C_{1-4}$alkyl and —NHC(=O)O$C_{1-4}$alkyl groups; wherein the substituents for substituted $C_{1-4}$ alkoxy, substituted $C_{3-6}$ cycloalkyl, $C_{3-6}$ heterocycloalkyl, and substituted phenyl are up to three groups selected from halo, $C_{1-4}$ alkyl, $C_{1-4}$ haloalkyl, $C_{1-4}$ alkoxy, amino, hydroxy, and CN. Preferred substituents for alkyl groups include halogen, CN, oxo, hydroxy, $C_{1-4}$ alkoxy, $C_{3-6}$ cycloalkyl, phenyl, amino, ($C_{1-4}$ alkyl)amino, alkyl)amino, $C_{1-4}$ alkylthio, $C_{1-4}$ alkylsulfonyl, —C(=O)—$C_{1-4}$ alkyl, COOH, —COO($C_{1-4}$ alkyl), —P(C=O)—$C_{1-4}$ alkyl, —NHC(=O) $C_{1-4}$ alkyl and —NHC(=O)O $C_{1-4}$ alkyl groups.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g, trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring atom. Unless otherwise provided, cycloalkyl refers to cyclic hydrocarbon groups having between 3 and 9 ring carbon atoms or between 3 and 7 ring carbon atoms. Preferably, cycloalkyl groups are saturated monocyclic rings having 3-7 ring atoms unless otherwise specified.

A substituted cycloalkyl is a cycloalkyl group substituted by one, or two, or three, or more than three substituents, up to the number of hydrogens on the unsubstituted group. Typically, a substituted cycloalkyl will have 1-4 or 1-2 substituents. Suitable substituents, unless otherwise specified, are independently selected from the group consisting of halogen, hydroxyl, thiol, cyano, nitro, oxo, $C_{1-4}$-alkoximino, hydroxyimino, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, $C_{1-4}$-alkylcarbonyl, carboxy, $C_{1-4}$-alkoxycarbonyl, amino, $C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, $C_{1-4}$-alkylsulfamoyl, and $C_{1-4}$-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents include $C_{1-4}$ alkyl and the substituent groups listed above as preferred substituents for alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring, that is unsubstituted or substituted with 1-2 groups. When optionally substituted, the substituents are typically selected from $C_{1-4}$ alkyl and those set forth above as suitable or preferred substituents for alkyl groups.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

A substituted aryl is an aryl group substituted by 1-5 (such as one, or two, or three) substituents independently selected from the group consisting of hydroxyl, thiol, cyano, nitro, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, halogen, $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, sulfamoyl, $C_{1-4}$-alkylsulfamoyl, and $C_{1-4}$-alkylaminosulfonyl where each of the afore-mentioned hydrocarbon groups (e.g., alkyl, alkenyl, alkynyl, alkoxy residues) may be further substituted by one or more groups independently selected at each occurrence from the groups listed above as suitable substituents for alkyl groups. Preferred substituents for a substituted aryl group are $C_{1-4}$ alkyl, halogen, CN, hydroxy, substituted or unsubstituted $C_{1-4}$ alkyl, substituted or unsubstituted $C_{1-4}$ alkoxy, substituted or unsubstituted $C_{3-6}$ cycloalkyl, substituted or unsubstituted $C_{3-6}$ heterocycloalkyl, amino, ($C_{1-4}$ alkyl)amino, di($C_{1-4}$alkyl)amino, $C_{1-4}$ alkylthio, $C_{1-4}$ alkylsulfonyl, —C(═O)—$C_{1-4}$ alkyl, COOH, COO($C_{1-4}$ alkyl), —O(C═O)—$C_{1-4}$ alkyl, —NHC(═O)$C_{1-4}$ alkyl and —NHC(═O)O$C_{1-4}$ alkyl groups; wherein the substituents for substituted $C_{1-4}$ alkoxy, substituted $C_{3-6}$ cycloalkyl, $C_{3-6}$ heterocycloalkyl, and substituted alkyl are up to three groups selected from halo, oxo, $C_{1-4}$ alkyl, $C_{1-4}$ haloalkyl, $C_{1-4}$ alkoxy, amino, hydroxy, and CN.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" or "heterocycloalkyl" refers to a heterocyclic radical that is saturated or partially unsaturated but not aromatic, and can be a monocyclic or a polycyclic ring, including a bicyclic, tricyclic or spirocyclic ring system; and has 3 to 14, more commonly 4 to 10, and most preferably 5 to 7 ring atoms; wherein one or more, preferably one to four, especially one or two ring atoms are heteroatoms independently selected from O, S and N (the remaining ring atoms therefore being carbon). Even though described as, e.g., a $C_{5-6}$ atom ring, a heterocycle contains at least one heteroatom as a ring atom and has the total number of ring atoms stated, e.g. 5 or 6 in this example. Preferably, a heterocyclyl group has one or two such heteroatoms as ring atoms, and preferably the heteroatoms are not directly connected to each other. The bonding ring (i.e. the ring connecting to the Formula of interest) preferably has 4 to 12, especially 5 to 7 ring atoms. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can comprise fused or bridged rings as well as spirocyclic ring systems (e.g., 2-oxa-6-azaspiro[3.3]heptane), and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above as suitable or preferred for a cycloalkyl group.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S. Typically, the heteroaryl is a 5-10 membered ring system, e.g., a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, 1- or 2-tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings, where the radical or point of attachment to the Formula of interest is on a heteroaromatic ring. Non-limiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents, typically 1, 2 or 3 substituents, selected from the substituents described above as suitable or preferred for an aryl group.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various embodiments of the invention are described herein. It will be recognized that features specified in each embodiment may be combined with other specified features to provide further embodiments of the present invention. The following enumerated embodiments are representative of the invention:

1. In a first embodiment, the invention provides a compound of the formula (I):

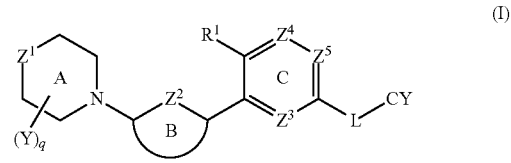

or a pharmaceutically acceptable salt thereof, wherein:

$Z^1$ is O, S, S(=O) or $SO_2$;

$Z^2$ is N, S or $CR^a$, where $R^a$ is H, $C_{1-4}$ alkyl or $C_{1-4}$ haloalkyl;

$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;

Ring B is selected from phenyl, pyridine, pyrimidine, pyrazine, pyridone, pyrimidone, pyrazinone, pyridazinone, and thiazole, each of which is optionally substituted with up to two groups selected from halo, OH, CN, $C_{1-4}$ alkyl, $C_{2-4}$ alkenyl, —O—($C_{1-4}$alkyl), $NH_2$, NH—($C_{1-4}$alkyl), —N($C_{1-4}$ alkyl)$_2$, —$SO_2R^2$, $NHSO_2R^2$, $NHC(O)R^2$, $NHCO_2R^2$, $C_{3-6}$ cycloalkyl, $C_{5-6}$ heteroaryl, —O—$C_{3-6}$ cycloalkyl, —O—$C_{5-6}$ heteroaryl, $C_{4-8}$ heterocycloalkyl, and —O—$C_{4-8}$ heterocycloalkyl, where each $C_{4-8}$ heterocycloalkyl and $C_{5-6}$ heteroaryl contains up to three heteroatoms selected from N, O and S as ring members, where each $C_{1-4}$ alkyl, $C_{2-4}$ alkenyl, $C_{3-6}$ cycloalkyl, $C_{5-6}$ heteroaryl, and $C_{4-8}$ heterocycloalkyl is each optionally substituted with up to three groups selected from oxo, hydroxyl, halo, $C_{1-4}$ alkyl, $C_{1-4}$ haloalkyl, $C_{1-4}$ alkoxy, and —$(CH_2)_{1-2}$Q where Q is OH, $C_{1-4}$ alkoxy, —CN, $NH_2$, —$NHR^3$, —$N(R^3)_2$, —$SO_2R^3$, $NHSO_2R^3$, NHC(O)$OR^3$, or NHC(O)$R^3$;

each $R^2$ and $R^3$ is independently $C_{1-4}$ alkyl; and

Ring B is optionally fused to a 5-6 membered aromatic or nonaromatic ring containing up to two heteroatoms selected from N, O and S, where the 5-6 membered ring can be substituted with halo, $C_{1-4}$ alkyl, $C_{1-4}$ haloalkyl, or $C_{1-4}$ alkoxy;

each Y is independently selected from $C_{1-4}$ alkyl, $C_{1-4}$ alkoxy, CN, halo, oxo, —$(CH_2)_pOR^4$, —$(CH_2)_p N(R^4)_2$, —$(CH_2)_pNHC(O)R^4$, —$(CH_2)_pNHCOO(C_{1-4}$ alkyl), or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, —$(CH_2)_pOR^4$, —$(CH_2)_p N(R^4)_2$, —$(CH_2)_pNHC(O)R^4$, and —$(CH_2)_pNHCOO(C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N;

L is —C(=O)—NH—[CY] or —NH—C(=O)—[CY], where [CY] indicates which atom of L is attached to CY; and CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, OH, $NH_2$, $NHR^5$, and —$N(R^5)_2$, wherein each $R^5$ is independently $C_{1-4}$ alkyl, $C_{4-6}$ heterocyclyl, or $C_{3-8}$ cycloalkyl, and $R^5$ is optionally substituted with up to three groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, $NHC(\!=\!O)R^6$, —$CH_2OR^7$, —$CH_2N(R^7)_2$, wherein each $R^6$ is independently $C_{1-4}$ alkyl, and each $R^7$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$alkoxy.

2. A compound according to embodiment 1 or a pharmaceutically acceptable salt thereof, wherein $Z^1$ is O.

3 (a). A compound according to embodiment 1 or embodiment 2 or a pharmaceutically acceptable salt thereof, wherein $Z^2$ is CH.

3 (b). In an alternative embodiment, $Z^2$ is N.

4. A compound according to any one of embodiments 1 to 3 or a pharmaceutically acceptable salt thereof, wherein CY is selected from phenyl, pyridine, pyrimidine, pyrazine, pyridazine, pyridone, thiazole, and oxazole, each of which is optionally substituted as described for embodiment 1.

5. A compound according to any of the preceding embodiments or a pharmaceutically acceptable salt thereof, wherein $R^1$ is methyl or $CF_3$.

6. A compound according to any of the preceding embodiments or a pharmaceutically acceptable salt thereof, wherein Ring B is pyridine or pyrimidine or pyridone.

7. A compound according to any of the preceding embodiments or a pharmaceutically acceptable salt thereof, wherein CY is phenyl or pyridin-4-yl, and is optionally substituted with one or two groups selected from methyl, ethyl, isopropyl, $CF_3$, —$CHF_2$, $CH_2F$, $CF_2CH_3$, $CH_2CF_3$, 1-piperazinyl, 4-methyl-1-piperazinyl, 4-ethyl-1-piperazinyl, cyclopropyl, 1-cyanocyclopropyl, —$CH_2CN$, —CHMeCN, —$CMe_2CN$, OMe, OEt, F, Cl, —$SO_2Me$, —$SO_2NMe_2$, —$CH_2NH_2$, —$CH_2NMe_2$, —$CH_2NHMe$, and —$CH_2OMe$.

8. A compound according to any of the preceding embodiments or a pharmaceutically acceptable salt thereof, wherein CY is substituted with at least one group selected from $CF_3$, $OCF_3$, t-butyl, —$C(Me)_2CN$, and —$SO_2Me$.

9. A compound according to any of the preceding embodiments or a pharmaceutically acceptable salt thereof, wherein $Z^4$ is CH.

10. A compound according to any of embodiments 1-8 or a pharmaceutically acceptable salt thereof, wherein $Z^4$ is N.

11. A compound according to any of the preceding embodiments or a pharmaceutically acceptable salt thereof, wherein L is —C(=O)—NH—[CY], where [CY] indicates which atom of L is attached to ring CY.

12. A compound according to any of embodiments 1-10 or a pharmaceutically acceptable salt thereof, wherein L is —NH—C(=O)-[CY], where [CY] indicates which atom of L is attached to ring CY.

13. A compound according to any of the preceding embodiments or a pharmaceutically acceptable salt thereof, wherein $Z^3$ is N.

14. A compound of any of the preceding embodiments, wherein ring B is selected from

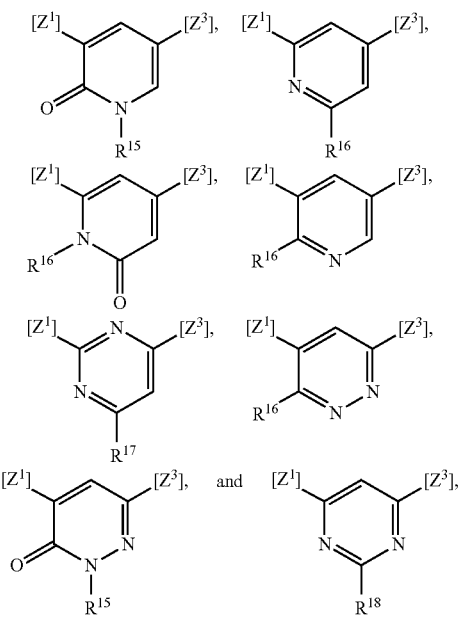

wherein [$Z^1$] indicates where the ring containing $Z^1$ is attached to ring B, and [$Z^3$] indicates where the ring containing $Z^3$ is attached to ring B, and $R^{15}$, $R^{16}$, $R^{17}$ and $R^{18}$ are each selected from CN, halo, $R^{20}$, —$N)(R^{20})_2$, —$OR^{20}$, and $C_{4-8}$ heterocycloalkyl optionally substituted with up to two groups selected from hydroxyl, $C_{1-4}$ alkyl, oxo, and halo; where each $R^{20}$ is independently H or $C_{1-4}$ alkyl optionally substituted with up to three groups independently selected from halo, oxo, $C_{1-4}$ alkoxy, hydroxyl, amino, and CN.

15. A compound of embodiment 1, which is selected from the compounds in Table 1 and the pharmaceutically acceptable salts thereof.

16. A pharmaceutical composition comprising a compound of any of the preceding embodiments or a pharmaceutically acceptable salt thereof and one or more pharmaceutically acceptable carriers.

17. A combination comprising a therapeutically effective amount of a compound according to any one of embodiments 1 to 14 or a pharmaceutically acceptable salt thereof and one or more therapeutically active co-agents.

18. A method of treating a proliferative disorder, comprising administering to a subject in need thereof a therapeutically effective amount of a compound of any of embodiments 1-14 or a pharmaceutically acceptable salt thereof.

19. A compound according to any one of embodiments 1 to 14 or a pharmaceutically acceptable salt thereof, for use as a medicament.

20. A compound according to any one of embodiments 1 to 14 or a pharmaceutically acceptable salt thereof, for use in the treatment of cancer.

21. Use of a compound according to any one of embodiments 1 to 14 or a pharmaceutically acceptable salt thereof in the manufacture of a medicament for the treatment of cancer.

Unless otherwise specified, in any of the foregoing enumerated embodiments, Ring A can be unsubstituted morpholine or a substituted morpholine derivative as described for Formula (I) above. In specific embodiments, Ring A is selected from the following morpholinic groups:

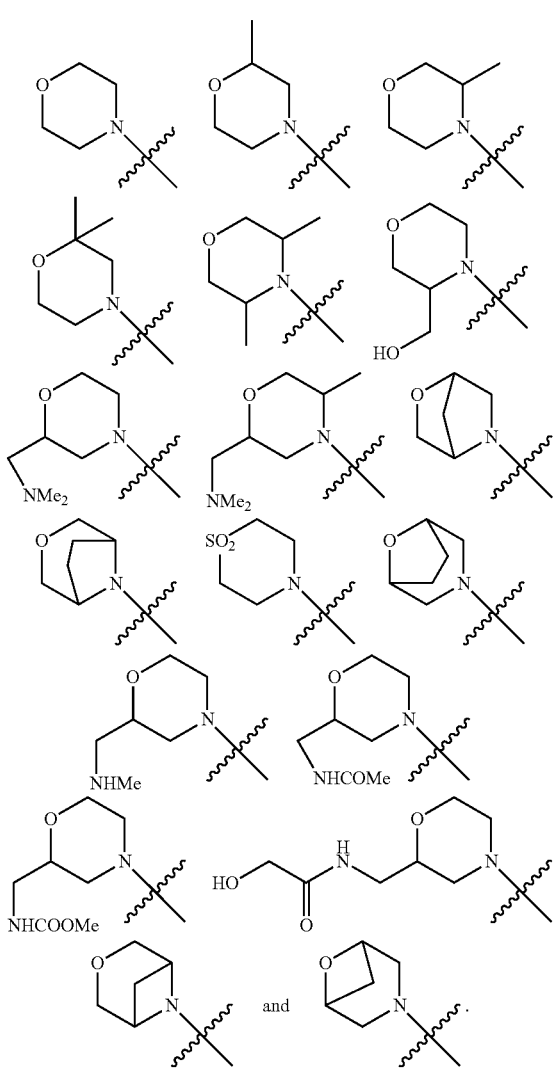

In certain embodiments, Ring A is unsubstituted morpholine.

In the foregoing enumerated embodiments, unless otherwise stated, Ring B is selected from phenyl, pyridine, pyrimidine, pyrazine, pyridone, pyrimidone, pyrazinone, pyridazinone, and thiazole. In certain of these embodiments, Ring B is selected from pyrazine, pyridazine, pyridone, pyrimidone, pyrazinone, and pyridazinone. Ring B in any of these embodiments can be substituted as described above for Formula (I); in some embodiments, Ring B is a six-membered ring that is substituted at positions 1, 3 and 5, where the N of ring A is at position 1 and $Z^2$ is at position 6. Where Ring B includes an oxo group (pyridone, pyridazinone, pyrazinone), oxo is sometimes at position 2 using this numbering. In some embodiments, Ring B is substituted by a group selected from methyl, ethyl, isopropyl, amino, hydroxyl, —NHMe, —NHEt, —NMe$_2$, —NHSO$_2$Me, —NH—CH$_2$CH$_2$OH, 4-tetrahydropyranyl, —O-4-tetrahydropyranyl, 1-pyrrolidinyl, 1-morpholinyl, —NH—CH(CH$_2$OH)$_2$, 1-pyrrolidin-2-one, 4-morpholin-3-one, 2-oxa-6-aza[3.3]heptan-6-yl, —CH$_2$CH$_2$OH, CF$_3$, SO$_2$Me, 2-propenyl, —CH$_2$CN, and —CH$_2$CH$_2$NHCOOMe.

Preferably, Ring B is selected from pyridine, pyrimidine, pyrazine, pyridone, pyrimidone, pyrazinone, and pyridazinone, optionally substituted and/or fused as described for Formula (I).

Where Ring B is pyridone, it is preferably a 2-pyridone, and optionally is N-alkylated with a C$_{1-4}$ alkyl, which may be substituted with one to three groups selected from OH, OMe, halo, and CN. In some embodiments, Ring B is substituted by a group selected from methyl, ethyl, isopropyl, amino, hydroxyl, —NHMe, —NHEt, —NMe$_2$, —NHSO$_2$Me, —NH—CH$_2$CH$_2$OH, 4-tetrahydropyranyl, —O-4-tetrahydropyranyl, 1-pyrrolidinyl, 1-morpholinyl, —NH—CH(CH$_2$OH)$_2$, 1-pyrrolidin-2-one, 4-morpholin-3-one, 2-oxa-6-aza[3.3]heptan-6-yl, 1-imidazolyl, 4-methyl-1,2,3-triazol-1-yl, 4-ethyl-1,2,3-triazol-1-yl, 4-isopropyl-1,2,3-triazol-1-yl, 4-(1-hydroxy-2-propyl)-1,2,3-triazol-1-yl, —CH$_2$CH$_2$OH, CF$_3$, SO$_2$Me, 2-propenyl, —CH$_2$CN, and —CH$_2$CH$_2$NHCOOMe.

Preferred embodiments of Ring B include

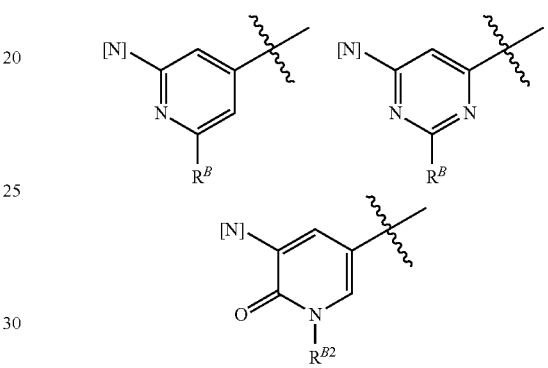

where [N] indicates the position attached to Ring A; R$^B$ is selected from amino, hydroxyl, —NHMe, —NHEt, —NMe$_2$, —NHSO$_2$Me, —NH—CH$_2$CH$_2$OH, —O-4-tetrahydropyranyl, 1-pyrrolidinyl, 1-morpholinyl, —NH—CH(CH$_2$OH)$_2$, 1-pyrrolidin-2-one, 4-morpholin-3-one, and 2-oxa-6-aza[3.3]heptan-6-yl; and R$^{B2}$ is selected from methyl, ethyl, isopropyl, —CH$_2$CH$_2$OH, 4-tetrahydropyranyl, CH$_2$CN, and —CH$_2$CH$_2$NHCOOMe.

In some of the foregoing embodiments, Ring C is phenyl or pyridine. When Ring C is pyridine, preferably Z$^4$ is N. Unless otherwise stated, R$^1$ is often methyl or CF$_3$.

In the enumerated embodiments where not otherwise specified, CY can be substituted with 1 or 2 groups selected from methyl, ethyl, isopropyl, CF$_3$, —CHF$_2$, CH$_2$F, CF$_2$CH$_3$, CH$_2$CF$_3$, 1-piperazinyl, 4-methyl-1-piperazinyl, 4-ethyl-1-piperazinyl, cyclopropyl, 1-cyanocyclopropyl, —CH$_2$CN, —CHMeCN, —CMe$_2$CN, OMe, OEt, F, Cl, —SO$_2$Me, —SO$_2$NMe$_2$, —CH$_2$NH$_2$, —CH$_2$NMe$_2$, —CH$_2$NHMe, and —CH$_2$OMe. It some of these embodiments, CY is phenyl or 4-pyridinyl, and at least one substituent is at position 3. In some embodiments, CY is a group of the formula

where [L] indicates which position is attached to L in Formula (I); $Z^{CY}$ is N or CH; R* is selected from methyl, ethyl, isopropyl, CF$_3$, —CHF$_2$, CH$_2$F, CF$_2$CH$_3$, CH$_2$CF$_3$, 1-piperazinyl, 4-methyl-1-piperazinyl, 4-ethyl-1-piperazinyl, cyclopropyl, 1-cyanocyclopropyl, —CH$_2$CN, —CHMeCN, —CMe$_2$CN, OMe, OEt, F, Cl, —SO$_2$Me, —SO$_2$NMe$_2$, —CH$_2$NH$_2$, —CH$_2$NMe$_2$, —CH$_2$NHMe, and —CH$_2$OMe; and R$^{CY}$ is selected from CF$_3$, OCF$_3$, t-butyl, —C(Me)$_2$CN, and —SO$_2$Me.

In certain embodiments, the compound of Formula (I) has this formula:

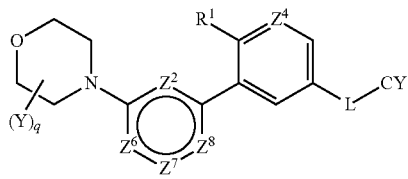

wherein Z$^2$ is N or CH;

Z$^4$ is N or CH;

Z$^6$ is C=O and Z$^7$ is NR$^Q$, where R$^Q$ is H or C$_{1-4}$ alkyl optionally substituted by OH, CN, OMe, SO$_2$Me, or 1-3 halogens;

or Z$^6$ is CH and Z$^7$ is C-Q;

Z$^8$ is CH or N (and preferably Z$^8$ and Z$^2$ are not both simultaneously N);

Q is selected from H, C$_{1-4}$ alkyl, C$_{1-4}$ haloalkyl, C$_{3-6}$ cycloalkyl, C$_{5-6}$ heteroaryl, C$_{4-7}$ heterocycloalkyl, including morpholine or any of the morpholinic groups shown above as options for Ring A, as well as 2-oxa-6-azaspiro[3.3]heptane, e.g.,

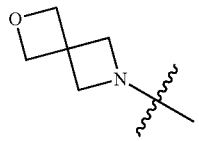 [SMILES: *N1CC2(COC2)C1]

and other spirocyclic systems; where the, C$_{1-4}$ alkyl, C$_{3-6}$ cycloalkyl, C$_{5-6}$ heteroaryl, or C$_{4-7}$ heterocycloalkyl is optionally substituted with a group selected from OH, NH$_2$, CN, OMe, SO$_2$Me, and NMe$_2$;

and R$_1$, Y, q, L, and CY are as defined for Formula (I) or any of the subgenera of Formula (I) described herein.

In a particular embodiment, the invention provides compounds of this formula:

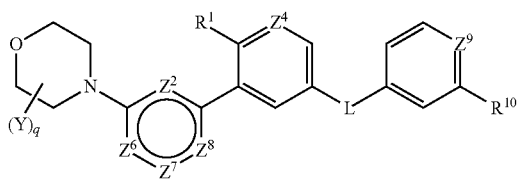

wherein:

Y is oxo, C$_{1-4}$ alkyl, or —CH$_2$T, where T is selected from hydroxyl, C$_{1-4}$ alkoxy, amino, C$_{1-4}$ alkylamino, di(C$_{1-4}$ alkyl) amino, —NHC(=O)(C$_{1-4}$ alkyl) and —NHC(=O)—O(C$_{1-4}$ alkyl);

q is 0, 1 or 2;

Z$^2$ is CH or N;

Z$^4$ is CH or N;

Z$^6$ is C=O, Z$^7$ is NR$^{20}$, and Z$^8$ is CH;

or Z$^6$ is N, Z$^7$ is CR$^{21}$, and Z$^8$ is CH;

or Z$^6$ is N, Z$^7$ is CR$^{22}$, and Z$^8$ is N, provided Z$^2$ and Z$^8$ are not both N;

Z$^9$ is N or CH;

R$^1$ is Me or CF$_3$;

L is —C(=O)NH— or —NH—C(=O)—;

R$^{10}$ is selected from C$_{1-4}$ alkyl, —O—C$_{1-3}$ alkyl, —SO$_2$—C$_{1-3}$ alkyl, and C$_{3-4}$ cycloalkyl, wherein each C$_{1-3}$ alkyl, —O—C$_{1-3}$ alkyl, —SO$_2$—C$_{1-3}$ alkyl, and C$_{3-4}$ cycloalkyl is optionally substituted with up to three groups selected from halo, CN, Me, CF$_3$, OH and OMe; and R$^{20}$, R$^{21}$, and R$^{22}$ are each selected from H, C$_{1-4}$ alkyl and C$_{4-8}$ heterocycloalkyl, wherein the C$_{1-4}$ alkyl and C$_{4-8}$ heterocycloalkyl are each optionally substituted with 1-2 groups selected from C$_{1-4}$ alkyl, oxo, halo, and —(CH$_2$)$_{1-2}$Q wherein Q is OH, C$_{1-4}$ alkoxy, —CN, NH$_2$, —NHR$^3$, —N(R$^3$)$_2$, —SO$_2$R$^3$, NHSO$_2$R$^3$, or NHC(O)R$^3$;

or a pharmaceutically acceptable salt thereof.

In specific embodiments of these compounds, Z$^6$ is C=O, Z$^7$ is NR$^{20}$, and Z$^8$ is CH. In some such embodiments, L is —NH—C(=O)—; in alternative embodiments, L is —C(=O)NH—. In some of these embodiments, Z$^4$ is N; in alternative embodiments, Z$^4$ is CH. In some of these embodiments, Z$^9$ is N; in other embodiments, Z$^9$ is CH. In some of these embodiments, R$^{10}$ is trifluoromethyl. In preferred embodiments of these compounds, R$^1$ is methyl.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for compounds of Formula (I) are tablets or gelatin capsules comprising an active ingredient of Formula (I) together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological activities, e.g. they modulate or inhibit activity of A-Raf, B-Raf and/or C-Raf, as indicated by test data provided in the next sections, and are therefore indicated for therapy or for use as research chemicals, e.g. as tool compounds. These compounds are especially useful for treatment of cancers driven by mutations in the Raf/Raf/MEK/ERK pathway, including cancers characterized by an activating Raf mutation such as RafV600E, including but not limited to melanoma, breast cancer, lung cancer, sarcoma, GI tumors such as gastrointestinal stromal tumors, ovarian cancer, colorectal cancer, thyroid cancer, and pancreatic cancer.

Thus, as a further embodiment, the present invention provides the use of a compound of formula (I) or any of the embodiments within the scope of Formula (I) as described herein, in therapy. In a further embodiment, the therapy is for a disease which may be treated by inhibition of A-Raf, B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula (I) or any of the embodiments within the scope of Formula (I) as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula (I) or any of the embodiments of such compounds described herein for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s). The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula (I) and the other therapeutic co-agent(s) together in the same pharmaceutical composition, or the compound of formula (I) and the other therapeutic co-agent(s) in separate form, e.g. in the form of a kit.

In one embodiment, the invention provides a pharmaceutical composition comprising a compound of formula (I) and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula (I).

The invention also provides a compound of formula (I) for use in a method of treating a disease or condition mediated by B-Raf or C-Raf, wherein the compound of formula (I) is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula (I). The invention also provides a compound of formula (I) for use in a method of treating a disease or condition mediated by B-Raf or C-Raf, wherein the compound of formula (I) is administered with another therapeutic co-agent. The invention also provides another therapeutic co-agent for use in a method of treating a disease or condition mediated by B-Raf or C-Raf, wherein the other therapeutic co-agent is administered with a compound of formula (I).

The invention also provides the use of a compound of formula (I) for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula (I).

General Synthesis Methods

The following Schemes and Examples illustrate representative methods useful for making the compounds of Formula (I).

Compounds of Formula (I) where ring B is a pyrimidine can be prepared from known halopyrimidine intermediates, introducing ring C by a Suzuki or similar arylation reactions. The group -L-CY can be attached to Ring C before it is installed, or a protected amine can be present at the position corresponding to L for the Suzuki, and can be converted into the amide linker to form -L-CY after the Suzuki reaction.

Scheme 1.

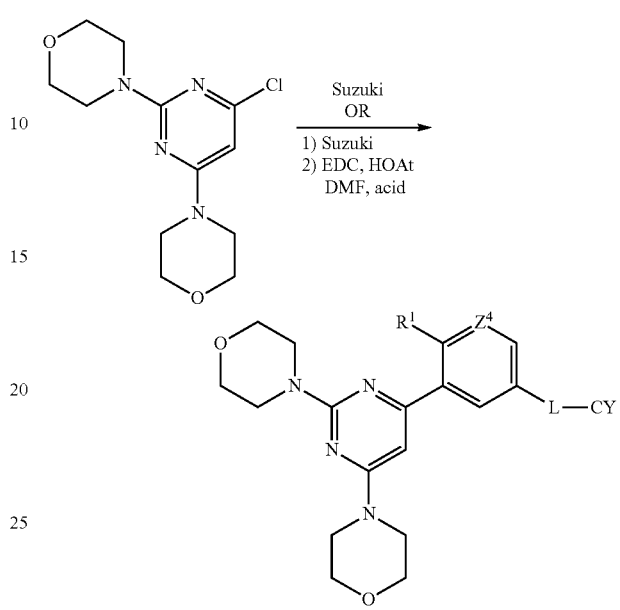

Compounds having different groups on Ring B, instead of two morpholine groups, can be prepared by using thioalkyl-substituted pyrimidines, as exemplified in the following scheme. A desired A-ring morpholine group (see Formula (I)) can be attached using nucleophilic aromatic substitution chemistry, and a Suzuki or similar arylation can be used to attach Ring C. The thioalkyl group can then be activated toward nucleophilic displacement by oxidation to an alkyl-sulfonyl group, which can be displaced by various nucleophilic groups.

Scheme 2.

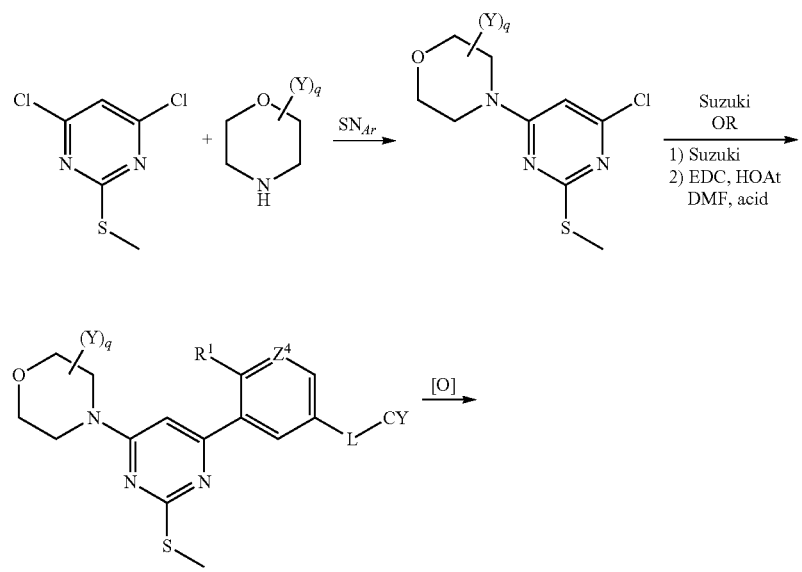

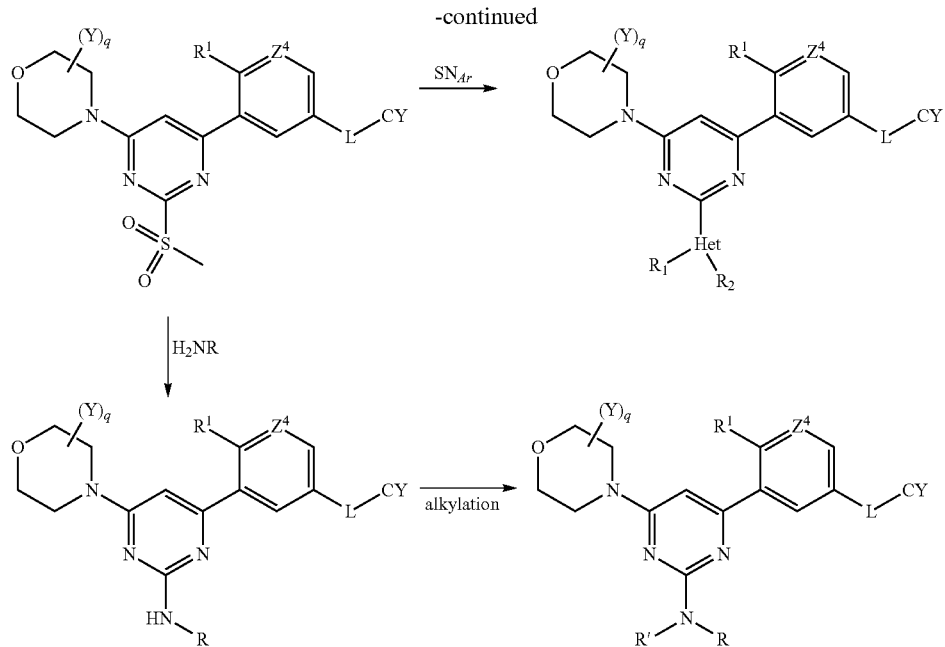

Alternatively, the oxidation can be done before the Suzuki reaction. This sequence can be used to install a heterocyclic or heteroaryl group on the B ring, or it can be used to introduce other nucleophiles such as alkoxy, amine or azide at this position. These can then be further modified as exemplified by amine alkylation (above) or, e.g., if azide is used as the nucleophile, a cycloaddition reaction can be used to make a heteroaryl substituent on Ring B as shown below.

Scheme 3.

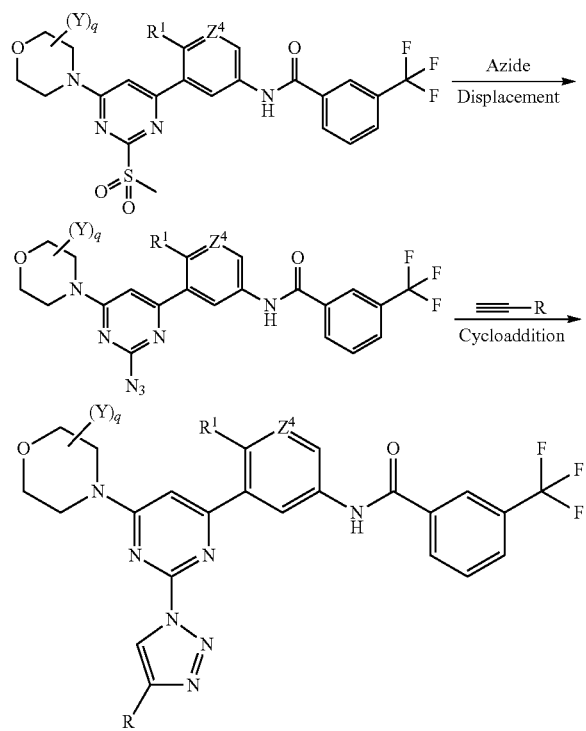

ing with a Suzuki reaction to introduce one group ($R_1$), providing a mixture of isomeric products, as shown in Scheme 4. A morpholine A-ring can then be attached by aromatic nucleophilic substitution chemistry, followed by another Suzuki reaction.

Scheme 4.

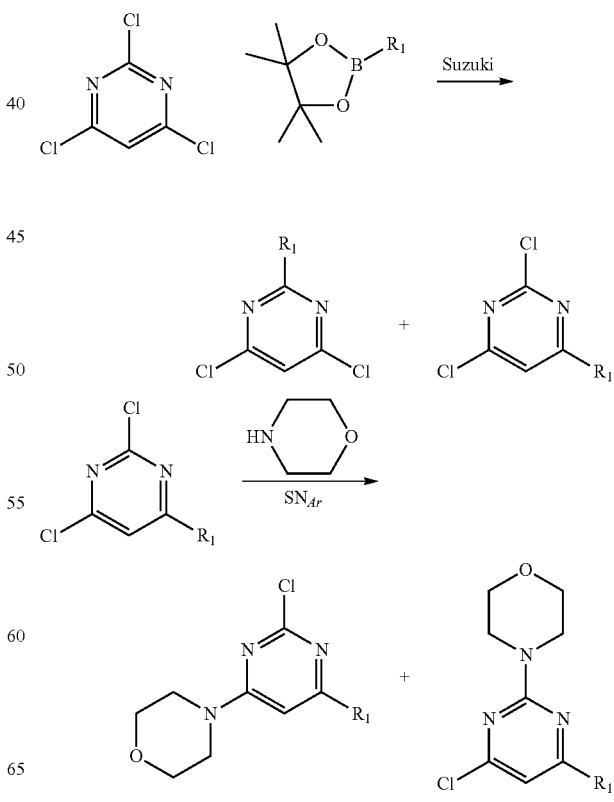

Other compounds of Formula (I) wherein Ring B is pyrimidine can be made from 2,4,6-trichloropyrimidine by start-

27
-continued
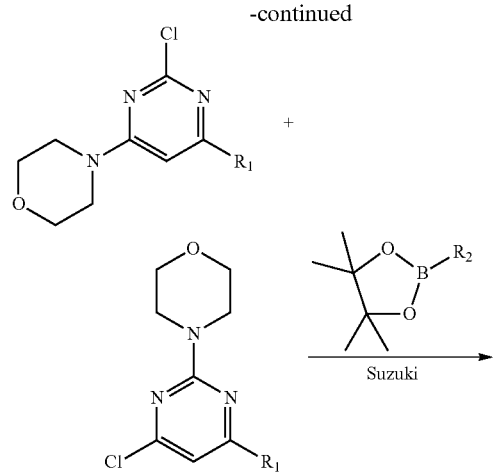
28
-continued
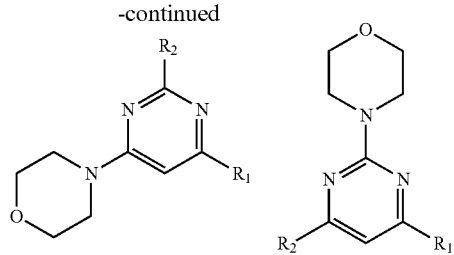
Compounds of Formula (I) wherein Ring B is pyridine can be made by the following general methods, which provide various pyridine isomers. Bromo-fluoropyridines allow selective use of nucleophilic aromatic substitution and Suzuki or similar arylation chemistry.
Scheme 5a.
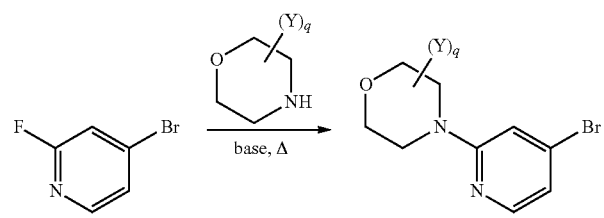
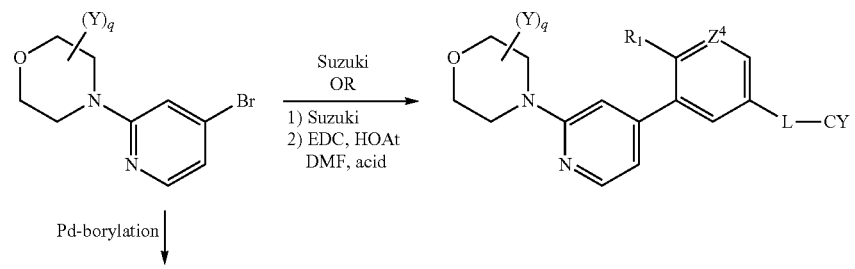
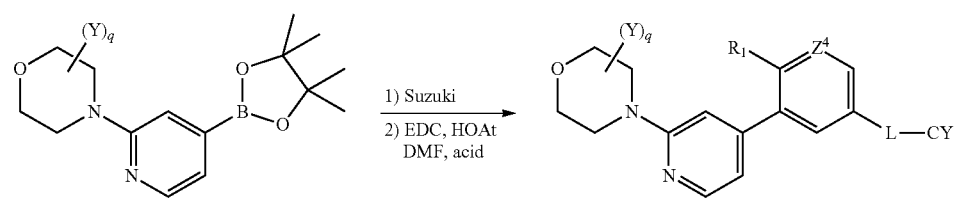

-continued
Scheme 5b.

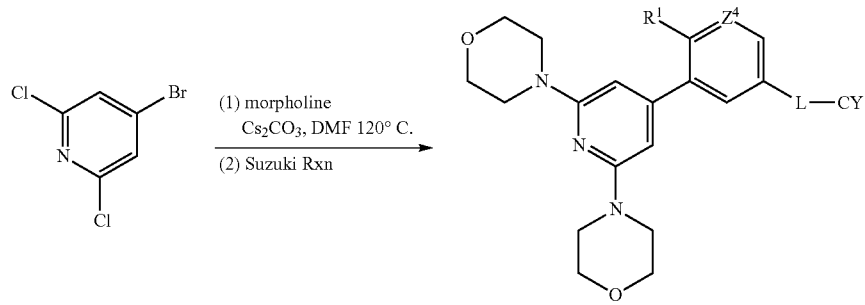

Various other substituent groups can be introduced onto pyridinyl B-ring compounds by introducing only one optionally substituted morpholine on a 2,4,6-trihalopyridine, then sequentially replacing the other two halogens with suitable groups as illustrated in the following schemes. Scheme 6 illustrates introduction of an aryl or heteroaryl group on the B ring, using Suzuki chemistry; Scheme 7 illustrates use of aromatic nucleophilic substitution chemistry to introduce other nucleophilic substituents such as amines, alkoxy groups, and alkylthio groups.

Scheme 6.

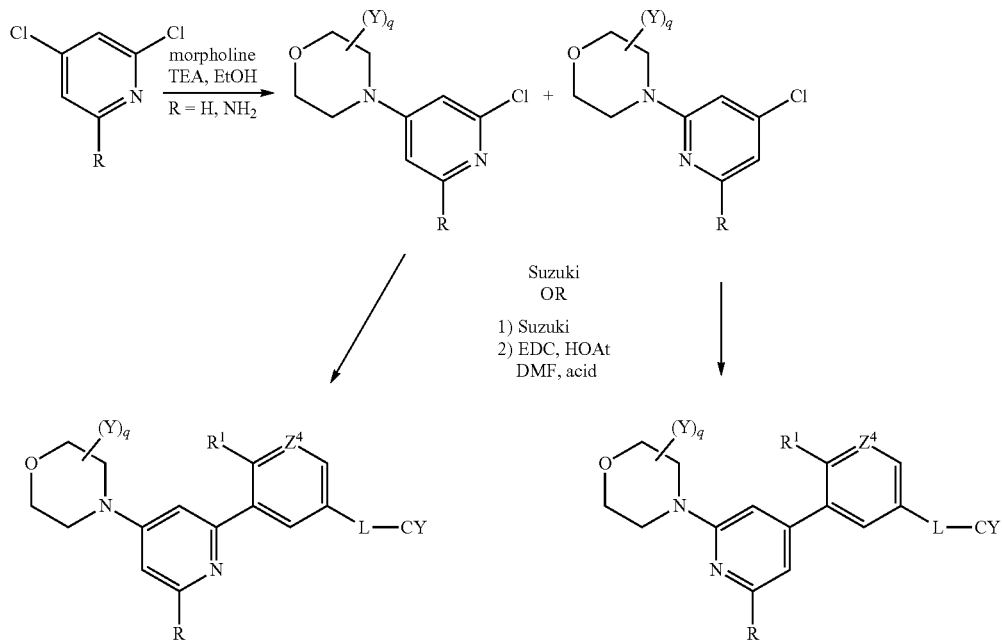

Scheme 7.

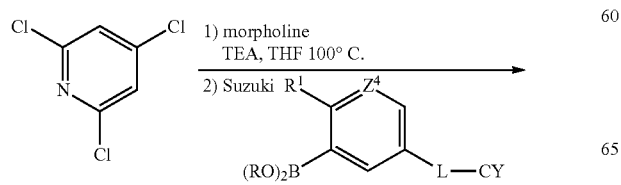

-continued

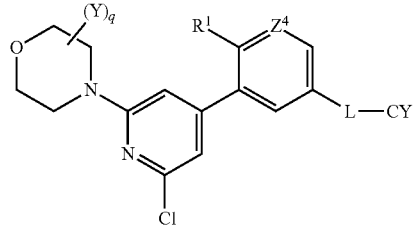

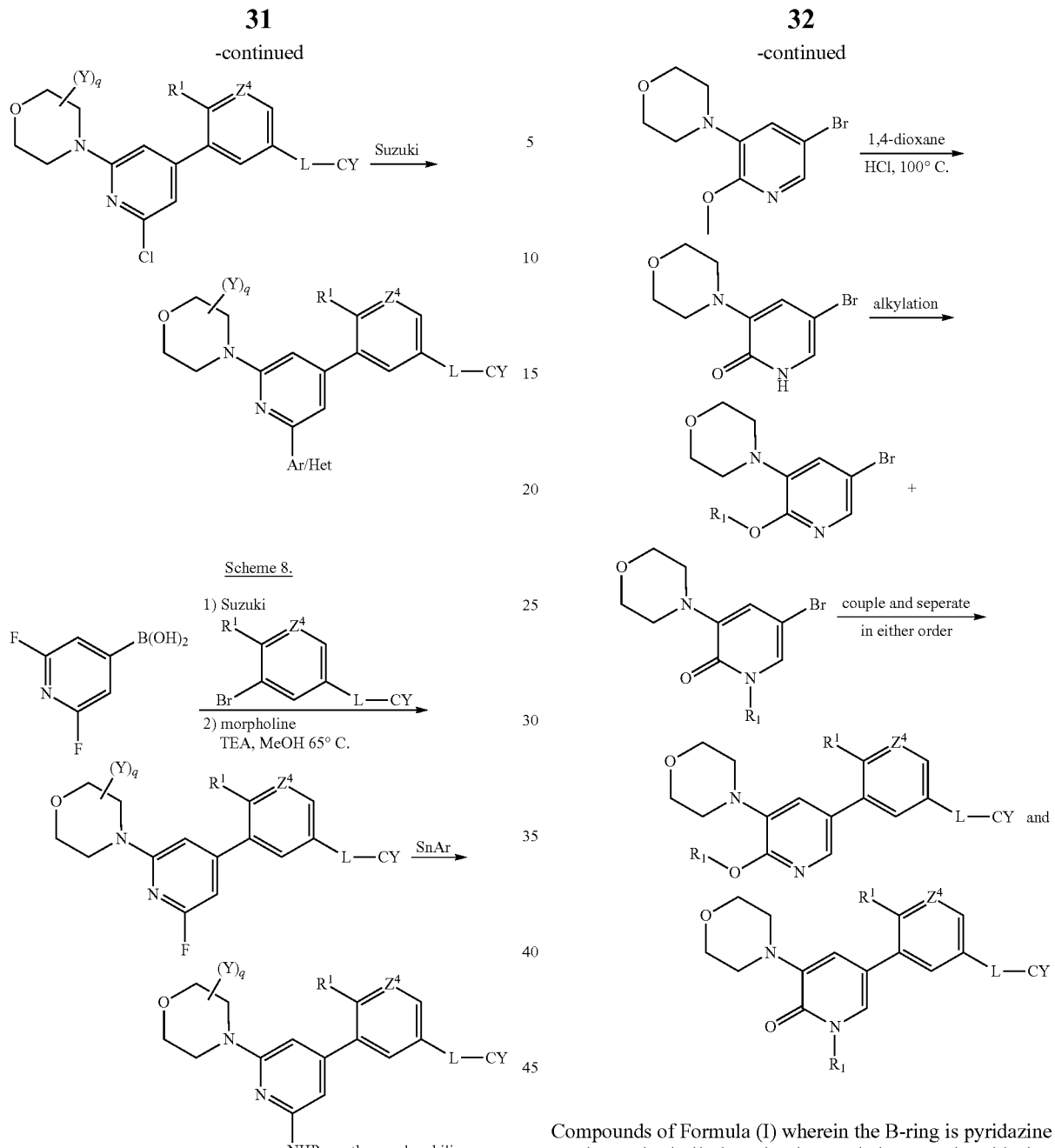

Scheme 8.

Scheme 9.

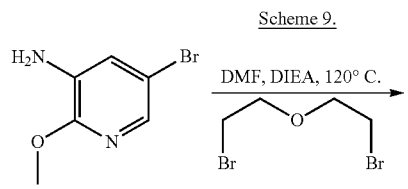

The following scheme illustrates a general route for synthesis of compound of Formula (I) wherein the B-ring is pyridone. The sequence also produces alkoxy-substituted pyridine B-ring compounds of Formula (I).

Compounds of Formula (I) wherein the B-ring is pyridazine can be made similarly, using known halogenated pyridazine starting materials with nucleophilic aromatic substitution reactions to attach Ring A (and/or other substituents on the B-ring), and Suzuki chemistry to attach Ring C.

Scheme 10.

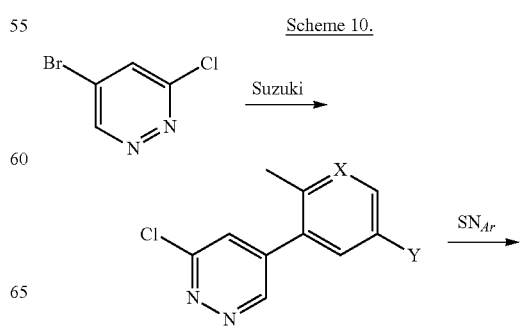

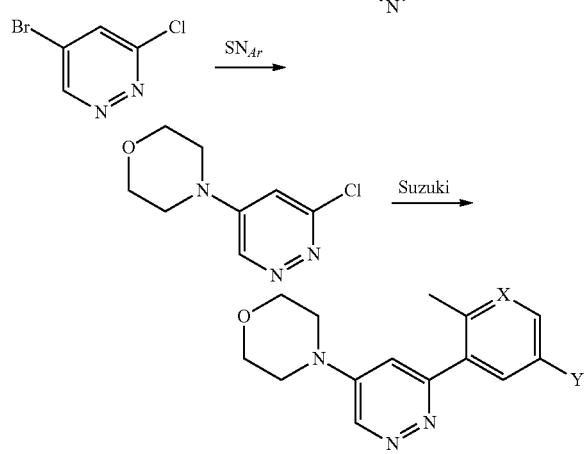

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

Compounds of the invention and intermediates can also be converted into each other according to methods generally known to those skilled in the art.

Terms used herein have their ordinary meaning to those of skill in the art unless otherwise defined. The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphosphine)palladium(0) |
| $Pd(dppf)Cl_2$—DCM | Dichloro-(1,2-bis(diphenylphosphino)ethan)-Palladium(II)-dichloromothethane adduct |
| RT or rt | room temperature |
| TBDMSCl | tert-butyldimethylsilylchloride |
| TEA | Triethylamine |
| THF | tetrahydrofuran |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; coneVoltage 20V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Compounds of the invention can be prepared using methods known in the art, along with methods disclosed herein, starting with known materials.

The syntheses of certain intermediates are outlined here, followed by description of syntheses of examples of compounds of Formula (I).

Synthesis of N-(4-methyl-3-(4,4,5,5-tetramethyl-1,3,2-dioxaborolan-2-yl)phenyl)-3-(trifluoromethyl)benzamide

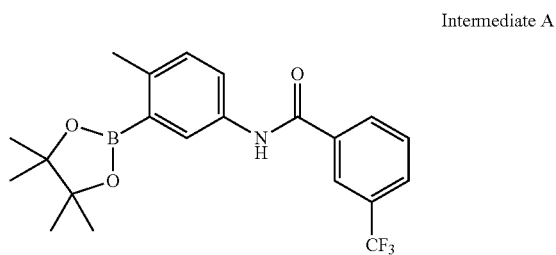 [SMILES: Cc1ccc(NC(=O)c2cccc(C(F)(F)F)c2)cc1B1OC(C)(C)C(C)(C)O1]

Intermediate A

To a solution of 4-methyl-3-(4,4,5,5-tetramethyl-1,3,2-dioxaborolan-2-yl)aniline (1.0 equiv.) in THF (0.1 M) at 0° C. was added 3-trifluoromethylbenzoylchloride (1.0 equiv.) and the reaction was stirred at room temperature for 3 h. The solution was concentrated and dried under vacuo to give N-(4-methyl-3-(4,4,5,5-tetramethyl-1,3,2-dioxaborolan-2-yl)phenyl)-3-(trifluoromethyl)benzamide as a tan solid in 96% yield. LCMS (m/z) (M+H)=406.2, Rt=1.24 min.

Synthesis of N-(6-methyl-5-(4,4,5,5-tetramethyl-1,3,2-dioxaborolan-2-yl)pyridin-3-yl)-3-(trifluoromethyl)benzamide

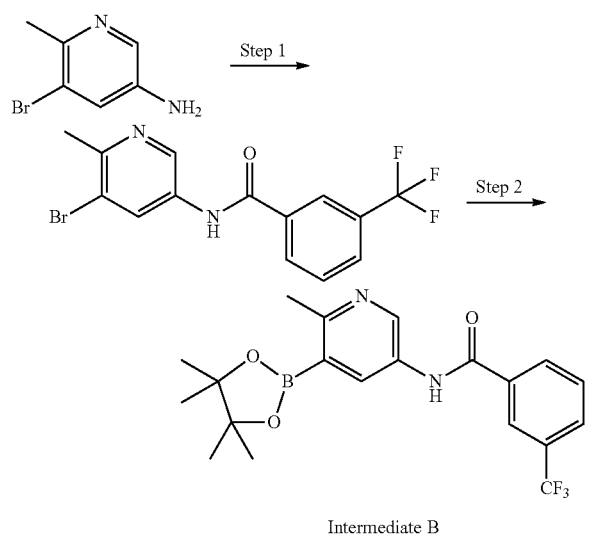

Intermediate B

Step 1: To a 0.4 M solution of 5-bromo-6-methylpyridin-3-amine (1.00 equiv.) in DCM was added DIEA (1.00 equiv.) and 3-(trifluoromethyl)benzoyl chloride (1.00 equiv.). The mixture was stirred at ambient temperature for 3 hr. The reaction mixture was diluted with DCM, washed with saturated aqueous sodium bicarbonate, dried over sodium sulfate, filtered, and concentrated to give N-(5-bromo-6-methylpyridin-3-yl)-3-(trifluoromethyl)benzamide as an off-white solid in 98% yield. LCMS (m/z) (M+H)=359.0/361.0, Rt=0.86 min.

Step 2: To a 0.27 M solution N-(5-bromo-6-methylpyridin-3-yl)-3-(trifluoromethyl)benzamide (1.00 equiv.) in 1,4-dioxane was added bis(pinacolato)diboron (1.50 equiv.), potassium acetate (2.00 equiv.) and PdCl$_2$(dppf).CH$_2$Cl$_2$ adduct (0.10 equiv.). The reaction was irradiated at 120° C. for 20 min. The cooled reaction mixture was diluted with ethyl acetate and filtered through Celite. The filtrate was concentrated to give N-(6-methyl-5-(4,4,5,5-tetramethyl-1,3,2-dioxaborolan-2-yl)pyridin-3-yl)-3-(trifluoromethyl)benzamide as a dark brown tacky solid in quantitative yield. LCMS (m/z) (M+H)=325.0, Rt=0.59 min.

Synthesis of 2-(2-cyanopropan-2-yl)-N-(4-methyl-3-(4,4,5,5-tetramethyl-1,3,2-dioxaborolan-2-yl)pthenyl)isonicotinamide

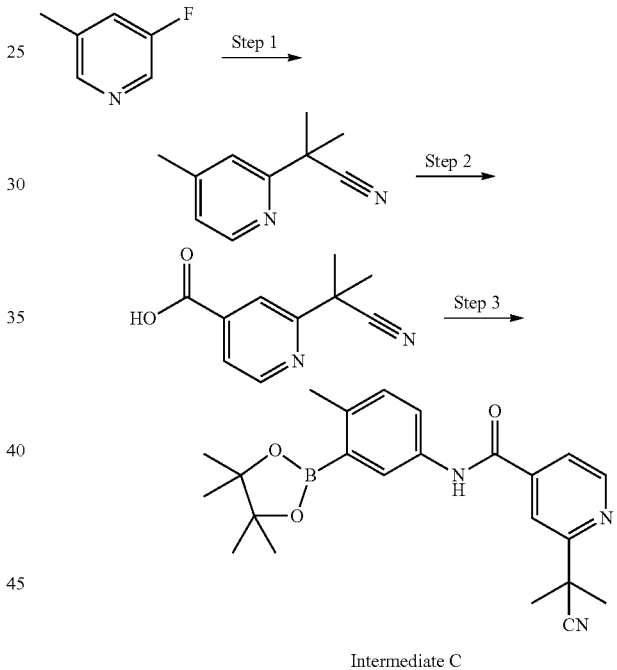

Intermediate C

Step 1: To a mixture of 2-fluoro-4-methylpyridine (1.0 equiv.) and isobutyronitrile (4.0 equiv.) was cannulated KHMDS (1.2 equiv.) in toluene. The mixture was heated to reflux for 1.5 hours at which time the reaction was cooled to RT, quenched with NH$_4$Cl (aq), extracted with EtOAc, dried over Na$_2$SO$_4$, filtered, and concentrated. The crude material was used in next step. LCMS (m/z) (M+H)=161.1, Rt=0.48 min.

Step 2: To a solution of 2-methyl-2-(4-methylpyridin-2-yl)propanenitrile (1.0 equiv.) in water (0.38 M) was added potassium permanganate (6.0 equiv.). The mixture was heated at 60° C. for 1 hr. The mixture was cooled to rt, acidified with 2 M HCl to pH 4 and extracted with EtOAc. The organic layer was washed with brine, dried over Na$_2$SO$_4$ and concentrated. LC-MS showed the crude yellowish solid still contained 15% of diacid. Redissolved the crude in EtOAc and washed with acidic water (pH 4). The organic layer was washed with brine, dried over Na₂SO₄ and concentrated to yield off white solid. NO diacid left. Used as is in next step. LCMS (m/z) (M+H)=191.0, Rt=0.53 min.

Step 3: EDC (1.3 equiv.) was added to a solution of 4-methyl-3-(4,4,5,5-tetramethyl-1,3,2-dioxaborolan-2-yl)aniline (1.0 equiv.), 2-(2-cyanopropan-2-yl)isonicotinic acid (1.2 equiv.), HOAt (1.3 equiv.) in DMF (0.19 M). The mixture was stirred at ambient temperature 3 hrs. The reaction mixture was diluted with water and extracted with ethyl acetate. The combined extracts were washed sequentially with 1M aqueous sodium hydroxide and brine, dried over sodium sulfate, filtered, and concentrated to yield 2-(2-cyanopropan-2-yl)-N-(4-methyl-3-(4,4,5,5-tetramethyl-1,3,2-dioxaborolan-2-yl)phenyl)isonicotinamide in 97% yield. LCMS (m/z) (M+H)=406.2, Rt=1.10 min.

Synthesis of N-(4-methyl-3-(4,4,5,5-tetramethyl-1,3,2-dioxaborolan-2-yl)phenyl)-3-(trifluoromethyl)benzamide

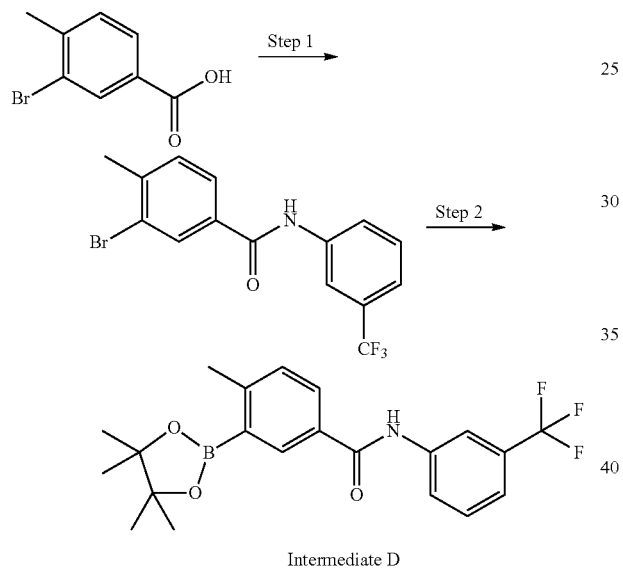

Intermediate D

Step 1: To a solution of 3-bromo-4-methylbenzoic acid (1.0 equiv.) in DMF (1.2M) was added EDC (1.0 equiv.) and HOBt (1.0 equiv.) followed by 3-trifluoromethylaniline (1.0 equiv.) and the reaction was stirred at ambient temperature for 48 h. The reaction mixture was partitioned between ethyl acetate and water. The separated organic layer was dried with sodium sulfate and concentrated under vacuo. The concentrated crude was purified via silica gel chromatography and eluted with 0 to 100% ethyl acetate in heptanes to give 3-bromo-4-methyl-N-(3-(trifluoromethyl)phenyl)benzamide in 83% yield. LCMS (m/z) (M+H)=358/360, Rt=1.1 min.

Step 2: To 3-bromo-4-methyl-N-(3-(trifluoromethyl)phenyl)benzamide (1.0 equiv.) in a microwave vial equipped with a stir bar was added dioxane (0.5M) was added 4,4,4',4',5,5,5',5'-octamethyl-2,2'-bi(1,3,2-dioxaborolane) (3 equiv.) and potassium acetate (6 equiv.) and nitrogen was bubbled through the reaction mixture for 5 min. To it was added PdCl₂(dppf)-DCM adduct (0.1 equiv) and the vial was sealed and heated to 120° C. for 16 h. The reaction mixture was filtered and the filter paper was washed with dichloromethane and the filtrate was concentrated under vacuo. It was then loaded on celite and purified via silica gel chromatography eluting with 0-100% ethyl acetate in heptanes to afford N-(4-methyl-3-(4,4,5,5-tetramethyl-1,3,2-dioxaborolan-2-yl)phenyl)-3-(trifluoromethyl)benzamide in quantitative yield. LCMS (m/z) (M+H)=406.2, Rt=1.2 min.

Synthesis of N-(4-methyl-3-(4,4,5,5-tetramethyl-1,3,2-dioxaborolan-2-yl)phenyl)-2-(trifluoromethyl)isonicotinamide

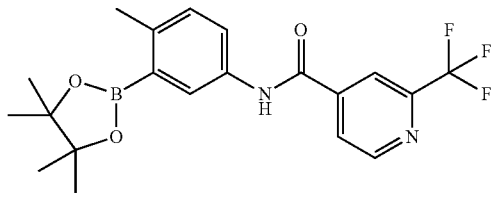

Intermediate E

To a mixture of 4-methyl-3-(4,4,5,5-tetramethyl-1,3,2-dioxaborolan-2-yl)aniline (1.0 equiv.) and 3-(trifluoromethyl)benzoic acid (1.1 equiv.) in DMF (0.27 M) was added HOAt (1.3 equiv.) and EDC (1.3 equiv.) After 3 h the reaction mixture was diluted with water and then extracted with EtOAc. The organic phase was washed sequentially with 1 M aqueous sodium hydroxide and brine and was then dried over sodium sulfate. The solution was concentrated and dried under vacuo to give N-(4-methyl-3-(4,4,5,5-tetramethyl-1,3,2-dioxaborolan-2-yl)phenyl)-2-(trifluoromethyl)isonicotinamide in 91% yield. LCMS (m/z) (M+H)=407.1, Rt=1.13 min.

2-(tert-butyl)-N-(4-methyl-3-(4,4,5,5-tetramethyl-1,3,2-dioxaborolan-2-yl)phenyl)isonicotinamide

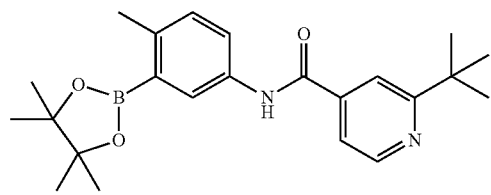

Intermediate F

A solution of 5-amino-2-methylphenylboronic acid, pinacol ester (1.0 equiv.), 2-(tert-butyl)isonicotinic acid (1.0 equiv.), EDC (1.0 equiv.) and 1-hydroxy-7-azabenzotriazole (0.380 g, 1.0 equiv.) in DMF (0.3 M) was stirred at RT for 68 hr. The reaction mixture was then diluted with EtOAc and water, the organic layer was isolated and the aqueous layer was extracted twice with EtOAc. The combined organics were dried over MgSO₄, filtered and concentrated in vaccuo to yield 2-(tert-butyl)-N-(4-methyl-3-(4,4,5,5-tetramethyl-1,3,2-dioxaborolan-2-yl)phenyl)isonicotinamide as a white solid in 91%. LCMS (m/z) (M+H)=395.1, Rt=0.71 min.

Synthesis of 2-(2-cyanopropan-2-yl)-N-(6-methyl-5-(4,4,5,5-tetramethyl-1,3,2-dioxaborolan-2-yl)pyridin-3-yl)isonicotinamide

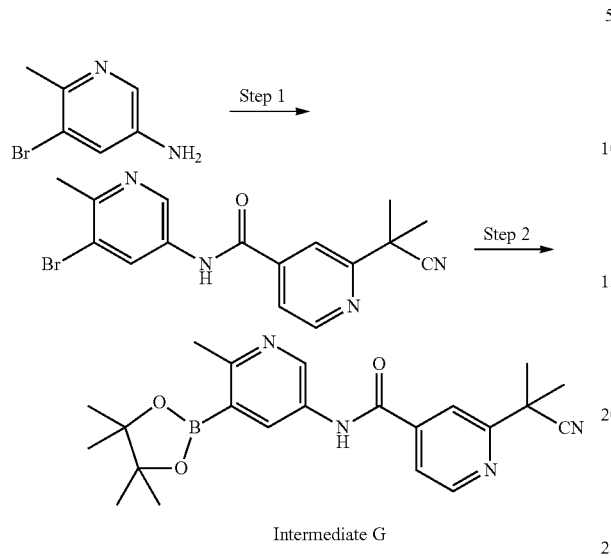

Intermediate G

Step 1: EDC (1.3 equiv.) was added to a solution of 5-bromo-6-methylpyridin-3-amine (1.05 equiv), 2-(2-cyanopropan-2-yl)isonicotinic acid (1.0 equiv), HOAt (1.3 equiv) in DMF (0.17 $\underline{M}$). The mixture was stirred at ambient temperature 3 hrs. The reaction mixture was diluted with water and extracted with ethyl acetate. The combined extracts were washed sequentially with 1$\underline{M}$ aqueous sodium hydroxide and brine, dried over sodium sulfate, filtered, and concentrated. The crude was purified by ISCO(50% EtOAc/Heptane). Combined fractions still contained 17% 5-bromo-6-methylpyridin-3-amine. Add 2-(2-cyanopropan-2-yl)isonicotinic acid (0.3 equiv), EDC (0.3 equiv), HOAt (0.3 equiv) in DMF (0.17 $\underline{M}$). After stirred at rt overnight, the reaction mixture was diluted with water and extracted with ethyl acetate. The combined extracts were washed sequentially with 1$\underline{M}$ aqueous sodium hydroxide and brine, dried over sodium sulfate, filtered, and concentrated to yield N-(5-bromo-6-methylpyridin-3-yl)-2-(2-cyanopropan-2-yl)isonicotinamide in 71% over three steps. LCMS (m/z) (M+H)=359.0, Rt=0.73 min.

Step 2: To a solution of N-(5-bromo-6-methylpyridin-3-yl)-2-(2-cyanopropan-2-yl)isonicotinamide (1.0 equiv.) in dioxane (0.18 $\underline{M}$) was added potassium acetate (5.0 equiv.) and 4,4,4',4',5,5,5',5'-octamethyl-2,2'-bi(1,3,2-dioxaborolane) (1.5 equiv.). The solution was degassed with nitrogen and Pd(dppf)Cl$_2$-DCM was added. The reaction was then heated to 80° C. overnight. The mixture was concentrated and diluted with EtOAc, washed with H$_2$O, brine. The organic layer was dried over Na$_2$SO$_4$ and concentrated. The residue was then titrated in hexane. Filtered and the solid was collected to yield 2-(2-cyanopropan-2-yl)-N-(6-methyl-5-(4,4,5,5-tetramethyl-1,3,2-dioxaborolan-2-yl)pyridin-3-yl)isonicotinamide in 82% yield. LCMS (m/z) (M+H)=325.1, Rt=0.49 min. 1H NMR (400 MHz, <cdcl3>) δ ppm 1.27 (s, 6H), 1.32-1.40 (m, 12H), 1.82 (s, 6H), 2.75 (s, 3H), 7.69 (d, J=3.91 Hz, 1H), 7.86-7.95 (m, 1H), 7.98 (s, 1H), 8.28 (br. s., 1H), 8.79 (d, J=5.09 Hz, 1H), 8.89 (br. s., 1H).

Synthesis of 3-(difluoromethyl)benzoic acid

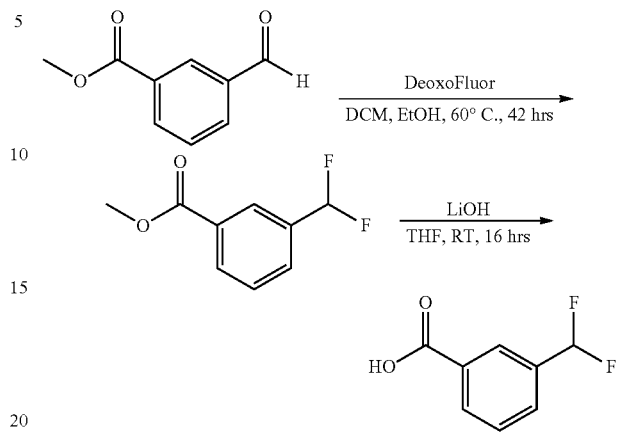

Step 1: In a high pressure vial, a solution of methyl 3-formylbenzoate (1 equiv.) in DCM/EtOH (867:1, 0.40$\underline{M}$) was added DeoxoFluor (2.0 equiv.). The reaction was purged with N$_2$, the vessel was sealed and heated at 60° C. After 18 hrs of stirring additional DeoxoFluor (2.0 equiv.) was added and allowed to stir for 42 hrs. The reaction was followed by TLC (25% EtOAc in heptanes). The reaction was partitioned between brine and EtOAc. The aqueous layer was further washed with EtOAc (3×) and the combined organics were dried over Na$_2$SO$_4$, filtered, and concentrated. The crude material was purified via flash chromatography over silica gel eluting with heptanes and 0-25% ethyl acetate gradient. Isolated methyl 3-(difluoromethyl)benzoate as a yellow oil in 62% yield. 1H NMR (400 MHz, <cdcl3>) δ ppm 3.94 (s, 3H) 6.53-6.84 (m, 1H) 7.54 (t, J=7.83 Hz, 1H) 7.71 (d, J=7.83 Hz, 1H) 8.15 (d, J=7.83 Hz, 1H) 8.18 (s, 1H).

Step 2: To a solution of methyl 3-(difluoromethyl)benzoate (1 equiv.) in THF (0.25$\underline{M}$) was added 1$\underline{M}$ LiOH (2.5 equiv.) and allowed to stir at RT. Upon initial addition of LiOH, the solution turned from clear to a burnt orange, and after 2 hrs the solution is light yellow. The reaction stirred for 18 hrs at RT. The volatiles were removed in vacuo, and the aqueous phase was acidified to ~pH 3. A white precipitate was formed, filtered and dried. Isolated 3-(difluoromethyl)benzoic acid in 78% yield. LCMS (m/z) (M+H)=245.1, Rt=0.73). 1H NMR (400 MHz, <dmso>) δ ppm 6.97-7.30 (m, 1H) 7.63-7.71 (m, 1H) 7.83 (d, J=7.43 Hz, 1H) 8.06-8.16 (m, 1H)

Synthesis of 2-(1,1-difluoroethyl)isonicotinic acid

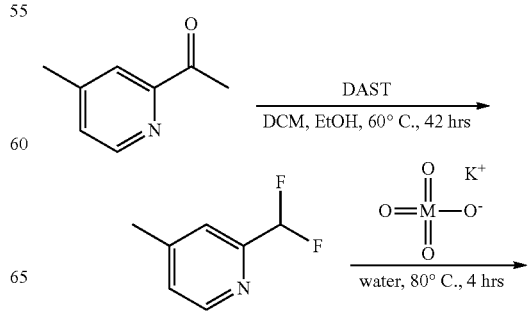

Synthesis of 3-(2-cyanopropan-2-yl)benzoic acid

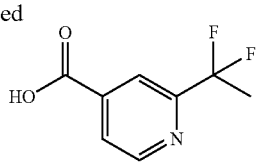

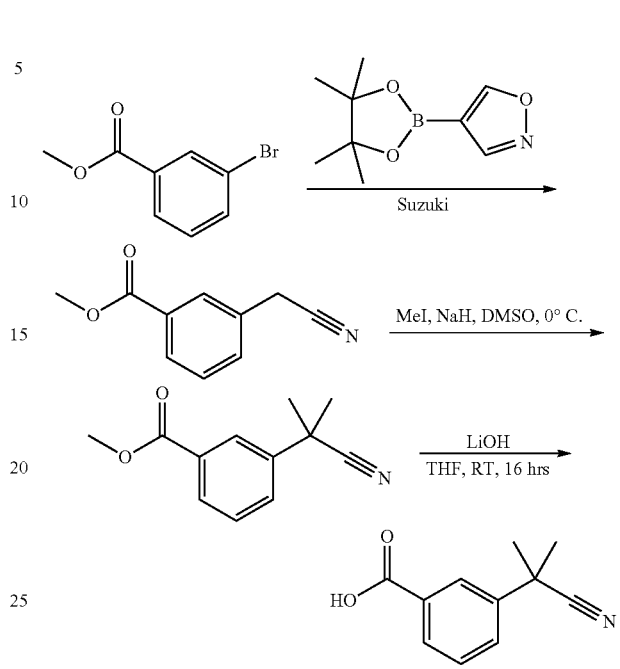

Step 1: In a high pressure vial charged with a solution of 1-(4-methylpyridin-2-yl)ethanone (1.0 equiv.) and EtOH (0.1 equiv) in DCM (2.0M) was added DAST (2.5 equiv.). The reaction was heated to 30° C. and heated for 48 hrs. LCMS analysis indicated the formation of the desired product (MH+—157.9, Rt—0.54 min). The reaction was diluted with DCM and quenched with NaHCO3, slowly at 0° oC. The phases were separated and the aqueous layer was washed with DCM (2×). The combined organics were dried over MgSO4, filtered, and concentrated. The crude material was purified via flash chromatography over silica gel eluting with heptanes and 0-100% ethyl acetate gradient. Isolated 2-(1,1-difluoroethyl)-4-methylpyridine in 27% yield. LCMS (m/z) (M+H)=157.9, Rt=0.54.

Step 2: To a solution of 2-(1,1-difluoroethyl)-4-methylpyridine (1 equiv.) in water (2.0 $\underline{M}$) was added KMnO$_4$ (3.0 equiv) and heated to 80° C. for 4 hrs. LCMS analysis indicated the formation of the desired product (MH$^+$—188.0, Rt—0.52 min). The reaction was acidified to pH 3 with 1$\underline{M}$ HCl. The white precipitate was filtered and dried. Isolated 2-(1,1-difluoroethyl)isonicotinic acid in 12% yield. LCMS (m/z) (M+H)=188.0, Rt=0.52). 1H NMR (400 MHz, <cd3od>) δ ppm 2.01 (t, J=18.78 Hz, 3H) 8.00 (d, J=4.70 Hz, 1H) 8.16 (s, 1H) 8.80 (d, J=5.09 Hz, 1H).

Synthesis of 2-(difluoromethyl)isonicotinic acid

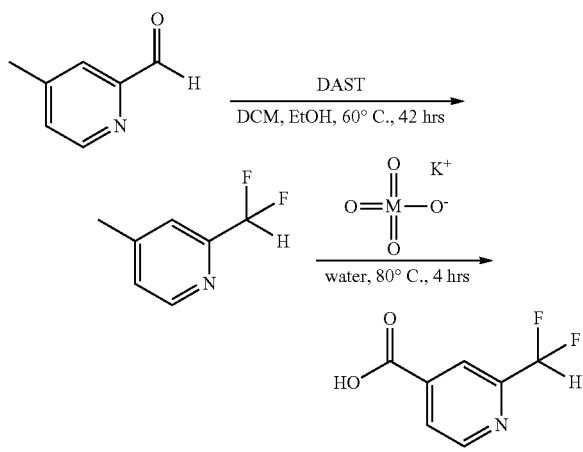

Procedure follows exactly as that of 2-(1,1-difluoroethyl) isonicotinic acid. Isolated 2-(difluoromethyl)isonicotinic acid in 23%. LCMS (m/z) (M+H)=174.0, Rt=0.48).

Step 1: To a vial with a stir bar was added methyl 3-bromobenzoate (1.0 equiv.) 4-isoxazoleboronic acid (1.2 equiv.), PdCl$_2$(dppf).CH$_2$Cl$_2$ adduct (0.1 equiv.), 1$\underline{M}$ KF (2.0) and DMSO (0.10 $\underline{M}$). The reaction mixture was degassed with bubbling nitrogen and the vial capped and heated at 130° C. for 18 hr. LCMS analysis indicated the formation of the desired product (MH$^+$—176, Rt—0.62 min). The reaction mixture was diluted with a saturated solution of NH$_4$Cl and extracted with EtOAc (2×). The combined organics were washed with water and brine, dried over MgSO$_4$, filtered and concentrated. The crude material was purified via flash chromatography over silica gel eluting with heptanes and 0-100% ethyl acetate gradient. Isolated methyl 3-(cyanomethyl)benzoate in 69% yield. LCMS (m/z) (M+H)=176.1, Rt=0.62). 1H NMR (400 MHz, <cd3od>) δ ppm 3.92 (s, 3H), 3.99 (s, 2H), 7.49-7.55 (m, 1H), 7.62 (d, J=7.83 Hz, 1H), 7.99 (d, J=7.83 Hz, 1H), 8.04 (s, 1H).

Step 2: To a solution of methyl 3-(cyanomethyl)benzoate (1.0 equiv.) in DMSO (0.50 $\underline{M}$) was slowly added NaH (3 equiv.) at 0° C. and allowed to stir for 20 mins. To the mixture was added MeI (3.0 equiv.) and allowed to stir 18 hrs at RT. LCMS analysis indicated the formation of the desired product (MH$^+$—204, Rt—0.78 min). Under ice-cooling, the reaction mixture was diluted with water and extracted with EtOAc. The organics were washed with water and brine, dried over MgSO$_4$, filtered, and concentrated. The crude material was purified via flash chromatography over silica gel eluting with heptanes and 0-50% ethyl acetate gradient. Isolated methyl 3-(2-cyanopropan-2-yl)benzoate in 63% yield. LCMS (m/z) (M+H)=204.1, Rt=0.78).

Step 3: To a solution of methyl 3-(2-cyanopropan-2-yl) benzoate (1 equiv.) in THF (0.10 $\underline{M}$) was added 1$\underline{M}$ LiOH (2.5 equiv.) and allowed to stir at RT for 18 hrs. LCMS analysis indicated the formation of the desired product (MH$^+$—190, Rt—0.60 min). The volatiles were removed in vacuo, and the aqueous phase was acidified to ~pH3 with 1$\underline{M}$ HCl. A white precipitate was formed, filtered and dried. Isolated 3-(2-cyanopropan-2-yl)benzoic acid in 63% yield. LCMS (m/z)

(M+H)=190.1, Rt=0.60. 1H NMR (400 MHz, <cd3od>) δ ppm 1.76 (s, 6H) 7.54 (t, J=7.83 Hz, 1H) 7.74-7.80 (m, 1H) 8.00 (d, J=7.43 Hz, 1H) 8.16-8.21 (m, 1H).

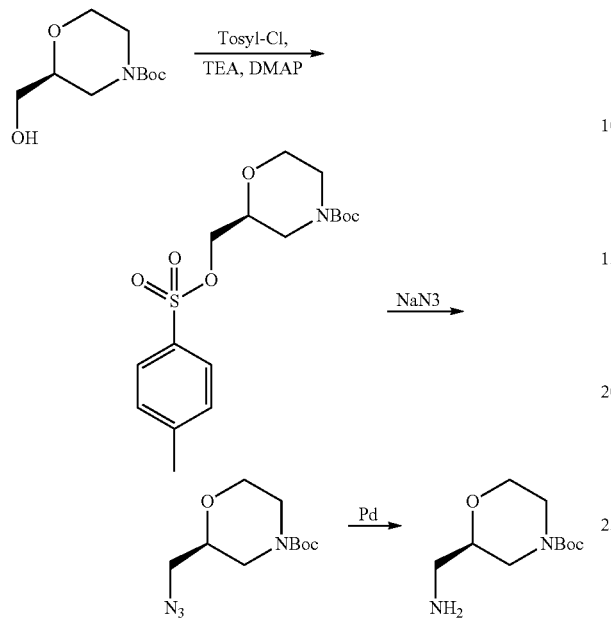

Synthesis of (R)-tert-butyl 2-(aminomethyl)morpholine-4-carboxylate

Step 1. A solution of (S)-tert-butyl 2-(hydroxymethyl)morpholine-4-carboxylate (1.0 equiv.), tosyl chloride (1.10 equiv.), triethylamine (1.40 equiv.) and N,N-dimethylpyridin-4-amine (0.1 equiv.) in dichloromethane (0.1 M) at RT. The resulting mixture was stirred at RT for 2 hours. The reaction mixture was then diluted with water and the aqueous layer was separated and washed sequentially with NaOH (1 M), water, brine dried over sodium sulfate then concentrated in vaccuo to yield (S)-tert-butyl 2-((tosyloxy)methyl)morpholine-4-carboxylate as a pale yellow oil in 99% yield. LCMS (m/z) (M+H)=390.2, Rt=0.84 min.

Step 2. To a solution of (S)-tert-butyl 2-((tosyloxy)methyl) morpholine-4-carboxylate (1.0 equiv.) in DMF (0.1 M) at RT was added sodium azide (2.00). The resulting mixture was heated to 60° C. for 24 h. The reaction then cooled to RT and partitioned between water and diethyl ether. The organic layer was separated then washed with water followed by brine then dried over sodium sulfate. The organic layer was then concentrated in vaccuo to yield (S)-tert-butyl 2-(azidomethyl) morpholine-4-carboxylateas a white solid oil in 83% yield.

Step 3. A solution of (S)-tert-butyl 2-(azidomethyl)morpholine-4-carboxylateas (1.0 equiv.) in ethanol (0.1 M) was evacuated and back filled with argon (×3). To the solution was then added Pd/C (0.20 eq.) and the mixture was evacuated and back filled with hydrogen (×3). The mixture was then stirred at RT under a positive pressure of atmospheric hydrogen (balloon) for 24 h. The hydrogen gas was removed by evacuation and the reaction backfilled with argon. The reaction mixture was then filtered through a pad of celite and then concentrated in vaccuo to afford (R)-tert-butyl 2-(aminomethyl)morpholine-4-carboxylate as a white solid in 91% yield. LCMS (m/z) (M+H)=217.1, Rt=0.43 min.

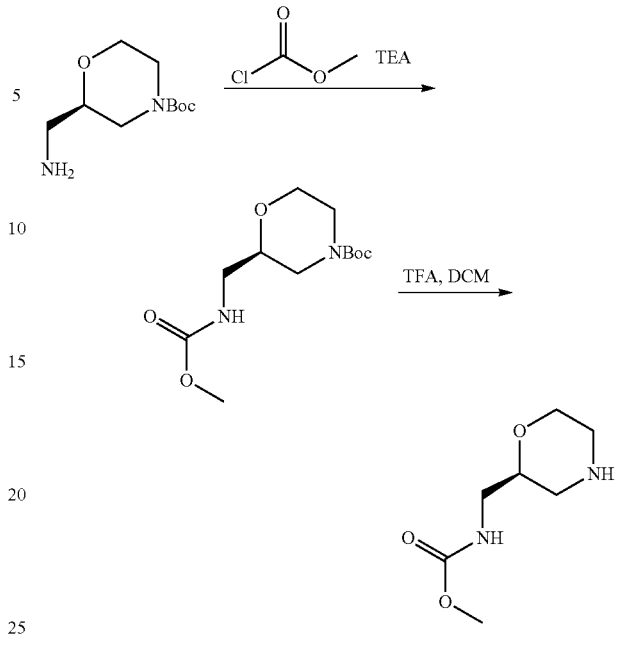

Synthesis of (S)-methyl(morpholin-2-ylmethyl)carbamate

Step 1. To a solution of (R)-tert-butyl 2-(aminomethyl) morpholine-4-carboxylate (1.0 equiv.) and triethylamine (3.0 equiv.) in dichloromethane (0.1 M) was added methyl chloroformate (1.1 equiv.). The resulting mixture was stirred at RT for 45 min. After concentration, the residue was partitioned between EtOAc and water. The organic phase was washed with water and then with brine. After drying over sodium sulfate the solution was concentrated in vaccuo to give crude (R)-tert-butyl 2-(((methoxycarbonyl)amino)methyl)morpholine-4-carboxylate which was used in the next step without further purification. LCMS (m/z) (M+H)=175.1 (-Boc), Rt=0.63 min.

Step 2. To a 4:1 solution of dichloromethane and TFA (0.1 M) was added (R)-tert-butyl 2-(((methoxycarbonyl)amino) methyl)morpholine-4-carboxylate. After 1 h the solution was then concentrated in vaccuo to give crude (S)-methyl(morpholin-2-ylmethyl)carbamate which was used in the next step without further purification. LCMS (m/z) (M+H)=175.0, Rt=0.11 min.

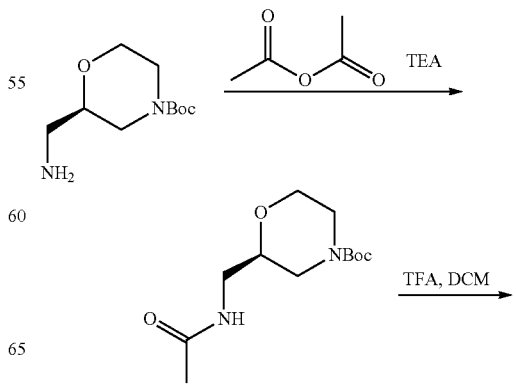

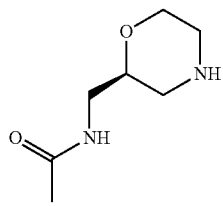

Synthesis of (S)—N-(morpholin-2-ylmethyl)acetamide

Step 1. To a solution of (R)-tert-butyl 2-(aminomethyl)morpholine-4-carboxylate (1.0 equiv.) and triethylamine (1.5 equiv.) in dichloromethane (0.1 M) was added acetic anhydride (1.1 equiv.). The resulting mixture was stirred at RT for 45 min. After concentration, the residue was partitioned between EtOAc and water. The organic phase was washed with water and then with brine. After drying over sodium sulfate the solution was concentrated in vaccuo to give crude (R)-tert-butyl 2-(acetamidomethyl)morpholine-4-carboxylate which was used in the next step without further purification. LCMS (m/z) (M+H)=159.1 (-Boc), Rt=0.53 min.

Step 2. To a 4:1 solution of dichloromethane and TFA (0.1 M) was added (R)-tert-butyl 2-(acetamidomethyl)morpholine-4-carboxylate. After 1 h the solution was then concentrated in vacuo to give crude (S)—N-(morpholin-2-ylmethyl)acetamide which was used in the next step without further purification. LCMS (m/z) (M+H)=159.0, Rt=0.11 min.

Synthesis of (S)-2-hydroxy-N-(morpholin-2-ylmethyl)acetamide

Step 1. A mixture of (R)-tert-butyl 2-(aminomethyl)morpholine-4-carboxylate (1.0 equiv.), 2-hydroxyacetic acid (1.80 equiv.), N1-((ethylimino)methylene)-N3,N3-dimethylpropane-1,3-diamine hydrochloride (2.0 equiv.), and N,N-dimethylpyridin-4-amine (0.20 equiv.) was stirred in DCM (0.1 M) at room temperature overnight. The reaction was quenched with water and washed (3×) with water. The combined aqueous fractions were then back-extracted with chloroform (4×) and the combined organics were dried over Na$_2$SO$_4$, filtered, and concentrated. The resulting oil was passed through a pad of SiO$_2$ gel using 5-50% MeOH/DCM and concentrated to yield (R)-tert-butyl 2-((2-hydroxyacetamido)methyl)morpholine-4-carboxylate as an oil. LCMS (m/z) (M+H)=175.1 (-Boc), Rt=0.55 min.

Step 2. (R)-tert-butyl 2-((2-hydroxyacetamido)methyl)morpholine-4-carboxylate (1.0 equiv.) was dissolved in DCM:TFA (4:1, 0.5 M) and stirred at room temperature. After one hour the solution was concentrated to yield (S)-2-hydroxy-N-(morpholin-2-ylmethyl)acetamide. LCMS (m/z) (M+H)=175.1, Rt=0.12 min.

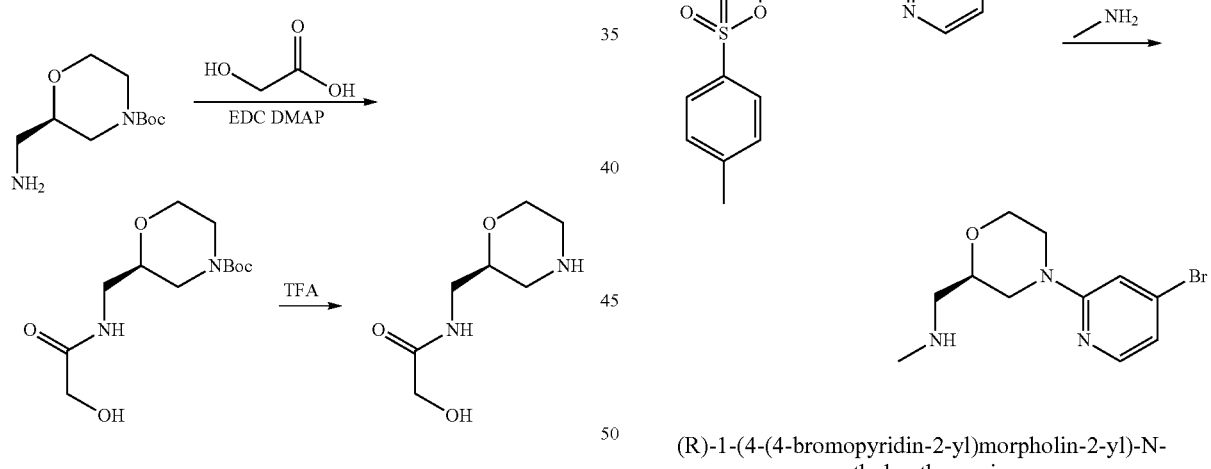

(R)-1-(4-(4-bromopyridin-2-yl)morpholin-2-yl)-N-methylmethanamine

Step 1. To a 4:1 solution of dichloromethane and TFA (0.1 M) was added (S)-tert-butyl 2-(hydroxymethyl)morpholine-4-carboxylate. After 1 h the solution was then concentrated in vaccuo to give crude (S)-morpholin-2-ylmethanol which was used in the next step without further purification. LCMS (m/z) (M+H)=60.0, Rt=0.11 min.

Step 2. Refer to standard.

Step 3. A solution of (S)-(4-(4-bromopyridin-2-yl)morpholin-2-yl)methanol (1.0 equiv.), tosyl chloride (1.0 equiv.), triethylamine (1.40 equiv.) and N,N-dimethylpyridin-4-amine (0.1 equiv.) in dichloromethane (0.1 M) at RT. The resulting mixture was stirred at RT for 18 hours. The reaction mixture was then diluted with water and the aqeuous layer was separated and washed sequentially with NaOH (1 M), water, brine dried over sodium sulfate then concentrated in vacuo to yield (S)-(4-(4-bromopyridin-2-yl)morpholin-2-yl)methyl 4-methylbenzenesulfonate in 56% yield. LCMS (m/z) (M+H)=427.1/429.0, Rt=0.77 min.

Step 4. To a 2 M solution of methylamine in methanol was added (S)-(4-(4-bromopyridin-2-yl)morpholin-2-yl)methyl 4-methylbenzenesulfonate (1.0 eq). This solution was microwave heated at 80° C. After 1 h the solution was then concentrated in vacuo and water was added. The resulting suspension was sonicated and centrifuged. The water soluble portion was separated from the solids. The resulting aqueous solution of (R)-1-(4-(4-bromopyridin-2-yl)morpholin-2-yl)-N-methylmethanamine was used in the next step without further purification. LCMS (m/z) (M+H)=286.0/288.0, Rt=0.34 min.

Synthesis of
5-bromo-3-morpholinopyridin-2(1H)-one

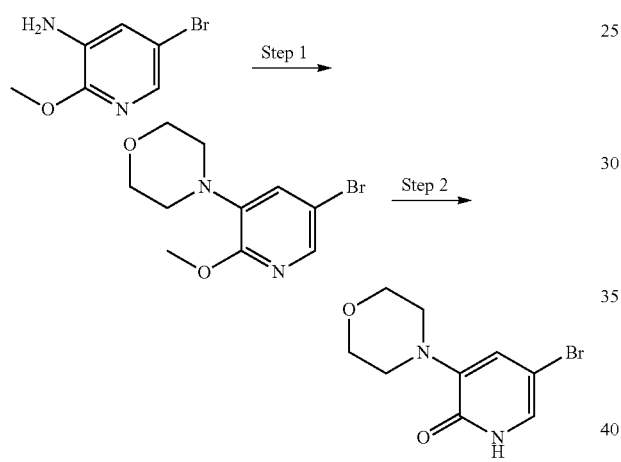

Step 1: To a solution of 5-bromo-2-methoxypyridin-3-amine (1.0 equiv.) in DMF was added 1-bromo-2-(2-bromoethoxy)ethane (1.2 equiv.), followed by DIEA (3.0 equiv.). The solution was heated at 120° C. for 24 hours. Cooled to room temperature and partitioned between ethyl acetate and water. The organic phase was washed with brine, dried over sodium sulfate, filtered and concentrated. The crude material was purified via flash chromatography over silica gel eluting with heptanes and 0-25% ethyl acetate gradient). Isolated 4-(5-bromo-2-methoxypyridin-3-yl)morpholine as a yellow solid in 69% yield. LCMS (m/z) (M+H)=273.0/274.9, Rt=0.82 min. ¹H NMR (400 MHz, <cdcl3>) δ ppm 2.90-3.18 (m, 4H) 3.76-3.91 (m, 4H) 3.97 (s, 3H) 7.14 (d, J=1.96 Hz, 1H) 7.84 (d, J=1.96 Hz, 1H).

Step 2: To a solution of 4-(5-bromo-2-methoxypyridin-3-yl)morpholine (1.0 equiv.) in 1,4-dioxane (0.3 M) was added concentrated HCl (5 equiv.) and the solution was heated to 100° C. for 1 h. Upon cooling to room temperature, the solution was concentrated to dryness under vacuo, then dissolved in water and neutralized with solid sodium bicarbonate. The precipitate was filtered, washed with water and dried under vacuo to give 5-bromo-3-morpholinopyridin-2(1H)-one as a beige solid in 93% yield. LCMS (M+H)=258.9/260.9, Rt=0.48 min.

Synthesis of 4-(6-chloropyrazin-2-yl)morpholine

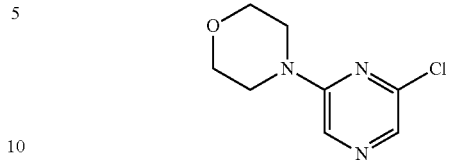

To a solution of 2,6-dichloropyrazine (1.0 equiv.) in acetonitrile (0.3 M) was added morpholine (3.5 equiv.) and the reaction was stirred at room temperature for 20 h. The resulting precipitate was filtered off and the filtrate was concentrated under vacuo. The crude material was partitioned between water and ethyl acetate, the organic phase was dried with sodium sulfate, filtered and concentrated to afford 4-(6-chloropyrazin-2-yl)morpholine in 75% yield. LCMS m/z (M+H)=200.0, Rt=0.61 min.

Synthesis of
5-bromo-3-morpholinopyridin-2(1H)-one

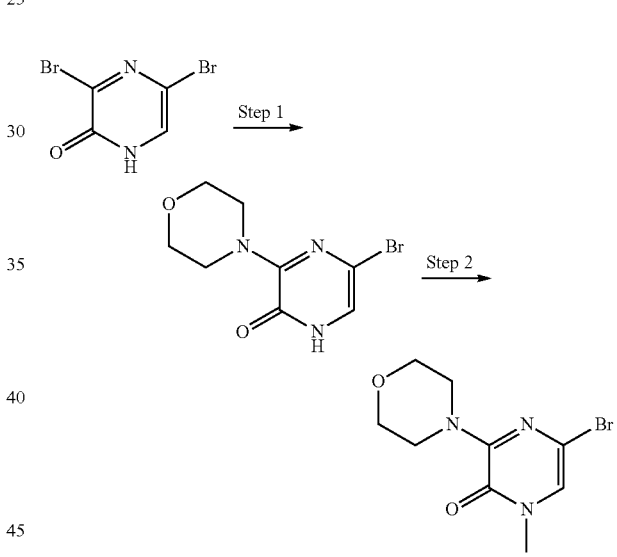

Step 1: A solution of 3,5-dibromopyrazin-2(1H)-one (1.0 equiv.) in morpholine (5 equiv.) was heated to 100° C. for 24 h. Cooled to room temperature and filtered off the precipitate. The filtrate was partitioned between water and ethyl acetate. The organic phase was dried with sodium sulfate, filtered and concentrated. The crude material was purified via silica gel column chromatography eluting with ethyl acetate and heptanes (0-50%). The pure fractions were concentrated to yield 5-bromo-3-morpholinopyrazin-2(1H)-one as a white solid in 43% yield. LCMS m/z (M+H)=259.9, Rt=0.41 min.

Step 2: To a solution of 5-bromo-3-morpholinopyrazin-2(1H)-one (1.0 equiv.) in DMF (0.1 M) was added potassium carbonate (2.0 equiv.) and iodomethane (1.0 equiv.) at 0° C. and the solution was allowed to warm to room temperature and stirred for 2 hours. Upon completion, the reaction was partitioned between water and ethyl acetate, the organic phase was washed with brine, dried with sodium sulfate, filtered and concentrated. The crude material was used for the next step without further purification. Isolated 5-bromo-1-methyl-3-morpholinopyrazin-2(1H)-one in 91% yield.

LCMS m/z (M+H)=274/276, Rt=0.60 min. ¹H NMR (400 MHz, <cdcl3>) δ ppm 3.42 (s, 3H) 3.66-3.83 (m, 4H) 3.85-4.00 (m, 4H), 6.77 (s, 1H).

Synthesis of 3-bromo-1-methyl-5-morpholinopyridin-2(1H)-one

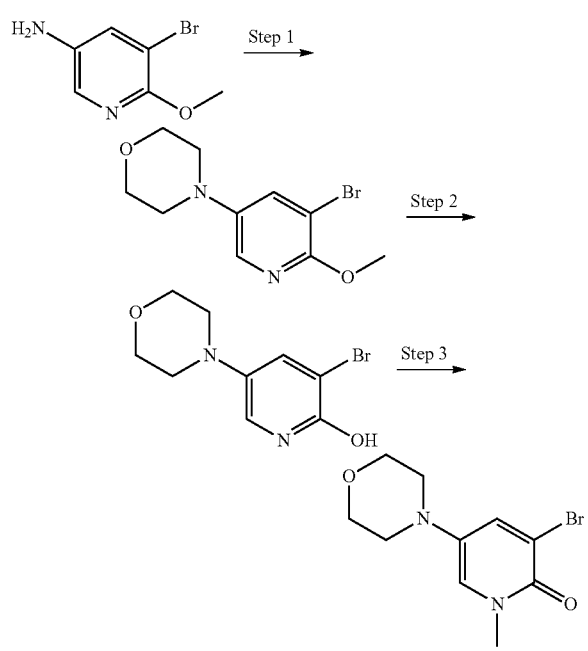

Step 1: To a solution of 5-bromo-6-methoxypyridin-3-amine (1.0 equiv.) in DMF was added DIEA (3.0 equiv.) and 1-bromo-2-(2-bromoethoxy)ethane (1.0 equiv.). The solution was heated to 120° C. for 24 hours. Upon cooling to room temperature, the reaction was partitioned between water and ethyl acetate, the aqueous phase was extracted three times with ethyl acetate, the organics were combined, dried with sodium sulfate, filtered and concentrated. The crude material was purified via silica gel column chromatography eluting with 0-50% ethyl acetate in heptanes. The pure fractions were concentrated to yield 4-(5-bromo-6-methoxypyridin-3-yl)morpholine in 53% yield as an orange oil. LCMS m/z (M+H)=273/275, Rt=0.61 min. ¹H NMR (400 MHz, <cdcl3>) δ ppm 2.93-3.18 (m, 4H) 3.80-4.05 (m, 7H) 7.50 (d, J=2.74 Hz, 1H) 7.74 (d, J=2.74 Hz, 1H).

Step 2: A solution of 4-(5-bromo-6-methoxypyridin-3-yl)morpholine (1.0 equiv.) in 4M HCl in dioxane (20 equiv.) was heated to 110° C. for 24 hours. Upon cooling to room temperature, the reaction was neutralized with aqueous NaOH to pH ~6 then extracted with ethyl acetate three times. The organic phase was dried with sodium sulfate, filtered and concentrated. Isolated 3-bromo-5-morpholinopyridin-2-ol as the desired product in 32% yield. LCMS (m/z) (M+H)=259.0/261/0, Rt=0.36 min.

Step 3: To a solution of 3-bromo-5-morpholinopyridin-2-ol (1.0 equiv.) in DMF (0.1 M) was added potassium carbonate (2.0 equiv.) and iodomethane (1.0 equiv.). The solution was stirred at room temperature for 3 hours. Partitioned between water and ethyl acetate, the organic phase was washed with brine, dried with sodium sulfate, filtered and concentrated to dryness. Isolated 3-bromo-1-methyl-5-morpholinopyridin-2(1H)-one in 87% yield. LCMS (m/z) (M+H)=273.0/275.0, Rt=0.41 min.

Synthesis of 4-bromo-1-methyl-6-morpholinopyridin-2(1H)-one and 6-chloro-1-methyl-4-morpholinopyridin-2(1H)-one

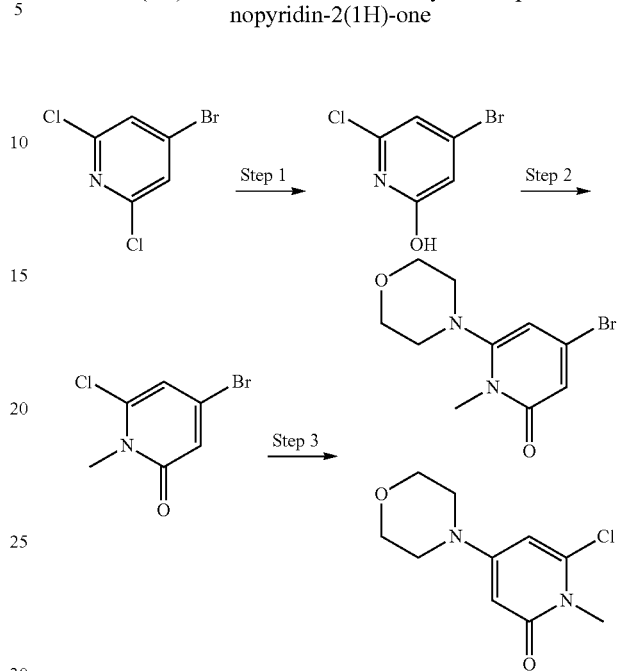

Step 1: A solution of 4-bromo-2,6-dichloropyridine (1.0 equiv.) in dioxane and aqueous sodium hydroxide (15% by weight solution, 1:1 ratio, 0.55 M) was heated in the microwave for 30 min at 150° C. The solution was cooled to room temperature and neutralized with concentrated HCl (pH=~6) and extracted with ethyl acetate three times. The organic phase was dried with sodium sulfate, filtered and concentrated. The crude material was dried under vacuo to give 4-bromo-6-chloropyridin-2-ol as an off-white solid in 76% yield. LCMS (m/z) (M+H)=207.9/209.9, Rt=0.60 min.

Step 2: To a solution of 4-bromo-6-chloropyridin-2-ol (1.0 equiv.) in DMF (0.16 M) was added potassium carbonate (2.0 equiv.) and iodomethane (1.2 equiv.) at room temperature. The solution was stirred for 2 hours, then partitioned between water and ethyl acetate. The aqueous phase was extracted with ethyl acetate two more times, the organic phase was washed with brine, dried with sodium sulfate, filtered and concentrated. The crude material was purified via silica gel column chromatography eluting with ethyl acetate and heptanes (0-50% ethyl acetate). The pure fractions were concentrated to yield 4-bromo-6-chloro-1-methylpyridin-2(1H)-one in 38% yield. LCMS (m/z) (M+H)=221.9/223.9, Rt=0.64 min.

Step 3: To a solution of 4-bromo-6-chloro-1-methylpyridin-2(1H)-one (1.0 equiv.) in NMP (0.18 M) was added morpholine (1.1 equiv.) and DIEA (1.1 equiv). The solution was stirred at 100° C. for 4 hours. Upon cooling to room temperature, the solution was partitioned between water and ethyl acetate. The organic phase was washed with water, then brine, dried with sodium sulfate, filtered and concentrated. The crude material was purified via silica gel column chromatography eluting with ethyl acetate and heptanes (0-100% ethyl acetate then 90% ethyl acetate and 10% methanol). Isolated 4-bromo-1-methyl-6-morpholinopyridin-2(1H)-one in 51% yield and 6-chloro-1-methyl-4-morpholinopyridin-2(1H)-one in 15% yield. LCMS (m/z) (M+H)=273/274.9, Rt=0.53 min and LCMS (m/z) (M+H)=229.1/230.9, Rt=0.47 min respectively.

Synthesis of
6-chloro-2-methyl-4-morpholinopyridazin-3(2H)-one

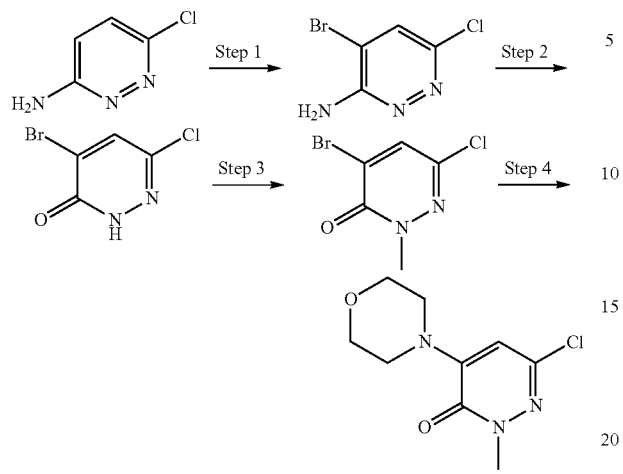

Step 1: To a solution of 6-chloropyridazin-3-amine (1.0 equiv) in MeOH (1M) at room temperature was added sodium bicarbonate (2.0 equiv.) and the resulting suspension was stirred at room temperature for 30 min before the dropwise addition of bromine (1.0 equiv.). The reaction mixture was stirred for 20 h. Upon concentration under vacuo, the crude residue was purified via silica gel column chromatography eluting with 100% heptanes to 80% ethyl acetate:heptanes to yield 4-bromo-6-chloropyridazin-3-amine in 50% yield. LCMS (m/z) (M+H)=207.8/209.8, Rt=0.47 min. $^1$H NMR (400 MHz, <cdcl3>) δ ppm 5.31-5.63 (m, 2H) 7.46-7.61 (m, 1H).

Step 2: To a cooled solution (0-5° C.) of NaNO$_2$ (2.4 equiv.) in H$_2$SO$_4$ conc. (23 equiv.) was added 4-bromo-6-chloropyridazin-3-amine (1.0 equiv.) in acetic acid (0.25 M). The reaction mixture was stirred at 0° C. for 30 min before warming to room temperature and stirring for 1 hour. Water was added and stirred at room temperature for a further 4 hours. The reaction mixture was then extracted with ethyl acetate, dried over MgSO$_4$ and concentrated in vacuo to yield a brown oil. The oil was further purified by silica gel column chromatography eluting with 100% heptanes to 80% ethyl acetate/heptanes to yield 4-bromo-6-chloropyridazin-3(2H)-one as an off-white solid in 83% yield. LCMS (m/z) (M+H)=208.9/210.9, Rt=0.42 min. $^1$H NMR (400 MHz, <dmso>) δ ppm 8.08-8.32 (m, 1H) 13.25-13.71 (m, 1H).

Step 3: To a solution of 4-bromo-6-chloropyridazin-3(2H)-one (1.0 equiv.) and Cs$_2$CO$_3$ (1.2 equiv.) in DMF (0.07 M) was added iodomethane (1.5 equiv.) drop-wise over 20 min. The resulting mixture was stirred for 3 h. The reaction mixture was then diluted with ammonium chloride, then extracted with ethyl acetate, dried over MgSO$_4$ and concentrated in vacuo to yield as a brown solid. The oil was further purified via silica gel column chromatography eluting with 100% heptanes to 80% ethyl acetate:heptanes to yield 4-bromo-6-chloro-2-methylpyridazin-3(2H)-one as an off-white solid in 79% yield. LCMS (m/z) (M+H)=222.9/224.9, Rt=0.54 min. $^1$H NMR (400 MHz, <cdcl3>) δ ppm 3.77-3.86 (m, 3H) 7.56-7.69 (m, 1H).

Step 4: To a solution of 4-bromo-6-chloro-2-methylpyridazin-3(2H)-one (1.0 equiv.) in DMF (0.3 M) was added DIEA (1.0 equiv.) and morpholine (1.0 equiv.) at room temperature. The resulting mixture was heated to 120° C. for 5 h and 30 min. The reaction mixture was diluted with water, extracted with ethyl acetate, dried over MgSO$_4$ and concentrated in vacuo to yield. 6-chloro-2-methyl-4-morpholinopyridazin-3(2H)-one as an off-white solid in 97% yield. LCMS (m/z) (M+H)=230.0/232.0, Rt=0.63 min.

Synthesis of 4-(5-bromo-2-((tetrahydro-2H-pyran-4-yl)oxy)pyridin-3-yl)morpholine AND 5-bromo-3-morpholino-1-(tetrahydro-2H-pyran-4-yl)pyridin-2(1H)-one

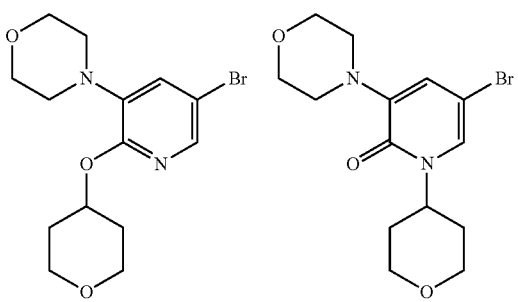

To a 0.45 M solution of triphenylphosphine (1.50 equiv.) in DMF was added DIAD (1.50 equiv.). The mixture was stirred at ambient temperature for 10 min. Tetrahydro-2H-pyran-4-ol (2.00 equiv.) was added, and the mixture was stirred for 15 min. 5-Bromo-3-morpholinopyridin-2(1H)-one (1.00 equiv.) was added. The mixture was stirred for 2 hr. The reaction mixture was diluted with water and extracted with ethyl acetate. The combined organics were washed with brine, dried over sodium sulfate, filtered and concentrated with silica gel. The material was purified by flash chromatography over silica gel (heptanes with 0-100% ethyl acetate gradient) to give both the O-alkylated isomer (88% yield) and the N-alkylated isomer (11% yield).

4-(5-bromo-2-((tetrahydro-2H-pyran-4-yl)oxy)pyridin-3-yl)morpholine: $^1$H NMR (400 MHz, <cdcl3>) δ ppm 1.82 (td, J=8.51, 4.30 Hz, 2H) 2.09 (dt, J=8.99, 4.33 Hz, 2H) 3.02-3.17 (m, 4H) 3.56-3.73 (m, 2H) 3.77-3.89 (m, 4H) 3.90-4.03 (m, 2H) 5.29 (dt, J=8.01, 3.99 Hz, 1H) 7.13 (d, J=2.10 Hz, 1H) 7.78 (d, J=2.20 Hz, 1H). LCMS (m/z) (M+H)=343.0/345.0, Rt=0.92 min.

5-bromo-3-morpholino-1-(tetrahydro-2H-pyran-4-yl)pyridin-2(1H)-one: $^1$H NMR (400 MHz, <cdcl3>) δ ppm 1.26 (s, 2H) 1.72-1.96 (m, 4H) 3.08-3.24 (m, 4H) 3.47-3.67 (m, 2H) 3.79-3.95 (m, 4H) 4.04-4.19 (m, 2H) 5.14 (s, 1H) 6.64 (d, J=2.40 Hz, 1H) 7.13 (d, J=2.40 Hz, 1H). LCMS (m/z) (M+H)=342.9/344.9, Rt=0.63 min.

Synthesis of 4-(5-bromo-2-isopropoxypyridin-3-yl)morpholine AND 5-bromo-1-isopropyl-3-morpholinopyridin-2(1H)-one

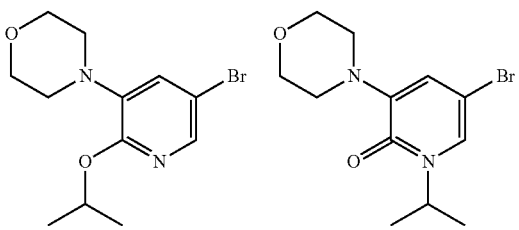

A 0.3 M solution of 5-bromo-3-morpholinopyridin-2(1H)-one (1.00 equiv.) in DMF was treated with sodium hydride (1.20 equiv.). The mixture was stirred for 20 min at ambient temperature. 2-bromopropane (1.20 equiv.) was added. The mixture was stirred at 70° C. for 18 hr. The cooled reaction mixture was diluted with water and extracted with ethyl acetate. The combined extracts were washed with brine, dried over sodium sulfate, filtered, and concentrated. The crude material was purified by flash chromatography over silica gel (heptanes with 20-100% ethyl acetate gradient) to give both the O-alkylated isomer (56% yield) and the N-alkylated isomer (26% yield).

4-(5-bromo-2-isopropoxypyridin-3-yl)morpholine: $^1$H NMR (400 MHz, <cdcl3>) δ ppm 1.39 (d, J=6.16 Hz, 6H) 3.04-3.15 (m, 4H) 3.82-3.93 (m, 4H) 5.24-5.44 (m, 1H) 7.12 (d, J=2.10 Hz, 1H) 7.82 (d, J=2.15 Hz, 1H). LCMS (m/z) (M+H)=301.0/303.0, Rt=0.99 min.

5-bromo-1-isopropyl-3-morpholinopyridin-2(1H)-one: $^1$H NMR (400 MHz, <cdcl3>) δ ppm 1.30-1.40 (m, 6H) 3.12-3.21 (m, 4H) 3.82-3.93 (m, 4H) 5.19-5.33 (m, 1H) 6.62 (d, J=2.35 Hz, 1H) 7.11 (d, J=2.35 Hz, 1H). LCMS (m/z) (M+H)=301.0/303.0, Rt=0.70 min.

Synthesis of tert-butyl (2-(5-bromo-3-morpholino-2-oxopyridin-1(2H)-yl)ethyl)carbamate

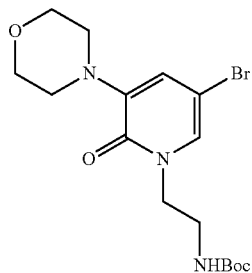 [SMILES: CC(C)(C)OC(=O)NCCn1cc(Br)cc(N2CCOCC2)c1=O]

A 0.3 M solution of 5-bromo-3-morpholinopyridin-2(1H)-one (1.00 equiv.) in DMF was treated with sodium hydride (1.20 equiv.). The mixture was stirred for 15 min at ambient temperature. Tert-butyl (2-bromoethyl)carbamate (1.20 equiv.) was added. The mixture was stirred at 60° C. for 3 hr. The cooled reaction mixture was diluted with water and extracted with ethyl acetate. The combined organics were washed with saturated aqueous sodium bicarbonate, dried over sodium sulfate, filtered, and concentrated to give tert-butyl (2-(5-bromo-3-morpholino-2-oxopyridin-1(2H)-yl) ethyl)carbamate. LCMS (m/z) (M+H)=402.1/404.1, Rt=0.78 min.

Method 1:
To a solution of the starting pyridone or pyrazinone (1.0 equiv.) in DMF (0.1-0.2 M) was added the electrophile (1.0-1.5 equiv.) followed by potassium carbonate or cesium carbonate (1.0-2.0 equiv.). The solution was stirred at room temperature (or alternatively heated up to 80° C.) for 2-24 hours. Upon cooling to room temperature, the solution was partitioned between water and ethyl acetate, the organic phase was washed with water, then brine, dried over sodium sulfate, filtered and concentrated under vacuo. The crude material was a mixture of N-alkyl and O-alkyl products. The material could be used for the next step without further purification as a mixture of isomers or it could be purified via silica gel column chromatography eluting with 0-100% ethyl acetate in heptanes.

Synthesis of 5-bromo-1-methyl-3-morpholinopyridin-2(1H)-one AND 4-(5-bromo-2-methoxypyridin-3-yl)morpholine

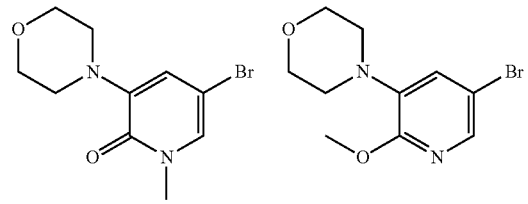

To a solution of 5-bromo-3-morpholinopyridin-2(1H)-one (1.0 equiv.) in DMF (0.2 M) was added potassium carbonate (2.0 equiv.), followed by iodomethane (1.0 equiv.). The solution was stirred at room temperature for 3 hours. The solution was partitioned between water and ethyl acetate, the organic phase was washed with brine, dried with sodium sulfate, filtered and concentrated. The crude material was a mixture of N-methylated and O-methylated products (90:10). The material could be used for the next step without further purification as a mixture of isomers or it could be purified via silica gel column chromatography eluting with 0-100% ethyl acetate in heptanes to afford 5-bromo-1-methyl-3-morpholinopyridin-2(1H)-one in 71% yield LCMS (m/z) (M+H)=273/275, Rt=0.55 min and 4-(5-bromo-2-methoxypyridin-3-yl)morpholine in 10% yield. LCMS (m/z) (M+H)=273/275, Rt=0.82 min.

The intermediates listed below were prepared using methods similar to those described for the preparation of 5-bromo-1-methyl-3-morpholinopyridin-2(1H)-one AND 4-(5-bromo-2-methoxypyridin-3-yl)morpholine (Method 1) using the appropriate starting materials.

Synthesis of 5-bromo-1-(2-hydroxyethyl)-3-morpholinopyridin-2(1H)-one and 2-((5-bromo-3-morpholinopyridin-2-yl)oxy)ethanol

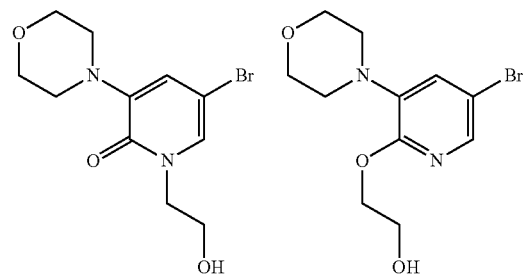

Method 1 was followed using 5-bromo-3-morpholinopyridin-2(1H)-one (1.0 equiv.), 2-iodoethanol (1.0 equiv.) and potassium carbonate (2.0 equiv.) at room temperature to give 5-bromo-1-(2-hydroxyethyl)-3-morpholinopyridin-2(1H)-one and 2-((5-bromo-3-morpholinopyridin-2-yl)oxy)ethanol as a mixture of two isomers (~5:1 ratio). LCMS (m/z) (M+H)=303/305, Rt=0.47 min and 0.62 min.

Synthesis of 5-bromo-1-(2-(methylsulfonyl)ethyl)-3-morpholinopyridin-2(1H)-one

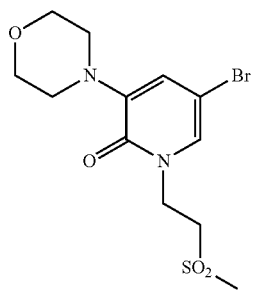 [SMILES: CS(=O)(=O)CCn1cc(Br)cc(N2CCOCC2)c1=O]

Method 1 was followed using 5-bromo-3-morpholinopyridin-2(1H)-one (1.0 equiv.), (methylsulfonyl)ethene (1.2 equiv.) and cesium carbonate (1.2 equiv.) at room temperature to give 5-bromo-1-(2-(methylsulfonyl)ethyl)-3-morpholinopyridin-2(1H)-one in 98% yield. $^1$H NMR (400 MHz, <cdcl3>) δ ppm 2.92 (s, 3H) 3.09-3.23 (m, 4H) 3.53 (t, J=6.65 Hz, 2H) 3.78-3.96 (m, 4H) 4.32 (t, J=6.65 Hz, 2H) 6.69 (s, 1H) 7.23 (d, J=2.35 Hz, 1H). LCMS (m/z) (M+H)=365.1/366.9, Rt=0.57 min.

Synthesis of 5-bromo-1-ethyl-3-morpholinopyridin-2(1H)-one and 4-(5-bromo-2-ethoxypyridin-3-yl)morpholine

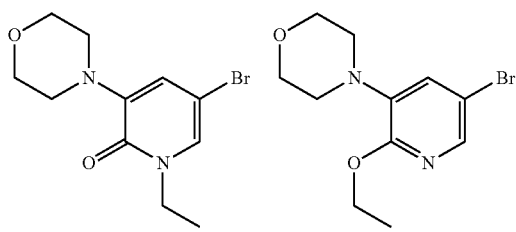

Method 1 was followed using 5-bromo-3-morpholinopyridin-2(1H)-one (1.0 equiv.), iodoethane (1.0 equiv.) and cesium carbonate (1.0 equiv.) at 50° C. to afford a mixture of 5-bromo-1-ethyl-3-morpholinopyridin-2(1H)-one and 4-(5-bromo-2-ethoxypyridin-3-yl)morpholine in about 2:1 ratio. LCMS (m/z) (M+H)=286.9/288.9, Rt=0.62 min and 0.88 min.

Synthesis of 2-(5-bromo-3-morpholino-2-oxopyridin-1(2H)-yl)acetonitrile and 2-((5-bromo-3-morpholinopyridin-2-yl)oxy)acetonitrile

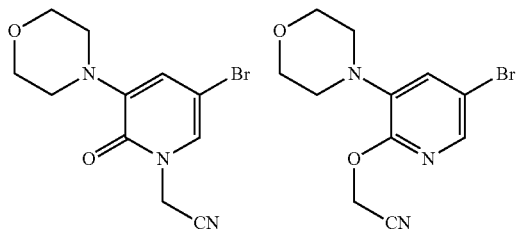

Method 1 was followed using 5-bromo-3-morpholinopyridin-2(1H)-one (1.0 equiv.), 2-bromoacetonitrile (1.2 equiv.) and potassium carbonate (1.0 equiv.) at 80° C. and the isomers were purified via silica gel column chromatography (0-50% ethyl acetate and heptanes). Isolated 2-(5-bromo-3-morpholino-2-oxopyridin-1(2H)-yl)acetonitrile in 61% yield. LCMS (m/z) (M+H)=298/299.8, Rt=0.60 min. And 2-((5-bromo-3-morpholinopyridin-2-yl)oxy)acetonitrile in 12% yield. LCMS (m/z) (M+H)=298/299.8, Rt=0.82 min.

Synthesis of 2-(5-bromo-3-morpholino-2-oxopyridin-1(2H)-yl)propanenitrile and 2-((5-bromo-3-morpholinopyridin-2-yl)oxy)propanenitrile

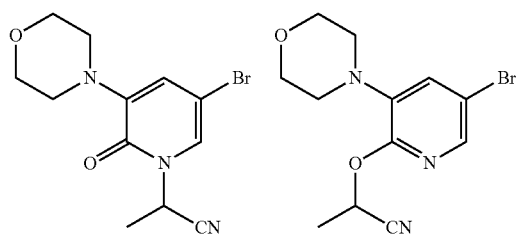

Method 1 was followed using 5-bromo-3-morpholinopyridin-2(1H)-one (1.0 equiv.), 2-bromopropanenitrile (1.2 equiv.) and potassium carbonate (1.0 equiv.) at 80° C. and the isomers were purified via silica gel column chromatography (0-50% ethyl acetate and heptanes). Isolated 2-(5-bromo-3-morpholino-2-oxopyridin-1(2H)-yl)propanenitrile in 50% yield. LCMS (m/z) (M+H)=312/314, Rt=0.63 min. And 2-((5-bromo-3-morpholinopyridin-2-yl)oxy)propanenitrile in 39% yield. LCMS (m/z) (M+H)=312/314, Rt=0.84 min.

Synthesis of (R)-2-(5-bromo-3-morpholino-2-oxopyridin-1(2H)-yl)propanenitrile and (S)-2-(5-bromo-3-morpholino-2-oxopyridin-1(2H)-yl)propanenitrile

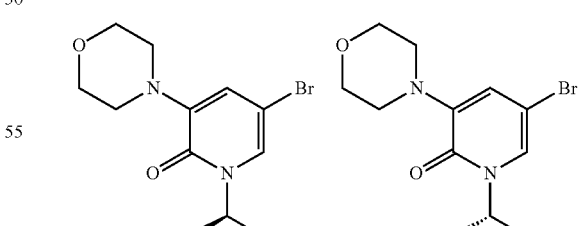

2-(5-bromo-3-morpholino-2-oxopyridin-1(2H)-yl)propanenitrile was further purified via chiral HPLC (SFC, Methanol, AD-column) to give: Peak 1 (Rt=1.13 min, 99% ee) and Peak 2 (Rt=1.74 min, 95% ee).

Synthesis of (R)-2-((5-bromo-3-morpholinopyridin-2-yl)oxy)propanenitrile and (S)-2-(5-bromo-3-morpholinopyridin-2-yl)oxy)propanenitrile

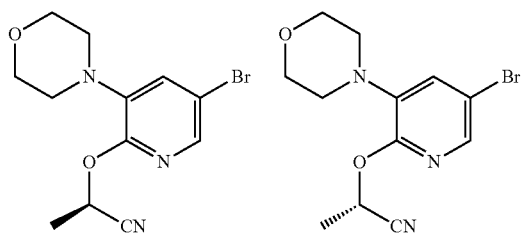

2-((5-bromo-3-morpholinopyridin-2-yl)oxy)propanenitrile was further purified via chiral HPLC (Heptanes/ethanol 95:5, AD-H column) to give: Peak 1 (Rt=4.808 min, 99% ee) and Peak 2 (Rt=7.274 min, 99% ee).

Method 2:

To a solution of the aryl halide (1.0 equiv.) and the boronic ester (Intermediate A-G, 1.0-1.2 equiv.) in DME and 2M sodium carbonate (3:1, 0.1 M) was added $PdCl_2$(dppf)-DCM adduct (0.1-0.5 equiv.) in a microwave vial equipped with a stir bar. The reaction was heated to 120° C. for 10-20 min in the microwave. The solution was partitioned between ethyl acetate and water, the organic phase was dried with sodium sulfate or magnesium sulfate, filtered and concentrated. The crude material was purified via preparative reverse phase HPLC. Upon lyophilization, the TFA salt of the product was obtained.

Compounds of Formula (I) were prepared by the synthetic schemes shown above, using the intermediates depicted above and analogs made similarly. Other compounds of the invention can be made by the same methods, based on the Examples described herein and known starting materials, in combination with methods known in the art.

Example 1

Synthesis of N-(4-methyl-3-(6-morpholinopyrimidin-4-yl)phenyl)-3-trifluoromethyl)benzamide

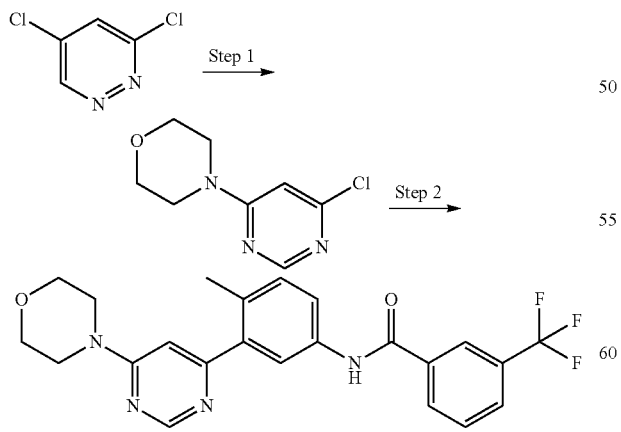

Step 1. To a solution of 4,6-dichloropyrimidine (1.0 equiv.) in EtOH (0.44 M) was added morpholine (1.0 equiv.) followed by triethylamine (1.10 equiv.). The resulting mixture was stirred at RT for 16 hours. The reaction mixture was then concentrated in vacuo and dried under high vacuum over 20 h to yield 4-(6-chloropyrimidin-4-yl)morpholine as a white solid in 93% yield. LCMS (m/z) (M+H)=200.0/201.8, Rt=0.35 min. $^1$H NMR (400 MHz, <cdcl3>) δ ppm 3.53-3.71 (m, 4H) 3.72-3.83 (m, 4H) 6.51 (s, 1H) 8.39 (s, 1H) 11.75 (br. s., 1H).

Step 2. To a solution of 4-(6-chloropyrimidin-4-yl)morpholine (1.0 equiv.) and Intermediate A (1.1 equiv.) in DME and 2M sodium carbonate (3:1, 0.2 M) was added $PdCl_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(4-methyl-3-(6-morpholinopyrimidin-4-yl)phenyl)-3-(trifluoromethyl)benzamide was isolated as the TFA salt in 52% yield. $^1$H NMR (400 MHz, <cd3od>) δ ppm 2.28 (s, 3H) 3.67-4.02 (m, 8H) 7.09 (s, 1H) 7.35 (d, J=8.22 Hz, 1H) 7.65 (s, 2H) 7.78-7.84 (m, 1H) 7.92 (d, J=2.35 Hz, 1H) 8.16 (s, 2H) 8.64 (s, 1H). LCMS (m/z) (M+H)=443.2, Rt=0.77 min.

The compounds listed below were prepared using methods similar to those described for the preparation of Example 1 using the appropriate starting materials.

Example 2

2-(2-cyanopropan-2-yl)-N-(4-methyl-3-(6-morpholinopyrimidin-4-yl)phenyl)isonicotinamide

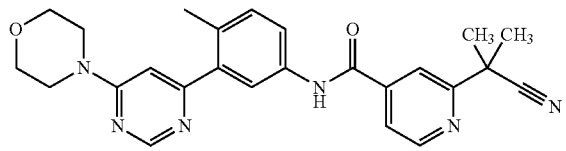 [SMILES: Cc1ccc(NC(=O)c2ccnc(C(C)(C)C#N)c2)cc1-c1cc(N2CCOCC2)ncn1]

1H NMR (400 MHz, <dmso>) δ ppm 1.70-1.81 (m, 6H) 2.30 (s, 3H) 3.67-3.92 (m, 8H) 7.11-7.22 (m, 1H) 7.34-7.45 (m, 1H) 7.73-7.83 (m, 1H) 7.83-7.92 (m, 2H) 7.99 (s, 1H) 8.73-8.86 (m, 2H) 10.70 (s, 1H). LCMS (m/z) (M+H)=443.2, Rt=0.64 min.

Example 3

Synthesis of N-(4-methyl-3-(2-morpholino-6-(3-oxomorpholino)pyrimidin-4-yl)phenyl)-3-(trifluoromethyl)benzamide

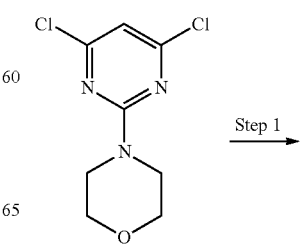

-continued

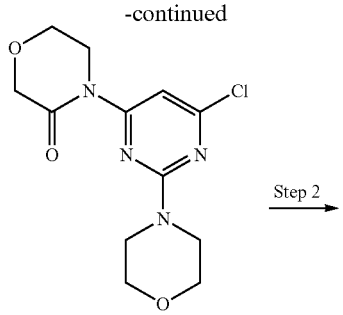

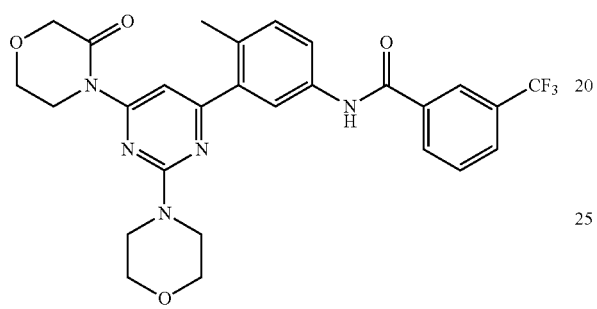

Step 1. To a solution 4-(4,6-dichloropyrimidin-2-yl)morpholine (1.0 equiv.), morpholin-3-one (1.2 equiv.), tribasic potassium phosphate (4.00 equiv), (9,9-dimethyl-9H-xanthene-4,5-diyl)bis(diphenylphosphine) (0.16 equiv) and Pd₂(dba)₃.HCCl₃ (20 mol %) in dioxane (0.5 M) was heated to 100° C. for 90 min. The reaction mixture was then cooled to room temperature and diluted with EtOAc (20 ml) and water (20 ml). The aqueous layer was separated and extracted with EtOAc (×2, 20 ml). The combined organic layer was dried over magnesium sulfate, filtered and concentrated in vacuo. The compound was utilized in the subsequent reactions without further purification. LCMS (m/z) (M+H)=299.2/300.9, Rt=0.77 min.

Step 2. To a solution of 4-(6-chloro-2-morpholinopyrimidin-4-yl)morpholin-3-one (1.0 equiv.) and Intermediate A (1.1 equiv.) in DME and 2M sodium carbonate (3:1, 0.2 M) was added PdCl₂(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(4-methyl-3-(1-methyl-5-morpholino-6-oxo-1,6-dihydropyridin-3-yl)phenyl)-3-(trifluoromethyl)benzamide was isolated as the TFA salt in 19% yield. LCMS (m/z) (M+H)=542.4, Rt=1.04 min. ¹H NMR (400 MHz, <dmso>) δ ppm 2.36 (s, 3H) 3.56-3.81 (m, 8H) 4.01 (d, J=5.09 Hz, 4H) 4.28 (s, 5H) 7.31 (d, J=8.22 Hz, 1H) 7.72-7.82 (m, 2H) 7.85 (d, J=1.96 Hz, 1H) 7.97 (d, J=7.83 Hz, 1H) 8.20-8.35 (m, 2H) 10.53 (s, 1H).

The compounds listed below were prepared using methods similar to those described for the preparation of Example 3 using the appropriate starting materials.

Example 4

4-methyl-3-(2-morpholino-6-(3-oxomorpholino)pyrimidin-4-yl)-N-(3-(trifluoromethyl)phenyl)benzamide

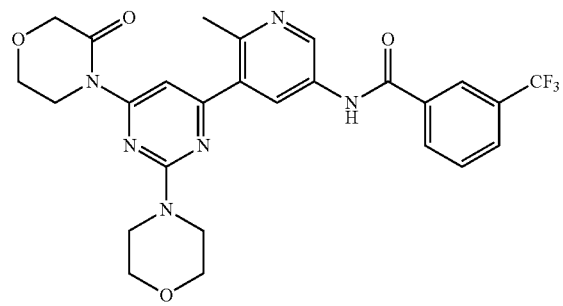 [SMILES: Cc1ncc(NC(=O)c2cccc(C(F)(F)F)c2)cc1-c1cc(N2CCOCC2=O)nc(N2CCOCC2)n1]

¹H NMR (400 MHz, <dmso>) δ ppm 2.45 (s, 3H) 3.69 (d, J=4.70 Hz, 5H) 3.74 (d, J=4.70 Hz, 5H) 4.01 (d, J=5.09 Hz, 3H) 4.29 (s, 2H) 7.36-7.54 (m, 3H) 7.60 (t, J=8.02 Hz, 2H) 7.93-8.02 (m, 2H) 8.05 (d, J=8.22 Hz, 1H) 8.24 (s, 1H) 10.55 (s, 1H) LCMS (m/z) (M+H)=542.3, Rt=1.08 min.

Example 5

N-(6-methyl-5-(2-morpholino-6-(3-oxomorpholino)pyrimidin-4-yl)pyridin-3-O-3-(trifluoromethyl)benzamide ¹H NMR (400 MHz, <dmso>) δ ppm 3.61-3.72 (m, 6H) 3.75 (d, J=4.70 Hz, 5H) 3.88-4.08 (m, 9H) 4.29 (s, 3H) 7.41-7.51 (m, 4H) 7.51-7.58 (m, 3H) 7.77-7.88 (m, 3H) 8.01 (t, J=6.46 Hz, 3H) 8.22-8.32 (m, 4H) 9.01 (dd, J=4.30, 2.35 Hz, 2H) 10.83 (s, 1H) 10.88 (s, 1H), LCMS (m/z) (M+H)= 543.3, Rt=0.78 min.

Example 6

Synthesis of N-(3-(6-(1,1-dioxidothiomorpholino)-2-morpholinopyrimidin-4-yl)-4-methylphenyl)-3-(trifluoromethyl)benzamide

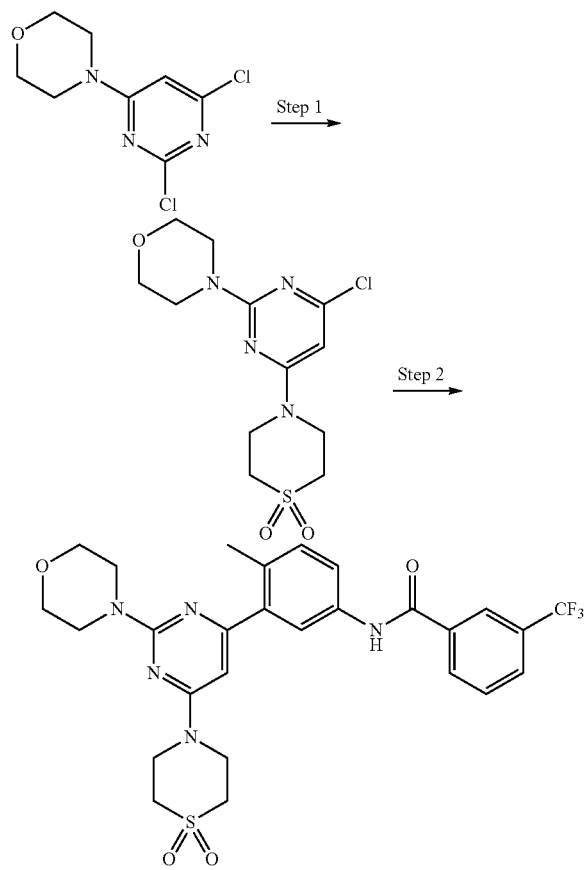

Step 1. To a solution of 4-(4,6-dichloropyrimidin-2-yl)morpholine (1.0 equiv.) in EtOH:THF (1:1, 0.25 M) was added thiomorpholine 1,1-dioxide (1.0 equiv.) in one portion. The resulting mixture was heated to 100° C. for 42 h. The resulting mixture was then cooled to RT and concentrated in vacuo to yield an off white solid in The reaction mixture was then concentrated in vacuo and dried under high vacuum over 20 h to yield 4-(6-chloropyrimidin-4-yl)morpholine as a white solid in 97% yield. LCMS (m/z) (M+H)=333.0/334.9, Rt=0.68 min.

Step 2. To a solution of 4-(6-chloro-2-morpholinopyrimidin-4-yl)thiomorpholine 1,1-dioxide (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(6-(1,1-dioxidothiomorpholino)-2-morpholinopyrimidin-4-yl)-4-methylphenyl)-3-(trifluoromethyl)benzamide was isolated as the TFA salt in 35% yield. LCMS (m/z) (M+H)=576.3, Rt=0.79 min, $^1$H NMR (400 MHz, <dmso>) δ ppm 2.33 (s, 3H) 2.54 (s, 1H) 3.21 (br. s., 4H) 3.70 (d, J=10.56 Hz, 8H) 4.16 (br. s., 4H) 6.56 (br. s., 1H) 7.32 (d, J=7.83 Hz, 1H) 7.67-7.87 (m, 3H) 7.98 (d, J=7.83 Hz, 1H) 8.21-8.44 (m, 2H) 10.55 (br. s., 1H).

The compounds listed below were prepared using methods similar to those described for the preparation of Example 6 using the appropriate starting materials.

Example 7

Synthesis of 3-(6-(1,1-dioxidothiomorpholino)-2-morpholinopyrimidin-4-yl)-4-methyl-N-(3-(trifluoromethyl)phenyl)benzamide

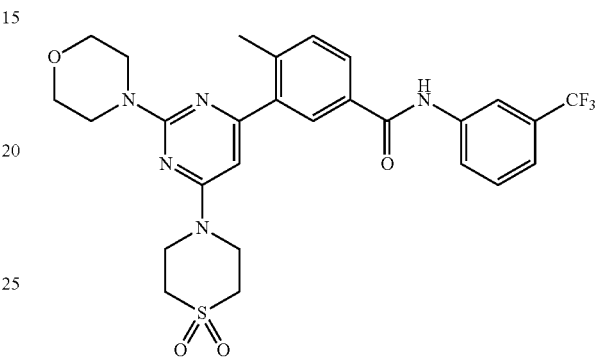

LCMS (m/z) (M+H)=576.3, Rt=0.78 min, $^1$H NMR (400 MHz, <dmso>) δ ppm 2.44 (s, 3H) 3.08-3.30 (m, 4H) 3.41-3.88 (m, 46H) 4.15 (br. s., 4H) 6.49-6.68 (m, 1H) 7.39-7.52 (m, 2H) 7.56-7.66 (m, 1H) 7.91-8.00 (m, 1H) 8.01 (d, J=1.57 Hz, 1H) 8.06 (d, J=8.22 Hz, 1H) 8.25 (s, 1H) 10.40-10.60 (m, 1H).

Example 8

Synthesis of N-(3-(2-(1,1-dioxidothiomorpholino)-6-morpholinopyrimidin-4-yl)-4-methylphenyl)-3-(trifluoromethyl)benzamide

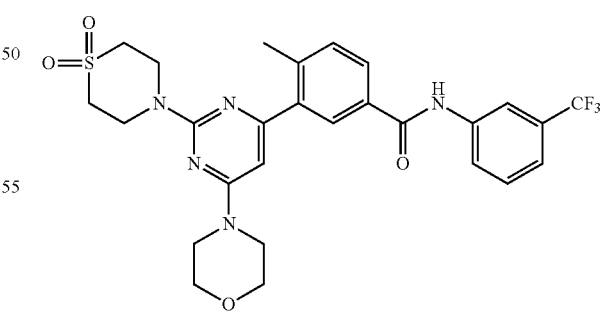

LCMS (m/z) (M+H)=576.3, Rt=0.78 min, $^1$H NMR (400 MHz, <dmso>) δ ppm 2.32 (s, 3H) 2.54 (s, 2H) 3.20 (br. s., 4H) 3.69 (br. s., 8H) 4.01-4.30 (m, 4H) 6.45 (br. s., 1H) 7.32 (d, J=8.22 Hz, 1H) 7.71-7.80 (m, 2H) 7.82 (d, J=4.30 Hz, 1H) 7.98 (d, J=7.43 Hz, 1H) 8.27 (d, J=8.22 Hz, 1H) 8.30 (s, 1H) 10.55 (s, 1H).

Example 9

Synthesis of 3-(2-(1,1-dioxidothiomorpholino)-6-morpholinopyrimidin-4-yl)-4-methyl-N-(3-(trifluoromethyl)phenyl)benzamide

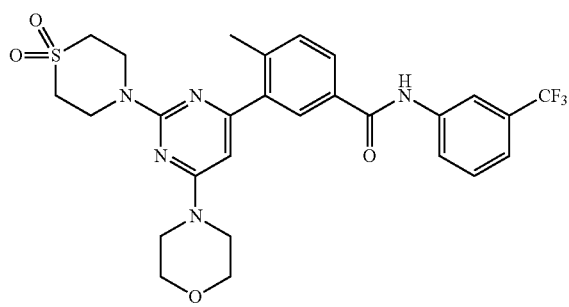 [SMILES: Cc1ccc(C(=O)Nc2cccc(C(F)(F)F)c2)cc1-c1cc(N2CCOCC2)nc(N2CCS(=O)(=O)CC2)n1]

LCMS (m/z) (M+H)=576.3, Rt=0.80 min, $^1$H NMR (400 MHz, <dmso>) δ ppm 2.43 (s, 3H) 2.54 (s, 2H) 3.04-3.23 (m, 4H) 3.68 (br. s., 10H) 4.20 (br. s., 4H) 6.46 (br. s., 1H) 7.26-7.53 (m, 2H) 7.60 (t, J=7.83 Hz, 1H) 7.98 (d, J=7.83 Hz, 1H) 8.00 (s, 1H) 8.06 (d, J=8.22 Hz, 1H) 8.25 (s, 1H) 10.52 (s, 1H).

Example 10

Synthesis of N-(3-(2,6-dimorpholinopyrimidin-4-yl)-4-methylphenyl)-3-(trifluoromethyl)benzamide

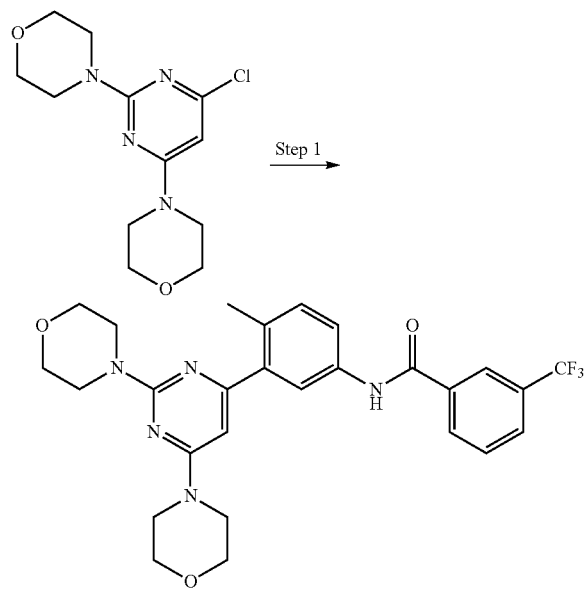

Step 1. To a solution of 4,4'-(6-chloropyrimidine-2,4-diyl) dimorpholine (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(2,6-dimorpholinopyrimidin-4-yl)-4-methylphenyl)-3-(trifluoromethyl)benzamide was isolated as the TFA salt in 37% yield. LCMS (m/z) (M+H)=528.3, Rt=0.80 min, $^1$H NMR (400 MHz, <dmso>) δ ppm 2.21-2.35 (m, 3H) 3.68 (br. s., 8H) 3.71 (d, J=4.30 Hz, 8H) 6.50 (br. s., 1H) 7.34 (d, J=8.22 Hz, 1H) 7.70-7.89 (m, 3H) 7.97 (d, J=7.83 Hz, 1H) 8.26 (d, J=7.83 Hz, 1H) 8.29 (s, 1H) 10.59 (br. s., 1H).

The compounds listed below were prepared using methods similar to those described for the preparation of Example 10 using the appropriate starting materials.

Example 11

3-(2,6-dimorpholinopyrimidin-4-yl)-4-methyl-N-(3-(trifluoromethyl)phenyl)benzamide

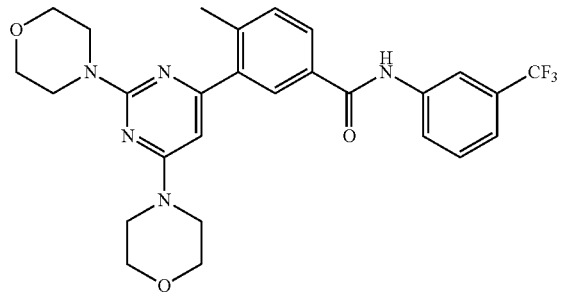 [SMILES: Cc1ccc(C(=O)Nc2cccc(C(F)(F)F)c2)cc1-c1cc(N2CCOCC2)nc(N2CCOCC2)n1]

LCMS (m/z) (M+H)=528.3, Rt=0.80 min. $^1$H NMR (400 MHz, <dmso>) δ ppm 2.29-2.37 (m, 3H) 3.42-3.72 (m, 19H) 3.84 (br. s., 8H) 7.35-7.50 (m, 2H) 7.54 (t, J=8.02 Hz, 1H) 7.95 (s, 2H) 8.00 (d, J=8.22 Hz, 1H) 8.18 (s, 1H) 10.47 (s, 1H).

Example 12

N-(5-(2,6-dimorpholinopyrimidin-4-yl)-6-methylpyridin-3-yl)-3-(trifluoromethyl)benzamide

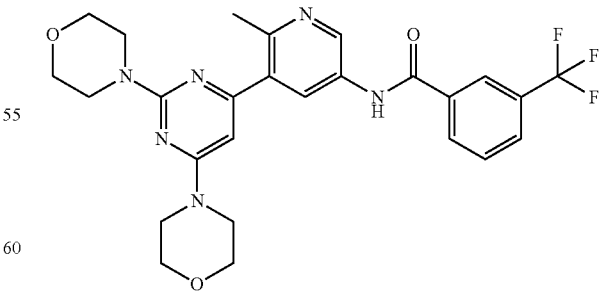

$^1$H NMR (400 MHz, <dmso>) δ ppm 10.86 (s, 1H), 8.99 (d, J=2.3 Hz, 1H), 8.24-8.40 (m, 3H), 8.01 (d, J=7.8 Hz, 1H), 7.75-7.89 (m, 1H), 6.51 (br. s., 1H), 3.68 (d, J=6.6 Hz, 16H), 2.56 (s, 3H). LCMS (m/z) (M+H)=529.4, Rt=0.70 min.

Example 13

Synthesis of N-(3-(4,6-dimorpholinopyrimidin-2-yl)-4-methylphenyl)-3-(trifluoromethyl)benzamide

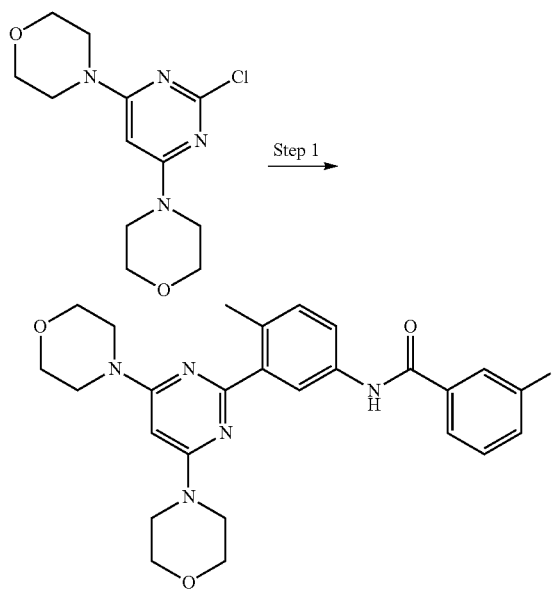

To a solution of 4,4'-(2-chloropyrimidine-4,6-diyl)dimorpholine (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(4,6-dimorpholinopyrimidin-2-yl)-4-methylphenyl)-3-(trifluoromethyl)benzamide was isolated as the TFA salt in 35% yield. LCMS (m/z) (M+H)=528.3, Rt=0.82 min, $^1$H NMR (400 MHz, <dmso>) δ ppm 2.35-2.45 (m, 3H) 3.40-3.63 (m, 9H) 3.66 (d, J=4.30 Hz, 9H) 5.97 (s, 1H) 7.26 (d, J=8.22 Hz, 1H) 7.69-7.84 (m, 2H) 7.95 (d, J=7.83 Hz, 1H) 8.04 (d, J=2.35 Hz, 1H) 8.21-8.31 (m, 2H) 10.49 (s, 1H).

The compounds listed below were prepared using methods similar to those described for the preparation of Example 13 using the appropriate starting materials.

Example 14

Synthesis of 3-(4,6-dimorpholinopyrimidin-2-yl)-4-methyl-N-(3-(trifluoromethyl)phenyl)benzamide

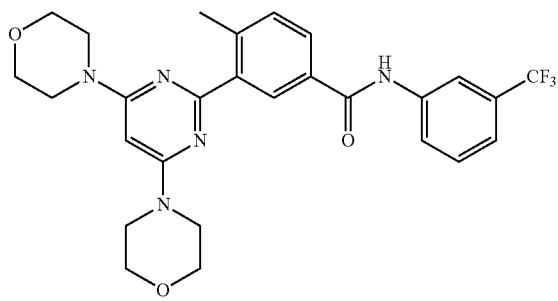 [SMILES: Cc1ccc(C(=O)Nc2cccc(C(F)(F)F)c2)cc1-c1nc(N2CCOCC2)cc(N2CCOCC2)n1]

LCMS (m/z) (M+H)=528.3, Rt=0.84 min, $^1$H NMR (400 MHz, <dmso>) δ ppm 2.51-2.62 (m, 4H) 3.58 (d, J=4.30 Hz, 9H) 3.62-3.77 (m, 9H) 5.96 (s, 1H) 7.30-7.47 (m, 2H) 7.51-7.65 (m, 2H) 7.92 (dd, J=8.02, 1.76 Hz, 1H) 8.03 (d, J=8.22 Hz, 1H) 8.16-8.34 (m, 2H) 10.53 (s, 1H).

Example 15

Synthesis of 2-(2-cyanopropan-2-yl)-N-(3-(2,6-dimorpholinopyrimidin-4-yl)-4-methylphenyl)isonicotinamide

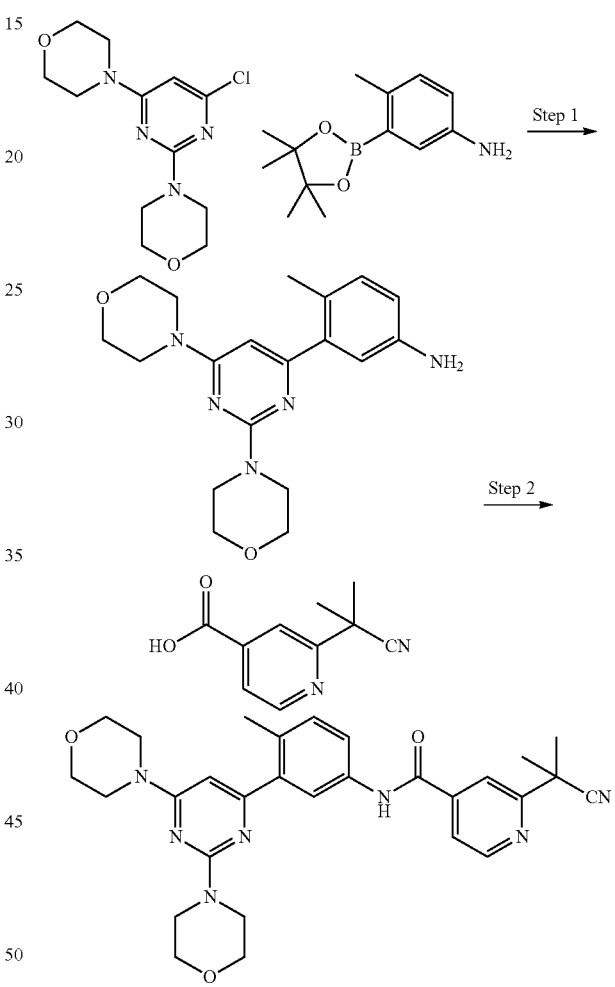

Step 1. To a solution of 4,4'-(6-chloropyrimidine-2,4-diyl)dimorpholine (1.0 equiv.) and 4-methyl-3-(4,4,5,5-tetramethyl-1,3,2-dioxaborolan-2-yl)aniline (1.5 equiv.) in DME and 2M sodium carbonate (3:1, 0.2 M) was added PdCl$_2$(dppf)-DCM adduct (0.100 equiv.) in a microwave vial equipped with a stir bar. The reaction was heated to 120° C. for 20 min in the microwave. The reaction mixture qas quenched with water and the aqueous layer was separated and extracted with EtOAc (×3). The combined organic layer was dried over magnesium sulfate, filtered and concentrated in vacuo. The material was purified via silica gel column chromatography eluting with 100% DCM to 10% MeOH/DCM to afford 3-(2,6-dimorpholinopyrimidin-4-yl)-4-methylaniline in 96% yield. LCMS (m/z) (M+H)=356.2, Rt=0.44 min.

Step 2. To a solution of 3-(2,6-dimorpholinopyrimidin-4-yl)-4-methylaniline (1.0 equiv.) in DMF (0.10 M) was added 2-(2-cyanopropan-2-yl)isonicotinic acid (1.2 equiv.), EDC-HCl (1.2 equiv.) and aza-HOBt (1.2 equiv.). The reaction was stirred at room temperature for 6 hours. Upon completion, the solution was filtered through a HPLC filter and purified via reverse phase preparative HPLC. Upon lyophilization of the pure fractions, 2-(2-cyanopropan-2-yl)-N-(3-(2,6-dimorpholinopyrimidin-4-yl)-4-methylphenyl)isonicotinamide was isolated as the TFA salt in 40% yield. $^1$H NMR (400 MHz, <cd3od>) δ ppm 1.81 (s, 6H) 2.38 (s, 3H) 3.79 (s, 13H) 3.89 (br. s., 3H) 6.57 (s, 1H) 7.43 (d, J=8.41 Hz, 1H) 7.65 (dd, J=8.27, 2.30 Hz, 1H) 7.81 (dd, J=5.04, 1.57 Hz, 1H) 7.97 (d, J=2.25 Hz, 1H) 8.04-8.10 (m, 1H) 8.78 (dd, J=5.04, 0.78 Hz, 1H). LCMS (m/z) (M+H)=528.3, Rt=0.69 min.

The compounds listed below were prepared using methods similar to those described for the preparation of Example 15 using the appropriate starting materials.

Example 16

3-(2-cyanopropan-2-yl)-N-(3-(2,6-dimorpholinopyrimidin-4-yl)-4-methylphenyl)benzamide

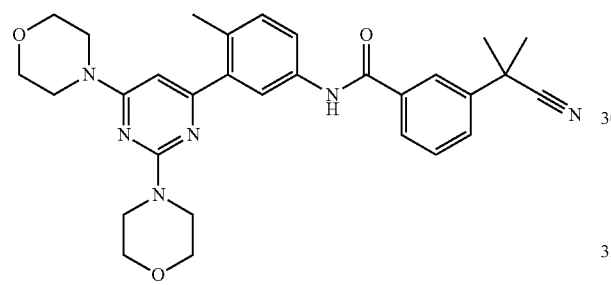

$^1$H NMR (400 MHz, <cd3od>) δ ppm 1.79 (s, 7H) 2.38 (s, 3H) 3.80 (s, 13H) 6.58 (s, 1H) 7.41 (d, J=8.36 Hz, 1H) 7.53-7.68 (m, 2H) 7.78 (ddd, J=7.92, 2.05, 1.03 Hz, 1H) 7.86-7.99 (m, 2H) 8.10 (t, J=1.71 Hz, 1H). LCMS (m/z) (M+H)=527.3, Rt=0.75 min.

Example 17

2-chloro-3-(1-cyanocyclopropyl)-N-(3-(2,6-dimorpholinopyrimidin-4-yl)-4-methylphenyl)benzamide

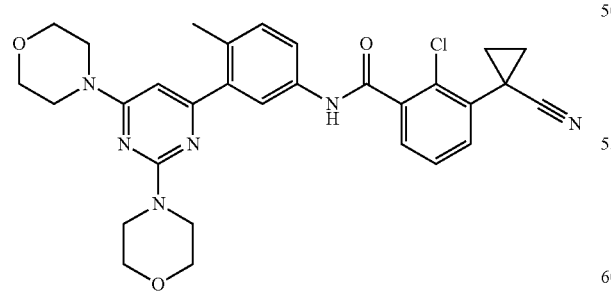

$^1$H NMR (400 MHz, <cd3od>) δ ppm 1.31-1.41 (m, 2H) 1.65-1.76 (m, 2H) 2.26 (s, 3H) 3.69 (s, 17H) 6.47 (s, 1H) 7.30 (d, J=8.36 Hz, 1H) 7.35-7.41 (m, 1H) 7.44-7.50 (m, 2H) 7.53 (dd, J=7.65, 1.74 Hz, 1H) 7.87 (d, J=2.30 Hz, 1H). LCMS (m/z) (M+H)=560.2, Rt=0.72 min.

Example 18

5-(dimethylamino)-N-(3-(2,6-dimorpholinopyrimidin-4-yl)-4-methylphenyl)nicotinamide

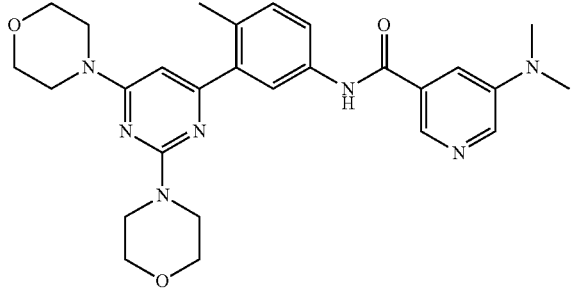 [SMILES: Cc1ccc(NC(=O)c2cncc(N(C)C)c2)cc1-c1cc(N2CCOCC2)nc(N2CCOCC2)n1]

$^1$H NMR (400 MHz, <cd3od>) δ ppm 2.38 (s, 3H) 3.17 (s, 6H) 3.71-3.99 (m, 16H) 6.56 (s, 1H) 7.43 (d, J=8.36 Hz, 1H) 7.67 (dd, J=8.31, 2.30 Hz, 1H) 7.95 (d, J=2.35 Hz, 1H) 8.03 (dd, J=2.86, 1.54 Hz, 1H) 8.26 (d, J=2.84 Hz, 1H) 8.44 (d, J=1.22 Hz, 1H). LCMS (m/z) (M+H)=504.3, Rt=0.53 min.

Example 19

5-(tert-butyl)-N-(3-(2,6-dimorpholinopyrimidin-4-yl)-4-methylphenyl)nicotinamide

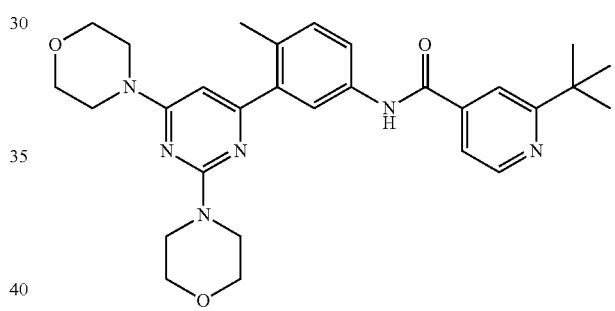

$^1$H NMR (400 MHz, <cd3od>) δ ppm 1.40-1.48 (m, 9H) 2.38 (s, 3H) 3.80 (s, 13H) 6.58 (s, 1H) 7.43 (d, J=8.41 Hz, 1H) 7.62-7.68 (m, 1H) 7.72 (d, J=5.28 Hz, 1H) 7.97 (d, J=2.15 Hz, 2H) 8.69 (d, J=5.18 Hz, 1H). LCMS (m/z) (M+H)=517.3, Rt=0.60 min.

Example 20

3-((dimethylamino)methyl)-N-(3-(2,6-dimorpholinopyrimidin-4-O-4-methylphenyl)-5-(trifluoromethyl)benzamide

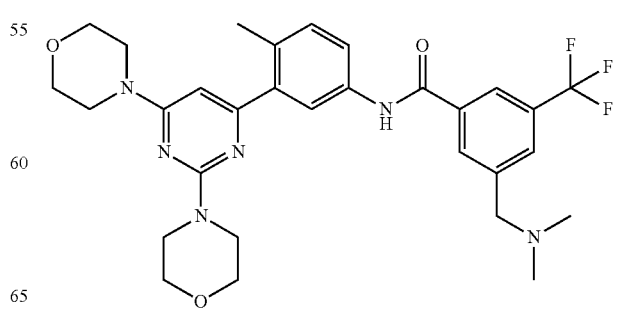

¹H NMR (400 MHz, <cd3od>) δ ppm 2.38 (s, 3H) 2.92 (s, 6H) 3.68-3.98 (m, 16H) 4.51 (s, 2H) 6.53 (s, 1H) 7.42 (d, J=8.41 Hz, 1H) 7.66-7.73 (m, 1H) 7.93 (d, J=2.15 Hz, 1H) 8.12 (s, 1H) 8.38 (s, 1H) 8.43 (s, 1H). LCMS (m/z) (M+H)=585.3, Rt=0.61 min.

Example 21

N-(3-(2,6-dimorpholinopyrimidin-4-yl)-4-methylphenyl)-3-(4-ethylpiperazin-1-yl)-5-(trifluoromethyl)benzamide

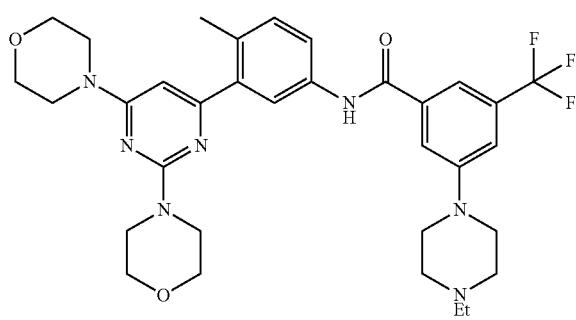

¹H NMR (400 MHz, <cd3od>) δ ppm 1.41 (t, J=7.34 Hz, 3H) 2.38 (s, 3H) 3.70-3.93 (m, 15H) 6.52 (s, 1H) 7.40 (d, J=8.36 Hz, 1H) 7.52 (s, 1H) 7.66 (dd, J=8.39, 1.98 Hz, 1H) 7.79 (s, 1H) 7.82 (d, J=2.01 Hz, 1H) 7.91 (d, J=2.25 Hz, 1H). LCMS (m/z) (M+H)=640.3, Rt=0.66 min.

Example 22

N-(3-(2,6-dimorpholinopyrimidin-4-O-4-methylphenyl)-3-trifluoromethoxy)benzamide

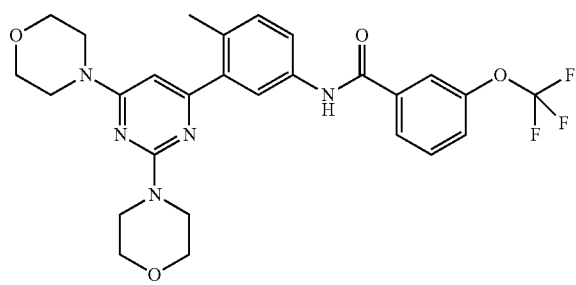 [SMILES: Cc1ccc(NC(=O)c2cccc(OC(F)(F)F)c2)cc1-c1cc(N2CCOCC2)nc(N2CCOCC2)n1]

¹H NMR (400 MHz, <cd3od>) δ ppm 2.38 (s, 3H) 3.72-3.94 (m, 15H) 6.57 (s, 1H) 7.42 (d, J=8.36 Hz, 1H) 7.51-7.57 (m, 1H) 7.60-7.69 (m, 2H) 7.87 (s, 1H) 7.94-8.00 (m, 1H). LCMS (m/z) (M+H)=544.3, Rt=0.84 min.

Example 23

N-(3-(2,6-dimorpholinopyrimidin-4-yl)-4-methylphenyl)-3-(methylsulfonyl)benzamide

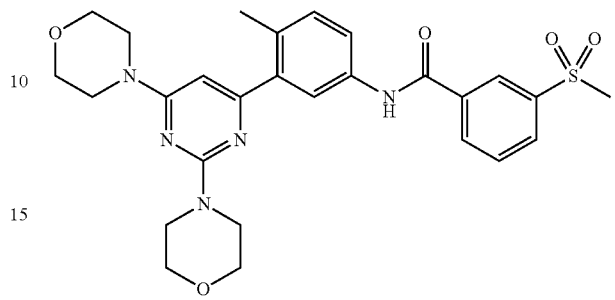

¹H NMR (400 MHz, <cd3od>) δ ppm 2.38 (s, 3H) 3.19 (s, 3H) 3.65-4.06 (m, 16H) 6.58 (s, 1H) 7.42 (d, J=8.22 Hz, 1H) 7.65 (dd, J=8.41, 2.15 Hz, 1H) 7.81 (t, J=7.83 Hz, 1H) 7.97 (d, J=2.35 Hz, 1H) 8.19 (d, J=7.83 Hz, 1H) 8.28 (d, J=7.83 Hz, 1H) 8.51 (s, 1H). LCMS (m/z) (M+H)=538.3, Rt=0.64 min.

Example 24

3-(tert-butyl)-N-(3-(2,6-dimorpholinopyrimidin-4-yl)-4-methylphenyl)isoxazole-5-carboxamide

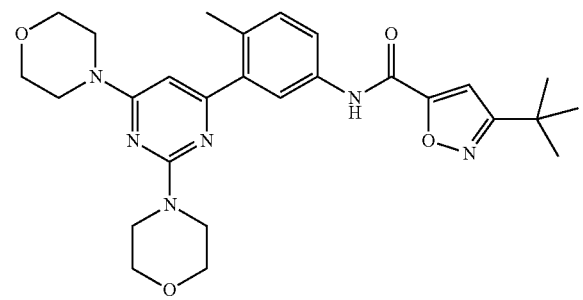 [SMILES: Cc1ccc(NC(=O)c2cc(C(C)(C)C)no2)cc1-c1cc(N2CCOCC2)nc(N2CCOCC2)n1]

¹H NMR (400 MHz, <cd3od>) δ ppm 1.42 (s, 9H) 2.37 (s, 3H) 3.80 (m, 16H) 6.52 (s, 1H) 7.10 (s, 1H) 7.42 (d, J=5.28 Hz, 1H) 7.71 (d, J=5.28 Hz, 1H) 7.92 (s, 1H). LCMS (m/z) (M+H)=507.3, Rt=0.79 min.

Example 25

5-(tert-butyl)-N-(3-(2,6-dimorpholinopyrimidin-4-yl)-4-methylphenyl)isoxazole-3-carboxamide

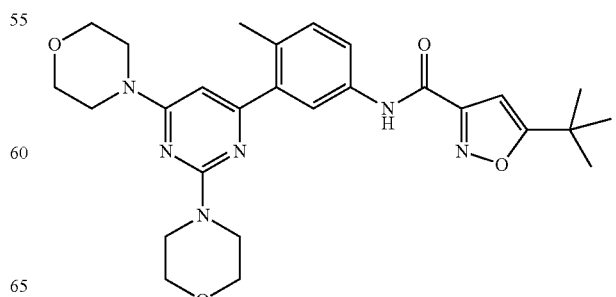

¹H NMR (400 MHz, <cd3od>) δ ppm 1.39 (s, 9H) 2.30 (s, 3H) 3.80 (m, 16H) 6.52 (m, 2H) 7.40 (d, J=5.28 Hz, 1H) 7.71 (d, J=5.28 Hz, 1H) 7.87 (s, 1H). LCMS (m/z) (M+H)=507.3, Rt=0.84 min.

Example 26

N-(3-(2,6-dimorpholinopyrimidin-4-yl)-4-methylphenyl)-2-(trifluoromethyl)thiazole-4-carboxamide

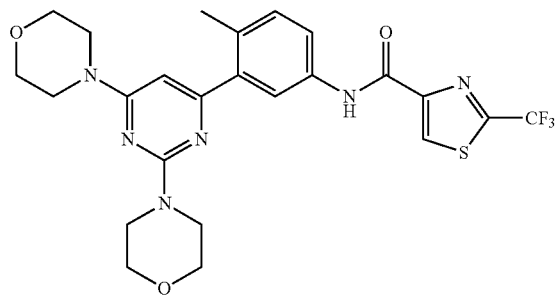 [SMILES: Cc1ccc(NC(=O)c2csc(C(F)(F)F)n2)cc1-c1cc(N2CCOCC2)nc(N2CCOCC2)n1]

LCMS (m/z) (M+H)=535.2, Rt=0.78 min. ¹H NMR (400 MHz, <cd3od>) δ ppm 2.37 (s, 3H) 3.71-4.00 (m, 16H) 6.57 (s, 1H) 7.42 (d, J=8.22 Hz, 1H) 7.77 (dd, J=8.22, 2.35 Hz, 1H) 7.92 (d, J=1.96 Hz, 1H) 8.70 (s, 1H).

Example 27

N-(4-methyl-3-(2-(methylsulfonyl)-6-morpholinopyrimidin-4-yl)phenyl)-3-trifluoromethyl)benzamide Step 1. To a solution of 4,6-dichloro-2-(methylthio)pyrimidine (1.0 equiv.) and triethylamine (0.8 equiv.) in EtOH (0.256 M) at RT was added morpholine (1.0 equiv.) in one portion. The resulting mixture was stirred at RT for 6 hours; a precipitate formed during this time. LCMS analysis indicated the formation of the desired product. The precipitate was filtered and washed with EtOH. Isolated 4-(6-chloro-2-(methylthio)pyrimidin-4-yl)morpholine as a white solid in 76% yield. LCMS (m/z) (M+H)=245.1, Rt=0.73 min.

Step 2. To a solution of 4-(6-chloro-2-(methylthio)pyrimidin-4-yl)morpholine (1.0 equiv.), N-(4-methyl-3-(4,4,5,5-tetramethyl-1,3,2-dioxaborolan-2-yl)phenyl)-3-(trifluoromethyl)benzamide (1.05 equiv.) in DME/2M sodium carbonate (3:1, 0.20M) was added PdCl₂(dppf).CH₂Cl₂ adduct (0.1 equiv.). The reaction was purged with N₂ for 5 mins, the vial was sealed and subjected to microwave irradiation for 10 min at 120° C. LCMS shows complete formation of desired product. The reaction was partitioned between water and EtOAc. The aqueous layer was further washed EtOAc (2×100 mL). The combined organics were dried over MgSO₄, filtered and concentrated. The crude material was purified via flash chromatography over silica gel eluting with heptanes and 0-60% ethyl acetate gradient. Isolated N-(4-methyl-3-(2-(methylthio)-6-morpholinopyrimidin-4-yl)phenyl)-3-(trifluoromethyl)benzamide as a white solid in 60% yield. LCMS (m/z) (M+H)=489.1, Rt=0.81 min.

Step 3. To a solution of N-(4-methyl-3-(2-(methylthio)-6-morpholinopyrimidin-4-yl)phenyl)-3-(trifluoromethyl)benzamide (1.0 equiv.) in DCM (0.1 M) was added m-CPBA (2.2 equiv.) portion wise. The reaction was stirred at RT for 4 hours. After which time LCMS shows complete oxidation to

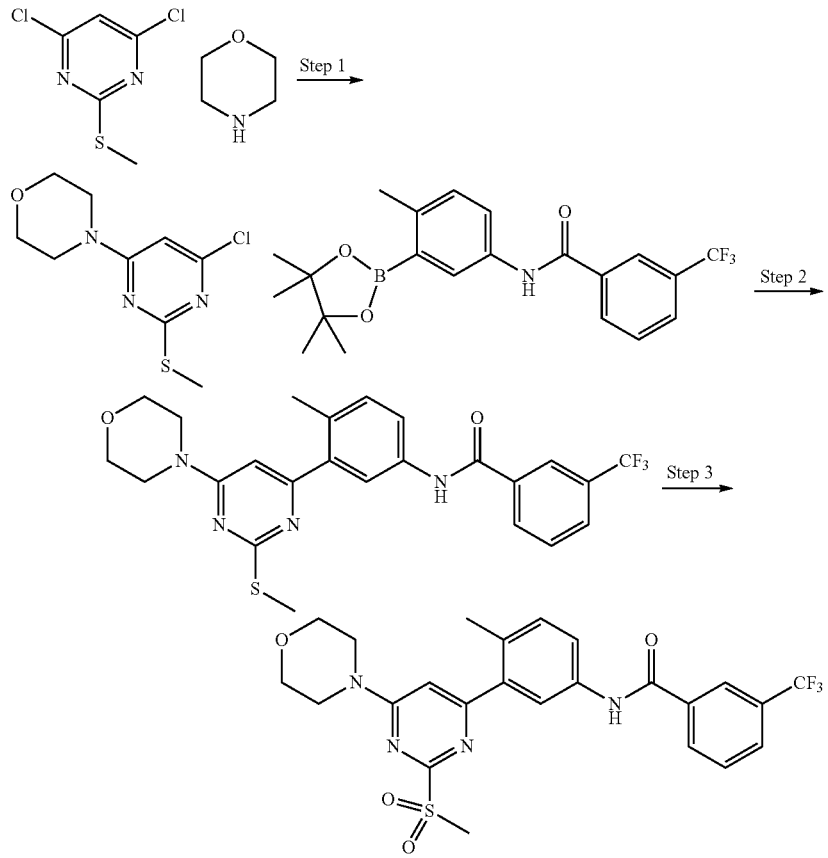

desired product. The reaction was diluted with DCM and washed with 0.5M Na₂CO₃. The resulting emulsion was filtered through a pad of celite and the cake was washed with DCM. The organics were dried over MgSO₄, filtered and concentrated. The material was purified via preparative reverse phase HPLC. Upon lyophilization of the pure fractions, N-(4-methyl-3-(2-(methylsulfonyl)-6-morpholinopyrimidin-4-yl)phenyl)-3-(trifluoromethyl)benzamide was isolated as the TFA salt in 33% yield. LCMS (m/z) (M+H)= 521.2, Rt=0.97 min. 1H NMR (400 MHz, <dmso>) δ ppm 2.36 (s, 3H) 3.68-3.81 (m, 9H) 4.03 (br. s., 2H) 7.14 (s, 1H) 7.35 (d, J=9.00 Hz, 1H) 7.76-7.82 (m, 1H) 7.82-7.87 (m, 2H) 7.98 (d, J=7.83 Hz, 1H) 8.28 (d, J=7.83 Hz, 1H) 8.31 (s, 1H) 10.57 (s, 1H).

Example 28

Synthesis of N-(3-(2-(ethylamino)-6-morpholinopyrimidin-4-yl)-4-methylphenyl)-3-(trifluoromethyl)benzamide

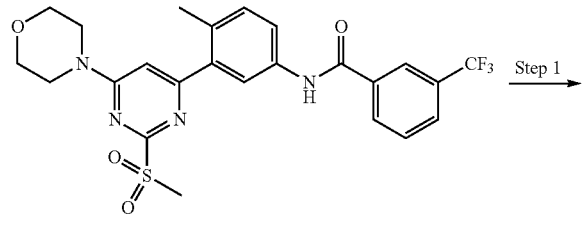

Step 1. To a solution of N-(4-methyl-3-(2-(methylsulfonyl)-6-morpholinopyrimidin-4-yl)phenyl)-3-(trifluoromethyl)benzamide (1.0 equiv.) and 2-oxa-6-azaspiro[3.3]heptane (1.0 equiv.) in THF (0.20M) was added triethylamine (3.5 equiv.) and the allowed to stir at 75° C. for 48 hours. LCMS analysis indicated formation of the desired product. The volatiles were removed in vacuo. The crude material was purified via preparative reverse phase HPLC. Upon lyophilization of the pure fractions, N-(3-(2-(ethylamino)-6-morpholinopyrimidin-4-yl)-4-methylphenyl)-3-(trifluoromethyl)benzamide was isolated as the TFA salt in 21% yield. 1H NMR (400 MHz, <cd3od>) δ ppm 1.28 (t, J=7.24 Hz, 3H) 2.38 (s, 3H) 3.52 (q, J=6.65 Hz, 2H) 3.80 (br. s., 6H) 4.05 (br. s., 2H) 6.50 (s, 1H) 7.41 (d, J=8.61 Hz, 1H) 7.66 (dd, J=8.22, 2.35 Hz, 1H) 7.72-7.78 (m, 1H) 7.91 (d, J=7.83 Hz, 1H) 7.96 (d, J=2.35 Hz, 1H) 8.21 (d, J=7.83 Hz, 1H) 8.26 (s, 1H). LCMS (m/z) (M+H)=486.3, Rt=0.86 min.

The compounds listed below were prepared using methods similar to those described for the preparation of Example 28 using the appropriate starting materials.

Example 29

N-(4-methyl-3-(6-morpholino-2-(2-oxa-6-azaspiro[3.3]heptan-6-yl)pyrimidin-4-yl)phenyl)-3-(trifluoromethyl)benzamide

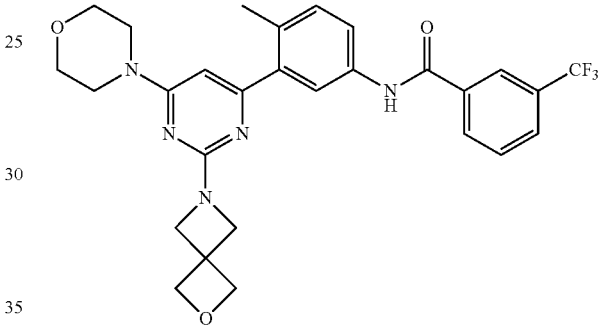

LCMS (m/z) (M+H)=540.3, Rt=0.81 min. 1H NMR (400 MHz, <cd3od>) δ ppm 2.36 (s, 3H) 3.69-3.83 (m, 12H) 4.44 (s, 4H) 6.51 (s, 1H) 7.41 (d, J=8.61 Hz, 1H) 7.63 (dd, J=8.22, 2.35 Hz, 1H) 7.72-7.78 (m, 1H) 7.92 (d, J=7.83 Hz, 1H) 7.95 (d, J=1.96 Hz, 1H) 8.21 (d, J=7.83 Hz, 1H) 8.26 (s, 1H).

Example 30

N-(4-methyl-3-(2-(methylamino)-6-morpholinopyrimidin-4-yl)phenyl)-3-(trifluoromethyl)benzamide

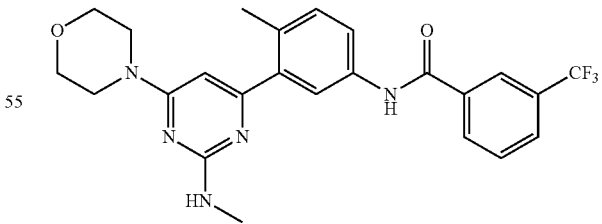

1H NMR (400 MHz, <cd3od>) δ ppm 2.37 (s, 3H) 3.03 (s, 3H) 3.80 (br. s., 6H) 4.08 (br. s., 2H) 6.50 (s, 1H) 7.41 (d, J=8.22 Hz, 1H) 7.66 (dd, J=8.22, 2.35 Hz, 1H) 7.71-7.78 (m, 1H) 7.91 (d, J=7.83 Hz, 1H) 7.96 (d, J=2.35 Hz, 1H) 8.21 (d, J=7.83 Hz, 1H) 8.26 (s, 1H). LCMS (m/z) (M+H)=472.3, Rt=0.82 min.

Example 31

N-(3-(2-((2-hydroxyethyl)amino)-6-morpholinopyrimidin-4-yl)-4-methylphenyl)-3-(trifluoromethyl)benzamide

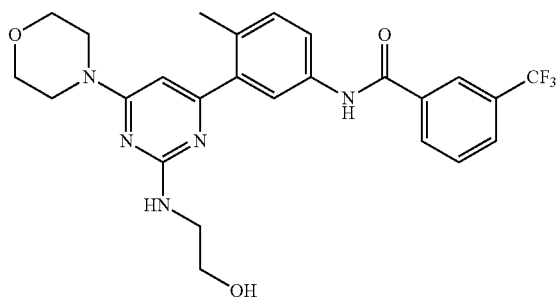 [SMILES: Cc1ccc(NC(=O)c2cccc(C(F)(F)F)c2)cc1-c1cc(N2CCOCC2)nc(NCCO)n1]

1H NMR (400 MHz, <cd3od>) δ ppm 2.02-2.26 (m, 2H) 2.38 (s, 3H) 3.62-3.85 (m, 9H) 4.04 (br. s., 2H) 4.56 (br. s., 1H) 6.52 (s, 1H) 7.41 (d, J=8.22 Hz, 1H) 7.66 (dd, J=8.22, 2.35 Hz, 1H) 7.72-7.78 (m, 1H) 7.92 (d, J=7.83 Hz, 1H) 7.94 (d, J=1.96 Hz, 1H) 8.21 (d, J=7.83 Hz, 1H) 8.26 (s, 1H). LCMS (m/z) (M+H)=502.3, Rt=0.77 min.

Example 32

N-(3-(2-(3-hydroxypyrrolidin-1-yl)-6-morpholinopyrimidin-4-yl)-4-methylphenyl)-3-(trifluoromethyl)benzamide

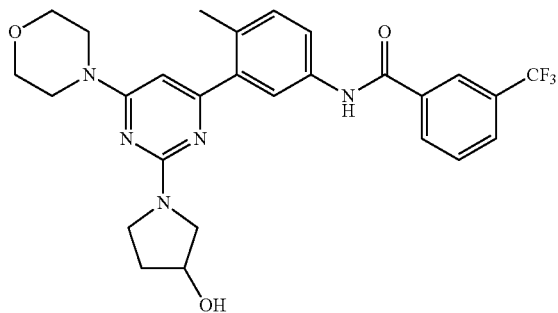 [SMILES: Cc1ccc(NC(=O)c2cccc(C(F)(F)F)c2)cc1-c1cc(N2CCOCC2)nc(N2CCC(O)C2)n1]

1H NMR (400 MHz, <cd3od>) δ ppm 2.02-2.27 (m, 2H) 2.38 (s, 3H) 3.63-3.87 (m, 10H) 4.05 (br. s., 2H) 4.56 (br. s., 1H) 6.52 (s, 1H) 7.41 (d, J=8.61 Hz, 1H) 7.66 (dd, J=8.41, 2.15 Hz, 1H) 7.72-7.78 (m, 1H) 7.92 (d, J=7.83 Hz, 1H) 7.94 (d, J=2.35 Hz, 1H) 8.21 (d, J=7.83 Hz, 1H) 8.26 (s, 1H). LCMS (m/z) (M+H)=528.3, Rt=0.79 min.

Example 33

N-(3-(2-(1H-imidazol-1-yl)-6-morpholinopyrimidin-4-yl)-4-methylphenyl)-3-(trifluoromethyl)benzamide

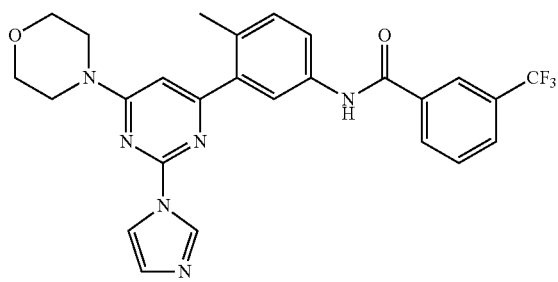 [SMILES: Cc1ccc(NC(=O)c2cccc(C(F)(F)F)c2)cc1-c1cc(N2CCOCC2)nc(-n2ccnc2)n1]

1H NMR (400 MHz, <cd3od>) δ ppm 2.46 (s, 3H) 3.78-3.93 (m, 8H) 6.99 (s, 1H) 7.36 (d, J=8.22 Hz, 1H) 7.60 (s, 1H) 7.63 (dd, J=8.22, 2.35 Hz, 1H) 7.71-7.78 (m, 1H) 7.91 (d, J=7.83 Hz, 1H) 7.99 (d, J=1.96 Hz, 1H) 8.22 (d, J=7.83 Hz, 1H) 8.27 (s, 1H) 8.36 (s, 1H) 9.61 (s, 1H). LCMS (m/z) (M+H)=509.4, Rt=0.84 min.

Example 34

Synthesis of N-(3-(2-(2-hydroxyethoxy)-6-morpholinopyrimidin-4-yl)-4-methylphenyl)-3-(trifluoromethyl)benzamide

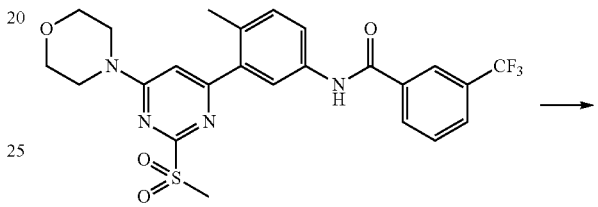

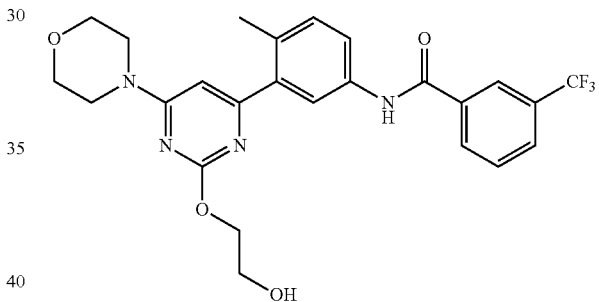

To a solution of N-(4-methyl-3-(2-(methylsulfonyl)-6-morpholinopyrimidin-4-yl)phenyl)-3-(trifluoromethyl)benzamide (1.0 equiv.) and ethylene glycol (1.0 equiv.) in acetonitrile (0.10M) was added potassium carbonate (1.0 equiv.) and the allowed to stir at 120° C. for 24 hours. LCMS analysis indicated formation of the desired product. The volatiles were removed in vacuo. The crude material was purified via preparative reverse phase HPLC. Upon lyophilization of the pure fractions, N-(4-methyl-3-(2-(methylsulfonamido)-6-morpholinopyrimidin-4-yl)phenyl)-3-(trifluoromethyl)benzamide was isolated as the TFA salt in 6% yield. LCMS (m/z) (M+H)=536.3, Rt=0.80 min, ¹H NMR (400 MHz, <cd3od>) δ ppm 2.37 (s, 3H) 3.79-3.85 (m, 4H) 3.86-3.97 (m, 6H) 4.60-4.65 (m, 2H) 6.78 (s, 1H) 7.41 (d, J=8.22 Hz, 1H) 7.67 (dd, J=8.22, 2.35 Hz, 1H) 7.74 (t, J=7.83 Hz, 1H) 7.91 (d, J=8.22 Hz, 1H) 7.94 (d, J=1.96 Hz, 1H) 8.21 (d, J=7.83 Hz, 1H) 8.26 (s, 1H). LCMS (m/z) (M+H)=503.1, Rt=0.73 min.

The compounds listed below were prepared using methods similar to those described above using the appropriate starting materials.

Example 35

N-(4-methyl-3-(2-(methylsulfonamido)-6-morpholinopyrimidin-4-yl)phenyl)-3-(trifluoromethyl)benzamide

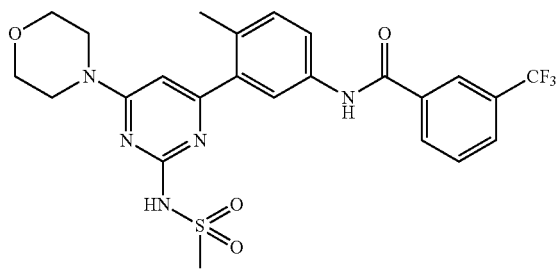 [SMILES: Cc1ccc(NC(=O)c2cccc(C(F)(F)F)c2)cc1-c1cc(N2CCOCC2)nc(NS(C)(=O)=O)n1]

LCMS (m/z) (M+H)=536.3, Rt=0.80 min. 1H NMR (400 MHz, <cd3od>) δ ppm 2.37 (s, 3H) 3.23 (s, 3H) 3.76-3.83 (m, 4H) 3.86 (br. s., 4H) 6.50 (s, 1H) 7.38 (d, J=8.22 Hz, 1H) 7.68-7.78 (m, 2H) 7.84 (d, J=2.35 Hz, 1H) 7.91 (d, J=7.83 Hz, 1H) 8.21 (d, J=7.83 Hz, 1H) 8.26 (s, 1H).

Example 36

Synthesis of N-(4-methyl-3-(6-morpholino-2-(2-oxopyrrolidin-1-yl)pyrimidin-4-yl)phenyl)-3-(trifluoromethyl)benzamide

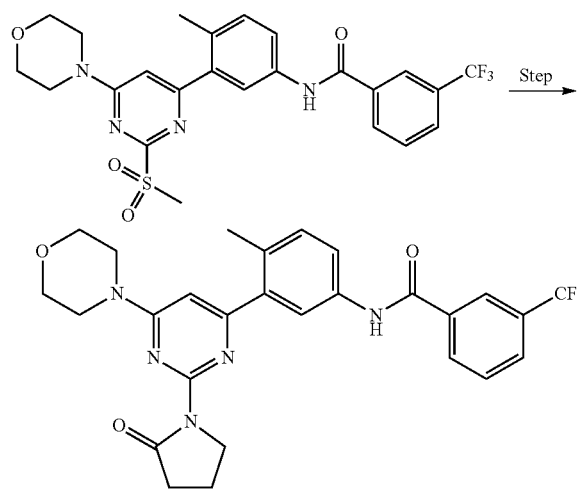

To a solution of N-(4-methyl-3-(2-(methylsulfonyl)-6-morpholinopyrimidin-4-yl)phenyl)-3-(trifluoromethyl)benzamide (1.0 equiv.) and pyrrolidin-2-one (2.0 equiv.) in dioxane (0.10M) was added cesium carbonate (1.0 equiv.) and the allowed to stir at 120° C. for 24 hours. LCMS analysis indicated formation of the desired product. The volatiles were removed in vacuo. The crude material was purified via preparative reverse phase HPLC. Upon lyophilization of the pure fractions, N-(4-methyl-3-(6-morpholino-2-(2-oxopyrrolidin-1-yl)pyrimidin-4-yl)phenyl)-3-(trifluoromethyl)benzamide was isolated as the TFA salt in 12% yield. LCMS (m/z) (M+H)=526.3, Rt=0.83 min. ¹H NMR (400 MHz, <cd3od>) δ ppm 2.25 (quin, J=7.73 Hz, 2H) 2.47 (s, 3H) 2.81 (t, J=8.02 Hz, 2H) 3.82-3.87 (m, 8H) 4.15 (t, J=7.43 Hz, 2H) 7.03 (s, 1H) 7.47 (d, J=8.61 Hz, 1H) 7.71 (dd, J=8.41, 2.15 Hz, 1H) 7.75 (t, J=7.83 Hz, 1H) 7.92 (d, J=7.83 Hz, 1H) 8.11 (d, J=2.35 Hz, 1H) 8.22 (d, J=7.83 Hz, 1H) 8.27 (s, 1H).

Example 37

Synthesis of N-(3-(2-(4-(2-hydroxypropan-2-yl)-1H-1,2,3-triazol-1-yl)-6-morpholinopyrimidin-4-yl)-4-methylphenyl)-3-(trifluoromethyl)benzamide

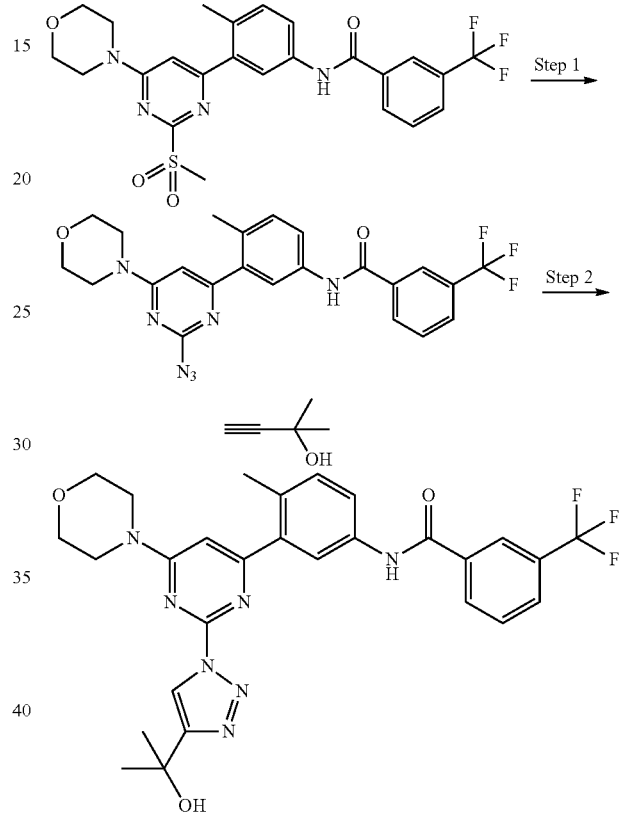

Step 1. A solution of N-(4-methyl-3-(2-(methylsulfonyl)-6-morpholinopyrimidin-4-yl)phenyl)-3-(trifluoromethyl) benzamide (1.0 equiv.) and Sodium azide in DMF (0.2 M) was heated at 90° C. for 3 hours. The reaction mixture was then cooled to room temperature and quenched with water then the aqueous layer was separated and extracted with EtOAc (×2). The combined organic layer was dried over sodium sulfate, filtered and concentrated in vacuo to afford N-(3-(2-azido-6-morpholinopyrimidin-4-yl)-4-methylphenyl)-3-(trifluoromethyl)benzamide. The compound was utilized in the subsequent reaction without further purification. LCMS (m/z) (M+H)=484.0/485.1, Rt=0.96 min.

Step 2. To a mixture of N-(3-(2-azido-6-morpholinopyrimidin-4-yl)-4-methylphenyl)-3-(trifluoromethyl)benzamide (1.0 equiv.), 2-methylbut-3-yn-2-ol (5.0 equiv.) and triethylamine (2.0 equiv.) in dioxane (0.25 M) was added Copper (I) Oxide on carbon (0.2 equiv.). The resulting mixture was heated to 90° C. for 3 hours. The reaction mixture was then cooled to room temperature and filtered, concentrated in vacuo. The crude material was purified via preparative reverse phase HPLC. Upon lyophilization of the pure fractions, N-(3-(2-(4-(2-hydroxypropan-2-yl)-1H-1,2,3-triazol- 1-yl)-6-morpholinopyrimidin-4-yl)-4-methylphenyl)-3-(trifluoromethyl)benzamide was isolated as the TFA salt in 14% yield. 1H NMR (400 MHz, <cd3od>) δ ppm 1.66 (s, 6H) 2.55 (s, 3H) 2.66 (s, 1H) 3.71-4.06 (m, 8H) 6.99 (s, 1H) 7.43 (d, J=7.83 Hz, 1H) 7.47-7.61 (m, 2H) 7.92-8.02 (m, 2H) 8.11 (d, J=1.96 Hz, 1H) 8.17 (s, 1H) 8.62 (s, 1H). LCMS (m/z) (M+H)=568.3, Rt=0.96 min.

Example 38

Synthesis of N-(3-(2-amino-6-morpholinopyrimidin-4-yl)-4-methylphenyl)-3-(trifluoromethyl)benzamide

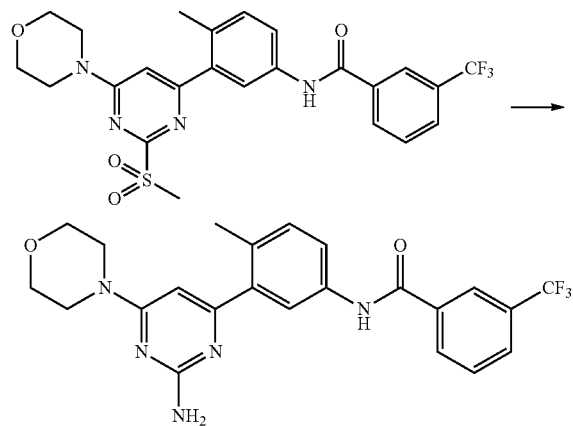

To a solution of N-(4-methyl-3-(2-(methylsulfonyl)-6-morpholinopyrimidin-4-yl)phenyl)-3-(trifluoromethyl)benzamide (1.0 equiv.) in DMSO (0.05M) was added ammonium acetate (2 equiv.) in a microwave vial equipped with a stir bar. The reaction was heated to 100° C. for 15 min in the microwave. The crude material was purified via preparative reverse phase HPLC. Upon lyophilization of the pure fractions, N-(3-(2-amino-6-morpholinopyrimidin-4-yl)-4-methylphenyl)-3-(trifluoromethyl)benzamide was isolated as the TFA salt in 23% yield. LCMS (m/z) (M+H)=458.0, Rt=0.79 min. 1H NMR (400 MHz, <cd3od>) δ ppm 2.48 (s, 3H) 3.79 (br. s., 8H) 6.57 (s, 1H) 7.45 (d, J=7.83 Hz, 1H) 7.54-7.60 (m, 2H) 7.94 (d, J=8.61 Hz, 1H) 8.03 (d, J=1.57 Hz, 1H) 8.08 (dd, J=8.02, 1.76 Hz, 1H) 8.17 (s, 1H).

Example 39

Synthesis of N-(3-(2-((1,3-dihydroxypropan-2-yl)amino)-6-morpholinopyrimidin-4-yl)-4-methylphenyl)-3-(trifluoromethyl)benzamide

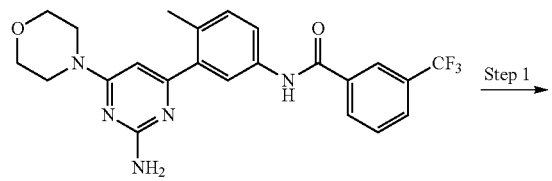

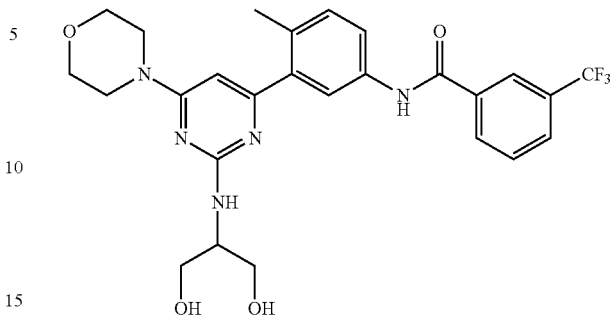

To a solution of N-(4-methyl-3-(2-(methylsulfonyl)-6-morpholinopyrimidin-4-yl)phenyl)-3-(trifluoromethyl)benzamide (1.0 equiv.) and 2-aminopropane-1,3-diol (1.0 equiv.) in DMF (0.05M) was added 60% sodium hydride (1.0 equiv.) at 0° C. The reaction was allowed to warm to room temperature and stir for 24 hours. LCMS analysis indicated the formation of the desired product. The crude material was purified via preparative reverse phase HPLC. Upon lyophilization of the pure fractions, N-(3-(2-((1,3-dihydroxypropan-2-yl)amino)-6-morpholinopyrimidin-4-yl)-4-methylphenyl)-3-(trifluoromethyl)benzamide was isolated as the TFA salt in 28% yield. LCMS (m/z) (M+H)=532.1, Rt=0.68 min. 1H NMR (400 MHz, <cd3od>) δ ppm 2.45 (s, 3H) 3.64-3.71 (m, 1H) 3.79 (s, 10H) 3.85-3.91 (m, 1H) 4.53-4.59 (m, 1H) 4.63-4.69 (m, 1H) 6.67 (s, 1H) 7.44 (d, J=7.43 Hz, 1H) 7.51 (d, J=7.83 Hz, 1H) 7.56 (t, J=8.02 Hz, 1H) 7.93 (d, J=8.22 Hz, 1H) 7.96-8.01 (m, 3H) 8.16 (s, 1H).

Step 2. To a solution of 4-(6-chloro-2-(methylthio)pyrimidin-4-yl)morpholine (1.0 equiv.) in DCM (0.10M) was added mCPBA (2.2 equiv.) portion-wise. The reaction was stirred at RT for 3 hours. After which time LCMS shows complete oxidation to desired product. The reaction was diluted with DCM (150 mL) and washed with 0.5M Na₂CO₃. The organics were dried over MgSO₄, filtered and concentrated. Isolated 4-(6-chloro-2-(methylsulfonyl)pyrimidin-4-yl)morpholine in 100% yield. LCMS (m/z) (M+H)=277.9, Rt=0.49 min.

Step 3. To a solution of 4-(6-chloro-2-(methylsulfonyl)pyrimidin-4-yl)morpholine (1.0 equiv) in dioxane (0.20M) was added ethane-1,2-diol (90 equiv.). To this stirring solution was added 60% NaH (1.0 equiv.) at 0° C. The reaction was allowed to warm to room temperature stirring for 24 hours. LCMS analysis indicated the formation of the desired product. The reaction was partitioned between NH₄Cl and EtOAc. The organics were washed with brine, water, then dried over MgSO₄ filtered and concentrated. Isolated 2-((4-chloro-6-morpholinopyrimidin-2-yl)oxy)ethanol in 75% yield. LCMS (m/z) (M+H)=260.0, Rt=0.49 min. ¹H NMR (400 MHz, <cdcl3>) δ ppm 3.71-3.82 (m, 8H) 3.91-3.98 (m, 2H) 4.40-4.47 (m, 2H) 6.18-6.24 (m, 1H).

Example 40

N-(3-(2-(2-hydroxyethoxy)-6-morpholinopyrimidin-4-yl)-4-methylphenyl)-3-(trifluoromethyl)benzamide

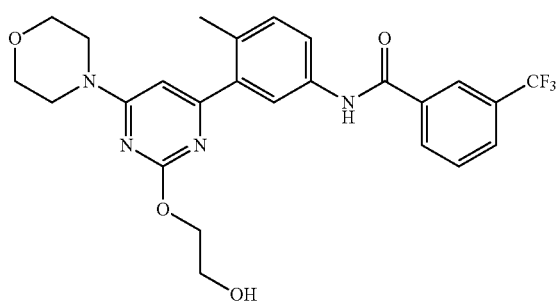 [SMILES: Cc1ccc(NC(=O)c2cccc(C(F)(F)F)c2)cc1-c1cc(N2CCOCC2)nc(OCCO)n1]

To a solution of 2-((4-chloro-6-morpholinopyrimidin-2-yl)oxy)ethanol (1.0 equiv.) and N-(4-methyl-3-(4,4,5,5-tetramethyl-1,3,2-dioxaborolane-2-yl)phenyl)-3-(trifluoromethyl)benzamide (1.2 equiv.) in DME and 2M sodium carbonate (3:1, 0.2 M) was added PdCl₂(dppf)-DCM adduct (0.1 equiv.) in a microwave vial equipped with a stir bar. The reaction was heated to 120° C. for 20 min in the microwave. The reaction was partitioned between water and ethyl acetate, the organic phase was washed with brine, was dried with sodium sulfate, filtered and concentrated. The crude material was purified via preparative reverse phase HPLC. Upon lyophilization of the pure fractions, N-(3-(2-(2-hydroxyethoxy)-6-morpholinopyrimidin-4-yl)-4-methylphenyl)-3-(trifluoromethyl)benzamide was isolated as the TFA salt in 18% yield. 1H NMR (400 MHz, <cd3od>) δ ppm 2.37 (s, 3H) 3.79-3.85 (m, 4H) 3.86-3.97 (m, 6H) 4.60-4.65 (m, 2H) 6.78 (s, 1H) 7.41 (d, J=8.22 Hz, 1H) 7.67 (dd, J=8.22, 2.35 Hz, 1H) 7.74 (t, J=7.83 Hz, 1H) 7.91 (d, J=8.22 Hz, 1H) 7.94 (d, J=1.96 Hz, 1H) 8.21 (d, J=7.83 Hz, 1H) 8.26 (s, 1H). LCMS (m/z) (M+H)=503.1, Rt=0.73 min.

Example 42 and Example 43

Synthesis of N-(4-methyl-3-(2-morpholino-6-(prop-1-en-2-yl)pyrimidin-4-yl)phenyl)-3-(trifluoromethyl)benzamide and N-(4-methyl-3-(4-morpholino-6-(prop-1-en-2-yl)pyrimidin-2-yl)phenyl)-3-(trifluoromethyl)benzamide

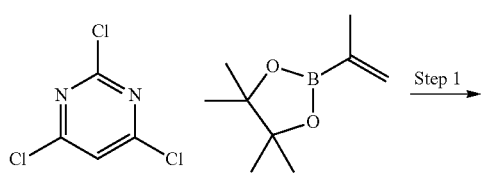

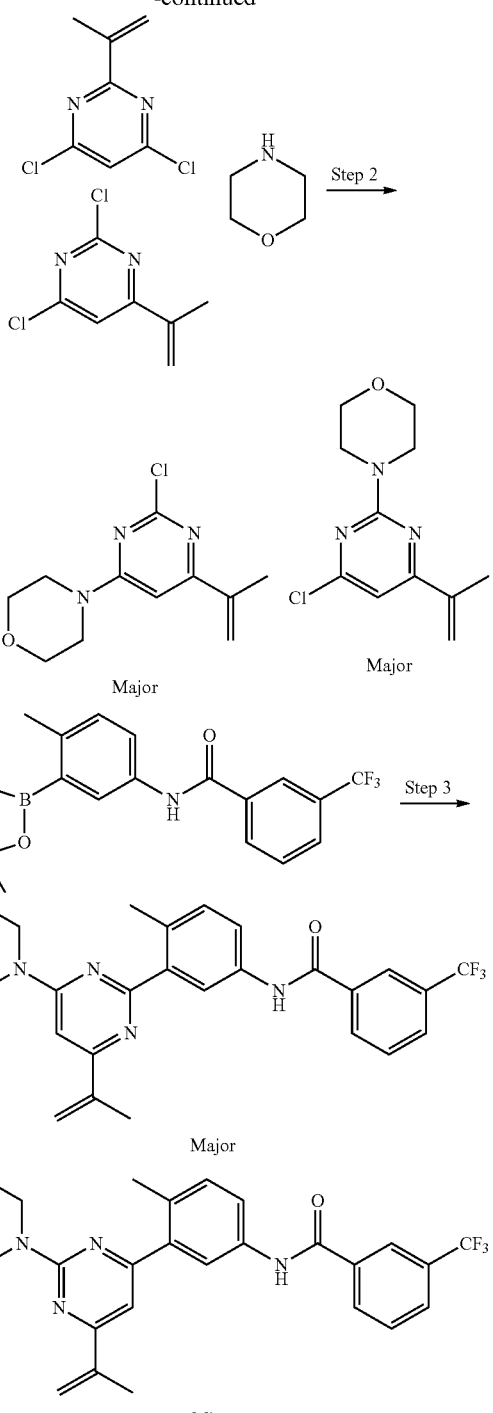

Step 1. To a solution of 2,4,6-trichloropyrimidine (1.0 equiv.) and 4,4,5,5-tetramethyl-2-(prop-1-en-2-yl)-1,3,2-dioxaborolane (1.05 equiv.) in dioxane and 2M sodium carbonate (3:1, 0.31 M) was added PdCl₂(dppf)-DCM adduct (0.05 equiv.). The reaction mixture was heated to 110° C. for 45 min. The reaction mixture was then cooled to room temperature and diluted with EtOAc and water. The aqueous layer was separated and extracted with EtOAc (×2). The combined organic layer was dried over sodium sulfate, filtered and concentrated in vacuo. The mixture of regioisomers was utilized in the subsequent reactions without further purification. LCMS (m/z) (M+H)=189.0/191.1, Rt=0.92 min two overlapping.

Step 2. To a solution of 2,4-dichloro-6-(prop-1-en-2-yl)pyrimidine and 4,6-dichloro-2-(prop-1-en-2-yl)pyrimidine (total 1.0 equiv.) in t-Butanol (0.2 M) was added morpholine (1.0 equiv.) followed by N,N-diisopropylethylamine (1.20 equiv.). The resulting mixture was heated to 120 at ° C. for 45 min. The reaction mixture was then cooled to RT, concentrated in vacuo and utilized in the subsequent reactions without further purification. LCMS Major (m/z) (M+H)=240.1/242.1, Rt=0.74 min and Minor (m/z) (M+H)=240.1/242.1, 0.94 min.

Step 3. To a solution of 4-(2-chloro-6-(prop-1-en-2-yl)pyrimidin-4-yl)morpholine and 4-(4-chloro-6-(prop-1-en-2-yl)pyrimidin-2-yl)morpholine (total 1.0 equiv.) and Intermediate A (1.1 equiv.) in dioxane and 2M sodium carbonate (4:1, 0.17 M) was added PdCl$_2$(dppf)-DCM adduct (0.150 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, two regioisomers were isolated in order of elution, major N-(4-methyl-3-(4-morpholino-6-(prop-1-en-2-yl)pyrimidin-2-yl)phenyl)-3-(trifluoromethyl)benzamide as the TFA salt in 4% yield. 1H NMR (400 MHz, <dmso>) δ ppm 2.13 (s, 3H) 3.30 (s, 3H) 3.69 (s, 8H) 5.38 (s, 1H) 6.15 (d, J=0.78 Hz, 1H) 6.83 (s, 1H) 7.26 (d, J=8.61 Hz, 1H) 7.72-7.84 (m, 2H) 7.95 (d, J=7.83 Hz, 1H) 8.16 (d, J=2.35 Hz, 1H) 8.22-8.34 (m, 2H) 10.48 (s, 1H). LCMS (m/z) (M+H)=483.2, Rt=0.87 min and minor N-(4-methyl-3-(2-morpholino-6-(prop-1-en-2-yl)pyrimidin-4-yl)phenyl)-3-(trifluoromethyl)benzamide 2% as the TFA salt in 2% yield. 1H NMR (400 MHz, <dmso>) ppm 2.11 (s, 3H) 2.35 (s, 3H) 3.75 (d, J=4.70 Hz, 8H) 5.45 (s, 1H) 6.12 (s, 1H) 6.99 (s, 1H) 7.30 (d, J=8.22 Hz, 1H) 7.73-7.87 (m, 3H) 7.95 (s, 1H) 8.21-8.35 (m, 2H) 10.49 (s, 1H). LCMS (m/z) (M+H)=483.2, Rt=1.22 min.

Example 44

Synthesis of N-(3-(4-isopropyl-6-morpholinopyrimidin-2-yl)-4-methylphenyl)-3-(trifluoromethyl)benzamide

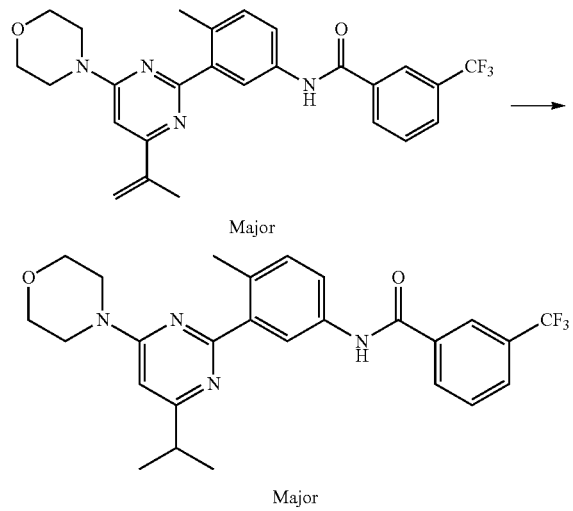

A solution of N-(4-methyl-3-(4-morpholino-6-(prop-1-en-2-yl)pyrimidin-2-yl)phenyl)-3-(trifluoromethyl)benzamide in Methanol (0.083 M) was evacuated and back filled with argon (×3). To the solution was then added Pd/C (1.00 eq.) and the mixture was evacuated and back filled with hydrogen (×3). The mixture was then stirred at RT under a positive pressure of atmospheric hydrogen (balloon) for 2 h. The hydrogen gas was removed by evacuation and the reaction backfilled with argon. The reaction mixture was then concentrated in vacuo. The crude material was purified via preparative reverse phase HPLC. Upon lyophilization of the pure fractions N-(3-(4-isopropyl-6-morpholinopyrimidin-2-yl)-4-methylphenyl)-3-(trifluoromethyl)benzamide as the TFA salt in 30% yield. 1H NMR (400 MHz, <dmso>) δ ppm 1.29 (d, J=6.65 Hz, 6H) 2.38 (br. s., 3H) 2.91-3.07 (m, 1H) 3.71 (br. s., 8H) 7.27-7.47 (m, 1H) 7.74-7.88 (m, 2H) 7.93-8.01 (m, 1H) 8.06 (s, 1H) 8.28 (s, 2H) 10.54-10.70 (m, 1H). LCMS (m/z) (M+H)= 485.4, Rt=0.85 min.

Example 45

Synthesis of N-(3-(6-isopropyl-2-morpholinopyrimidin-4-yl)-4-methylphenyl)-3-(trifluoromethyl)benzamide

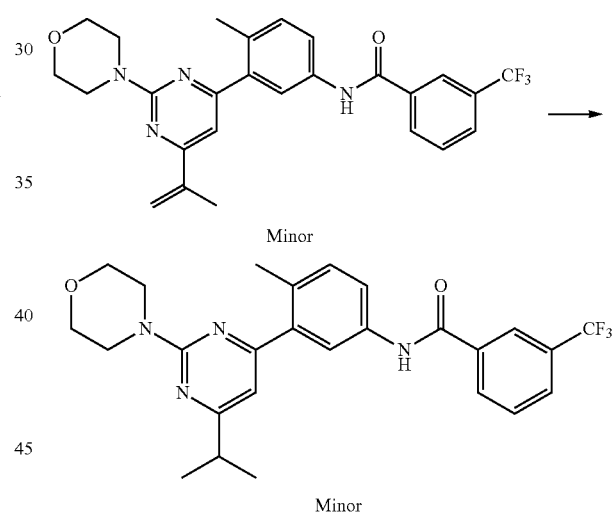

A solution of N-(4-methyl-3-(2-morpholino-6-(prop-1-en-2-yl)pyrimidin-4-yl)phenyl)-3-(trifluoromethyl)benzamide in Methanol (0.083 M) was evacuated and back filled with argon (×3). To the solution was then added Pd/C (1.00 eq.) and the mixture was evacuated and back filled with hydrogen (×3). The mixture was then stirred at RT under a positive pressure of atmospheric hydrogen (balloon) for 2 h. The hydrogen gas was removed by evacuation and the reaction backfilled with argon. The reaction mixture was then concentrated in vacuo. The crude material was purified via preparative reverse phase HPLC. Upon lyophilization of the pure fractions N-(3-(6-isopropyl-2-morpholinopyrimidin-4-yl)-4-methylphenyl)-3-(trifluoromethyl)benzamide was obtained as the TFA salt in 43% yield. 1H NMR (400 MHz, <dmso>) δ ppm 1.22 (d, J=6.65 Hz, 6H) 2.34 (s, 3H) 2.86 (dt, J=13.69, 6.85 Hz, 1H) 3.62-3.79 (m, 8H) 6.70 (s, 1H) 7.29 (d, J=8.22 Hz, 1H) 7.74-7.84 (m, 3H) 7.95 (d, J=7.83 Hz, 1H) 8.21-8.33 (m, 2H) 10.49 (s, 1H). LCMS (m/z) (M+H)=485.4, Rt=1.09 min.

Example 46

Synthesis of N-(3-(6-(2,2-dimethylmorpholino)-2-morpholinopyrimidin-4-yl)-4-methylphenyl)-3-(trifluoromethyl)benzamide

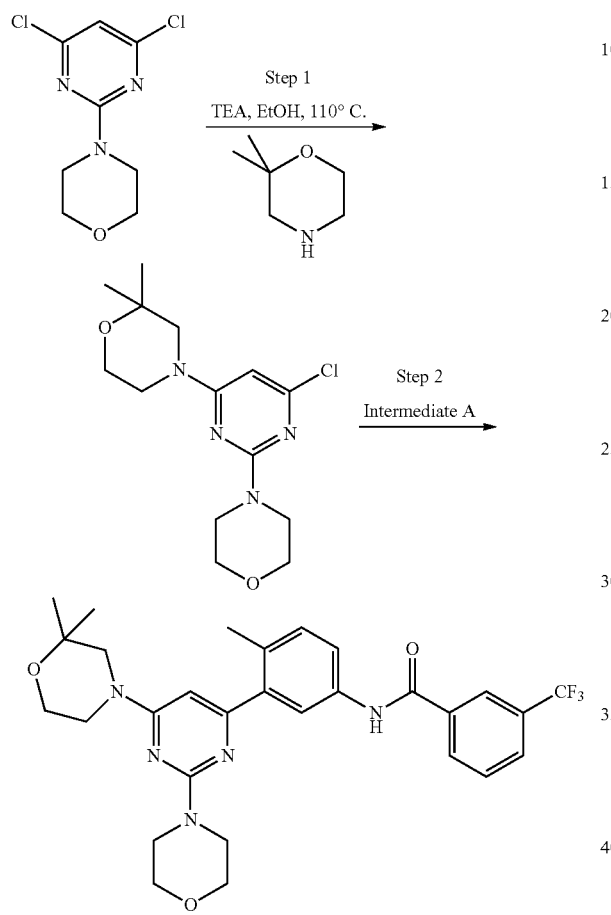

Step 1: A mixture of 2,2-dimethylmorpholine (2.0 equiv.), 4-(4,6-dichloropyrimidin-2-yl)morpholine (1 equiv.) and triethylamine (6 equiv.) in EtOH (0.2 M) were heated to 110° C. for 25 min in the microwave. The reaction mixture was partitioned between EtOAc and water. The organic phase was dried over sodium sulfate. The resulting solution was concentrated and dried under vacuo to give 4-(6-chloro-2-morpholinopyrimidin-4-yl)-2,2-dimethylmorpholine and was used in the next step without further purification. LCMS (m/z) (M+H)=313.2, Rt=0.86 min.

Step 2: A mixture of 4-(6-chloro-2-morpholinopyrimidin-4-yl)-2,2-dimethylmorpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(3-(6-(2,2-dimethylmorpholino)-2-morpholinopyrimidin-4-yl)-4-methylphenyl)-3-(trifluoromethyl)benzamide was isolated as the TFA salt in 36% yield. $^1$H NMR (400 MHz, <dmso>) δ ppm 1.08-1.18 (m, 6H) 2.29 (s, 3H) 3.39-3.90 (m, 14H) 7.34 (d, J=6.26 Hz, 1H) 7.45-7.65 (m, 1H) 7.70-7.88 (m, 3H) 7.92-8.03 (m, 1H) 8.18-8.36 (m, 2H) 10.58 (br. s., 1H). LCMS (m/z) (M+H)=556.4, Rt=0.87 min.

The compounds listed below were prepared using methods similar to those described above using the appropriate starting materials.

Example 47

N-(4-methyl-3-(2-morpholino-6-(2-oxa-6-azaspiro[3.3]heptan-6-yl)pyrimidin-4-yl)phenyl)-3-(trifluoromethyl)benzamide

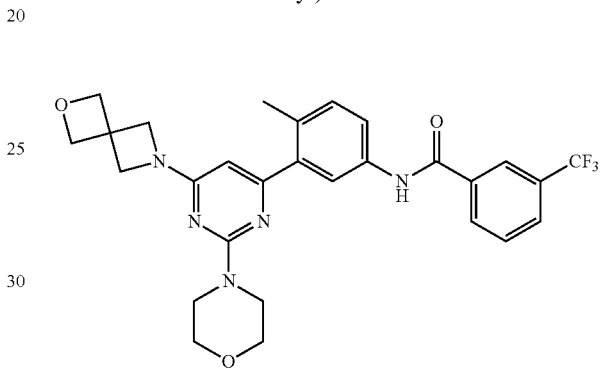

LCMS (m/z) (M+H)=540.2, Rt=0.79 min.

Example 48

(R)—N-(3-(6-(3-(hydroxymethyl)morpholino)-2-morpholinopyrimidin-4-yl)-4-methylphenyl)-3-(trifluoromethyl)benzamide

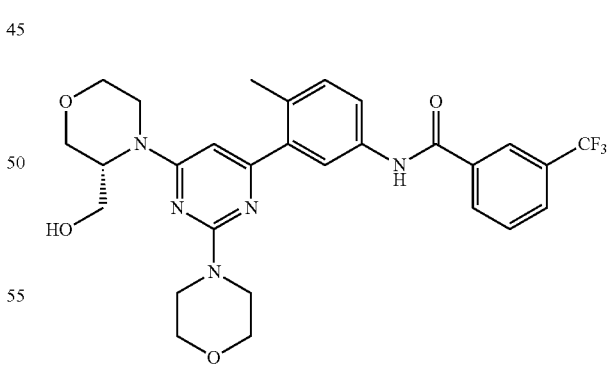

$^1$H NMR (400 MHz, <dmso>) δ ppm 2.29 (s, 3H) 3.16 (br. s., 1H) 3.36-3.55 (m, 3H) 3.68 (d, J=7.43 Hz, 10H) 3.85-4.04 (m, 3H) 6.43 (br. s., 1H) 7.34 (d, J=6.65 Hz, 1H) 7.69-7.88 (m, 3H) 7.97 (d, J=7.83 Hz, 1H) 8.20-8.35 (m, 2H) 10.57 (br. s., 1H). LCMS (m/z) (M+H)=558.3, Rt=0.75 min.

Example 49

N-(3-(6-(3-oxa-8-azabicyclo[3.2.1]octan-8-yl)-2-morpholinopyrimidin-4-yl)-4-methylphenyl)-3-(trifluoromethyl)benzamide

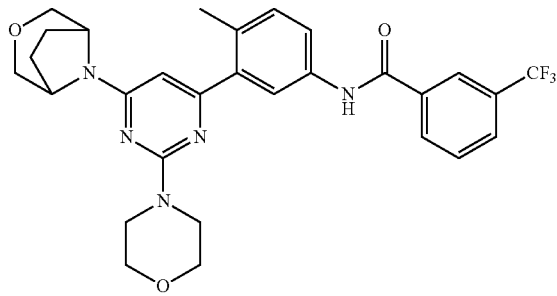 [SMILES: Cc1ccc(NC(=O)c2cccc(C(F)(F)F)c2)cc1-c1cc(N2C3CCC2COC3)nc(N2CCOCC2)n1]

¹H NMR (400 MHz, <dmso>) δ ppm 1.82-2.06 (m, 4H) 2.31 (s, 3H) 3.58-3.73 (m, 14H) 7.33 (br. s., 1H) 7.45-7.67 (m, 1H) 7.71-7.88 (m, 3H) 7.91-8.02 (m, 1H) 8.16-8.39 (m, 2H) 10.55 (br. s., 1H). LCMS (m/z) (M+H)=554.3, Rt=0.85 min.

Example 50

N-(4-methyl-3-(2-morpholino-6-(1,4-oxazepan-4-yl)pyrimidin-4-yl)phenyl)-3-(trifluoromethyl)benzamide

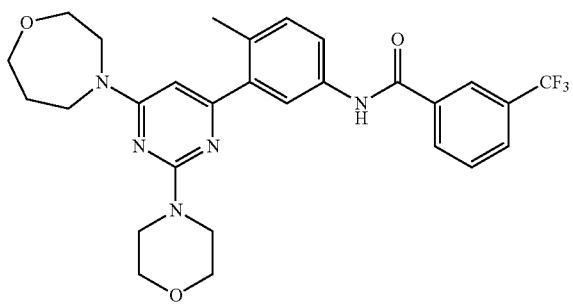 [SMILES: Cc1ccc(NC(=O)c2cccc(C(F)(F)F)c2)cc1-c1cc(N2CCCOCC2)nc(N2CCOCC2)n1]

¹H NMR (400 MHz, <dmso>) δ ppm 1.85 (br. s., 2H) 2.30 (s, 3H) 3.58-3.80 (m, 16H) 7.35 (br. s., 1H) 7.44-7.69 (m, 1H) 7.72-7.90 (m, 3H) 7.97 (d, J=7.83 Hz, 1H) 8.18-8.36 (m, 2H) 10.57 (br. s., 1H). LCMS (m/z) (M+H)=542.3, Rt=0.85 min.

Example 51

N-(3-(6-(2-oxa-5-azabicyclo[2.2.1]heptan-5-yl)-2-morpholinopyrimidin-4-yl)-4-methylphenyl)-3-(trifluoromethyl)benzamide

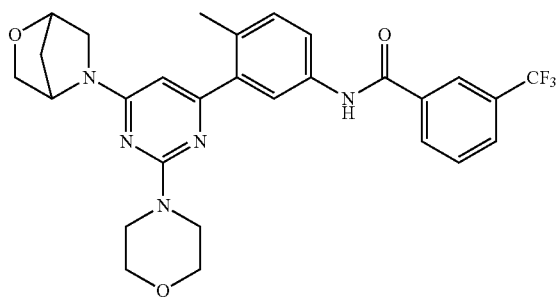 [SMILES: Cc1ccc(NC(=O)c2cccc(C(F)(F)F)c2)cc1-c1cc(N2CC3CC2CO3)nc(N2CCOCC2)n1]

LCMS (m/z) (M+H)=540.4, Rt=0.79 min.

Example 52

N-(3-(6-(8-oxa-3-azabicyclo[3.2.1]octan-3-yl)-2-morpholinopyrimidin-4-yl)-4-methylphenyl)-3-(trifluoromethyl)benzamide

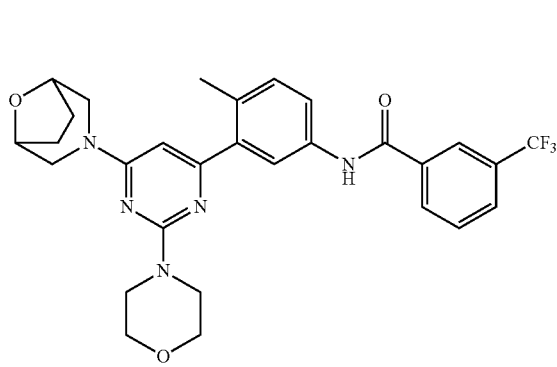 [SMILES: Cc1ccc(NC(=O)c2cccc(C(F)(F)F)c2)cc1-c1cc(N2CC3CCC(C2)O3)nc(N2CCOCC2)n1]

¹H NMR (400 MHz, <dmso>) δ ppm 1.58-1.72 (m, 2H) 1.74-1.92 (m, 2H) 2.29 (s, 3H) 2.94-3.29 (m, 2H) 3.68 (d, J=7.04 Hz, 8H) 4.42 (br. s., 2H) 7.33 (d, J=7.04 Hz, 1H) 7.46-7.68 (m, 1H) 7.70-7.86 (m, 3H) 7.97 (d, J=7.83 Hz, 1H) 8.19-8.34 (m, 2H) 10.56 (br. s., 1H). LCMS (m/z) (M+H)= 554.4, Rt=0.83 min.

Example 53

(R)—N-(4-methyl-3-(6-(2-methylmorpholino)-2-morpholinopyrimidin-4-yl)phenyl)-3-(trifluoromethyl)benzamide

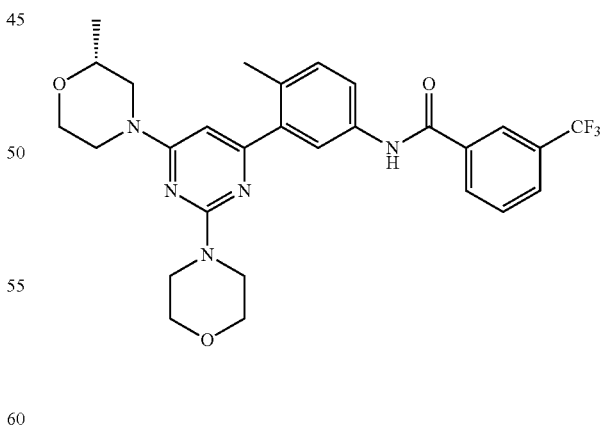

¹H NMR (400 MHz, <dmso>) δ ppm 1.00-1.26 (m, 3H) 2.29 (s, 3H) 3.41-3.57 (m, 2H) 3.68 (d, J=8.61 Hz, 8H) 3.89 (d, J=10.96 Hz, 1H) 7.32 (br. s., 1H) 7.42-7.66 (m, 1H) 7.70-7.87 (m, 3H) 7.92-8.02 (m, 1H) 8.19-8.33 (m, 2H) 10.54 (br. s., 1H). LCMS (m/z) (M+H)=542.3, Rt=0.85 min.

Example 54

(S)—N-(4-methyl-3-(6-(2-methylmorpholino)-2-morpholinopyrimidin-4-yl)phenyl)-3-(trifluoromethyl)benzamide

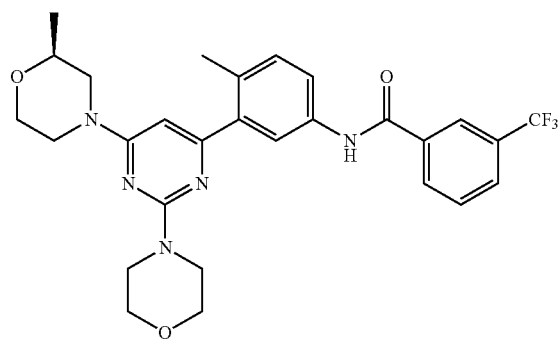 [SMILES: Cc1ccc(NC(=O)c2cccc(C(F)(F)F)c2)cc1-c1cc(N2CCO[C@@H](C)C2)nc(N2CCOCC2)n1]

$^1$H NMR (400 MHz, <dmso>) δ ppm 1.13 (d, J=6.26 Hz, 3H) 2.29 (s, 3H) 2.52 (s, 2H) 3.41-3.61 (m, 2H) 3.68 (d, J=9.39 Hz, 8H) 3.90 (d, J=10.17 Hz, 1H) 7.33 (d, J=6.26 Hz, 1H) 7.42-7.62 (m, 1H) 7.69-7.88 (m, 3H) 7.93-8.03 (m, 1H) 8.20-8.35 (m, 2H) 10.57 (br. s., 1H). LCMS (m/z) (M+H)=542.4, Rt=0.85 min.

Example 55

N-(3-(6-(3-oxa-8-azabicyclo[3.2.1]octan-8-yl)-2-morpholinopyrimidin-4-yl)-4-methylphenyl)-3-(trifluoromethyl)benzamide

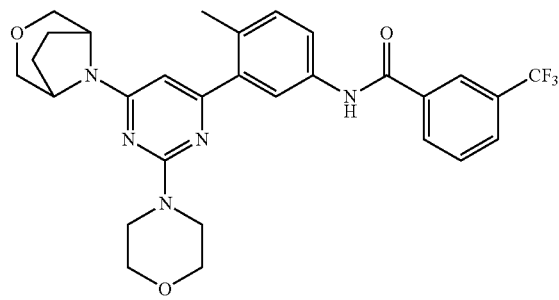 [SMILES: Cc1ccc(NC(=O)c2cccc(C(F)(F)F)c2)cc1-c1cc(N2C3CCC2COC3)nc(N2CCOCC2)n1]

$^1$H NMR (400 MHz, <dmso>) δ ppm 1.82-2.06 (m, 4H) 2.31 (s, 3H) 3.58-3.73 (m, 14H) 7.33 (br. s., 1H) 7.45-7.67 (m, 1H) 7.71-7.88 (m, 3H) 7.91-8.02 (m, 1H) 8.16-8.39 (m, 2H) 10.55 (br. s., 1H). LCMS (m/z) (M+H)=554.3, Rt=0.79 min.

Example 56

Synthesis of N-(4-methyl-3-(2-morpholino-6-((tetrahydro-2H-pyran-4-yl)oxy)pyrimidin-4-yl)phenyl)-3-(trifluoromethyl)benzamide

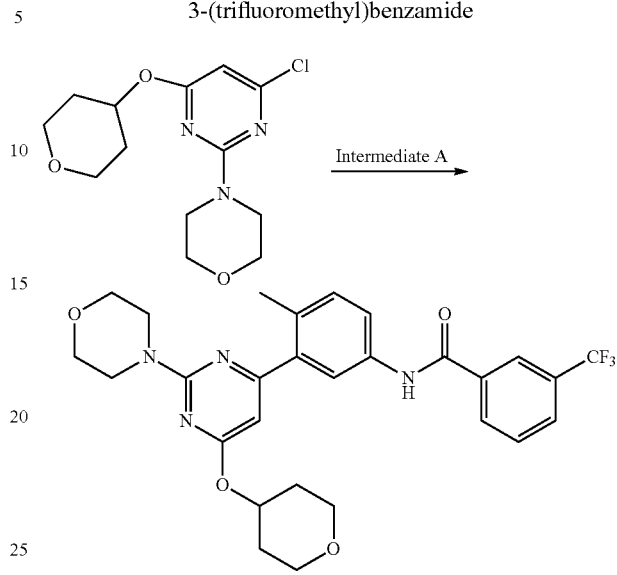

A mixture of 4-(4-chloro-6-((tetrahydro-2H-pyran-4-yl)oxy)pyrimidin-2-yl)morpholine (prepared according to WO2007/084786) (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(3-(6-(2,2-dimethylmorpholino)-2-morpholinopyrimidin-4-yl)-4-methylphenyl)-3-(trifluoromethyl)benzamide was isolated as the TFA salt in 44% yield. $^1$H NMR (400 MHz, <dmso>) δ ppm 1.59-1.71 (m, 2H) 1.95-2.09 (m, 2H) 2.35 (s, 3H) 3.64-3.72 (m, 10H) 3.80-3.91 (m, 2H) 5.24 (dt, J=8.71, 4.45 Hz, 1H) 6.18 (s, 1H) 7.27 (d, J=8.22 Hz, 1H) 7.72-7.87 (m, 3H) 7.96 (d, J=7.43 Hz, 1H) 8.18-8.38 (m, 2H) 10.45 (s, 1H). LCMS (m/z) (M+H)=543.3, Rt=0.96 min.

Example 57

Synthesis of N-(4-methyl-3-(5-methyl-2,6-dimorpholinopyrimidin-4-yl)phenyl)-3-(trifluoromethyl)benzamide

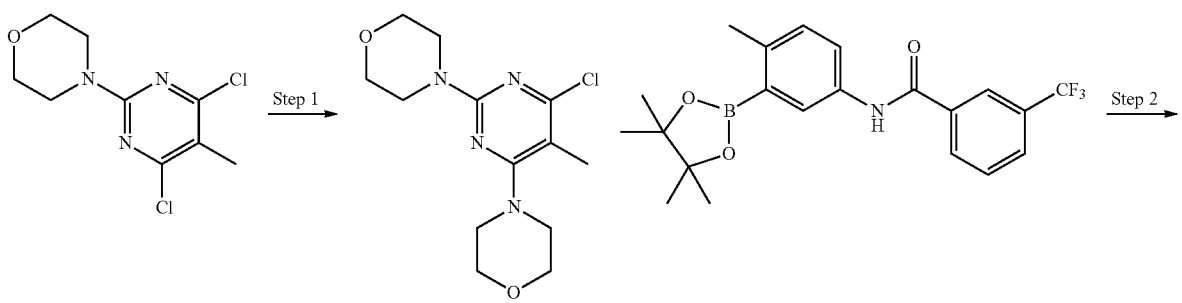

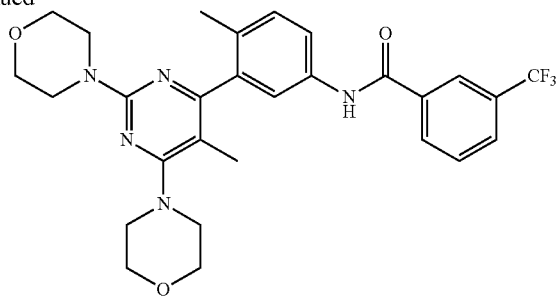

Step 1. To a solution of 4-(4,6-dichloro-5-methylpyrimidin-2-yl)morpholine in EtOH (0.15 M) was added morpholine (2.0 equiv.) followed by triethylamine (4.00 equiv.). The resulting mixture was heated under microwave irradiation at 125° C. for 50 min (2×25 min). The reaction mixture was then concentrated in vacuo to yield 4,4'-(6-chloro-5-methylpyrimidine-2,4-diyl)dimorpholine as a white solid in 96% yield which was utilized without further purification in the subsequent reaction. LCMS (m/z) (M+H)=299.1, Rt=0.85 min.

Step 2. To a solution of 4,4'-(6-chloro-5-methylpyrimidine-2,4-diyl)dimorpholine (1.0 equiv.) and Intermediate A (1.20 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 110° C. for 10 min under microwave irradiation. The organic phase was dried with sodium sulfate, filtered and concentrated. The crude material was purified via preparative reverse phase HPLC. Upon lyophilization of the pure fractions, N-(4-methyl-3-(5-methyl-2,6-dimorpholinopyrimidin-4-yl)phenyl)-3-(trifluoromethyl)benzamide was isolated as the TFA salt in 6% yield. $^1$H NMR (400 MHz, <dmso>) δ ppm 1.81 (s, 3H) 2.10 (br. s., 3H) 3.63 (br. s., 11H) 3.70 (d, J=3.91 Hz, 5H) 7.30 (br. s., 1H) 7.65-7.82 (m, 2H) 7.95 (d, J=7.43 Hz, 1H) 8.15-8.35 (m, 3H) 10.48 (br. s., 1H). LCMS (m/z) (M+H)=542.2, Rt=0.85 min.

Example 58

Synthesis of N-(6-methyl-5-(6-morpholinopyridazin-4-yl)pyridin-3-yl)-3-(trifluoromethyl)benzamide

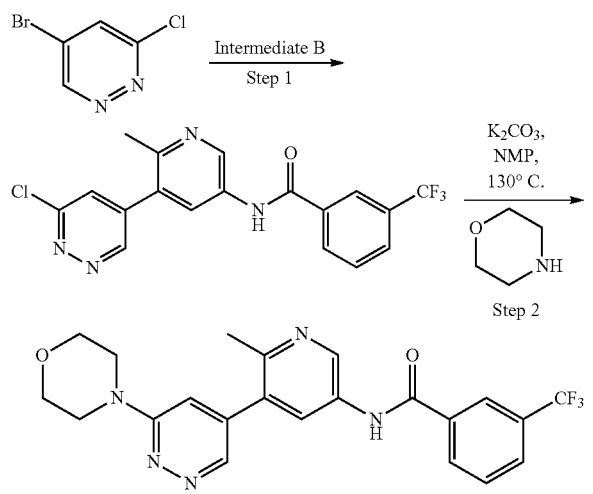

Step 1: A mixture of 5-bromo-3-chloropyridazine (1.0 equiv.), N-(6-methyl-5-(4,4,5,5-tetramethyl-1,3,2-dioxaborolan-2-yl)pyridin-3-yl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over sodium sulfate. After concentration, the crude material was purified via preparative reverse phase HPLC. Volatiles were removed by rotary evaporation and the remaining aqueous solution was basified with sodium bicarbonate. This solution was extracted with EtOAc, washed with brine and dried over sodium sulfate. The solution was concentrated and dried under vacuo to give crude N-(5-(6-chloropyridazin-4-yl)-6-methylpyridin-3-yl)-3-(trifluoromethyl)benzamide and was used in the next step without further purification. LCMS (m/z) (M+H)=393.1, Rt=0.73 min.

Step 2: A mixture of N-(5-(6-chloropyridazin-4-yl)-6-methylpyridin-3-yl)-3-(trifluoromethyl)benzamide (1.0 equiv.), morpholine (5 equiv.) and potassium carbonate (10 equiv.) in NMP (0.15 M) were heated to 130° C. for 18 h in an oil bath. The reaction mixture was centrifuged and the soluble portion was removed from solids. The soluble portion was purified via preparative reverse phase HPLC. Upon lyophilization of the pure fractions, N-(6-methyl-5-(6-morpholinopyridazin-4-yl)pyridin-3-yl)-3-(trifluoromethyl)benzamide was isolated as the TFA salt in 1% yield. LCMS (m/z) (M+H)=444.2, Rt=0.63 min.

Example 59

Synthesis of N-(4-methyl-3-(5-morpholinopyridazin-3-yl)phenyl)-3-(trifluoromethyl)benzamide

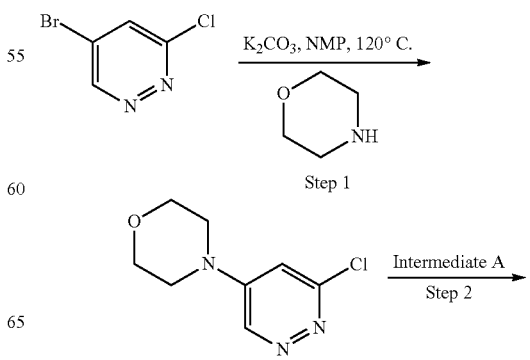

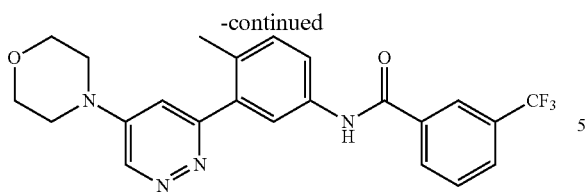

Step 1: A mixture of 5-bromo-3-chloropyridazine (1.0 equiv.), morpholine (1 equiv.) and potassium carbonate (6 equiv.) in NMP (0.2 M) were heated to 110° C. for 4 hours in an oil bath. The reaction mixture was partitioned between EtOAc and water. The organic phase was dried over sodium sulfate, concentrated and purified by normal phase chromatography. The combined fractions were concentrated and dried under vacuo to give crude 4-(6-chloropyridazin-4-yl) morpholine and was used in the next step without further purification. LCMS (m/z) (M+H)=200.0, Rt=0.34 min.

Step 2: A mixture of 4-(6-chloropyridazin-4-yl)morpholine (1.0 equiv.), N-(4-methyl-3-(4,4,5,5-tetramethyl-1,3,2-dioxaborolan-2-yl)phenyl)-3-(trifluoromethyl)benzamide (1.0 equiv.), sodium carbonate (2 M, 10 equiv.) and PdCl$_2$ (dppf) (0.5 equiv.) in DME (0.1 M) were heated to 110° C. for 15 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(4-methyl-3-(5-morpholinopyridazin-3-yl)phenyl)-3-(trifluoromethyl)benzamide was isolated as the TFA salt in 14% yield. $^1$H NMR (400 MHz, <dmso>) δ ppm 2.37 (s, 3H) 3.73-3.86 (m, 8H) 7.46 (d, J=7.83 Hz, 1H) 7.51 (d, J=2.35 Hz, 1H) 7.55-7.69 (m, 2H) 8.01-8.10 (m, 2H) 8.14 (d, J=8.22 Hz, 1H) 8.21 (s, 1H) 9.07 (d, J=2.74 Hz, 1H) 10.60 (s, 1H). LCMS (m/z) (M+H)=443.1, Rt=0.74 min.

The compound listed below were prepared using methods similar to those described above using the appropriate starting materials.

Example 60

N-(6-methyl-5-(5-morpholinopyridazin-3-yl)pyridin-3-yl)-3-(trifluoromethyl)benzamide

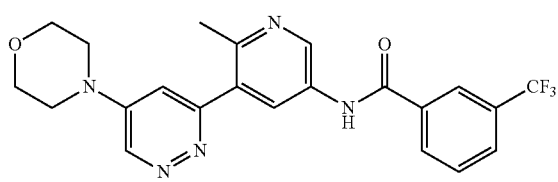 [SMILES: Cc1ncc(NC(=O)c2cccc(C(F)(F)F)c2)cc1-c1cc(N2CCOCC2)cnn1]

$^1$H NMR (400 MHz, <dmso>) δ ppm 2.46 (s, 3H) 3.73-3.90 (m, 9H) 7.55 (br. s., 1H) 7.76-7.88 (m, 1H) 8.01 (d, J=7.83 Hz, 1H) 8.28 (d, J=7.83 Hz, 1H) 8.32 (s, 1H) 8.38 (d, J=2.35 Hz, 1H) 8.95 (d, J=1.96 Hz, 1H) 9.07 (d, J=3.13 Hz, 1H) 10.87 (s, 1H). LCMS (m/z) (M+H)=444.0, Rt=0.62 min.

Example 61

N-(4-methyl-3-(2-morpholino-6-(trifluoromethyl)pyrimidin-4-yl)phenyl)-3-trifluoromethyl)benzamide

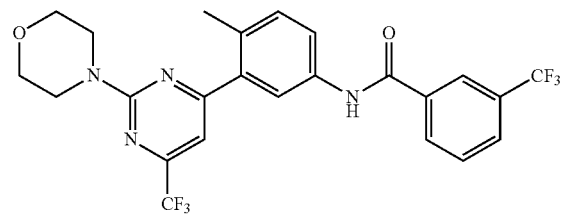 [SMILES: Cc1ccc(NC(=O)c2cccc(C(F)(F)F)c2)cc1-c1cc(C(F)(F)F)nc(N2CCOCC2)n1]

$^1$H NMR (400 MHz, <dmso>) δ ppm 2.40 (s, 3H) 3.65-3.85 (m, 8H) 7.19 (s, 1H) 7.35 (d, J=8.22 Hz, 1H) 7.75-7.83 (m, 1H) 7.87 (dd, J=8.22, 1.96 Hz, 1H) 7.91 (d, J=1.96 Hz, 1H) 7.97 (d, J=7.43 Hz, 1H) 8.22-8.34 (m, 2H) 10.54 (s, 1H). LCMS (m/z) (M+H)=511.2, Rt=1.23 min.

Example 62

Synthesis of N-(4-methyl-3-(2-morpholinopyridin-4-yl)phenyl)-3-trifluoromethyl)benzamide

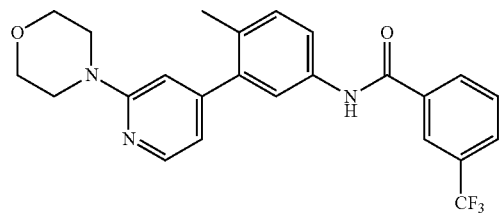

Synthesis of 4-(4-bromopyridin-2-yl)morpholine

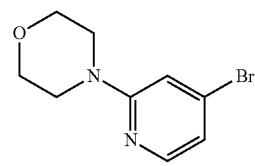 [SMILES: Brc1ccnc(N2CCOCC2)c1]

To a solution of triethylamine (1.0 equiv.) and 2-fluoro-4-bromopyridine (1.0 equiv.) at RT was added morpholine (1.0 equiv) in one portion, the resulting mixture was then heated in an oil bath at 100° C. for 66 hr. LCMS analysis indicated the formation of the desired product (m/z=244.9, Rt=0.36 min). The reaction mixture was concentrated in vacuo to yield 4-(4-bromopyridin-2-yl)morpholine as a light brown solid, (>100%, TEA impurity). LCMS (m/z) (M+H)=244.9, Rt=0.36 min. $^1$H NMR (400 MHz, <dmso>) δ ppm 3.39-3.55 (m, 4H) 3.59-3.75 (m, 4H) 6.87 (dd, J=5.28, 1.37 Hz, 1H) 7.05 (d, J=1.17 Hz, 1H) 8.00 (d, J=5.48 Hz, 1H).

Synthesis of 4-(4-(4,4,5,5-tetramethyl-1,3,2-dioxaborolan-2-yl)pyridin-2-yl)morpholine

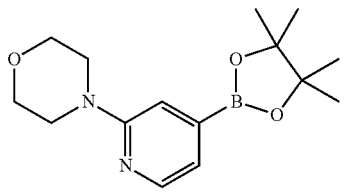 [SMILES: CC1(C)OB(c2ccnc(N3CCOCC3)c2)OC1(C)C]

4-(4-bromopyridin-2-yl)morpholine (1.10 equiv), bis(pinacolato)diboron (1.0 equiv.), potassium acetate (4.0 equiv), and PdCl$_2$(dppf)CH$_2$Cl$_2$ (0.05 equiv.) were added to a rb flask which was purged with nitrogen. DMF (0.20 M) was added and the mixture was heated to 80° C. overnight. The reaction was cooled to rt, quenched with water, and the product was extracted into EtOAc (3×). The combined organics were dried over Na$_2$SO$_4$, filtered, and concentrated. The crude was loaded onto silica gel and purified via ISCO to yield 4-(4-(4,4,5,5-tetramethyl-1,3,2-dioxaborolan-2-yl)pyridin-2-yl)morpholine as a light brown foam (56%). $^1$H NMR (400 MHz, <cdcl3>) δ ppm 1.33 (s, 12H) 3.49-3.55 (m, 4H) 3.79-3.83 (m, 4H) 6.98 (d, J=4.70 Hz, 1H) 7.03 (s, 1H) 8.21 (d, J=4.70 Hz, 1H).

Synthesis of 2-methyl-2'-morpholino-[3,4'-bipyridin]-5-amine

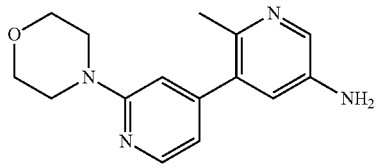 [SMILES: Cc1ncc(N)cc1-c1ccnc(N2CCOCC2)c1]

To a solution of 5-bromo-6-methylpyridin-3-amine (1.0 equiv.) and 4-(4-(4,4,5,5-tetramethyl-1,3,2-dioxaborolan-2-yl)pyridin-2-yl)morpholine (1.7 equiv.) in DME and 2M sodium carbonate (4:1, 0.14 M) was added PdCl$_2$(dppf)-DCM adduct (0.1 equiv.) in a microwave vial equipped with a stir bar. The reaction was heated to 110° C. for 15 min in the microwave. The cooled reaction mixture was partitioned between water and ethyl acetate. The organic phase was dried with sodium sulfate, filtered and concentrated. The crude material was purified by flash chromatography over silica gel (DCM with a 0-20% methanol gradient). The pure fractions were concentrated in vacuo to afford 2-methyl-2'-morpholino-[3,4'-bipyridin]-5-amine in quantitative yield. LCMS (m/z) (M+H)=271.1, Rt=0.26 min.

Synthesis of N-(4-methyl-3-(2-morpholinopyridin-4-yl)phenyl)-3-(trifluoromethyl)benzamide To a solution of 4-(4-bromopyridin-2-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(2-morpholinopyridin-4-yl)phenyl)-3-(trifluoromethyl)benzamide was isolated as the TFA salt in 16% yield. LCMS (m/z) (M+H)=442.3, Rt=0.76 min. $^1$H NMR (400 MHz, <dmso>) δ ppm 2.25 (s, 3H) 3.44-3.59 (m, 5H) 3.64-3.87 (m, 22H) 6.82 (d, J=5.48 Hz, 1H) 7.00 (s, 1H) 7.27-7.41 (m, 1H) 7.67-7.82 (m, 3H) 7.90-8.03 (m, 1H) 8.17 (d, J=5.48 Hz, 1H) 8.26 (d, J=7.83 Hz, 1H) 8.30 (s, 1H) 10.40-10.61 (m, 1H).

The compounds listed below were prepared using methods similar to those described for the preparation of Example 62 using the appropriate starting materials.

Example 63

4-Methyl-3-(2-morpholinopyridin-4-yl)-N-(3-(trifluoromethyl)phenyl)benzamide

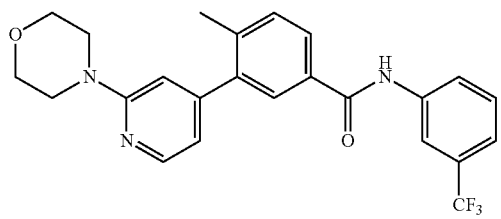 [SMILES: Cc1ccc(C(=O)Nc2cccc(C(F)(F)F)c2)cc1-c1ccnc(N2CCOCC2)c1]

1H NMR (400 MHz, <dmso>) δ ppm 2.28-2.38 (m, 3H) 3.50-3.58 (m, 5H) 3.61-3.93 (m, 36H) 6.83 (d, J=5.09 Hz, 1H) 6.97 (br. s., 1H) 7.37-7.69 (m, 6H) 7.89 (d, J=1.57 Hz, 1H) 7.96 (dd, J=7.83, 1.57 Hz, 1H) 8.06 (d, J=8.22 Hz, 1H) 8.20 (d, J=5.48 Hz, 1H) 8.23 (s, 1H) 10.50 (s, 1H). LCMS (m/z) (M+H)=442.3, Rt=0.79 min.

Example 64

4-methyl-3-(4-morpholinopyridin-2-yl)-N-(3-(trifluoromethyl)phenyl)benzamide

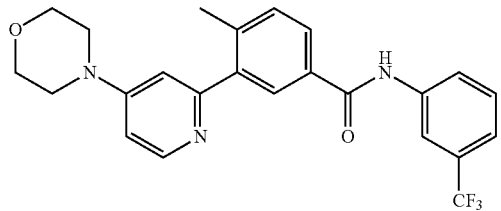

1H NMR (400 MHz, <dmso>) δ ppm 2.36 (s, 3H) 2.54 (s, 1H) 7.27 (dd, J=7.24, 2.54 Hz, 1H) 7.32 (d, J=2.74 Hz, 1H) 7.48 (d, J=7.83 Hz, 1H) 7.56-7.65 (m, 2H) 8.03-8.10 (m, 2H) 8.14 (dd, J=8.02, 1.76 Hz, 1H) 8.23 (s, 1H) 8.36 (d, J=7.04 Hz, 1H) 10.50-10.65 (m, 1H) 13.75 (br. s., 1H). LCMS (m/z) (M+H)=442.3, Rt=0.74 min.

Example 65

N-(3-(2,6-dimorpholinopyridin-4-yl)-4-methylphenyl)-3-(trifluoromethyl)benzamide

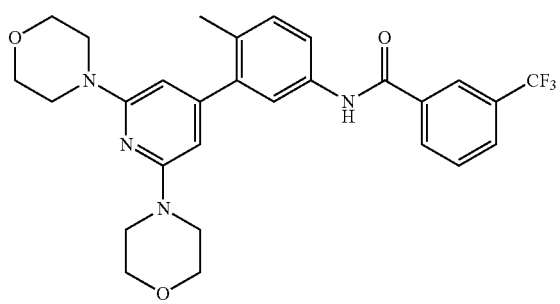 [SMILES: Cc1ccc(NC(=O)c2cccc(C(F)(F)F)c2)cc1-c1cc(N2CCOCC2)nc(N2CCOCC2)c1]

1H NMR (400 MHz, <dmso>) δ ppm 2.14-2.27 (m, 3H) 3.28-3.51 (m, 8H) 3.54-3.82 (m, 8H) 5.97-6.12 (m, 2H) 7.21-7.33 (m, 1H) 7.56-7.63 (m, 2H) 7.68-7.74 (m, 1H) 7.78 (t, J=7.83 Hz, 1H) 7.96 (d, J=7.83 Hz, 1H) 8.17-8.27 (m, 1H) 8.29 (s, 1H) 10.36-10.50 (m, 1H), LCMS (m/z) (M+H)= 527.4, Rt=1.04 min.

Example 66

2-(2-cyanopropan-2-yl)-N-(4-methyl-3-(2-morpholinopyridin-4-yl)phenyl)isonicotinamide

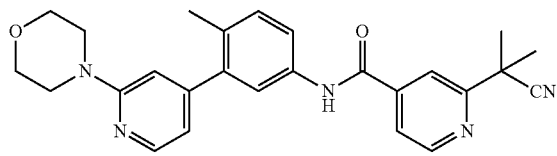 [SMILES: Cc1ccc(NC(=O)c2ccnc(C(C)(C)C#N)c2)cc1-c1ccnc(N2CCOCC2)c1]

1H NMR (400 MHz, <dmso>) δ ppm 2.25 (s, 3H) 3.45-3.61 (m, 4H) 3.67-3.79 (m, 4H) 6.81 (d, J=5.48 Hz, 1H) 6.98 (br. s., 1H) 7.35 (d, J=8.22 Hz, 1H) 7.69 (s, 1H) 7.73 (dd, J=8.22, 1.96 Hz, 1H) 7.86 (dd, J=5.09, 1.17 Hz, 1H) 8.00 (s, 1H) 8.17 (d, J=5.87 Hz, 1H) 8.81 (d, J=5.09 Hz, 1H) 10.60 (s, 1H), LCMS (m/z) (M+H)=442.4, Rt=0.67 min.

Example 67

N-(4-methyl-3-(2-morpholinopyridin-4-yl)phenyl) pyridazine-3-carboxamide

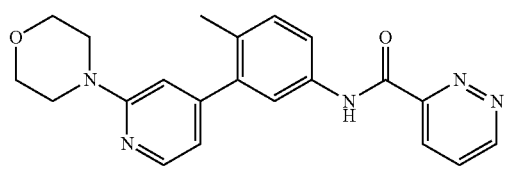 [SMILES: Cc1ccc(NC(=O)c2cccnn2)cc1-c1ccnc(N2CCOCC2)c1]

1H NMR (400 MHz, <dmso>) δ ppm 2.17-2.34 (m, 3H) 3.49-3.65 (m, 4H) 3.69-3.82 (m, 4H) 6.88 (d, J=5.48 Hz, 1H) 7.09 (s, 1H) 7.27-7.44 (m, 1H) 7.86-7.95 (m, 2H) 7.98 (dd, J=8.61, 5.09 Hz, 1H) 8.13-8.22 (m, 1H) 8.27-8.37 (m, 1H) 9.38-9.55 (m, 1H) 11.03-11.24 (m, 1H), LCMS (m/z) (M+H)=376.3.0, Rt=0.56 min.

Example 68

N-(4-methyl-3-(2-morpholinopyridin-4-yl)phenyl)-3-(methylsulfonyl)benzamide

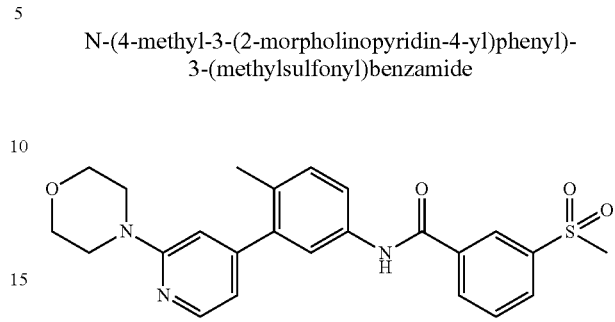

1H NMR (400 MHz, <dmso>) δ ppm 2.17-2.30 (m, 3H) 3.23-3.35 (m, 3H) 3.52-3.64 (m, 4H) 3.69-3.85 (m, 4H) 6.85 (d, J=5.48 Hz, 1H), 7.06 (br. s., 1H) 7.35 (d, J=8.22 Hz, 1H) 7.65-7.79 (m, 2H) 7.79-7.89 (m, 1H) 8.09-8.20 (m, 2H) 8.29 (d, J=7.83 Hz, 1H) 8.43-8.53 (m, 1H) 10.50-10.65 (m, 1H), LCMS (m/z) (M+H)=452.1, Rt=0.61 min.

Example 69

2-(tert-butyl)-N-(4-methyl-3-(2-morpholinopyridin-4-yl)phenyl)isonicotinamide

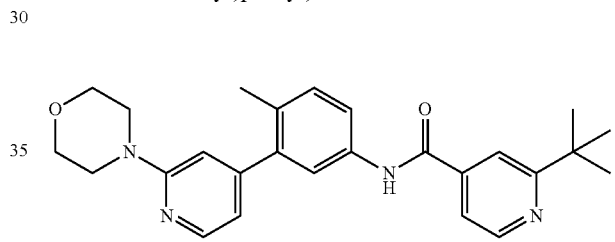

1H NMR (400 MHz, <dmso>) δ ppm 1.29-1.42 (m, 9H) 2.25 (s, 3H) 3.51-3.65 (m, 4H) 3.69-3.81 (m, 4H) 6.85 (d, J=5.48 Hz, 1H) 6.95-7.13 (m, 1H) 7.35 (d, J=8.22 Hz, 1H) 7.59-7.78 (m, 3H) 7.86 (s, 1H) 8.16 (d, J=5.48 Hz, 1H) 8.72 (d, J=5.09 Hz, 1H) 10.52 (s, 1H), LCMS (m/z) (M+H)=431.3, Rt=0.54 min.

Example 70

N-(4-methyl-3-(2-morpholinopyridin-4-yl)phenyl) pyrazine-2-carboxamide

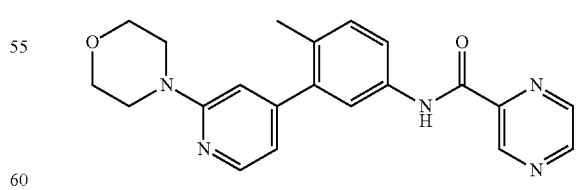

1H NMR (400 MHz, <dmso>) δ ppm 2.18-2.31 (m, 3H) 3.48-3.65 (m, 4H) 3.68-3.83 (m, 4H) 6.85 (d, J=5.48 Hz, 1H) 6.95-7.13 (m, 1H), 7.27-7.39 (m, 1H) 7.79-7.92 (m, 2H) 8.05-8.22 (m, 1H) 8.81 (dd, J=2.35, 1.57 Hz, 1H) 8.94 (d, J=2.35 Hz, 1H) 9.23-9.37 (m, 1H) 10.79 (s, 1H), LCMS (m/z) (M+H)=376.2, Rt=0.57 min.

Example 71

N-(4-methyl-3-(2-morpholinopyridin-4-yl)phenyl)pyrimidine-5-carboxamide

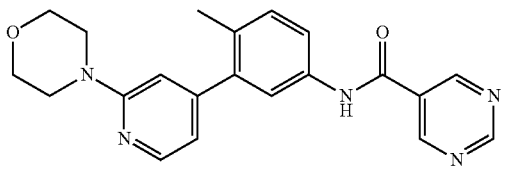 [SMILES: Cc1ccc(NC(=O)c2cncnc2)cc1-c1ccnc(N2CCOCC2)c1]

1H NMR (400 MHz, <dmso>) δ ppm 2.19-2.28 (m, 3H) 3.49-3.63 (m, 4H) 3.68-3.81 (m, 4H) 6.85 (d, J=5.48 Hz, 1H) 6.97-7.12 (m, 1H) 7.32-7.41 (m, 1H) 7.65-7.78 (m, 2H) 8.11 (dd, J=5.28, 2.15 Hz, 1H) 8.17 (d, J=5.48 Hz, 1H) 9.50 (dd, J=5.48, 0.78 Hz, 1H) 9.64 (d, J=0.78 Hz, 1H) 10.68-10.86 (m, 1H), LCMS (m/z) (M+H)=376.2, Rt=0.52 min.

Example 72

N-(4-methyl-3-(2-morpholinopyridin-4-yl)phenyl)pyridazine-4-carboxamide

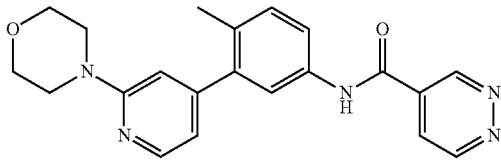 [SMILES: Cc1ccc(NC(=O)c2ccnnc2)cc1-c1ccnc(N2CCOCC2)c1]

1H NMR (400 MHz, <dmso>) δ ppm 2.19-2.29 (m, 3H) 3.58 (d, J=3.91 Hz, 4H) 3.67-3.82 (m, 4H) 6.83 (d, J=5.09 Hz, 1H) 7.03 (br. s., 1H), 7.29-7.42 (m, 1H) 7.64-7.76 (m, 2H) 8.10-8.24 (m, 1H) 9.27 (s, 2H) 9.37 (s, 1H) 10.66 (s, 1H), LCMS (m/z) (M+H)=376.2, Rt=0.50 min.

Example 73

N-(4-methyl-3-(2-morpholinopyridin-4-yl)phenyl)-2-(methylsulfonyl)isonicotinamide

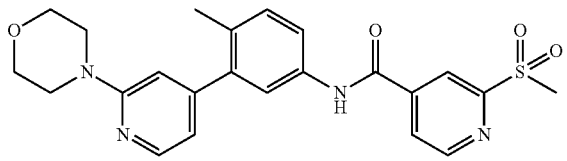 [SMILES: Cc1ccc(NC(=O)c2ccnc(S(C)(=O)=O)c2)cc1-c1ccnc(N2CCOCC2)c1]

1H NMR (400 MHz, <dmso>) δ ppm 2.18-2.34 (m, 3H) 3.35 (s, 3H) 3.47-3.63 (m, 4H) 3.69-3.84 (m, 4H) 6.72-6.88 (m, 1H) 6.95-7.07 (m, 1H) 7.37 (d, J=8.22 Hz, 1H) 7.72 (s, 1H) 7.76 (dd, J=8.22, 2.35 Hz, 1H) 8.17 (d, J=5.48 Hz, 1H) 8.20-8.26 (m, 1H) 8.53 (s, 1H) 8.94-9.05 (m, 1H) 10.75-10.90 (m, 1H), LCMS (m/z) (M+H)=453.3, Rt=0.57 min.

Example 74

3-(4-ethylpiperazin-1-yl)-N-(4-methyl-3-(2-morpholinopyridin-4-yl)phenyl)-5-(trifluoromethyl)benzamide

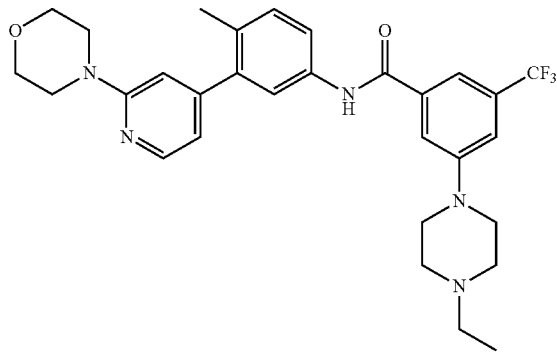 [SMILES: CCN1CCN(c2cc(C(=O)Nc3ccc(C)c(-c4ccnc(N5CCOCC5)c4)c3)cc(C(F)(F)F)c2)CC1]

1H NMR (400 MHz, <dmso>) δ ppm 1.27 (t, J=7.24 Hz, 4H) 2.24 (s, 3H) 2.54 (s, 1H) 3.13 (d, J=8.22 Hz, 5H) 3.18-3.28 (m, 3H) 3.44-3.56 (m, 6H) 3.61 (d, J=6.26 Hz, 3H) 3.66-3.81 (m, 6H) 4.11 (d, J=8.61 Hz, 3H) 6.76 (d, J=5.09 Hz, 1H) 6.89 (s, 1H) 7.33 (d, J=8.61 Hz, 1H) 7.52 (s, 1H) 7.65 (d, J=1.96 Hz, 1H) 7.73 (s, 2H) 7.75-7.81 (m, 2H) 8.18 (d, J=5.48 Hz, 1H) 9.72 (br. s., 1H) 10.42 (s, 1H), LCMS (m/z) (M+H)=554.4, Rt=0.61 min.

Example 75

3-(difluoromethyl)-N-(4-methyl-3-(2-morpholinopyridin-4-yl)phenyl)benzamide

1H NMR (400 MHz, <dmso>) δ ppm 2.54 (s, 1H) 3.46-3.63 (m, 4H) 3.66-3.82 (m, 4H) 6.84 (d, J=5.09 Hz, 1H) 7.01 (s, 1H) 7.03 (br. s., 1H), 7.15 (s, 1H) 7.28 (s, 1H) 7.33 (d, J=8.22 Hz, 1H) 7.62-7.84 (m, 4H) 8.06-8.20 (m, 3H) 10.46 (s, 1H), LCMS (m/z) (M+H)=424.1, Rt=0.73 min.

Example 76

N-(3-(2-(dimethylamino)-6-morpholinopyridin-4-yl)-4-methylphenyl)-3-(trifluoromethyl)benzamide

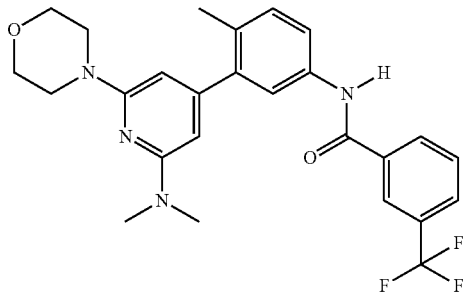 [SMILES: Cc1ccc(NC(=O)c2cccc(C(F)(F)F)c2)cc1-c1cc(N(C)C)nc(N2CCOCC2)c1]

1H NMR (400 MHz, DMSO-d6) δ ppm 2.21 (s, 3H) 2.99 (s, 6H) 3.30-3.49 (m, 4H) 5.89 (d, J=19.95 Hz, 2H) 7.12-7.32 (m, 1H) 7.63-7.84 (m, 2H) 7.90-8.04 (m, 1H) 8.17-8.35 (m, 2H) 10.30-10.53 (m, 1H). LCMS (m/z) (M+H) 485.4, Rt=0.93 min.

Example 77

N-(2-methyl-2',6'-dimorpholino-[3,4'-bipyridin]-5-yl)-3-(trifluoromethyl)benzamide

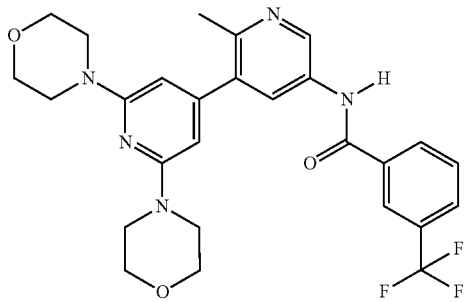 [SMILES: Cc1ncc(NC(=O)c2cccc(C(F)(F)F)c2)cc1-c1cc(N2CCOCC2)nc(N2CCOCC2)c1]

1H NMR (400 MHz, DMSO-d6) δ 2.13-2.32 (m, 1H) 2.54-2.66 (m, 2H) 3.54-3.70 (m, 9H) 7.65-8.11 (m, 4H) 7.83-8.02 (m, 3H) 8.26 (s, 3H) 8.76-8.94 (m, 1H) 10.53-10.79 (m, 1H). LCMS (m/z) (M+H) 528.3, Rt=0.8 min.

Example 78

(S)—N-(3-(2-(2-(hydroxymethyl)morpholino)pyridin-4-yl)-4-methylphenyl)-3-(trifluoromethyl)benzamide

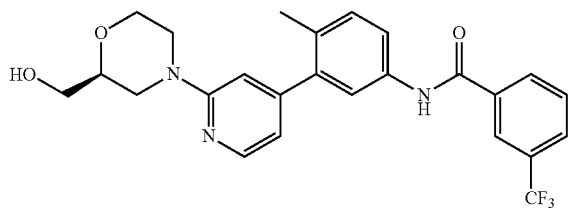 [SMILES: Cc1ccc(NC(=O)c2cccc(C(F)(F)F)c2)cc1-c1ccnc(N2CCO[C@H](CO)C2)c1]

1H NMR (400 MHz, <cd3od>) δ ppm 2.33 (s, 3H) 3.13 (t, J=11.54 Hz, 1H) 3.60-3.73 (m, 3H) 3.77 (td, J=11.74, 2.74 Hz, 1H) 4.02 (d, J=13.30 Hz, 1H) 4.11 (d, J=12.91 Hz, 2H) 7.02 (d, J=6.26 Hz, 1H) 7.29 (s, 1H) 7.37 (d, J=8.61 Hz, 1H) 7.61 (dd, J=8.22, 2.35 Hz, 1H) 7.70-7.76 (m, 1H) 7.81 (d, J=2.35 Hz, 1H) 7.90 (d, J=7.83 Hz, 1H) 8.04 (d, J=6.26 Hz, 1H) 8.20 (d, J=7.83 Hz, 1H) 8.26 (s, 1H). LCMS (m/z) (M+H)=472.3, Rt=0.74 min.

Example 79

2-(2-cyanopropan-2-yl)-N-(3-(2-((2R,5R)-2-((dimethylamino)methyl)-5-methylmorpholino)pyridin-4-yl)-4-methylphenyl)isonicotinamide

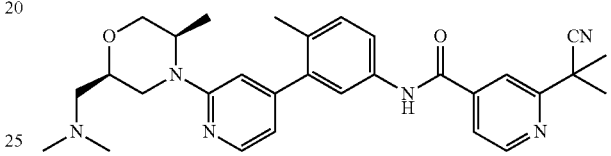

1H NMR (400 MHz, <dmso>) δ ppm 1.18 (d, J=6.26 Hz, 3H) 1.75 (s, 6H) 2.23 (s, 3H) 2.81 (br. s., 6H) 3.11 (br. s., 1H) 3.43 (dd, J=13.69, 4.70 Hz, 1H) 3.52 (dd, J=11.74, 2.35 Hz, 1H) 3.70-3.80 (m, 1H) 3.91 (d, J=12.91 Hz, 1H) 4.04 (dd, J=11.93, 3.33 Hz, 1H) 4.22-4.31 (m, 1H) 4.37 (d, J=10.56 Hz, 1H) 6.70 (d, J=5.09 Hz, 1H) 6.75 (s, 1H) 7.33 (d, J=8.22 Hz, 1H) 7.62-7.76 (m, 2H) 7.80-7.88 (m, 1H) 7.99 (s, 1H) 8.19 (d, J=5.09 Hz, 1H) 8.80 (d, J=5.09 Hz, 1H) 10.56-10.66 (m, 1H). LCMS (m/z) (M+H)=513.5, Rt=0.59 min.

Example 80

2-(2-cyanopropan-2-yl)-N-(3-(2-((2S,5S)-2-((dimethylamino)methyl)-5-methylmorpholino)pyridin-4-yl)-4-methylphenyl)isonicotinamide

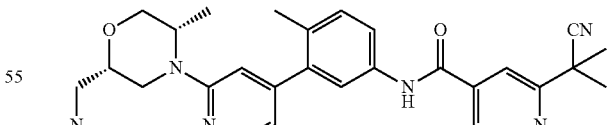

1H NMR (400 MHz, <dmso>) δ ppm 1.14 (d, J=6.65 Hz, 3H) 1.75 (s, 6H) 2.22 (s, 3H) 2.75-2.89 (m, 7H) 3.23-3.36 (m, 2H) 3.79-3.85 (m, 2H) 3.92 (t, J=9.78 Hz, 1H) 4.11 (d, J=12.52 Hz, 1H) 4.40 (d, J=6.26 Hz, 1H) 6.68 (d, J=5.48 Hz, 1H) 6.74 (s, 1H) 7.32 (d, J=8.61 Hz, 1H) 7.64-7.72 (m, 2H) 7.84 (d, J=4.70 Hz, 1H) 7.98 (s, 1H) 8.18 (d, J=5.09 Hz, 1H) 8.79 (d, J=5.09 Hz, 1H) 10.57 (s, 1H). LCMS (m/z) (M+H)=513.4, Rt=0.57 min.

Example 81

5-(dimethylamino)-N-(2-methyl-2'-morpholino-[3,4'-bipyridin]-5-yl)nicotinamide

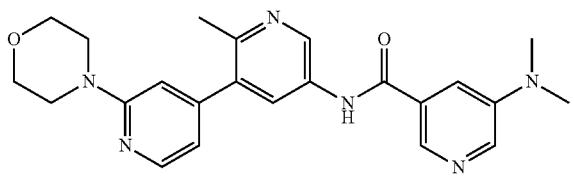 [SMILES: Cc1ncc(NC(=O)c2cncc(N(C)C)c2)cc1-c1ccnc(N2CCOCC2)c1]

1H NMR (400 MHz, <dmso>) δ ppm 2.49 (s, 9H) 3.50-3.62 (m, 4H) 3.68-3.77 (m, 4H) 6.86 (d, J=5.48 Hz, 1H) 7.07 (s, 1H) 7.87 (br. s., 1H) 8.18 (d, J=2.35 Hz, 1H) 8.22 (d, J=5.48 Hz, 1H) 8.34 (d, J=2.74 Hz, 1H) 8.50 (s, 1H) 8.97 (d, J=2.35 Hz, 1H) 10.96 (s, 1H). LCMS (m/z) (M+H)=419.3, Rt=0.37 min.

Example 82

(R)-2-(2-cyanopropan-2-yl)-N-(4-methyl-3-(2-(3-methylmorpholino)pyridin-4-yl)phenyl)isonicotinamide

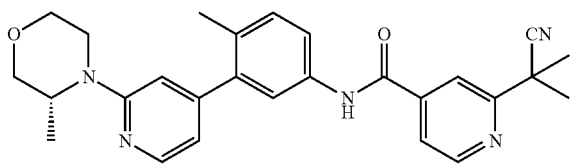 [SMILES: Cc1ccc(NC(=O)c2ccnc(C(C)(C)C#N)c2)cc1-c1ccnc(N2CCOC[C@H]2C)c1]

LCMS (m/z) (M+H)=456.3, Rt=0.66 min.

Example 83

(S)-2-(2-cyanopropan-2-yl)-N-(3-(2-(2-(hydroxymethyl)morpholino)pyridin-4-yl)-4-methylphenyl)isonicotinamide

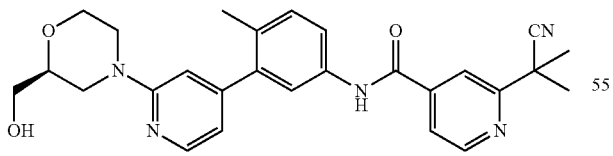

1H NMR (400 MHz, <dmso>) δ ppm 1.75 (s, 6H) 2.23 (s, 3H) 2.76 (t, J=11.35 Hz, 1H) 2.99 (t, J=10.96 Hz, 1H) 3.36-3.66 (m, 4H) 3.96 (dd, J=11.54, 2.15 Hz, 1H) 4.07 (d, J=12.91 Hz, 1H) 4.19 (d, J=12.52 Hz, 1H) 6.81 (d, J=5.09 Hz, 1H) 6.99 (br. s., 1H) 7.34 (d, J=8.61 Hz, 1H) 7.68 (d, J=1.57 Hz, 1H) 7.72 (dd, J=8.41, 2.15 Hz, 1H) 7.85 (dd, J=5.09, 1.17 Hz, 1H) 7.99 (s, 1H) 8.15 (d, J=5.48 Hz, 1H) 8.80 (d, J=5.09 Hz, 1H) 10.59 (s, 1H). LCMS (m/z) (M+H)=472.1, Rt=0.63 min.

Example 84

(R)-2-(2-cyanopropan-2-yl)-N-(4-methyl-3-(2-(2-((methylamino)methyl)morpholino)pyridin-4-yl)phenyl)isonicotinamide

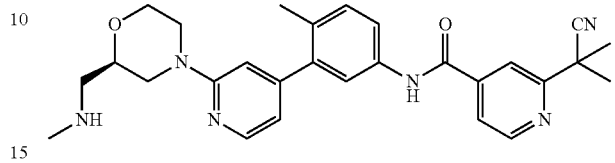

¹H NMR (400 MHz, <dmso>) δ ppm 1.75 (s, 7H) 2.22 (s, 3H) 2.58 (t, J=5.28 Hz, 3H) 2.62-2.73 (m, 2H) 2.87-2.99 (m, 1H) 3.00-3.22 (m, 2H) 3.76-3.87 (m, 2H) 4.01 (d, J=11.35 Hz, 1H) 4.11 (d, J=12.52 Hz, 1H) 4.26 (d, J=12.13 Hz, 1H) 6.72 (d, J=5.09 Hz, 1H) 6.81 (s, 1H) 7.33 (d, J=9.00 Hz, 1H) 7.61-7.72 (m, 2H) 7.84 (dd, J=5.09, 1.17 Hz, 1H) 7.98 (s, 1H) 8.19 (d, J=5.09 Hz, 1H) 8.80 (d, J=5.09 Hz, 1H) 10.57 (s, 1H). LCMS (m/z) (M+H)=485.3, Rt=0.60 min.

Example 85

(R)—N-(3-(2-(2-(acetamidomethyl)morpholino)pyridin-4-yl)-4-methylphenyl)-2-(2-cyanopropan-2-yl)isonicotinamide

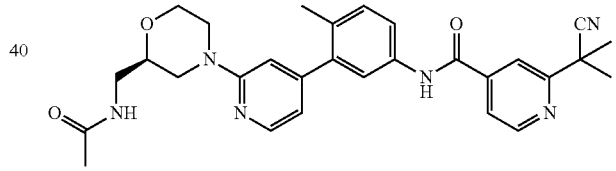

LCMS (m/z) (M+H)=513.2, Rt=0.64 min.

Example 86

(R)-methyl ((4-(2-methyl-5-(3-(trifluoromethyl)benzamido)-[3,4'-bipyridin]-2'-yl)morpholin-2-yl)methyl)carbamate

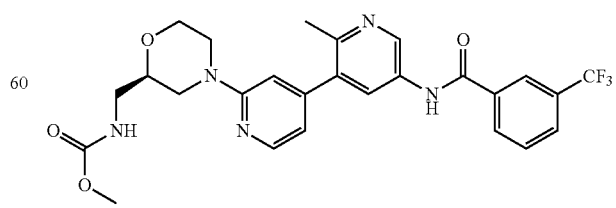

LCMS (m/z) (M+H)=530.2, Rt=0.65 min.

Example 87

(R)—N-(2'-(2-((2-hydroxyacetamido)methyl)morpholino)-2-methyl-[3,4'-bipyridin]-5-yl)-3-(trifluoromethyl)benzamide

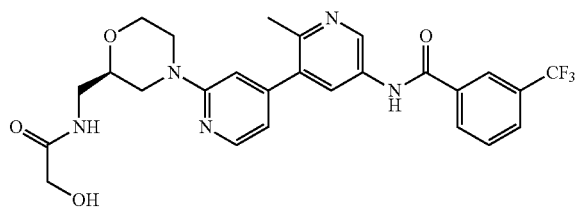 [SMILES: Cc1ncc(NC(=O)c2cccc(C(F)(F)F)c2)cc1-c1ccnc(N2CCO[C@H](CNC(=O)CO)C2)c1]

To a solution of (S)-2-hydroxy-N-(morpholin-2-ylmethyl)acetamide (1.0 equiv.) and N—(Z-fluoro-2-methyl-[3,4'-bipyridin]-5-yl)-3-(trifluoromethyl)benzamide (2.0 equiv.) in NMP (0.13 M) was added potassium carbonate (6.0 equiv.). The mixture was heated at 120° C. overnight. The reaction mixture was then filtered, and purified via reverse phase HPLC to yield (R)—N-(2'-(2-((2-hydroxyacetamido)methyl)morpholino)-2-methyl-[3,4'-bipyridin]-5-yl)-3-(trifluoromethyl)benzamide (5%, 99% purity by LC) as a white crystalline solid. LCMS (m/z) (M+H)=530.1, Rt=0.56 min.

Example 88

2-(2-cyanopropan-2-yl)-N-(2-methoxy-2'-morpholino-[3,4'-bipyridin]-5-yl)isonicotinamide

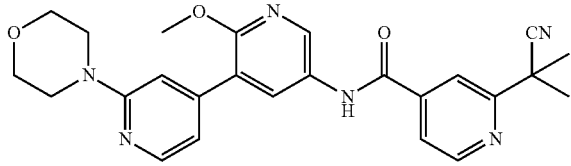 [SMILES: COc1ncc(NC(=O)c2ccnc(C(C)(C)C#N)c2)cc1-c1ccnc(N2CCOCC2)c1]

$^1$H NMR (400 MHz, <dmso>) δ ppm 1.75 (s, 6H) 3.53 (t, J=4.30 Hz, 4H) 3.67-3.76 (m, 4H) 3.90 (s, 3H) 6.98 (d, J=5.48 Hz, 1H) 7.15 (br. s., 1H) 7.88 (dd, J=4.89, 1.37 Hz, 1H) 8.02 (s, 1H) 8.11-8.23 (m, 2H) 8.58 (d, J=2.35 Hz, 1H) 8.82 (d, J=5.09 Hz, 1H) 10.73 (s, 1H). LCMS (m/z) (M+H)=459.2, Rt=0.69 min.

Example 89

2-(1,1-difluoroethyl)-N-(2'-morpholino-2-oxo-1,2-dihydro-[3,4'-bipyridin]-5-yl)isonicotinamide

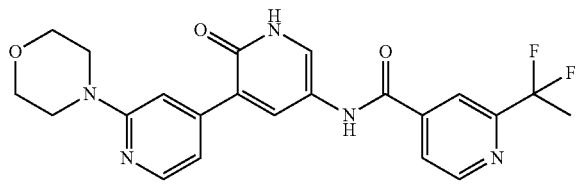

$^1$H NMR (400 MHz, <dmso>) δ ppm 1.94-2.12 (m, 3H) 3.54 (d, J=4.70 Hz, 4H) 3.68-3.79 (m, 4H) 7.19 (d, J=5.48 Hz, 1H) 7.56 (br. s., 1H) 8.00 (d, J=4.70 Hz, 1H) 8.04-8.15 (m, 3H) 8.17 (s, 1H) 8.88 (d, J=5.09 Hz, 1H) 10.54 (s, 1H). LCMS (m/z) (M+H)=442.2, Rt=0.60 min.

Example 90

N-(2'-morpholino-2-oxo-1,2-dihydro-[3,4'-bipyridin]-5-yl)-2-trifluoromethyl)isonicotinamide

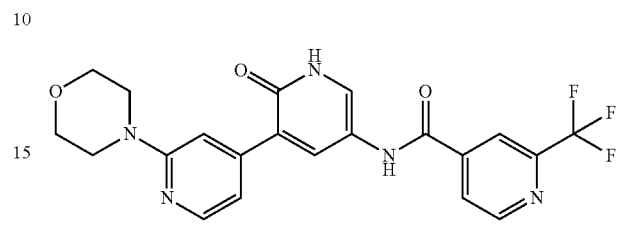

$^1$H NMR (400 MHz, <dmso>) δ ppm 3.53 (d, J=4.30 Hz, 4H) 3.68-3.77 (m, 4H) 7.17 (d, J=4.70 Hz, 1H) 7.52 (br. s., 1H) 8.00-8.14 (m, 3H) 8.17 (d, J=4.70 Hz, 1H) 8.34 (s, 1H) 9.00 (d, J=5.09 Hz, 1H) 10.59 (s, 1H). LCMS (m/z) (M+H)=446.2, Rt=0.61 min.

Example 91

2-(2-cyanopropan-2-yl)-N-(2'-morpholino-2-oxo-1,2-dihydro-[3,4'-bipyridin]-5-yl)isonicotinamide

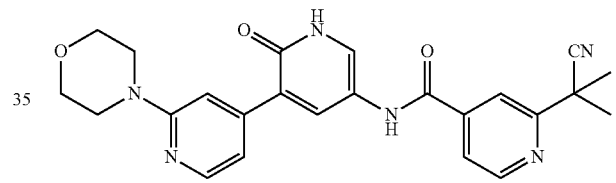

1H NMR (400 MHz, <dmso>) δ ppm 1.75 (s, 6H) 3.69-3.79 (m, 4H) 7.05-7.21 (m, 1H) 7.50 (br. s., 1H) 7.84 (dd, J=5.09, 1.57 Hz, 1H) 7.99 (s, 1H) 8.03 (br. s., 1H) 8.06-8.15 (m, 2H) 8.81 (d, J=5.09 Hz, 1H) 10.45 (s, 1H). LCMS (m/z) (M+H)=445.2, Rt=0.59 min.

Example 92

N-(3-(6-amino-4-morpholinopyridin-2-yl)-4-methylphenyl)-3-(trifluoromethyl)benzamide

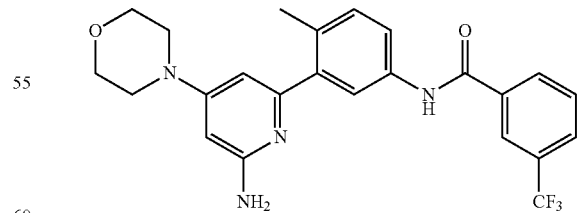

$^1$H NMR (400 MHz, <cd3od>) δ ppm 2.34 (s, 3H) 3.49-3.60 (m, 4H) 3.75-3.86 (m, 4H) 6.07 (d, J=2.35 Hz, 1H) 6.61 (d, J=2.35 Hz, 1H) 7.40 (d, J=8.61 Hz, 1H) 7.65 (dd, J=8.41, 2.15 Hz, 1H) 7.70-7.79 (m, 1H) 7.87-7.96 (m, 2H) 8.21 (d, J=7.83 Hz, 1H) 8.26 (s, 1H). LCMS (m/z) (M+H)=447.2, Rt=0.87 min.

Example 93

N-(3-(2-amino-6-morpholinopyridin-4-yl)-4-methylphenyl)-3-(trifluoromethyl)benzamide

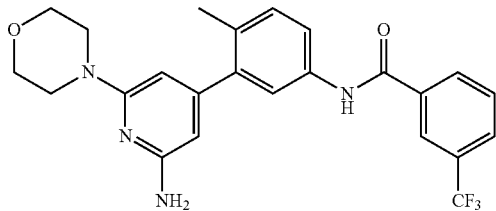

$^1$H NMR (400 MHz, <cd3od>) δ ppm 2.32 (s, 3H) 3.44-3.55 (m, 4H) 3.80-3.88 (m, 4H) 6.13-6.24 (m, 1H) 7.34 (d, J=8.22 Hz, 1H) 7.58 (dd, J=8.22, 2.35 Hz, 1H) 7.69-7.81 (m, 2H) 7.90 (d, J=7.83 Hz, 1H) 8.20 (d, J=7.83 Hz, 1H) 8.26 (s, 1H). LCMS (m/z) (M+H)=447.2, Rt=0.87 min.

Example 94

1-ethyl-N-(4-methyl-3-(2-morpholinopyridin-4-yl)phenyl)-6-oxo-5-(trifluoromethyl)-1,6-dihydropyridine-3-carboxamide

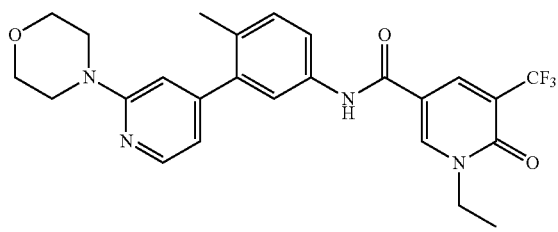 [SMILES: CCn1cc(C(=O)Nc2ccc(C)c(-c3ccnc(N4CCOCC4)c3)c2)cc(C(F)(F)F)c1=O]

1H NMR (400 MHz, <cd3od>) δ ppm 1.41 (t, J=7.24 Hz, 3H) 2.32 (s, 3H) 3.61-3.74 (m, 4H) 3.80-3.94 (m, 4H) 4.16 (q, J=7.04 Hz, 2H) 7.02 (d, J=5.87 Hz, 1H) 7.28 (s, 1H) 7.36 (d, J=8.61 Hz, 1H) 7.55 (dd, J=8.22, 1.96 Hz, 1H) 7.76 (d, J=1.96 Hz, 1H) 8.04 (d, J=6.26 Hz, 1H) 8.48 (s, 1H) 8.70 (d, J=2.74 Hz, 1H). LCMS (m/z) (M+H)=487.2, Rt=0.72 min.

Example 95

Synthesis of 2-(2-cyanopropan-2-yl)-N-(2-methyl-2'-morpholino-[3,4'-bipyridin]-5-yl)isonicotinamide

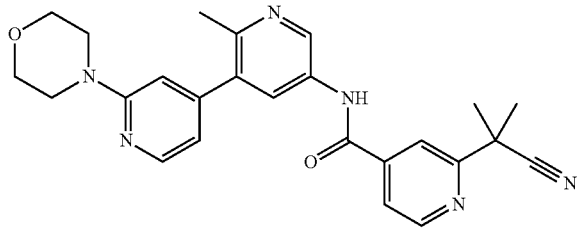 [SMILES: Cc1ncc(NC(=O)c2ccnc(C(C)(C)C#N)c2)cc1-c1ccnc(N2CCOCC2)c1]

To a 0.2 M solution of 2-methyl-2'-morpholino-[3,4'-bipyridin]-5-amine (1.0 equiv.) in DMF was added 2-(2-cyanopropan-2-yl)isonicotinic acid (1.0 equiv.), EDC·HCl (1.1 equiv.) and aza-HOBt (1.1 equiv.). The reaction was stirred at room temperature for 4 hours. The solution was filtered through a syringe filter and purified via reverse phase preparative HPLC. Upon lyophilization of the pure fractions, 2-(2-cyanopropan-2-yl)-N-(2-methyl-2'-morpholino-[3,4'-bipyridin]-5-yl)isonicotinamide was isolated as the TFA salt in 51% yield. $^1$H NMR (400 MHz, <dmso>) δ ppm 1.75 (s, 6H) 2.47 (br. s., 3H) 3.45-3.63 (m, 4H) 3.64-3.79 (m, 4H) 6.84 (d, J=5.09 Hz, 1H) 7.03 (br. s., 1H) 7.87 (dd, J=5.09, 1.17 Hz, 1H) 8.02 (s, 1H) 8.14 (d, J=2.35 Hz, 1H) 8.20 (d, J=5.48 Hz, 1H) 8.83 (d, J=5.09 Hz, 1H) 8.92 (d, J=2.35 Hz, 1H) 10.90 (s, 1H); LCMS (m/z) (M+H)=443.2, Rt=0.50 min.

Synthesis of 3-bromo-4-(bromomethyl)benzoic acid

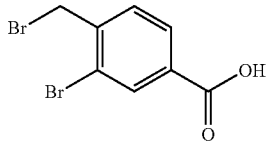 [SMILES: O=C(O)c1ccc(CBr)c(Br)c1]

To a solution of 3-bromo-4-methylbenzoic acid (1.0 equiv.) and AIBN (0.05 equiv.) in trifluorotoluene (0.28 M) was added NBS (1.1 equiv.). The mixture was heated at 90° C. overnight. The reaction mixture was partitioned between EtOAc and H$_2$O. The organic layer was washed with NaCl (sat.), dried over MgSO$_4$, filtered, concentrated to yield 3-bromo-4-(bromomethyl)benzoic acid in 60% yield. LC/MS (m/z)=294.8 (MH$^+$), Rt=0.80 min.

Synthesis of 3-bromo-4-(hydroxymethyl)benzoic acid

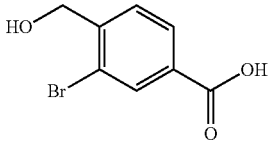 [SMILES: O=C(O)c1ccc(CO)c(Br)c1]

To a solution of yield 3-bromo-4-(bromomethyl)benzoic acid (1.0 equiv.) in Water (0.56 M) at 95° C. was added potassium carbonate K$_2$CO$_3$ (5.0 equiv.). The homogenous reaction mixture was stirred at 95° C. in an oil bath for 1 hr. The reaction mixture was COOLED OFF TO RT, neutralized with 6 M HCl. diluted with EtOAc and washed with brine. The organic layer was dried over Na$_2$SO$_4$, filtered and concentrated. The crude was used in next step. LC/MS (m/z)=294.8 (MH$^+$), Rt=0.80 min.

Synthesis of 3-bromo-4-(hydroxymethyl)-N-(3-(trifluoromethyl)phenyl)benzamide

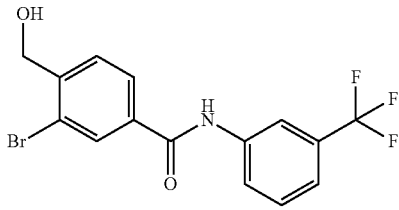 [SMILES: O=C(Nc1cccc(C(F)(F)F)c1)c1ccc(CO)c(Br)c1]

EDC (1.3 equiv.) was added to a solution of 3-bromo-4-(hydroxymethyl)benzoic acid (1.0 equiv), 3-(trifluoromethyl)aniline (1.1 equiv.), HOAt (1.3 equiv.) in DMF (0.43 M). The mixture was stirred at ambient temperature 3 hrs. The reaction mixture was diluted with water and extracted with ethyl acetate. The combined extracts were washed sequentially with 1M aqueous sodium hydroxide and brine, dried over sodium sulfate, filtered, and concentrated. The residue was purified by ISCO(50% EtOAc/Heptane) to yield 3-bromo-4-(hydroxymethyl)-N-(3-(trifluoromethyl)phenyl)benzamide in 35% yield. LC/MS (m/z)=374.0 (MH$^+$), Rt=0.93 min.

The compounds listed below were prepared using methods similar to those described for the preparation of Example 95 using the appropriate starting materials.

Example 96

N-(2-methyl-2'-morpholino-[3,4'-bipyridin]-5-yl)-3-trifluoromethyl)benzamide

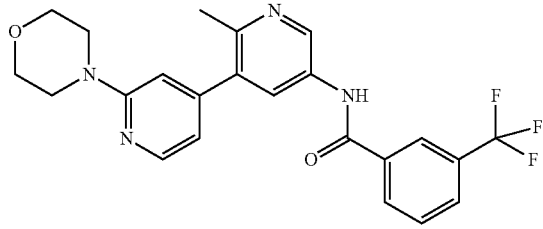 [SMILES: Cc1ncc(NC(=O)c2cccc(C(F)(F)F)c2)cc1-c1ccnc(N2CCOCC2)c1]

$^1$H NMR (400 MHz, <dmso>) δ ppm 2.47 (br. s., 3H) 3.49-3.59 (m, 4H) 3.67-3.75 (m, 4H) 6.85 (d, J=4.65 Hz, 1H) 7.03 (s, 1H) 7.81 (t, J=7.83 Hz, 1H) 8.00 (d, J=7.87 Hz, 1H) 8.18 (d, J=2.40 Hz, 1H) 8.21 (d, J=5.67 Hz, 1H) 8.27 (d, J=7.92 Hz, 1H) 8.32 (s, 1H) 8.96 (d, J=2.40 Hz, 1H) 10.82 (s, 1H). LCMS (m/z) (M+H)=443.3, Rt=0.61 min.

Example 97

4-methoxy-N-(2-methyl-2'-morpholino-[3,4'-bipyridin]-5-yl)-3-(trifluoromethyl)benzamide

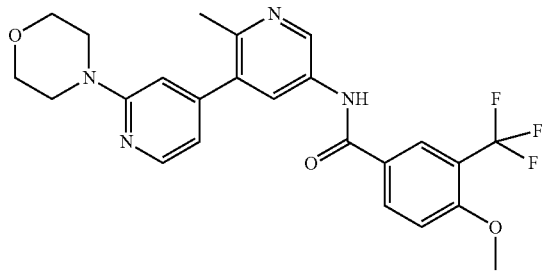 [SMILES: COc1ccc(C(=O)Nc2cnc(C)c(-c3ccnc(N4CCOCC4)c3)c2)cc1C(F)(F)F]

$^1$H NMR (400 MHz, <cd3od>) δ ppm 2.60 (s, 3H) 3.63-3.73 (m, 4H) 3.81-3.91 (m, 4H) 4.01 (s, 3H) 6.98-7.06 (m, 1H) 7.29 (s, 1H) 7.36 (d, J=8.22 Hz, 1H) 8.14 (d, J=5.87 Hz, 1H) 8.22-8.33 (m, 2H) 8.42 (d, J=2.35 Hz, 1H) 9.04 (d, J=2.35 Hz, 1H). LCMS (m/z) (M+H)=473.3, Rt=0.59 min.

Example 98

4-fluoro-3-methoxy-N-(2-methyl-2'-morpholino-[3,4'-bipyridin]-5-yl)benzamide

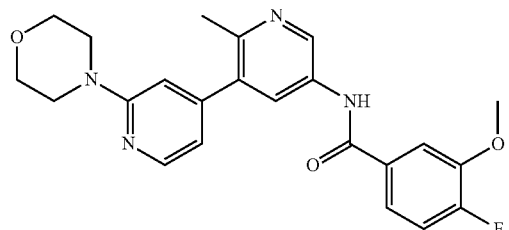

$^1$H NMR (400 MHz, <cd3od>) δ ppm 2.59 (s, 3H) 3.62-3.73 (m, 4H) 3.81-3.91 (m, 4H) 3.97 (s, 3H) 7.01 (dd, J=6.06, 0.98 Hz, 1H) 7.20-7.33 (m, 2H) 7.60 (ddd, J=8.41, 4.11, 2.35 Hz, 1H) 7.73 (dd, J=8.02, 2.15 Hz, 1H) 8.14 (d, J=6.26 Hz, 1H) 8.39 (d, J=2.35 Hz, 1H) 9.02 (d, J=2.35 Hz, 1H). LCMS (m/z) (M+H)=423.3, Rt=0.51 min.

Example 99

3-(difluoromethyl)-N-(2-methyl-2'-morpholino-[3,4'-bipyridin]-5-yl)benzamide

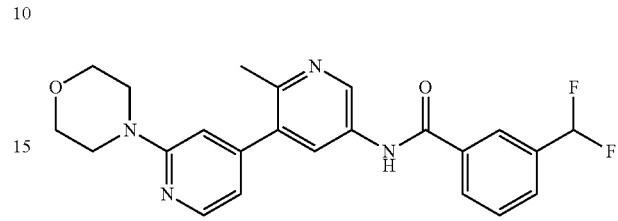

1H NMR (400 MHz, <cd3od>) δ ppm 2.59 (s, 3H) 3.65-3.70 (m, 4H) 3.84-3.89 (m, 4H) 6.75 (s, 1H) 6.89 (s, 1H) 7.01 (s, 1H) 7.03 (d, J=3.13 Hz, 1H) 7.27 (s, 1H) 7.66-7.72 (m, 1H) 7.81 (d, J=7.83 Hz, 1H) 8.11-8.16 (m, 2H) 8.19 (s, 1H) 8.41 (d, J=2.35 Hz, 1H) 9.01 (d, J=2.35 Hz, 1H). LCMS (m/z) (M+H)=425.1, Rt=0.56 min.

Example 100

2-(1,1-difluoroethyl)-N-(2-methyl-2'-morpholino-[3,4'-bipyridin]-5-yl)isonicotinamide

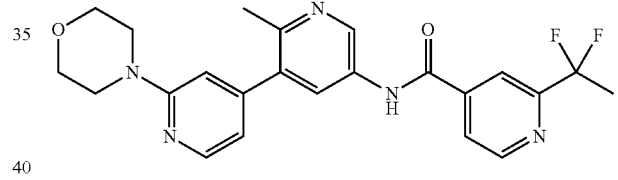

1H NMR (400 MHz, <cd3od>) δ ppm 2.05 (t, J=18.78 Hz, 3H) 2.59 (s, 3H) 3.67-3.73 (m, 4H) 3.84-3.91 (m, 4H) 7.05 (dd, J=6.26, 1.17 Hz, 1H) 7.34 (s, 1H) 8.00 (d, J=3.91 Hz, 1H) 8.13 (d, J=6.26 Hz, 1H) 8.23 (s, 1H) 8.41 (d, J=2.35 Hz, 1H) 8.85 (d, J=5.09 Hz, 1H) 8.98 (d, J=2.35 Hz, 1H). LCMS (m/z) (M+H)=440.1, Rt=0.51 min.

Example 101

3-(1,1-difluoroethyl)-N-(2-methyl-2'-morpholino-[3,4'-bipyridin]-5-yl)benzamide

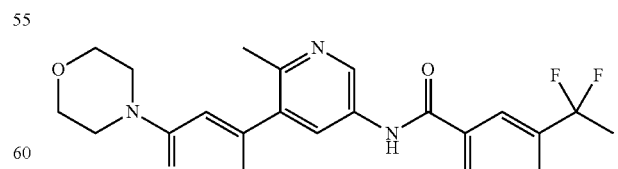

$^1$H NMR (400 MHz, <cd3od>) δ ppm 1.99 (t, J=18.39 Hz, 3H) 2.60 (s, 3H) 3.66-3.71 (m, 4H) 3.84-3.89 (m, 4H) 7.03 (dd, J=6.26, 1.17 Hz, 1H) 7.30 (s, 1H) 7.63-7.69 (m, 1H) 7.81 (d, J=7.43 Hz, 1H) 8.09 (d, J=7.83 Hz, 1H) 8.15 (d, J=6.26

Hz, 1H) 8.18 (s, 1H) 8.44 (d, J=2.35 Hz, 1H) 9.05 (d, J=2.35 Hz, 1H). LCMS (m/z) (M+H)=439.1, Rt=0.59 min.

Example 102

N-(2-methyl-2'-morpholino-[3,4'-bipyridin]-5-yl)-2-(methylsulfonyl)isonicotinamide

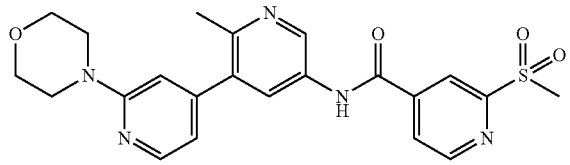

1H NMR (400 MHz, <dmso>) δ ppm 3.27-3.42 (m, 3H) 3.48-3.64 (m, 4H) 3.67-3.84 (m, 4H) 6.90 (d, J=5.09 Hz, 1H) 7.12 (s, 1H) 8.10-8.34 (m, 3H) 8.57 (s, 1H) 8.99 (d, J=2.35 Hz, 1H) 9.04 (d, J=5.09 Hz, 1H) 11.19 (s, 1H), LCMS (m/z) (M+H)=454.2, Rt=0.40 min.

Example 103

N-(2-methyl-2'-morpholino-[3,4'-bipyridin]-5-yl)-3-(methylsulfonyl)benzamide

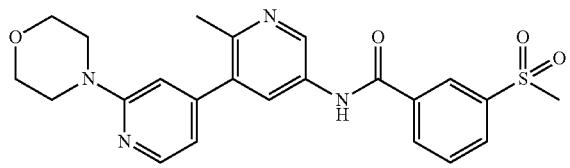 [SMILES: Cc1ncc(NC(=O)c2cccc(S(C)(=O)=O)c2)cc1-c1ccnc(N2CCOCC2)c1]

1H NMR (400 MHz, <dmso>) δ ppm 2.53 (s, 3H) 3.45-3.63 (m, 4H) 3.66-3.82 (m, 4H) 5.67 (br. s., 1H) 6.81-6.96 (m, 1H) 7.14 (s, 1H) 7.87 (t, J=7.83 Hz, 1H) 8.13-8.26 (m, 2H) 8.27-8.37 (m, 2H) 8.53 (s, 1H) 9.00-9.13 (m, 1H) 10.96-11.11 (m, 1H), LCMS (m/z) (M+H)=453.2, Rt=0.43 min.

Example 104

2-(tert-butyl)-N-(2-methyl-2'-morpholino-[3,4'-bipyridin]-5-yl)isonicotinamide

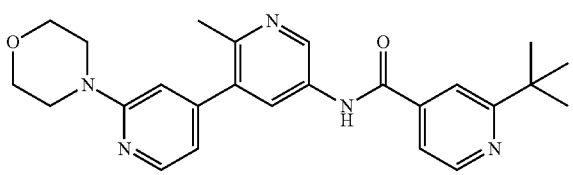 [SMILES: Cc1ncc(NC(=O)c2ccnc(C(C)(C)C)c2)cc1-c1ccnc(N2CCOCC2)c1]

1H NMR (400 MHz, <dmso>) δ ppm 1.38 (s, 9H) 2.51-2.54 (m, 3H) 3.52-3.63 (m, 4H) 3.68-3.79 (m, 4H) 6.85-6.97 (m, 1H) 7.10-7.17 (m, 1H) 7.74 (dd, J=5.09, 1.57 Hz, 1H) 7.87-7.95 (m, 1H) 8.23 (d, J=5.48 Hz, 1H) 8.25-8.30 (m, 1H) 8.77 (d, J=5.09 Hz, 1H) 9.00-9.06 (m, 1H) 10.98 (s, 1H), LCMS (m/z) (M+H)=432.3, Rt=0.46 min.

Example 106

2-(2-cyanopropan-2-yl)-N-(4-methyl-3-(2-morpholino-6-(tetrahydro-2H-pyran-4-yl)pyridin-4-yl)phenyl)isonicotinamide

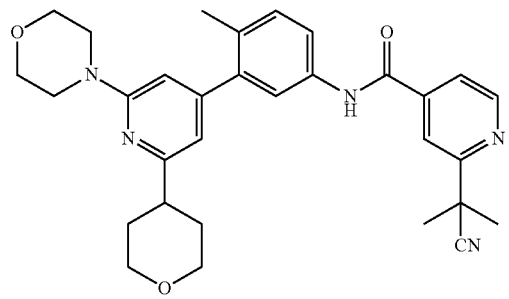 [SMILES: Cc1ccc(NC(=O)c2ccnc(C(C)(C)C#N)c2)cc1-c1cc(C2CCOCC2)nc(N2CCOCC2)c1]

¹H NMR (400 MHz, <cd3od>) δ ppm 1.81 (s, 6H) 1.85-2.01 (m, 4H) 2.31 (s, 3H) 3.02-3.17 (m, 1H) 3.48-3.61 (m, 2H) 3.65-3.76 (m, 3H) 3.80-3.92 (m, 4H) 4.01-4.14 (m, 2H) 6.87 (s, 1H) 7.02 (s, 1H) 7.37 (d, J=8.22 Hz, 1H) 7.61 (dd, J=8.22, 1.96 Hz, 1H) 7.73-7.86 (m, 2H) 8.06 (s, 1H) 8.76 (d, J=5.09 Hz, 1H). LCMS (m/z) (M+H)=526.3, Rt=0.76 min.

Example 107

N-(4-methyl-3-(2-morpholino-6-(tetrahydro-2H-pyran-4-yl)pyridin-4-yl)phenyl)-3-(trifluoromethyl)benzamide

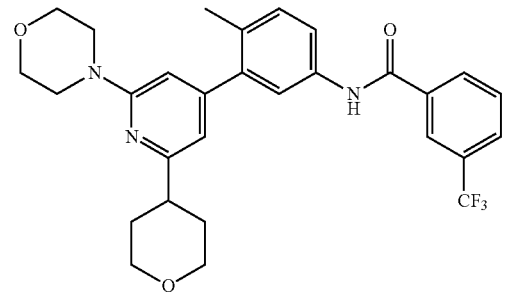 [SMILES: Cc1ccc(NC(=O)c2cccc(C(F)(F)F)c2)cc1-c1cc(C2CCOCC2)nc(N2CCOCC2)c1]

¹H NMR (400 MHz, <cd3od>) δ ppm 1.81-2.02 (m, 4H) 2.31 (s, 3H) 3.05-3.18 (m, 1H) 3.45-3.62 (m, 2H) 3.66-3.75 (m, 4H) 3.81-3.91 (m, 4H) 4.03-4.15 (m, 2H) 6.89 (s, 1H) 7.06 (s, 1H) 7.36 (d, J=8.22 Hz, 1H) 7.60 (dd, J=8.22, 2.35 Hz, 1H) 7.69-7.83 (m, 2H) 7.90 (d, J=7.83 Hz, 1H) 8.20 (d, J=7.83 Hz, 1H) 8.26 (s, 1H). LCMS (m/z) (M+H)=526.2, Rt=0.86 min.

Example 108

4-(hydroxymethyl)-3-(2-morpholinopyridin-4-yl)-N-(3-(trifluoromethyl)phenyl)benzamide

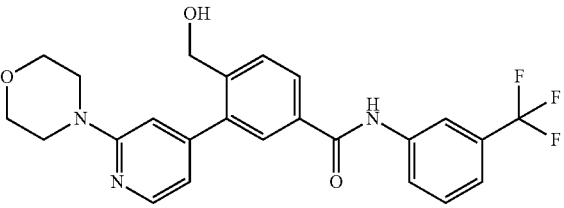 [SMILES: O=C(Nc1cccc(C(F)(F)F)c1)c1ccc(CO)c(-c2ccnc(N3CCOCC3)c2)c1]

The method used to prepare example X was followed using 3-bromo-4-(hydroxymethyl)-N-(3-(trifluoromethyl)phenyl)benzamide and 4-(4-(4,4,5,5-tetramethyl-1,3,2-dioxaborolan-2-yl)pyridin-2-yl)morpholine to afford 4-(hydroxymethyl)-3-(2-morpholinopyridin-4-yl)-N-(3-(trifluoromethyl)phenyl)benzamide in a 91% yield. $^1$H NMR (400 MHz, <cd3od>) δ ppm 3.61-3.73 (m, 4H), 3.83-3.90 (m, 4H), 4.63 (s, 2H), 7.09-7.15 (m, 1H), 7.39-7.47 (m, 2H), 7.53-7.60 (m, 1H), 7.75-7.82 (m, 1H), 7.91-7.99 (m, 2H), 8.04-8.13 (m, 2H), 8.14-8.19 (m, 1H). LC/MS (m/z)=458.1 (MH$^+$), R$_t$=0.73 min.

4-formyl-3-(2-morpholinopyridin-4-yl)-N-(3-(trifluoromethyl)phenyl)benzamide

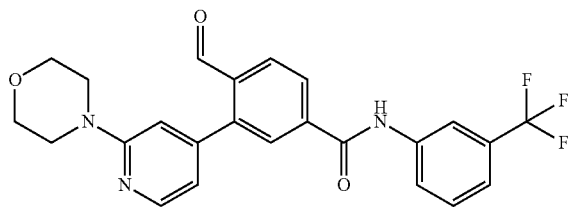 [SMILES: O=Cc1ccc(C(=O)Nc2cccc(C(F)(F)F)c2)cc1-c1ccnc(N2CCOCC2)c1]

MnO$_2$ (8.0 equiv.) was added into a solution of 4-(hydroxymethyl)-3-(2-morpholinopyridin-4-yl)-N-(3-(trifluoromethyl)phenyl)benzamide (1.0 equiv.) in DCM (0.05 M). The suspension was stirred at rt for 1 hr. The mixture was filtered over celite and concentrated to yield 4-formyl-3-(2-morpholinopyridin-4-yl)-N-(3-(trifluoromethyl)phenyl)benzamide in 100% yield. LC/MS (m/z)=456.1 (MH$^+$), R$_t$=0.76 min.

Example 109

4-(difluoromethyl)-3-(2-morpholinopyridin-4-yl)-N-(3-(trifluoromethyl)phenyl)benzamide

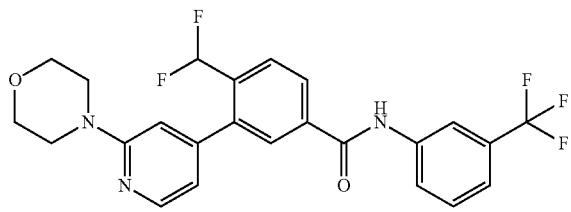 [SMILES: O=C(Nc1cccc(C(F)(F)F)c1)c1ccc(C(F)F)c(-c2ccnc(N3CCOCC3)c2)c1]

To a cooled solution of 4-formyl-3-(2-morpholinopyridin-4-yl)-N-(3-(trifluoromethyl)phenyl)benzamide (1.0 equiv.) in dry CH$_2$Cl$_2$ (0.05 M), (diethylamino)sulfur trifluoride (3.5 equiv.) was added under vigorous stirring. The resulting reaction mixture was stirred at 0° C. for 2 hrs. Quenched the reaction with sat NaHCO$_3$ and extracted with DCM. The organic layer was washed with Brine, filtered over Na$_2$SO$_4$ and concentrated. The crude was purified by prep HPLC to yield 4-(difluoromethyl)-3-(2-morpholinopyridin-4-yl)-N-(3-(trifluoromethyl)phenyl)benzamide in 12% yield. $^1$H NMR (400 MHz, <cd3od>) δ ppm 2.65 (s, 1H), 3.63-3.73 (m, 4H), 3.80-3.90 (m, 4H), 6.70-7.05 (m, 2H), 7.27 (s, 1H), 7.43-7.49 (m, 1H), 7.53-7.61 (m, 1H), 7.91-7.99 (m, 2H), 8.01-8.05 (m, 1H), 8.08-8.14 (m, 2H), 8.15-8.23 (m, 2H). LC/MS (m/z)=478.1 (MH$^+$), R$_t$=0.85 min.

Example 110

Synthesis of 4-(fluoromethyl)-3-(2-morpholinopyridin-4-yl)-N-(3-(trifluoromethyl)phenyl)benzamide

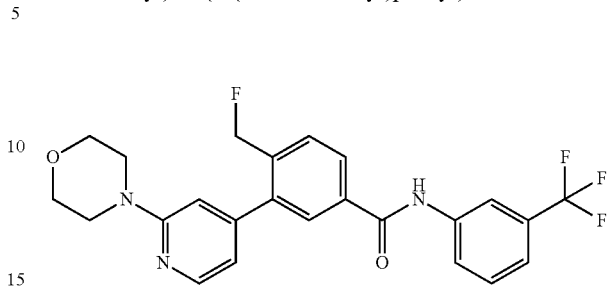

To a cooled solution of 4-(difluoromethyl)-3-(2-morpholinopyridin-4-yl)-N-(3-(trifluoromethyl)phenyl)benzamide (1.0 equiv.) in dry CH$_2$Cl$_2$ (0.05 M), (diethylamino)sulfur trifluoride (3.5 equiv.) was added portionwise under vigorous stirring. The resulting reaction mixture was stirred at −78° C. for 3 hrs, Quenched the reaction with sat NaHCO$_3$ and extracted with DCM. The organic layer was washed with Brine, filtered over Na$_2$SO$_4$ and concentrated. The residue was purified by PREP HPLC to yield 4-(fluoromethyl)-3-(2-morpholinopyridin-4-yl)-N-(3-(trifluoromethyl)phenyl)benzamide in 16% yield. $^1$H NMR (400 MHz, <cd3od>) δ ppm 3.68 (d, J=5.09 Hz, 4H), 3.86 (d, J=5.09 Hz, 4H), 5.40 (s, 1H), 5.52 (s, 1H), 7.01-7.11 (m, 1H), 7.24-7.31 (m, 1H), 7.41-7.48 (m, 1H), 7.52-7.60 (m, 1H), 7.77-7.83 (m, 1H), 7.91-7.98 (m, 1H), 7.99-8.04 (m, 1H), 8.07-8.19 (m, 3H). LC/MS (m/z)=460.1 (MH$^+$), R=0.85 min.

Synthesis of 4-(2-chloropyridin-4-yl)morpholine

To a solution of triethylamine (1.0 equiv.) and 2,4-dichloropyridine (1.0 equiv.) at RT was added morpholine (1.0 equiv) in one portion, the resulting mixture was then stirred at RT for 45 hr. LCMS analysis indicated the formation of the desired product (M+H=199, Rt=0.29 min, major) and the undesired isomer (M+H=199, Rt=0.33 min, minor). The reaction mixture was concentrated in vacuo and purified via ISCO to yield 4-(2-chloropyridin-4-yl)morpholine as a light brown solid (28%). LCMS (m/z) (M+H)=299.0, Rt=0.29 min. 1H NMR (400 MHz, <cdcl3>) δ ppm 3.18-3.37 (m, 4H) 3.72-3.91 (m, 4H) 6.51-6.61 (m, 1H) 6.61-6.69 (m, 1H) 8.05 (d, J=6.26 Hz, 1H)

Example 111

N-(4-methyl-3-(4-morpholinopyridin-2-yl)phenyl)-3-(trifluoromethyl)benzamide

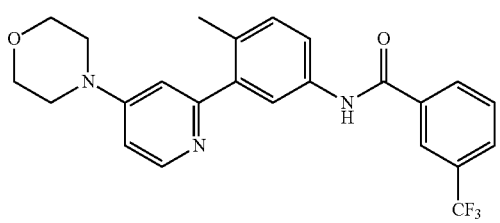 [SMILES: Cc1ccc(NC(=O)c2cccc(C(F)(F)F)c2)cc1-c1cc(N2CCOCC2)ccn1]

To a solution of 4-(2-chloropyridin-4-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(4-morpholinopyridin-2-yl)phenyl)-3-(trifluoromethyl)benzamide was isolated as the TFA salt in 16% yield. $^1$H NMR (400 MHz, <dmso>) δ ppm 2.17-2.30 (m, 3H) 7.17-7.29 (m, 2H) 7.44 (d, J=8.22 Hz, 1H) 7.74-7.86 (m, 2H) 7.93 (d, J=1.96 Hz, 1H) 7.99 (d, J=7.83 Hz, 1H) 8.17-8.41 (m, 3H) 10.68 (s, 1H) 13.74 (br. s., 1H). LCMS (m/z) (M+H)=442.3, Rt=0.73 min.

Synthesis of
4,4'-(4-bromopyridine-2,6-diyl)dimorpholine

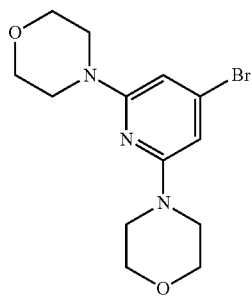 [SMILES: Brc1cc(N2CCOCC2)nc(N2CCOCC2)c1]

To a solution of Morpholine (5.0 equiv.) and 4-bromo-2,6-dichloropyridine (1.0 equiv.) in DMF (0.275 M) was added cesium carbonate (2.0 equiv.). The mixture was heated at 100° C. for 45 hours. LCMS analysis indicated formation of several products including the desired (M+H=288, Rt=0.87 min). The reaction mixture was then concentrated in vacuo to yield a glassy foam. Water was then added, and the mixture was extracted with ethyl acetate, and the combined extracts were washed with brine, dried over magnesium sulfate, filtered, and concentrated. The residue was chromatographed via ISCO to provide 4,4'-(4-bromopyridine-2,6-diyl)dimorpholine (44%, 80% purity by LC) as a white crystalline solid. LCMS (m/z) (M+H)=288.0, Rt=0.87 min

Example 112

3-(2,6-dimorpholinopyridin-4-yl)-4-methyl-N-(3-(trifluoromethyl)phenyl)benzamide

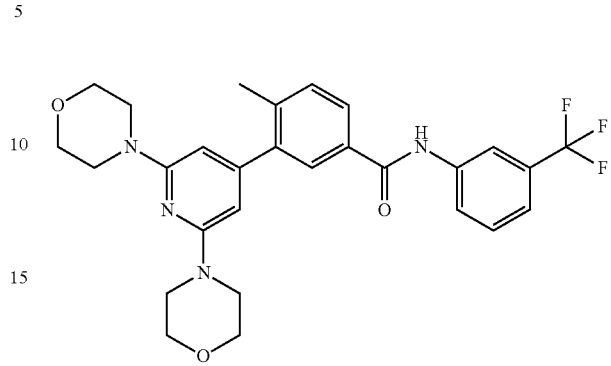

To a solution of 4-bromo-2,6-dichloropyridine (1.0 equiv.) and Intermediate D (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, 3-(2,6-dimorpholinopyridin-4-yl)-4-methyl-N-(3-(trifluoromethyl)phenyl)benzamide was isolated as the TFA salt in 8% yield. LCMS (m/z) (M+H)=527.3, Rt=1.07 min. 1H NMR (400 MHz, <dmso>) δ ppm 1.27 (s, 2H) 2.31 (s, 3H) 3.53-3.71 (m, 16H) 6.08 (s, 2H) 7.30-7.72 (m, 6H) 7.80-7.98 (m, 2H) 8.22 (s, 2H) 10.44 (s, 1H).

Synthesis of
4-(6-chloro-4-iodopyridin-2-yl)morpholine

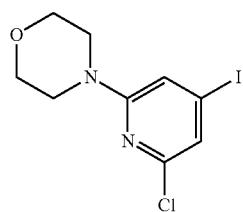 [SMILES: Clc1cc(I)cc(N2CCOCC2)n1]

To a solution of triethylamine (1.0 equiv.) and 2,6-dichloro-4-iodopyridine (1.0 equiv.) at RT was added morpholine (1.0 equiv) in one portion, the resulting mixture was then heated in an oil bath at 100° C. for 18 hours. LCMS analysis indicated the formation of the desired product (M+H=324.9/326.8, Rt=0.98 min). Water was then added, and the mixture was extracted with ethyl acetate, and the combined extracts were washed with brine, dried over magnesium sulfate, filtered, and concentrated. The residue was chromatographed via ISCO to yield 4-(6-chloro-4-iodopyridin-2-yl)morpholine as a light brown solid (63%). LCMS (m/z) (M+H)=324.9/326.8, Rt=0.98 min.

Synthesis of N-(3-(2-chloro-6-morpholinopyridin-4-yl)-4-methylphenyl)-3-(trifluoromethyl)benzamide

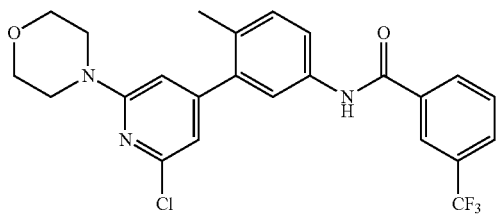

To a solution of 4-(6-chloro-4-iodopyridin-2-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a vial equipped with a stir bar. The reaction was heated to 80° C. for 18 hours. The reaction was quenched with water and extracted with ethyl acetate. The combined organic phase was dried with sodium sulfate, filtered and concentrated. The residue was chromatographed via ISCO to yield N-(3-(2-chloro-6-morpholinopyridin-4-yl)-4-methylphenyl)-3-(trifluoromethyl)benzamide as a light brown solid (>100%, 90% purity by UV). LCMS (m/z) (M+H)=476.0, Rt=1.16 min.

Example 113

N-(4-methyl-3-(2-(1-methyl-1H-pyrazol-4-yl)-6-morpholinopyridin-4-yl)phenyl)-3-(trifluoromethyl) benzamide

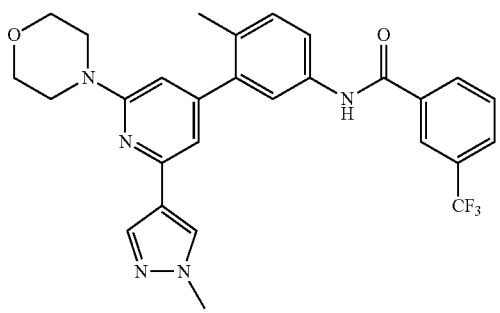 [SMILES: Cc1ccc(NC(=O)c2cccc(C(F)(F)F)c2)cc1-c1cc(-c2cnn(C)c2)nc(N2CCOCC2)c1]

To a solution of N-(3-(2-chloro-6-morpholinopyridin-4-yl)-4-methylphenyl)-3-(trifluoromethyl)benzamide (1.0 equiv.), 1-methyl-4-pyrazole-1H-boronic acid pinacol ester (2.0 equiv.), potassium fluoride (3.0 equiv.), and P(t-Bu)$_3$ (0.1 equiv./1.0 M in PhMe) in THF and water (1:1, 0.12 M) was added Pd$_2$(dba)$_3$ (0.1 equiv.) in a nitrogen purged microwave vial equipped with a stir bar. The reaction was heated to 80° C. for 2 hours. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(2-(1-methyl-1H-pyrazol-4-yl)-6-morpholinopyridin-4-yl)phenyl)-3-(trifluoromethyl)benzamide was isolated as the TFA salt in 6% yield. 1H NMR (400 MHz, <cd3od>) δ ppm 2.33 (s, 3H) 3.64-3.69 (m, 4H) 3.82-3.88 (m, 4H) 3.96 (s, 3H) 6.79 (s, 1H) 7.08 (s, 1H) 7.35 (d, J=8.61 Hz, 1H) 7.62 (dd, J=8.41, 2.15 Hz, 1H) 7.70-7.77 (m, 2H) 7.90 (d, J=7.83 Hz, 1H) 8.04 (s, 1H) 8.18-8.24 (m, 2H) 8.26 (s, 1H). LCMS (m/z) (M+H)=522.1, Rt=0.89 min.

Synthesis of 3-(2-(3,6-dihydro-2H-pyran-4-yl)-6-morpholinopyridin-4-yl)-4-methylaniline

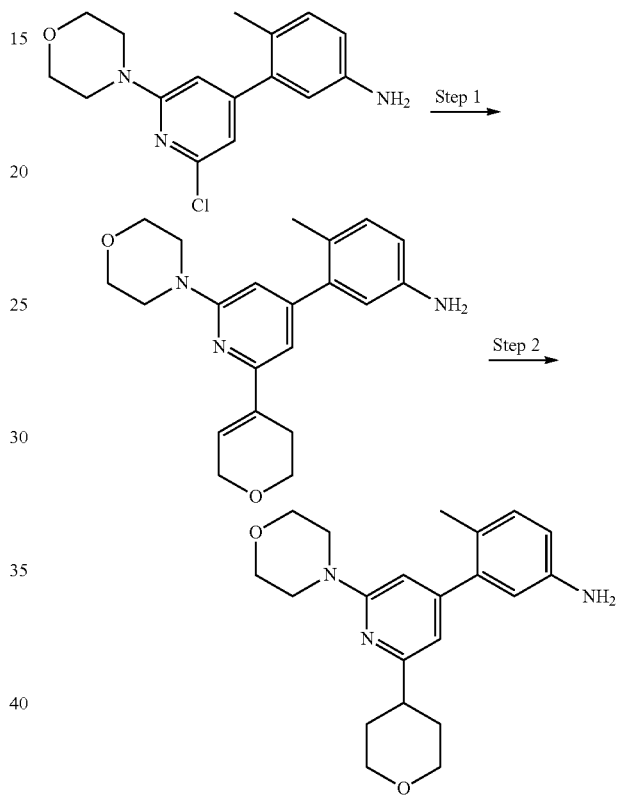

Step 1: To a solution of 3-(2-chloro-6-morpholinopyridin-4-yl)-4-methylaniline (1.0 equiv.) and 2-(3,6-dihydro-2H-pyran-4-yl)-4,4,5,5-tetramethyl-1,3,2-dioxaborolane (1.2 equiv.) in DME and 2M sodium carbonate (3:1, 0.1 M) was added PdCl2(dppf)-DCM adduct (0.1 equiv.). The solution was heated to 100 C for 5 hours. Upon cooling to room temperature, the solution was partitioned between water and ethyl acetate, the organic phase was dried with sodium sulfate, filtered and concentrated. The crude material was purified via silica gel column chromatography eluting with 0-50% ethyl acetate and heptanes). The pure fractions were concentrated to yield 3-(2-(3,6-dihydro-2H-pyran-4-yl)-6-morpholinopyridin-4-yl)-4-methylaniline in 69% yield. LCMS (m/z) (M+H)=352.3, Rt=0.50 min.

Step 2: To a solution of 3-(2-(3,6-dihydro-2H-pyran-4-yl)-6-morpholinopyridin-4-yl)-4-methylaniline (1.0 equiv.) in degassed ethanol (0.09 M) was added Pd/C (0.1 equiv.) and the solution was stirred under a hydrogen balloon for 1 h. Upon completion, the solution was filtered through Celite, and the filtrate was concentrated to dryness to give 4-methyl-3-(2-morpholino-6-(tetrahydro-2H-pyran-4-yl)pyridin-4-yl) aniline as desired product in 87% yield. LCMS (m/z) (M+H)=354.3, Rt=0.42 min.

Example 114

3-(2-cyanopropan-2-yl)-N-(4-methyl-3-(2-morpholino-6-(tetrahydro-2H-pyran-4-yl)pyridin-4-yl)phenyl)benzamide

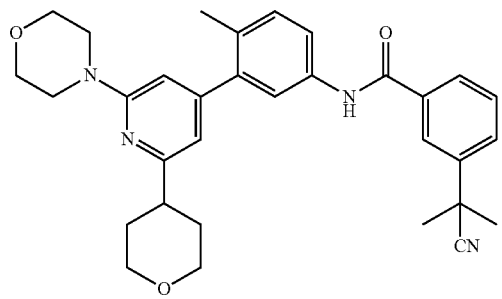 [SMILES: Cc1ccc(NC(=O)c2cccc(C(C)(C)C#N)c2)cc1-c1cc(C2CCOCC2)nc(N2CCOCC2)c1]

1H NMR (400 MHz, <cd3od>) δ ppm 1.79 (s, 6H) 1.85-1.96 (m, 4H) 2.31 (s, 3H) 3.05-3.17 (m, 1H) 3.48-3.62 (m, 2H) 3.66-3.76 (m, 4H) 3.82-3.92 (m, 4H) 4.07 (d, J=11.35 Hz, 2H) 6.89 (s, 1H) 7.06 (s, 1H) 7.36 (d, J=8.22 Hz, 1H) 7.54-7.64 (m, 2H) 7.77 (d, J=5.09 Hz, 2H) 7.91 (d, J=7.83 Hz, 1H) 8.09 (s, 1H). LCMS (m/z) (M+H)=525.3, Rt=0.82 min.

Synthesis of N-(3-(2,6-difluoropyridin-4-yl)-4-methylphenyl)-3-(trifluoromethyl)benzamide

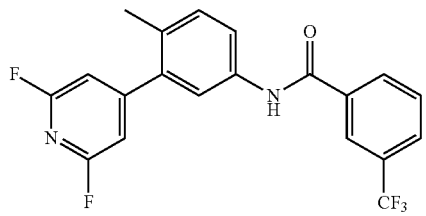 [SMILES: Cc1ccc(NC(=O)c2cccc(C(F)(F)F)c2)cc1-c1cc(F)nc(F)c1]

To a solution of (2,6-difluoropyridin-4-yl)boronic acid (1.5 equiv.) and Intermediate X (1.0 equiv.) in DME and 2M sodium carbonate (3:1, 0.2 M) was added PdCl₂(dppf)-DCM adduct (0.1 equiv.) in a vial equipped with a stir bar. The reaction was heated to 80° C. for 18 hours. The reaction was quenched with water and extracted with ethyl acetate. The combined organic phase was dried with sodium sulfate, filtered and concentrated. The residue was chromatographed via ISCO to yield N-(3-(2,6-difluoropyridin-4-yl)-4-methylphenyl)-3-(trifluoromethyl)benzamide as a light brown solid (37%). LCMS (m/z) (M+H)=393.0, Rt=1.09 min.

Synthesis of N-(3-(2-fluoro-6-morpholinopyridin-4-yl)-4-methylphenyl)-3-(trifluoromethyl)benzamide

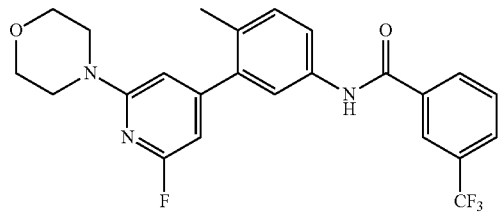 [SMILES: Cc1ccc(NC(=O)c2cccc(C(F)(F)F)c2)cc1-c1cc(F)nc(N2CCOCC2)c1]

To a solution of triethylamine (3.0 equiv.) and N-(3-(2,6-difluoropyridin-4-yl)-4-methylphenyl)-3-(trifluoromethyl)benzamide (1.0 equiv.) at RT in MeOH (0.12 M) was added morpholine (2.0 equiv) in one portion, the resulting mixture was then heated at 55° C. for 8 hours. LCMS analysis indicated 90% conversion to the desired product (M+H=460.1, Rt=0.43 min/non-polar). Water was then added, and the mixture was extracted with ethyl acetate, and the combined extracts were washed with brine, dried over magnesium sulfate, filtered, and concentrated to yield N-(3-(2-fluoro-6-morpholinopyridin-4-yl)-4-methylphenyl)-3-(trifluoromethyl)benzamide as a light brown solid (>100%). LCMS (m/z) (M+H)=460.1, Rt=0.43 min/non-polar.

Example 115

N-(3-(2-((2-hydroxyethyl)amino)-6-morpholinopyridin-4-yl)-4-methylphenyl)-3-(trifluoromethyl)benzamide

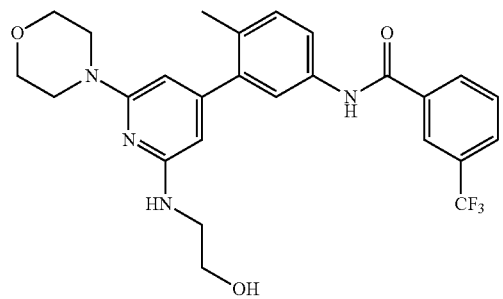 [SMILES: Cc1ccc(NC(=O)c2cccc(C(F)(F)F)c2)cc1-c1cc(NCCO)nc(N2CCOCC2)c1]

In a nitrogen purged microwave vial equipped with a stir bar N-(3-(2-fluoro-6-morpholinopyridin-4-yl)-4-methylphenyl)-3-(trifluoromethyl)benzamide (1.0 equiv.), in ethanolamine (276 equiv.) was heated to 180° C. for 15 minutes. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(3-(2-((2-hydroxyethyl)amino)-6-morpholinopyridin-4-yl)-4-methylphenyl)-3-(trifluoromethyl)benzamide was isolated as the TFA salt in 27% yield. ¹H NMR (400 MHz, <cd3od>) δ ppm 2.23 (s, 3H) 3.35-3.50 (m, 6H) 3.63-3.81 (m, 6H) 6.08-6.18 (m, 1H) 7.24 (d, J=8.22 Hz, 1H) 7.47 (dd, J=8.22, 2.35 Hz, 1H) 7.59-7.71 (m, 2H) 7.80 (d, J=7.83 Hz, 1H) 8.10 (d, J=7.83 Hz, 1H) 8.16 (s, 1H). LCMS (m/z) (M+H)=501.1, Rt=0.80 min.

Synthesis of 5-bromo-1-ethyl-3-(trifluoromethyl)pyridin-2(1H)-one

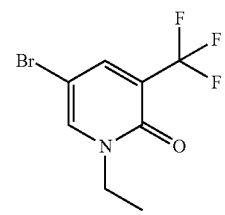

In a round bottom flask equipped with a stir bar and purged with nitrogen was added 5-bromo-3-(trifluoromethyl)pyridin-2-ol (1.0 equiv.), potassium carbonate (2.0 equiv.) and DMF (0.2 M). The mixture was stirred at room temperature and iodoethane (1.2 equiv.) was added via syringe. The mixture was warmed to 35° C. for 4 hours at which time LCMS indicated full conversion. The reaction was worked up by partitioning between water and ethyl acetate, the aqueous phase was extracted 3 more times with ethyl acetate, the organics were combined, washed with brine, dried with sodium sulfate, filtered and concentrated to yield 5-bromo-1-ethyl-3-(trifluoromethyl)pyridin-2(1H)-one (67%). $^1$H NMR (400 MHz, <cdcl3>) δ ppm 1.32-1.50 (m, 3H) 4.04 (q, J=7.17 Hz, 2H) 7.63 (br. s., 1H) 7.78 (br. s., 1H). LCMS (m/z) (M+H)=269.1/271.1, Rt=0.72 min Example 116

1-ethyl-N-(4-methyl-3-(1-methyl-5-morpholino-6-oxo-1,6-dihydropyridin-3-yl)phenyl)-6-oxo-5-(trifluoromethyl)-1,6-dihydropyridine-3-carboxamide

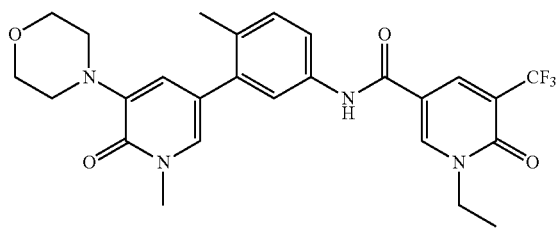 [SMILES: CCn1cc(C(=O)Nc2ccc(C)c(-c3cc(N4CCOCC4)c(=O)n(C)c3)c2)cc(C(F)(F)F)c1=O]

In a microwave tube was added 5-(5-amino-2-methylphenyl)-1-methyl-3-morpholinopyridin-2(1H)-one (1.0 equiv.), 5-bromo-1-ethyl-3-(trifluoromethyl)pyridin-2(1H)-one (2.0 equiv.), PdCl$_2$(dppf).CH$_2$Cl$_2$ adduct (0.1 equiv.), Mo(CO)$_6$ (1.0 equiv.), and THF (0.3 M). The mixture was capped and stirred while DBU (3.0 equiv.) was added, fizzing occurred and the tube was subsequently heated in the microwave at 150° C. for 15 min at which time LCMS indicated full conversion to product (M+H=517). The reaction was filtered, concentrated, and purified via preparative HPLC to yield 1-ethyl-N-(4-methyl-3-(1-methyl-5-morpholino-6-oxo-1,6-dihydropyridin-3-yl)phenyl)-6-oxo-5-(trifluoromethyl)-1,6-dihydropyridine-3-carboxamide (15% yield). $^1$H NMR (400 MHz, <cd3od>) δ ppm 1.42 (t, J=7.24 Hz, 3H) 2.30 (s, 3H) 3.08-3.21 (m, 4H) 3.64 (s, 3H) 3.80-3.92 (m, 4H) 4.16 (q, J=7.04 Hz, 2H) 6.93 (d, J=1.96 Hz, 1H) 7.28 (d, J=8.22 Hz, 1H) 7.34 (d, J=1.96 Hz, 1H) 7.47-7.60 (m, 2H) 8.48 (d, J=1.96 Hz, 1H) 8.70 (d, J=2.35 Hz, 1H). LCMS (m/z) (M+H)=517.1, Rt=0.81 min.

Example 117

Synthesis of N-(4-methyl-3-(1-methyl-5-morpholino-6-oxo-1,6-dihydropyridin-3-yl)phenyl)-3-(trifluoromethyl)benzamide

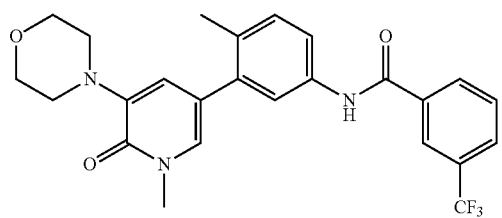 [SMILES: Cc1ccc(NC(=O)c2cccc(C(F)(F)F)c2)cc1-c1cc(N2CCOCC2)c(=O)n(C)c1]

To a solution of 5-bromo-1-methyl-3-morpholinopyridin-2(1H)-one (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 10 min in the microwave. The organic phase was dried with sodium sulfate, filtered and concentrated. The crude material was purified via preparative reverse phase HPLC. Upon lyophilization of the pure fractions, N-(4-methyl-3-(1-methyl-5-morpholino-6-oxo-1,6-dihydropyridin-3-yl)phenyl)-3-(trifluoromethyl)benzamide was isolated as the TFA salt in 11% yield. LCMS (m/z) (M+H)=472.2, Rt=0.87 min. $^1$H NMR (400 MHz, <cd3od>) δ ppm 2.30 (s, 3H) 3.13-3.21 (m, 4H) 3.64 (s, 3H) 3.81-3.92 (m, 4H) 7.01 (d, J=2.35 Hz, 1H) 7.29 (d, J=8.61 Hz, 1H) 7.39 (d, J=2.35 Hz, 1H) 7.57 (dd, J=8.22, 1.96 Hz, 1H) 7.62 (d, J=1.96 Hz, 1H) 7.69-7.77 (m, 1H) 7.89 (d, J=7.83 Hz, 1H) 8.19 (d, J=7.43 Hz, 1H) 8.25 (s, 1H).

The compounds listed below were prepared using methods similar to those described for the preparation of Example 117 using the corresponding aryl halide and intermediates (A-G).

Example 118

N-(4-methyl-3-(6-morpholinopyrazin-2-yl)phenyl)-3-(trifluoromethyl)benzamide

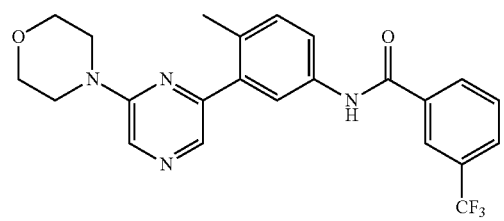 [SMILES: Cc1ccc(NC(=O)c2cccc(C(F)(F)F)c2)cc1-c1cncc(N2CCOCC2)n1]

1H NMR (400 MHz, <cd3od>) δ ppm 2.40 (s, 3H) 3.60-3.73 (m, 4H) 3.75-3.88 (m, 4H) 7.33 (d, J=8.22 Hz, 1H) 7.59-7.78 (m, 2H) 7.81-7.96 (m, 2H) 8.02 (s, 1H) 8.14-8.40 (m, 3H). LCMS (m/z) (M+H)=443.2, Rt=0.93 min.

Example 119

N-(4-methyl-3-(4-methyl-6-morpholino-5-oxo-4,5-dihydropyrazin-2-yl)phenyl)-3-(trifluoromethyl)benzamide

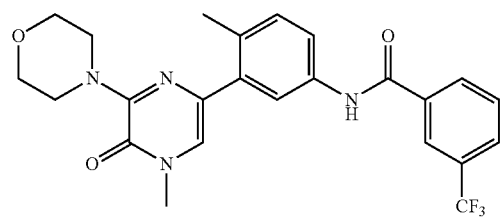

1H NMR (400 MHz, <cd3od>) δ ppm 2.39 (s, 3H) 3.56 (s, 3H) 3.80 (s, 9H) 7.18 (s, 1H) 7.26 (d, J=8.22 Hz, 1H) 7.56 (dd, J=8.22, 2.35 Hz, 1H) 7.67-7.80 (m, 2H) 7.89 (d, J=7.83 Hz, 1H) 8.20 (d, J=7.83 Hz, 1H) 8.25 (s, 1H). LCMS (m/z) (M+H)=473.1, Rt=0.92 min.

Example 120

N-(4-methyl-3-(6-morpholino-5-oxo-4,5-dihydropyrazin-2-yl)phenyl)-3-(trifluoromethyl)benzamide

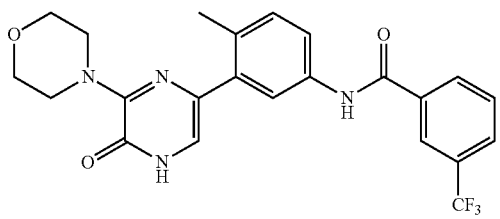 [SMILES: Cc1ccc(NC(=O)c2cccc(C(F)(F)F)c2)cc1-c1c[nH]c(=O)c(N2CCOCC2)n1]

1H NMR (400 MHz, <cd3od>) δ ppm 2.29 (s, 3H) 3.72 (d, J=4.70 Hz, 9H) 6.85 (s, 1H) 7.16 (d, J=8.22 Hz, 1H) 7.47 (dd, J=8.22, 2.35 Hz, 1H) 7.58-7.69 (m, 2H) 7.79 (d, J=7.83 Hz, 1H) 8.05-8.20 (m, 1H). LCMS (m/z) (M+H)=459.3, Rt=0.86 min.

Example 121

N-(6-methyl-5-(6-morpholino-5-oxo-4,5-dihydropyrazin-2-yl)pyridin-3-yl)-3-(trifluoromethyl)benzamide

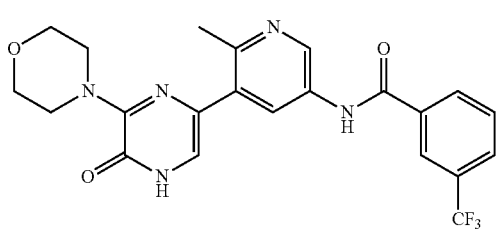 [SMILES: Cc1ncc(NC(=O)c2cccc(C(F)(F)F)c2)cc1-c1c[nH]c(=O)c(N2CCOCC2)n1]

1H NMR (400 MHz, <cd3od>) δ ppm 2.71 (s, 3H) 3.59-3.91 (m, 9H) 7.11 (s, 1H) 7.69 (t, J=7.83 Hz, 1H) 7.86 (d, J=7.83 Hz, 1H) 8.08-8.30 (m, 2H) 8.54 (d, J=2.35 Hz, 1H) 9.11 (d, J=1.96 Hz, 1H). LCMS (m/z) (M+H)=460.2, Rt=0.66 min.

Example 122

N-(3-(2-methoxy-5-morpholinopyridin-3-yl)-4-methylphenyl)-3-(trifluoromethyl)benzamide

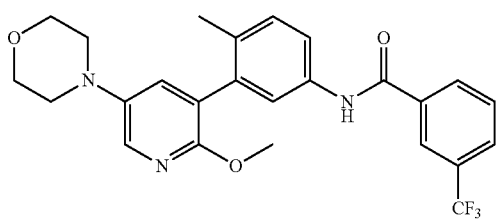 [SMILES: COc1ncc(N2CCOCC2)cc1-c1cc(NC(=O)c2cccc(C(F)(F)F)c2)ccc1C]

1H NMR (400 MHz, <cd3od>) δ ppm 2.11 (s, 3H) 3.21 (dd, J=5.48, 3.91 Hz, 4H) 3.81-3.92 (m, 7H) 7.27 (d, J=8.22 Hz, 1H) 7.45 (d, J=2.74 Hz, 1H) 7.52-7.62 (m, 2H) 7.68-7.77 (m, 1H) 7.83-7.97 (m, 2H) 8.10-8.36 (m, 2H). LCMS (m/z) (M+H)=472.2, Rt=0.93 min.

Example 123

N-(4-methyl-3-(1-methyl-5-morpholino-2-oxo-1,2-dihydropyridin-3-yl)phenyl)-3-(trifluoromethyl)benzamide

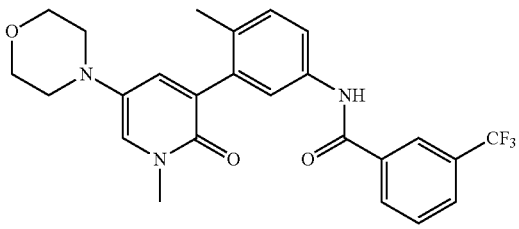 [SMILES: Cc1ccc(NC(=O)c2cccc(C(F)(F)F)c2)cc1-c1cc(N2CCOCC2)cn(C)c1=O]

1H NMR (400 MHz, <cd3od>) δ ppm 2.17 (s, 3H) 2.87-3.06 (m, 4H) 3.63 (s, 3H) 3.74-3.87 (m, 4H) 7.14-7.30 (m, 2H) 7.43-7.63 (m, 3H) 7.67-7.77 (m, 1H) 7.88 (d, J=7.83 Hz, 1H) 8.12-8.28 (m, 1H). LCMS (m/z) (M+H)=472.3, Rt=0.80 min.

Example 124

N-(1',2-dimethyl-5'-morpholino-2'-oxo-1',2'-dihydro-[3,3'-bipyridin]-5-yl)-3-(trifluoromethyl)benzamide

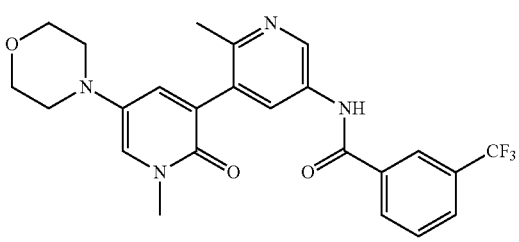 [SMILES: Cc1ncc(NC(=O)c2cccc(C(F)(F)F)c2)cc1-c1cc(N2CCOCC2)cn(C)c1=O]

¹H NMR (400 MHz, <cd3od>) δ ppm 2.61 (s, 3H) 2.92-3.08 (m, 4H) 3.67 (s, 3H) 3.77-3.92 (m, 4H) 7.42 (d, J=3.13 Hz, 1H) 7.68-7.83 (m, 2H) 7.96 (d, J=7.83 Hz, 1H) 8.17-8.37 (m, 2H) 8.47 (d, J=2.35 Hz, 1H) 9.37 (d, J=2.35 Hz, 1H). LCMS (m/z) (M+H)=473.2, Rt=0.63 min.

Example 125

N-(4-methyl-3-(5-morpholino-2-oxo-1,2-dihydropyridin-3-yl)phenyl)-3-(trifluoromethyl)benzamide

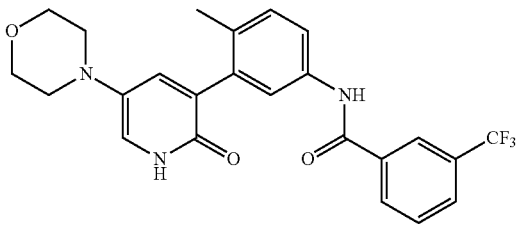 [SMILES: Cc1ccc(NC(=O)c2cccc(C(F)(F)F)c2)cc1-c1cc(N2CCOCC2)c[nH]c1=O]

¹H NMR (400 MHz, <cd3od>) δ ppm 2.11 (s, 3H) 2.84-2.98 (m, 4H) 3.66-3.79 (m, 4H) 6.93 (d, J=3.13 Hz, 1H) 7.18 (d, J=8.22 Hz, 1H) 7.39-7.55 (m, 3H) 7.57-7.68 (m, 1H) 7.79 (d, J=7.43 Hz, 1H) 8.02-8.22 (m, 1H). LCMS (m/z) (M+H)=458.2, Rt=0.78 min.

Example 126

N-(3-(6-methoxy-5-morpholinopyridin-3-yl)-4-methylphenyl)-3-(trifluoromethyl)benzamide

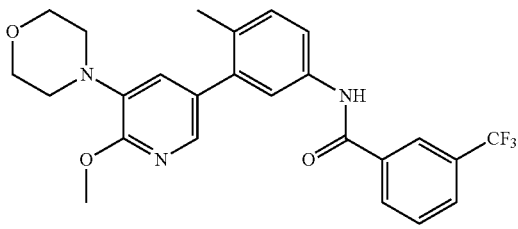 [SMILES: COc1ncc(-c2cc(NC(=O)c3cccc(C(F)(F)F)c3)ccc2C)cc1N1CCOCC1]

1H NMR (400 MHz, <cd3od>) δ ppm 2.27 (s, 3H) 3.04-3.22 (m, 4H) 3.81-3.93 (m, 4H) 4.04 (s, 3H) 7.27-7.34 (m, 2H) 7.61 (dd, J=4.11, 2.15 Hz, 2H) 7.68-7.76 (m, 1H) 7.80 (d, J=1.96 Hz, 1H) 7.88 (d, J=7.83 Hz, 1H) 8.20 (d, J=7.83 Hz, 1H) 8.25 (s, 1H). LCMS (m/z) (M+H)=472.4, Rt=1.04 min.

Example 127

N-(6'-methoxy-2-methyl-5'-morpholino-[3,3'-bipyridin]-5-yl)-3-(trifluoromethyl)benzamide

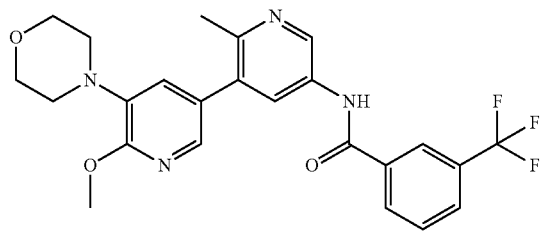 [SMILES: COc1ncc(-c2cc(NC(=O)c3cccc(C(F)(F)F)c3)cnc2C)cc1N1CCOCC1]

1H NMR (400 MHz, <cd3od>) δ ppm 2.67 (s, 3H) 3.09-3.18 (m, 4H) 3.80-3.91 (m, 4H) 4.05 (s, 3H) 7.31 (d, J=1.96 Hz, 1H) 7.78 (t, J=7.83 Hz, 1H) 7.88 (d, J=1.96 Hz, 1H) 7.96 (d, J=7.83 Hz, 1H) 8.28 (d, J=8.22 Hz, 1H) 8.34 (s, 1H) 8.43 (d, J=2.35 Hz, 1H) 9.32 (d, J=2.35 Hz, 1H). LCMS (m/z) (M+H)=473.3, Rt=0.72 min.

Example 128

2-(2-cyanopropan-2-yl)-N-(3-(6-methoxy-5-morpholinopyridin-3-yl)-4-methylphenyl)isonicotinamide

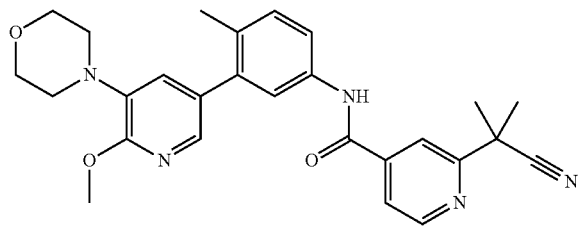 [SMILES: COc1ncc(-c2cc(NC(=O)c3ccnc(C(C)(C)C#N)c3)ccc2C)cc1N1CCOCC1]

1H NMR (400 MHz, <cd3od>) δ ppm 1.81 (s, 6H) 2.27 (s, 3H) 3.09-3.17 (m, 4H) 3.81-3.89 (m, 4H) 4.02 (s, 3H) 7.24 (d, J=1.96 Hz, 1H) 7.32 (d, J=8.22 Hz, 1H) 7.60 (d, J=1.96 Hz, 1H) 7.63 (dd, J=8.22, 2.35 Hz, 1H) 7.76 (d, J=1.96 Hz, 1H) 7.81 (dd, J=4.89, 1.37 Hz, 1H) 8.06 (s, 1H) 8.75 (d, J=5.09 Hz, 1H). LCMS (m/z) (M+H)=472.4, Rt=0.87 min.

Example 129

2-(2-cyanopropan-2-yl)-N-(6'-methoxy-2-methyl-5'-morpholino-[3,3'-bipyridin]-5-yl)isonicotinamide

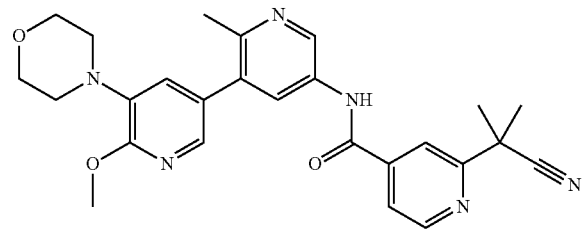 [SMILES: COc1ncc(-c2cc(NC(=O)c3ccnc(C(C)(C)C#N)c3)cnc2C)cc1N1CCOCC1]

$^1$H NMR (400 MHz, <cd3od>) δ ppm 1.82 (s, 6H) 2.69 (s, 3H) 3.07-3.21 (m, 4H) 3.78-3.92 (m, 4H) 4.05 (s, 3H) 7.31 (d, J=1.96 Hz, 1H) 7.82-7.94 (m, 2H) 8.14 (s, 1H) 8.45 (d, J=2.35 Hz, 1H) 8.82 (d, J=5.09 Hz, 1H) 9.34 (d, J=2.35 Hz, 1H). LCMS (m/z) (M+H)=473.3, Rt=0.62 min.

Example 130

N-(2-methyl-5'-morpholino-6'-oxo-1'-(tetrahydro-2H-pyran-4-yl)-1',6'-dihydro-[3,3'-bipyridin]-5-yl)-3-(trifluoromethyl)benzamide

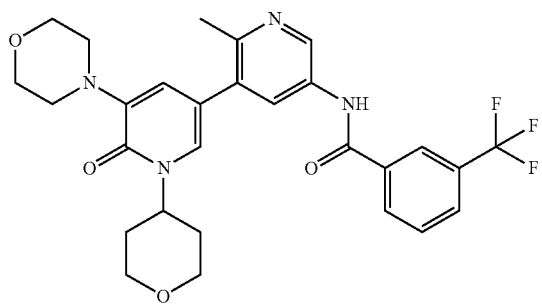 [SMILES: Cc1ncc(NC(=O)c2cccc(C(F)(F)F)c2)cc1-c1cc(N2CCOCC2)c(=O)n(C2CCOCC2)c1]

$^1$H NMR (400 MHz, <cd3od>) δ ppm 1.87 (dd, J=11.98, 2.15 Hz, 2H) 2.01 (qd, J=12.22, 4.52 Hz, 2H) 3.09-3.21 (m, 4H) 3.62 (td, J=11.77, 1.83 Hz, 2H) 3.79-3.91 (m, 4H) 4.10 (dd, J=11.27, 4.33 Hz, 2H) 5.19 (tt, J=12.06, 4.00 Hz, 1H) 6.94 (d, J=2.25 Hz, 1H) 7.55 (d, J=2.30 Hz, 1H) 7.74-7.83 (m, 1H) 7.96 (dd, J=7.87, 0.68 Hz, 1H) 8.27 (d, J=7.92 Hz, 1H) 8.34 (d, J=0.64 Hz, 1H) 8.40 (d, J=2.40 Hz, 1H) 9.22 (d, J=2.40 Hz, 1H). LCMS (m/z) (M+H)=543.1, Rt=0.70 min.

Example 131

N-(2-methyl-5'-morpholino-6'-((tetrahydro-2H-pyran-4-yl)oxy)-[3,3'-bipyridin]-5-yl)-3-(trifluoromethyl)benzamide

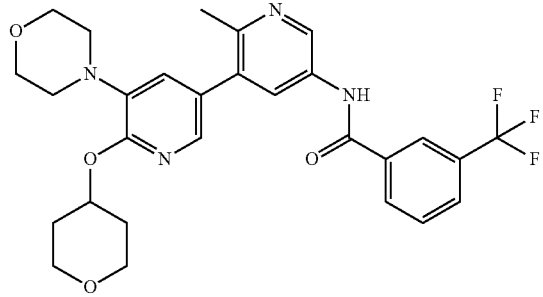 [SMILES: Cc1ncc(NC(=O)c2cccc(C(F)(F)F)c2)cc1-c1cnc(OC2CCOCC2)c(N2CCOCC2)c1]

¹H NMR (400 MHz, <cd3od>) δ ppm 1.77-1.91 (m, 2H) 2.06-2.20 (m, 2H) 2.71 (s, 3H) 3.12-3.22 (m, 4H) 3.67 (ddd, J=11.59, 8.22, 3.28 Hz, 2H) 3.81-3.91 (m, 4H) 3.92-4.03 (m, 2H) 5.45 (tt, J=7.92, 3.91 Hz, 1H) 7.33 (d, J=2.20 Hz, 1H) 7.74-7.82 (m, 1H) 7.87 (d, J=2.15 Hz, 1H) 7.93-8.00 (m, 1H) 8.29 (d, J=7.87 Hz, 1H) 8.35 (d, J=1.22 Hz, 1H) 8.50 (d, J=2.30 Hz, 1H) 9.40 (d, J=2.40 Hz, 1H). LCMS (m/z) (M+H)=543.1, Rt=0.80 min.

Example 132

N-(4-methyl-3-(5-morpholino-6-((tetrahydro-2H-pyran-4-yl)oxy)pyridin-3-yl)phenyl)-3-(trifluoromethyl)benzamide

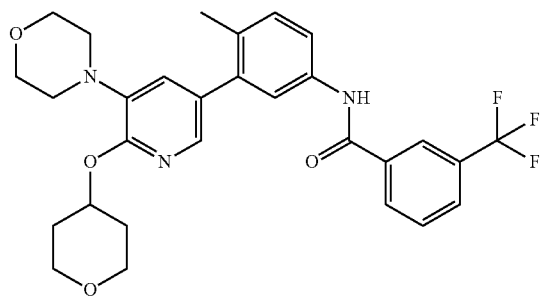 [SMILES: Cc1ccc(NC(=O)c2cccc(C(F)(F)F)c2)cc1-c1cnc(OC2CCOCC2)c(N2CCOCC2)c1]

¹H NMR (400 MHz, <cd3od>) δ 1.84 (dtd, J=12.67, 8.34, 8.34, 3.91 Hz, 2H) 2.03-2.20 (m, 2H) 2.27 (s, 3H) 3.06-3.22 (m, 4H) 3.67 (ddd, J=11.64, 8.31, 3.13 Hz, 2H) 3.78-3.91 (m, 4H) 3.92-4.04 (m, 2H) 5.39 (tt, J=7.83, 3.91 Hz, 1H) 7.24 (d, J=1.96 Hz, 1H) 7.30 (d, J=7.83 Hz, 1H) 7.56-7.66 (m, 2H) 7.68-7.78 (m, 2H) 7.88 (d, J=7.83 Hz, 1H) 8.20 (d, J=7.83 Hz, 1H) 8.25 (s, 1H). LCMS (m/z) (M+H)=542.1, Rt=1.06 min.

Example 133

N-(1'-isopropyl-2-methyl-5'-morpholino-6'-oxo-1',6'-dihydro-[3,3'-bipyridin]-5-yl)-3-(trifluoromethyl)benzamide

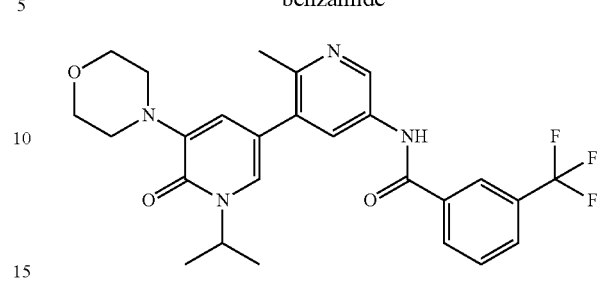

¹H NMR (400 MHz, <cd3od>) δ ppm 1.45 (d, J=6.80 Hz, 6H) 2.70 (s, 3H) 3.12-3.23 (m, 4H) 3.81-3.95 (m, 4H) 5.35 (quin, J=6.87 Hz, 1H) 6.95 (d, J=2.15 Hz, 1H) 7.56 (d, J=2.10 Hz, 1H) 7.80 (t, J=7.73 Hz, 1H) 7.98 (d, J=7.19 Hz, 1H) 8.30 (d, J=7.87 Hz, 1H) 8.36 (s, 1H) 8.41 (d, J=2.35 Hz, 1H) 9.26 (d, J=2.20 Hz, 1H). LCMS (m/z) (M+H)=501.3, Rt=0.78 min.

Example 134

N-(6'-isopropoxy-2-methyl-5'-morpholino-[3,3'-bipyridin]-5-yl)-3-(trifluoromethyl)benzamide

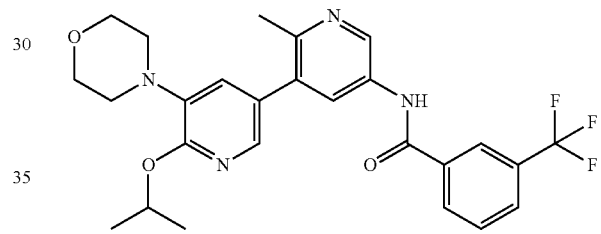

¹H NMR (400 MHz, <cd3od>) δ ppm 1.43 (d, J=6.16 Hz, 6H) 2.69 (s, 3H) 3.12-3.22 (m, 4H) 3.82-3.92 (m, 4H) 5.47 (quin, J=6.17 Hz, 1H) 7.30 (d, J=2.10 Hz, 1H) 7.76-7.84 (m, 1H) 7.87 (d, J=2.01 Hz, 1H) 7.98 (d, J=7.87 Hz, 1H) 8.30 (d, J=7.68 Hz, 1H) 8.36 (s, 1H) 8.43 (d, J=2.35 Hz, 1H) 9.31 (d, J=2.35 Hz, 1H). LCMS (m/z) (M+H)=501.3, Rt=0.90 min.

Example 135

N-(3-(1-isopropyl-5-morpholino-6-oxo-1,6-dihydropyridin-3-yl)-4-methylphenyl)-3-(trifluoromethyl)benzamide

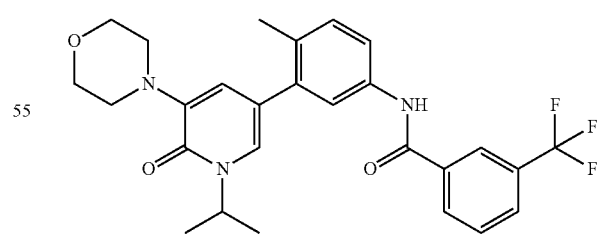

¹H NMR (400 MHz, <cd3od>) δ ppm 1.44 (d, J=6.80 Hz, 6H) 2.32 (s, 3H) 3.12-3.23 (m, 4H) 3.84-3.93 (m, 4H) 5.35 (quin, J=6.86 Hz, 1H) 6.98 (d, J=2.10 Hz, 1H) 7.32 (d, J=8.02 Hz, 1H) 7.39 (d, J=2.10 Hz, 1H) 7.58-7.66 (m, 2H) 7.71-7.79 (m, 1H) 7.91 (d, J=7.92 Hz, 1H) 8.23 (d, J=7.92 Hz, 1H) 8.28 (s, 1H). LCMS (m/z) (M+H)=500.3, Rt=1.02 min.

Example 136

N-(3-(6-isopropoxy-5-morpholinopyridin-3-yl)-4-methylphenyl)-3-(trifluoromethyl)benzamide

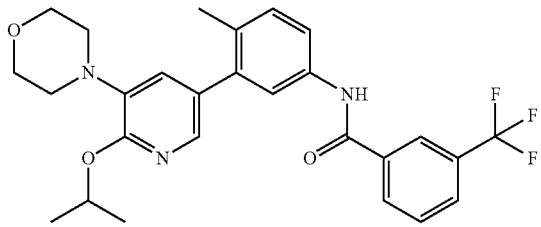 [SMILES: Cc1ccc(NC(=O)c2cccc(C(F)(F)F)c2)cc1-c1cnc(OC(C)C)c(N2CCOCC2)c1]

$^1$H NMR (400 MHz, <cd3od>) δ ppm 1.43 (d, J=6.16 Hz, 6H) 2.29 (s, 3H) 3.15-3.25 (m, 4H) 3.83-3.94 (m, 4H) 5.42 (spt, J=6.18 Hz, 1H) 7.27-7.35 (m, 2H) 7.59-7.66 (m, 2H) 7.70-7.77 (m, 1H) 7.79 (d, J=1.86 Hz, 1H) 7.90 (d, J=7.87 Hz, 1H) 8.22 (d, J=7.68 Hz, 1H) 8.27 (s, 1H). LCMS (m/z) (M+H)=500.4, Rt=1.17 min.

Example 137

4-methyl-3-(1-methyl-5-morpholino-6-oxo-1,6-dihydropyridin-3-yl)-N-(3-(trifluoromethyl)phenyl)benzamide

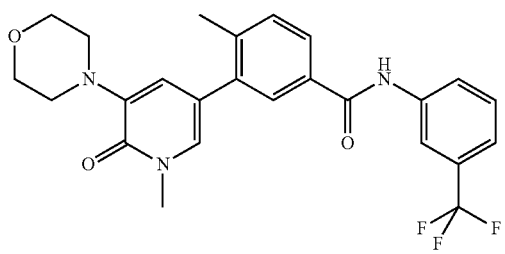 [SMILES: Cc1ccc(C(=O)Nc2cccc(C(F)(F)F)c2)cc1-c1cc(N2CCOCC2)c(=O)n(C)c1]

$^1$H NMR (400 MHz, <cd3od>) δ ppm 2.42 (s, 3H) 3.12-3.22 (m, 4H) 3.67 (s, 3H) 3.83-3.94 (m, 4H) 6.99 (d, J=2.25 Hz, 1H) 7.42 (d, J=2.25 Hz, 1H) 7.43-7.50 (m, 2H) 7.57 (t, J=8.02 Hz, 1H) 7.85 (d, J=2.01 Hz, 1H) 7.89 (dd, J=7.92, 2.01 Hz, 1H) 7.95 (d, J=8.22 Hz, 1H) 8.17 (s, 1H). LCMS (m/z) (M+H)=472.1, Rt=0.91 min.

Example 138

N-(1',2-dimethyl-5'-morpholino-6'-oxo-1',6'-dihydro-[3,3'-bipyridin]-5-yl)-3-trifluoromethyl)benzamide

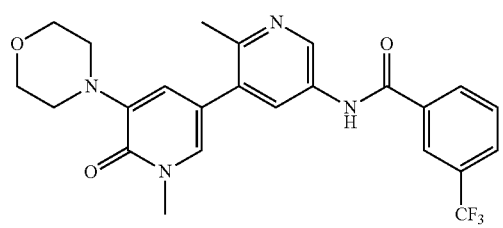 [SMILES: Cc1ncc(NC(=O)c2cccc(C(F)(F)F)c2)cc1-c1cc(N2CCOCC2)c(=O)n(C)c1]

$^1$H NMR (400 MHz, <cd3od>) δ ppm 2.71 (s, 3H) 3.12-3.21 (m, 4H) 3.65 (s, 3H) 3.82-3.90 (m, 4H) 6.96 (d, J=2.35 Hz, 1H) 7.53 (d, J=1.96 Hz, 1H) 7.74-7.83 (m, 1H) 7.96 (d, J=7.83 Hz, 1H) 8.28 (d, J=7.83 Hz, 1H) 8.34 (s, 1H) 8.45 (d, J=2.35 Hz, 1H) 9.27 (d, J=2.35 Hz, 1H). LCMS (m/z) (M+H)=473.3, Rt=0.64 min.

Example 139

2-(tert-butyl)-N-(4-methyl-3-(1-methyl-5-morpholino-6-oxo-1,6-dihydropyridin-3-yl)phenyl)isonicotinamide

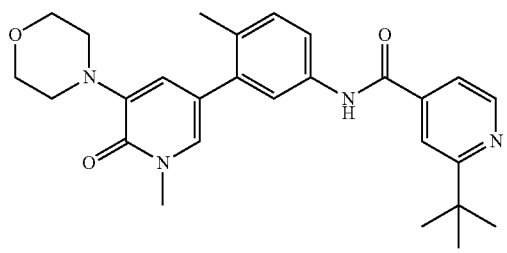 [SMILES: Cc1ccc(NC(=O)c2ccnc(C(C)(C)C)c2)cc1-c1cc(N2CCOCC2)c(=O)n(C)c1]

$^1$H NMR (400 MHz, <cd3od>) δ ppm 1.50 (s, 9H) 2.31 (s, 3H) 3.08-3.19 (m, 4H) 3.64 (s, 3H) 3.79-3.94 (m, 4H) 6.93 (d, J=1.96 Hz, 1H) 7.24-7.38 (m, 2H) 7.57-7.71 (m, 2H) 7.98 (d, J=5.48 Hz, 1H) 8.20 (s, 1H) 8.76 (d, J=5.87 Hz, 1H). LCMS (m/z) (M+H)=461.4, Rt=0.66 min.

Example 140

2-(2-cyanopropan-2-yl)-N-(4-methyl-3-(1-methyl-5-morpholino-6-oxo-1,6-dihydropyridin-3-yl)phenyl)isonicotinamide

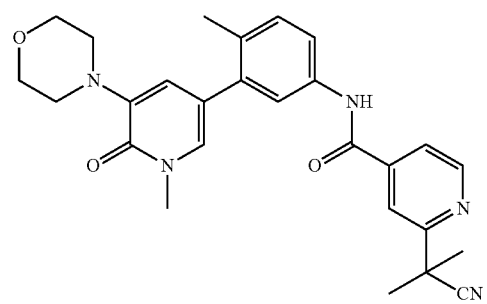 [SMILES: Cc1ccc(NC(=O)c2ccnc(C(C)(C)C#N)c2)cc1-c1cc(N2CCOCC2)c(=O)n(C)c1]

1H NMR (400 MHz, <cd3od>) δ ppm 1.81 (s, 6H) 2.31 (s, 3H) 3.10-3.23 (m, 4H) 3.64 (s, 3H) 3.82-3.95 (m, 4H) 7.01 (d, J=1.96 Hz, 1H) 7.30 (d, J=8.22 Hz, 1H) 7.40 (d, J=1.96 Hz, 1H) 7.58 (dd, J=8.22, 2.35 Hz, 1H) 7.63 (d, J=1.96 Hz, 1H) 7.80 (dd, J=5.09, 1.17 Hz, 1H) 8.06 (s, 1H) 8.76 (d, J=5.09 Hz, 1H). LCMS (m/z) (M+H)=472.2, Rt=0.73 min.

Example 141

2-(2-cyanopropan-2-yl)-N-(1',2-dimethyl-5'-morpholino-6'-oxo-1',6'-dihydro-[3,3'-bipyridin]-5-yl)isonicotinamide

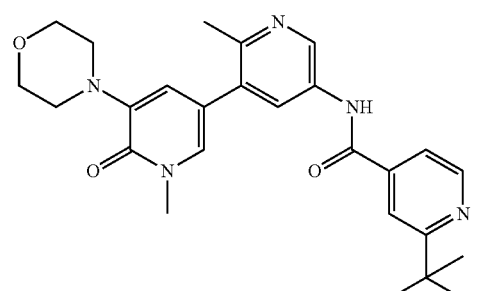

1H NMR (400 MHz, <cd3od>) δ ppm 1.78-1.86 (m, 6H) 2.70 (s, 3H) 3.16 (br. s., 4H) 3.65 (s, 3H) 3.85 (br. s., 4H) 6.90-6.99 (m, 1H) 7.49-7.56 (m, 1H) 7.82-7.89 (m, 1H) 8.09-8.16 (m, 1H) 8.38-8.45 (m, 1H) 8.78-8.85 (m, 1H) 9.20-9.26 (m, 1H). LCMS (m/z) (M+H)=473.2, Rt=0.54 min.

Example 142

N-(3-(1-(2-hydroxyethyl)-5-morpholino-6-oxo-1,6-dihydropyridin-3-yl)-4-methylphenyl)-3-(trifluoromethyl)benzamide

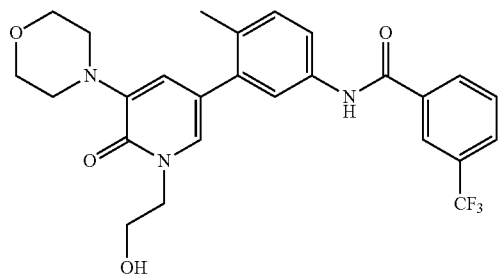 [SMILES: Cc1ccc(NC(=O)c2cccc(C(F)(F)F)c2)cc1-c1cc(N2CCOCC2)c(=O)n(CCO)c1]

$^1$H NMR (400 MHz, <cd3od>) δ ppm 2.31 (s, 3H) 3.13 (d, J=3.91 Hz, 4H) 3.80-3.95 (m, 6H) 4.17 (t, J=5.28 Hz, 2H) 6.93 (d, J=1.96 Hz, 1H) 7.26-7.33 (m, 2H) 7.54-7.63 (m, 2H) 7.72 (t, J=7.83 Hz, 1H) 7.89 (d, J=7.83 Hz, 1H) 8.20 (d, J=8.22 Hz, 1H) 8.25 (s, 1H). LCMS (m/z) (M+H)=502.2, Rt=0.78 min.

Example 143

2-(2-cyanopropan-2-yl)-N-(3-(1-(2-hydroxyethyl)-5-morpholino-6-oxo-1,6-dihydropyridin-3-yl)-4-methylphenyl)isonicotinamide

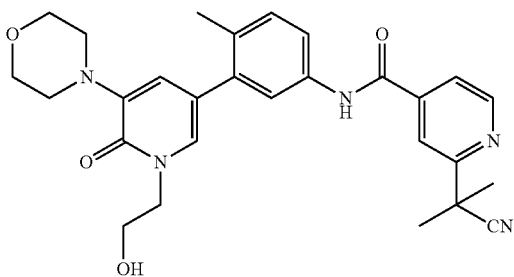 [SMILES: Cc1ccc(NC(=O)c2ccnc(C(C)(C)C#N)c2)cc1-c1cc(N2CCOCC2)c(=O)n(CCO)c1]

$^1$H NMR (400 MHz, <cd3od>) δ ppm 1.80 (s, 6H) 2.32 (s, 3H) 2.97-3.18 (m, 4H) 3.74-3.94 (m, 7H) 4.17 (t, J=5.28 Hz, 2H) 6.98 (d, J=2.35 Hz, 1H) 7.24-7.42 (m, 2H) 7.54-7.65 (m, 2H) 7.80 (dd, J=5.09, 1.17 Hz, 1H) 8.06 (s, 1H) 8.75 (d, J=5.09 Hz, 1H). LCMS (m/z) (M+H)=502.2, Rt=0.71 min.

Example 144

N-(1'-(2-hydroxyethyl)-2-methyl-5'-morpholino-6'-oxo-1',6'-dihydro-[3,3'-bipyridin]-5-yl)-3-(trifluoromethyl)benzamide

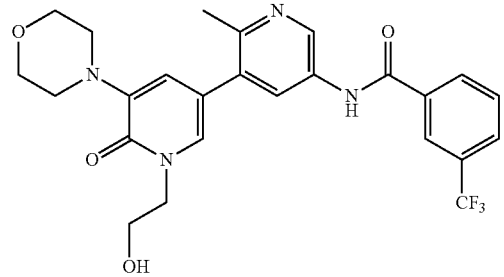 [SMILES: Cc1ncc(NC(=O)c2cccc(C(F)(F)F)c2)cc1-c1cc(N2CCOCC2)c(=O)n(CCO)c1]

$^1$H NMR (400 MHz, <cd3od>) δ ppm 2.72 (s, 3H) 3.07-3.20 (m, 4H) 3.80-3.99 (m, 6H) 4.19 (t, J=5.09 Hz, 2H) 6.98 (d, J=2.35 Hz, 1H) 7.50 (d, J=2.35 Hz, 1H) 7.78 (t, J=7.83 Hz, 1H) 7.96 (d, J=7.83 Hz, 1H) 8.28 (d, J=7.83 Hz, 1H) 8.34 (s, 1H) 8.47 (d, J=2.35 Hz, 1H) 9.30 (d, J=2.35 Hz, 1H). LCMS (m/z) (M+H)=503.2, Rt=0.63 min.

Example 145

N-(6'-(2-hydroxyethoxy)-2-methyl-5'-morpholino-[3,3'-bipyridin]-5-yl)-3-(trifluoromethyl)benzamide

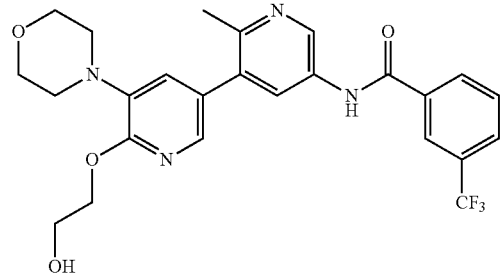 [SMILES: Cc1ncc(NC(=O)c2cccc(C(F)(F)F)c2)cc1-c1cnc(OCCO)c(N2CCOCC2)c1]

$^1$H NMR (400 MHz, <cd3od>) δ ppm 2.67 (s, 3H) 3.12-3.22 (m, 4H) 3.80-3.89 (m, 4H) 3.91-3.99 (m, 2H) 4.47-4.58 (m, 2H) 7.32 (d, J=1.96 Hz, 1H) 7.68-7.82 (m, 1H) 7.85 (d, J=1.96 Hz, 1H) 7.96 (d, J=7.83 Hz, 1H) 8.28 (d, J=7.83 Hz, 1H) 8.34 (s, 1H) 8.42 (d, J=1.96 Hz, 1H) 9.30 (d, J=2.35 Hz, 1H). LCMS (m/z) (M+H)=503.2, Rt=0.67 min.

Example 146

N-(4-methyl-3-(5-morpholino-6-oxo-1,6-dihydropyridin-3-yl)phenyl)-3-(trifluoromethyl)benzamide

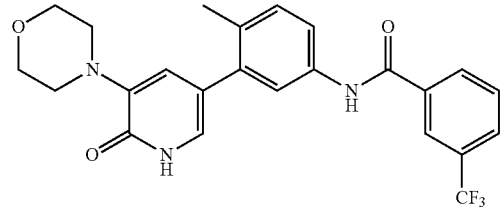

$^1$H NMR (400 MHz, <cd3od>) δ ppm 2.20 (s, 3H) 2.98-3.12 (m, 4H) 3.67-3.84 (m, 4H) 6.89 (d, J=1.96 Hz, 1H) 6.99 (d, J=1.96 Hz, 1H) 7.20 (d, J=8.22 Hz, 1H) 7.45-7.54 (m, 2H) 7.59-7.67 (m, 1H) 7.79 (d, J=7.83 Hz, 1H) 8.10 (d, J=7.83 Hz, 1H) 8.16 (s, 1H). LCMS (m/z) (M+H)=458.3, Rt=0.82 min.

Example 147

N-(3-(1-(cyanomethyl)-5-morpholino-6-oxo-1,6-dihydropyridin-3-yl)-4-methylphenyl)-3-(trifluoromethyl)benzamide

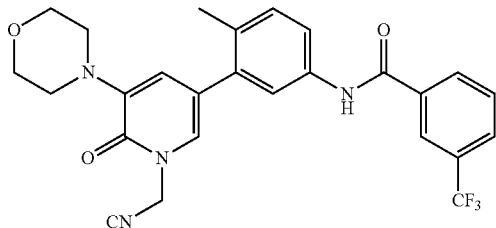

$^1$H NMR (400 MHz, <cd3od>) δ ppm 2.31 (s, 3H) 3.11-3.22 (m, 4H) 3.80-3.89 (m, 4H) 5.05 (s, 2H) 6.93 (d, J=1.96 Hz, 1H) 7.30 (d, J=8.22 Hz, 1H) 7.39 (d, J=1.96 Hz, 1H) 7.59 (dd, J=8.22, 1.96 Hz, 1H) 7.64 (d, J=1.96 Hz, 1H) 7.69-7.76 (m, 1H) 7.89 (d, J=7.83 Hz, 1H) 8.20 (d, J=7.83 Hz, 1H) 8.25 (s, 1H). LCMS (m/z) (M+H)=497.3, Rt=0.95 min.

Example 148

(R)—N-(3-(1-(1-cyanoethyl)-5-morpholino-6-oxo-1,6-dihydropyridin-3-yl)-4-methylphenyl)-3-(trifluoromethyl)benzamide

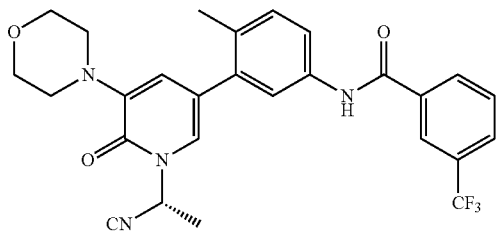

$^1$H NMR (400 MHz, <dmso>) δ ppm 1.72 (d, J=7.04 Hz, 6H) 2.25 (s, 6H) 3.11 (br. s., 8H) 3.71 (br. s., 8H) 5.87 (q, J=7.04 Hz, 2H) 6.73 (d, J=1.17 Hz, 2H) 7.28 (d, J=8.22 Hz, 2H) 7.43 (d, J=1.57 Hz, 2H) 7.63 (s, 2H) 7.71 (d, J=8.22 Hz, 2H) 7.77 (t, J=7.83 Hz, 2H) 7.95 (d, J=7.43 Hz, 2H) 8.21-8.32 (m, 5H) 10.45 (s, 1H). LCMS (m/z) (M+H)=511.2, Rt=1.00 min.

Example 149

(S)—N-(3-(1-(1-cyanoethyl)-5-morpholino-6-oxo-1,6-dihydropyridin-3-yl)-4-methylphenyl)-3-(trifluoromethyl)benzamide

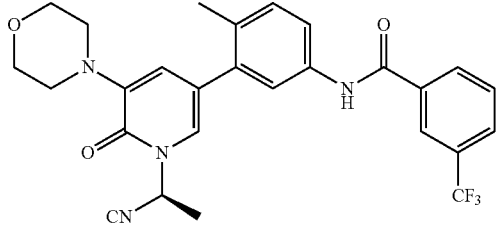

$^1$H NMR (400 MHz, <dmso>) δ ppm 1.80 (d, J=7.43 Hz, 3H) 2.33 (s, 3H) 3.20 (br. s., 4H) 3.78 (d, J=4.30 Hz, 4H) 5.95 (q, J=7.04 Hz, 1H) 6.81 (d, J=1.56 Hz, 1H) 7.36 (d, J=8.22 Hz, 1H) 7.51 (d, J=1.57 Hz, 1H) 7.71 (d, J=1.96 Hz, 1H) 7.79 (dd, J=8.22, 1.96 Hz, 1H) 7.83-7.90 (m, 1H) 8.04 (d, J=7.83 Hz, 1H) 8.28-8.44 (m, 2H) 10.53 (s, 1H). LCMS (m/z) (M+H)=511.3, Rt=1.01 min.

Example 150

N-(4-methyl-3-(1-(2-(methylsulfonyl)ethyl)-5-morpholino-6-oxo-1,6-dihydropyridin-3-yl)phenyl)-3-(trifluoromethyl)benzamide

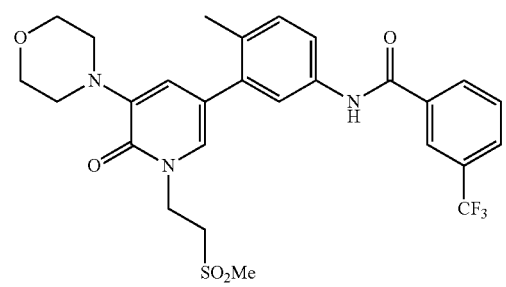 [SMILES: Cc1ccc(NC(=O)c2cccc(C(F)(F)F)c2)cc1-c1cc(N2CCOCC2)c(=O)n(CCS(C)(=O)=O)c1]

1H NMR (400 MHz, <cd3od>) δ ppm 2.31 (s, 3H) 3.02 (s, 3H) 3.14-3.24 (m, 4H) 3.67 (t, J=6.46 Hz, 2H) 3.83-3.90 (m, 4H) 4.50 (t, J=6.46 Hz, 2H) 6.99 (d, J=1.96 Hz, 1H) 7.29 (d, J=8.22 Hz, 1H) 7.42 (d, J=1.96 Hz, 1H) 7.57 (dd, J=8.22, 1.96 Hz, 1H) 7.61 (s, 1H) 7.69-7.76 (m, 1H) 7.89 (d, J=7.43 Hz, 1H) 8.20 (d, J=7.83 Hz, 1H) 8.25 (s, 1H). LCMS (m/z) (M+H)=564.3, Rt=0.90 min.

Example 151

N-(2-methyl-1'-(2-(methylsulfonyl)ethyl)-5'-morpholino-6'-oxo-1',6'-dihydro-[3,3'-bipyridin]-5-yl)-3-(trifluoromethyl)benzamide

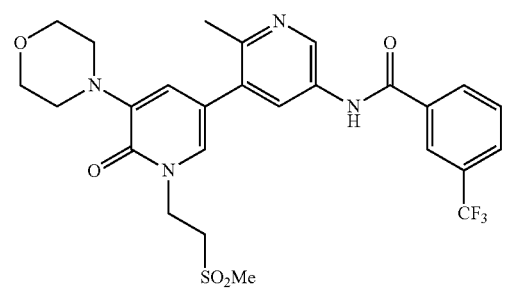 [SMILES: Cc1ncc(NC(=O)c2cccc(C(F)(F)F)c2)cc1-c1cc(N2CCOCC2)c(=O)n(CCS(C)(=O)=O)c1]

$^1$H NMR (400 MHz, <cd3od>) δ ppm 2.71 (s, 3H) 3.04 (s, 3H) 3.12-3.22 (m, 4H) 3.70 (t, J=6.06 Hz, 2H) 3.80-3.95 (m, 4H) 4.53 (t, J=6.06 Hz, 2H) 6.94 (d, J=1.96 Hz, 1H) 7.56 (d, J=1.96 Hz, 1H) 7.78 (t, J=8.02 Hz, 1H) 7.96 (d, J=7.43 Hz, 1H) 8.27 (d, J=7.43 Hz, 1H) 8.33 (s, 1H) 8.44 (d, J=2.35 Hz, 1H) 9.28 (d, J=2.35 Hz, 1H). LCMS (m/z) (M+H)=565.2, Rt=0.68 min.

Example 152

(S)—N-(3-(6-(1-cyanoethoxy)-5-morpholinopyridin-3-yl)-4-methylphenyl)-3-(trifluoromethyl)benzamide

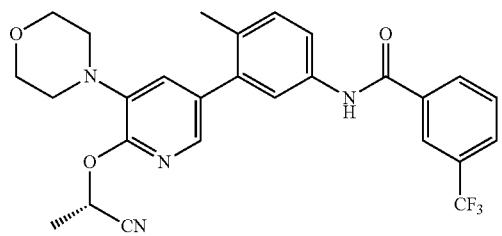 [SMILES: Cc1ccc(NC(=O)c2cccc(C(F)(F)F)c2)cc1-c1cnc(O[C@@H](C)C#N)c(N2CCOCC2)c1]

$^1$H NMR (400 MHz, <dmso>) δ ppm 1.73 (d, J=7.04 Hz, 3H) 2.22 (s, 3H) 3.06 (d, J=5.09 Hz, 4H) 3.74 (t, J=4.50 Hz, 4H) 5.78 (q, J=6.91 Hz, 1H) 7.26 (d, J=1.57 Hz, 1H) 7.30 (d, J=8.22 Hz, 1H) 7.65 (d, J=1.57 Hz, 1H) 7.70-7.82 (m, 3H) 7.95 (d, J=7.83 Hz, 1H) 8.22-8.30 (m, 2H) 10.44 (s, 1H). LCMS (m/z) (M+H)=511.5, Rt=1.13 min.

Example 153

(R)—N-(3-(6-(1-cyanoethoxy)-5-morpholinopyridin-3-yl)-4-methylphenyl)-3-(trifluoromethyl)benzamide

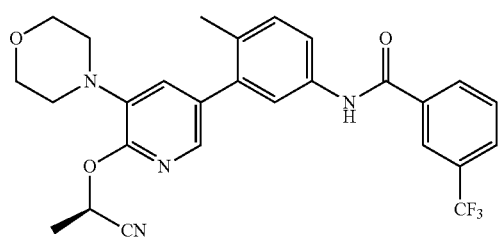 [SMILES: Cc1ccc(NC(=O)c2cccc(C(F)(F)F)c2)cc1-c1cnc(O[C@H](C)C#N)c(N2CCOCC2)c1]

$^1$H NMR (400 MHz, <dmso>) δ ppm 1.73 (d, J=7.04 Hz, 3H) 2.22 (s, 3H) 3.06 (d, J=5.09 Hz, 4H) 3.74 (t, J=4.50 Hz, 4H) 5.78 (q, J=6.65 Hz, 1H) 7.26 (d, J=1.57 Hz, 1H) 7.30 (d, J=8.22 Hz, 1H) 7.65 (d, J=1.96 Hz, 1H) 7.69-7.83 (m, 3H) 7.95 (d, J=7.83 Hz, 1H) 8.19-8.32 (m, 2H) 10.44 (s, 1H). LCMS (m/z) (M+H)=511.2, Rt=1.00 min.

Example 154

4-methyl-3-(1-(2-(methylsulfonyl)ethyl)-5-morpholino-6-oxo-1,6-dihydropyridin-3-yl)-N-(3-(trifluoromethyl)phenyl)benzamide

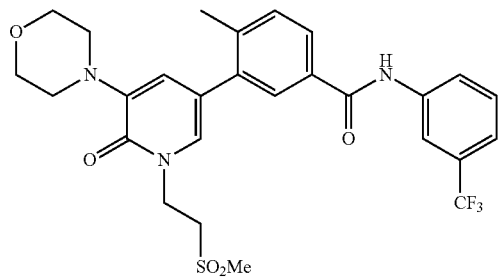

$^1$H NMR (400 MHz, <cd3od>) δ ppm 2.40 (s, 3H) 3.03 (s, 3H) 3.10-3.22 (m, 4H) 3.68 (t, J=6.46 Hz, 2H) 3.81-3.92 (m, 4H) 4.51 (t, J=6.46 Hz, 2H) 7.00 (d, J=1.96 Hz, 1H) 7.36-7.48 (m, 2H) 7.54 (t, J=8.02 Hz, 1H) 7.81-7.88 (m, 2H) 7.93 (d, J=8.22 Hz, 1H) 8.15 (s, 1H). LCMS (m/z) (M+H)=564.3, Rt=0.93 min.

Example 155

N-(3-(1-ethyl-5-morpholino-6-oxo-1,6-dihydropyridin-3-yl)-4-methylphenyl)-3-(trifluoromethyl)benzamide

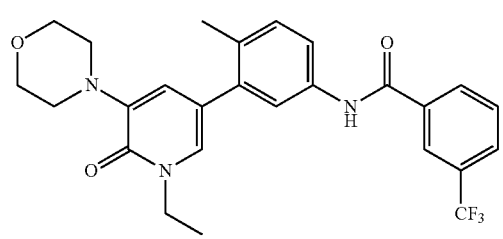 [SMILES: CCn1cc(-c2cc(NC(=O)c3cccc(C(F)(F)F)c3)ccc2C)cc(N2CCOCC2)c1=O]

$^1$H NMR (400 MHz, <cd3od>) δ ppm 1.38 (t, J=7.04 Hz, 3H) 2.31 (s, 3H) 3.11-3.21 (m, 4H) 3.82-3.91 (m, 4H) 4.11 (q, J=7.30 Hz, 2H) 6.96 (d, J=1.96 Hz, 1H) 7.29 (d, J=8.22 Hz, 1H) 7.38 (d, J=1.96 Hz, 1H) 7.58 (d, J=8.22 Hz, 1H) 7.62 (s, 1H) 7.69-7.76 (m, 1H) 7.89 (d, J=7.83 Hz, 1H) 8.20 (d, J=7.83 Hz, 1H) 8.25 (s, 1H). LCMS (m/z) (M+H)=486.2, Rt=0.95 min.

Example 156

N-(3-(6-ethoxy-5-morpholinopyridin-3-yl)-4-methylphenyl)-3-trifluoromethyl)benzamide

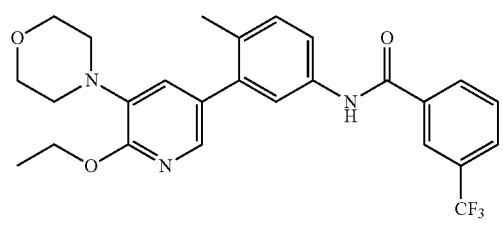 [SMILES: CCOc1ncc(-c2cc(NC(=O)c3cccc(C(F)(F)F)c3)ccc2C)cc1N1CCOCC1]

$^1$H NMR (400 MHz, <cd3od>) δ ppm 1.45 (t, J=7.04 Hz, 3H) 2.27 (s, 3H) 3.12-3.23 (m, 4H) 3.81-3.96 (m, 4H) 4.47 (q, J=7.04 Hz, 2H) 7.24-7.33 (m, 2H) 7.57-7.64 (m, 2H) 7.69-7.75 (m, 1H) 7.76 (d, J=1.96 Hz, 1H) 7.88 (d, J=7.83 Hz, 1H) 8.20 (d, J=7.83 Hz, 1H) 8.25 (s, 1H). LCMS (m/z) (M+H)=486.3, Rt=1.09 min.

Example 157

N-(1'-ethyl-2-methyl-5'-morpholino-6'-oxo-1',6'-dihydro-[3,3'-bipyridin]-5-yl)-3-(trifluoromethyl)benzamide

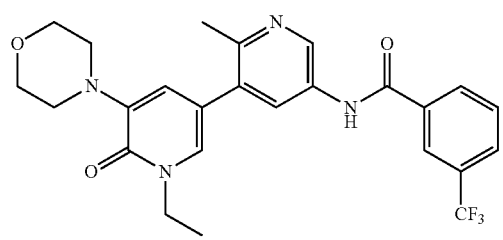 [SMILES: CCn1cc(-c2cc(NC(=O)c3cccc(C(F)(F)F)c3)cnc2C)cc(N2CCOCC2)c1=O]

1H NMR (400 MHz, <cd3od>) δ ppm 1.39 (t, J=7.24 Hz, 3H) 2.72 (s, 3H) 3.07-3.21 (m, 4H) 3.76-3.89 (m, 4H) 4.13 (q, J=7.30 Hz, 2H) 6.95 (d, J=1.96 Hz, 1H) 7.55 (d, J=2.35 Hz, 1H) 7.74-7.83 (m, 1H) 7.97 (d, J=7.83 Hz, 1H) 8.28 (d, J=7.83 Hz, 1H) 8.34 (s, 1H) 8.46 (d, J=2.35 Hz, 1H) 9.30 (d, J=2.35 Hz, 1H). LCMS (m/z) (M+H)=487.2, Rt=0.70 min.

Example 158

N-(3-(1-ethyl-5-morpholino-6-oxo-1,6-dihydropyridin-3-yl)-4-methylphenyl)-2-(trifluoromethyl)isonicotinamide

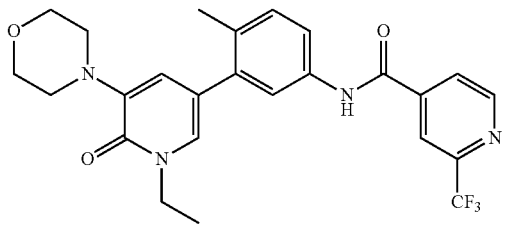 [SMILES: CCn1cc(-c2cc(NC(=O)c3ccnc(C(F)(F)F)c3)ccc2C)cc(N2CCOCC2)c1=O]

1H NMR (400 MHz, <cd3od>) δ ppm 1.29 (t, J=7.24 Hz, 3H) 2.22 (s, 3H) 3.03-3.13 (m, 4H) 3.71-3.82 (m, 4H) 4.03 (q, J=7.04 Hz, 2H) 6.93 (d, J=1.96 Hz, 1H) 7.22 (d, J=8.22 Hz, 1H) 7.32 (d, J=1.96 Hz, 1H) 7.51 (dd, J=8.22, 2.35 Hz, 1H) 7.56 (d, J=2.35 Hz, 1H) 8.02 (d, J=5.09 Hz, 1H) 8.20 (s, 1H) 8.81 (d, J=4.69 Hz, 1H). LCMS (m/z) (M+H)=487.2, Rt=0.89 min.

Example 159

N-(3-(6-ethoxy-5-morpholinopyridin-3-yl)-4-methylphenyl)-2-(trifluoromethyl)isonicotinamide

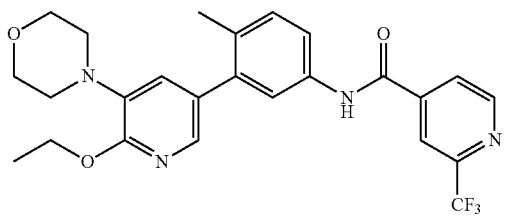 [SMILES: CCOc1ncc(-c2cc(NC(=O)c3ccnc(C(F)(F)F)c3)ccc2C)cc1N1CCOCC1]

1H NMR (400 MHz, <cd3od>) δ ppm 1.45 (t, J=7.04 Hz, 3H) 2.27 (s, 3H) 3.01-3.22 (m, 4H) 3.75-3.99 (m, 4H) 4.47 (q, J=7.04 Hz, 2H) 7.25 (d, J=1.96 Hz, 1H) 7.32 (d, J=8.22 Hz, 1H) 7.50-7.67 (m, 2H) 7.74 (d, J=1.96 Hz, 1H) 8.12 (d, J=5.09 Hz, 1H) 8.29 (s, 1H) 8.90 (d, J=5.09 Hz, 1H). LCMS (m/z) (M+H)=487.2, Rt=1.03 min.

Example 160

2-(2-cyanopropan-2-yl)-N-(3-(1-ethyl-5-morpholino-6-oxo-1,6-dihydropyridin-3-yl)-4-methylphenyl)isonicotinamide

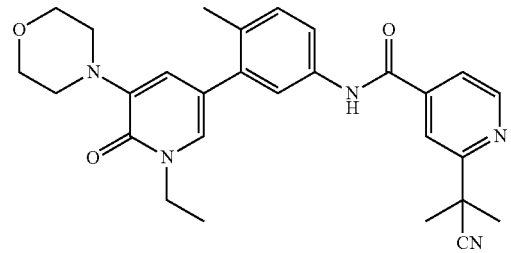 [SMILES: CCn1cc(-c2cc(NC(=O)c3ccnc(C(C)(C)C#N)c3)ccc2C)cc(N2CCOCC2)c1=O]

¹H NMR (400 MHz, <cd3od>) δ ppm 1.38 (t, J=7.04 Hz, 3H) 1.81 (s, 6H) 2.31 (s, 3H) 3.20 (d, J=3.91 Hz, 4H) 3.80-3.94 (m, 4H) 4.12 (q, J=7.04 Hz, 2H) 7.02 (d, J=1.96 Hz, 1H) 7.31 (d, J=8.61 Hz, 1H) 7.41 (d, J=1.96 Hz, 1H) 7.59 (d, J=8.22 Hz, 1H) 7.63 (s, 1H) 7.81 (d, J=4.70 Hz, 1H) 8.06 (s, 1H) 8.76 (d, J=5.09 Hz, 1H). LCMS (m/z) (M+H)=486.3, Rt=0.79 min.

Example 161

2-(2-cyanopropan-2-yl)-N-(3-(6-ethoxy-5-morpholinopyridin-3-yl)-4-methylphenyl)isonicotinamide

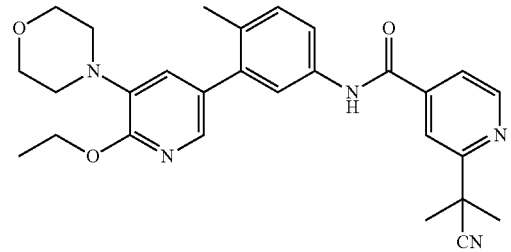 [SMILES: CCOc1ncc(-c2cc(NC(=O)c3ccnc(C(C)(C)C#N)c3)ccc2C)cc1N1CCOCC1]

¹H NMR (400 MHz, <cd3od>) δ ppm 1.46 (t, J=7.04 Hz, 3H) 1.81 (s, 6H) 2.27 (s, 3H) 3.12-3.25 (m, 4H) 3.75-3.94 (m, 4H) 4.49 (q, J=7.04 Hz, 2H) 7.24-7.36 (m, 2H) 7.47-7.67 (m, 2H) 7.75-7.90 (m, 2H) 8.06 (s, 1H) 8.75 (d, J=5.09 Hz, 1H). LCMS (m/z) (M+H)=486.3, Rt=0.93 min.

Example 162

N-(4-methyl-3-(1-methyl-6-morpholino-2-oxo-1,2-dihydropyridin-4-yl)phenyl)-3-(trifluoromethyl)benzamide

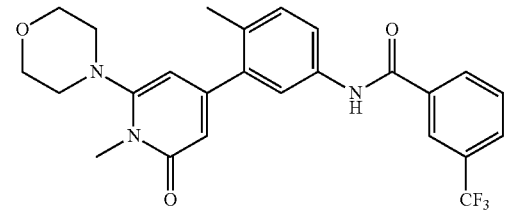 [SMILES: Cc1ccc(NC(=O)c2cccc(C(F)(F)F)c2)cc1-c1cc(N2CCOCC2)n(C)c(=O)c1]

¹H NMR (400 MHz, <cd3od>) δ ppm 2.30 (s, 3H) 3.05 (d, J=3.91 Hz, 4H) 3.66 (s, 3H) 3.82-3.91 (m, 4H) 6.13 (d, J=0.78 Hz, 1H) 6.31 (s, 1H) 7.31 (d, J=9.00 Hz, 1H) 7.61-7.67 (m, 2H) 7.72 (t, J=7.83 Hz, 1H) 7.89 (d, J=7.83 Hz, 1H) 8.20 (d, J=7.83 Hz, 1H) 8.25 (s, 1H). LCMS (m/z) (M+H)=472.3, Rt=0.96 min.

Example 163

N-(1',2-dimethyl-6'-morpholino-2'-oxo-1',2'-dihydro-[3,4'-bipyridin]-5-yl)-3-(trifluoromethyl)benzamide

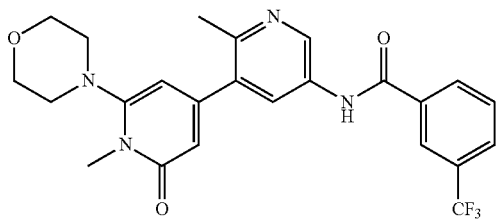 [SMILES: Cc1ncc(NC(=O)c2cccc(C(F)(F)F)c2)cc1-c1cc(N2CCOCC2)n(C)c(=O)c1]

¹H NMR (400 MHz, <cd3od>) δ ppm 2.64 (s, 3H) 2.99-3.11 (m, 4H) 3.65 (s, 3H) 3.80-3.96 (m, 4H) 6.12 (d, J=1.57 Hz, 1H) 6.35 (d, J=1.56 Hz, 1H) 7.73-7.81 (m, 1H) 7.95 (d, J=7.83 Hz, 1H) 8.26 (d, J=7.83 Hz, 1H) 8.33 (s, 1H) 8.36 (d, J=2.35 Hz, 1H) 9.21 (d, J=2.35 Hz, 1H). LCMS (m/z) (M+H)=473.2, Rt=0.69 min.

Example 164

N-(4-methyl-3-(1-methyl-5-morpholino-6-oxo-1,6-dihydropyridazin-3-yl)phenyl)-3-(trifluoromethyl)benzamide

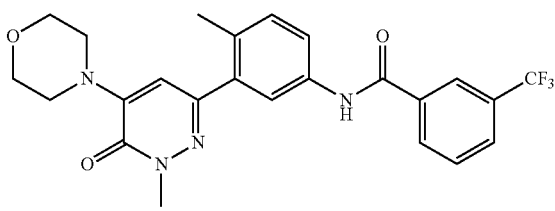 [SMILES: Cc1ccc(NC(=O)c2cccc(C(F)(F)F)c2)cc1-c1cc(N2CCOCC2)c(=O)n(C)n1]

1H NMR (400 MHz, <dmso>) δ ppm 2.29 (s, 3H) 3.37-3.51 (m, 4H) 3.67 (s, 3H) 3.68-3.77 (m, 5H) 6.59 (s, 1H) 7.28 (d, J=8.22 Hz, 1H) 7.69-7.83 (m, 3H) 7.95 (d, J=7.83 Hz, 1H) 8.21-8.27 (m, 1H) 8.29 (s, 1H) 10.47 (s, 1H). LCMS (m/z) (M+H)=473.1, Rt=0.94 min.

Example 165

4-methyl-3-(1-methyl-5-morpholino-6-oxo-1,6-dihydropyridazin-3-yl)-N-(3-(trifluoromethyl)phenyl)benzamide

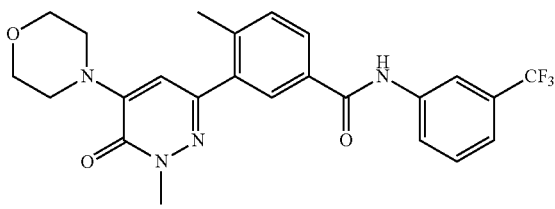 [SMILES: Cc1ccc(C(=O)Nc2cccc(C(F)(F)F)c2)cc1-c1cc(N2CCOCC2)c(=O)n(C)n1]

1H NMR (400 MHz, <dmso>) δ ppm 2.34 (s, 3H) 3.26 (br. s., 12H) 3.43 (br. s., 4H) 3.64 (br. s., 7H) 6.62 (s, 1H) 7.32-7.46 (m, 3H) 7.48-7.59 (m, 2H) 7.89 (d, J=8.22 Hz, 1H) 7.92 (s, 1H) 8.00 (d, J=7.83 Hz, 1H) 8.18 (s, 1H) 10.46 (s, 1H). LCMS (m/z) (M+H)=473.1, Rt=1.00 min.

Example 166

N-(6-methyl-5-(1-methyl-5-morpholino-6-oxo-1,6-dihydropyridazin-3-yl)pyridin-3-yl)-3-(trifluoromethyl)benzamide

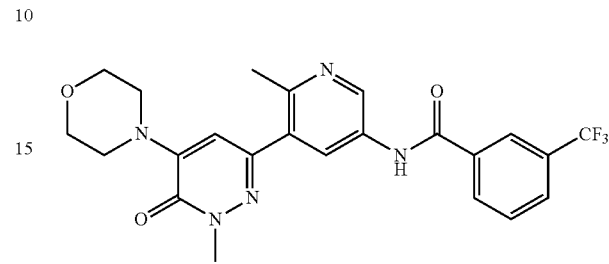

1H NMR (400 MHz, <dmso>) δ ppm 2.56 (s, 3H) 3.40-3.54 (m, 4H) 3.62-3.77 (m, 8H) 6.72 (s, 1H) 7.75-7.87 (m, 1H) 8.00 (d, J=7.83 Hz, 1H) 8.25-8.31 (m, 2H) 8.33 (s, 1H) 8.99 (d, J=2.35 Hz, 1H) 10.84 (s, 1H). LCMS (m/z) (M+H)=474.3, Rt=0.72 min.

Example 167

2-(2-cyanopropan-2-yl)-N-(6-methyl-5-(1-methyl-5-morpholino-6-oxo-1,6-dihydropyridazin-3-yl)pyridin-3-yl)isonicotinamide

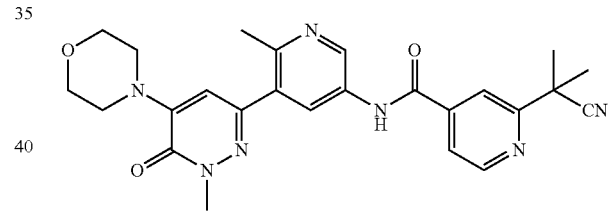

1H NMR (400 MHz, <dmso>) δ ppm 1.76 (s, 6H) 2.54 (s, 3H) 3.39-3.53 (m, 4H) 3.65-3.75 (m, 7H) 6.71 (s, 1H) 7.81-7.92 (m, 1H) 8.04 (s, 1H) 8.22 (d, J=2.35 Hz, 1H) 8.83 (d, J=5.09 Hz, 1H) 8.94 (d, J=1.96 Hz, 1H) 10.90 (s, 1H). LCMS (m/z) (M+H)=474.2, Rt=0.68 min.

Example 168

2-(2-cyanopropan-2-yl)-N-(6-methyl-5-(1-methyl-5-morpholino-6-oxo-1,6-dihydropyridazin-3-yl)pyridin-3-yl)isonicotinamide

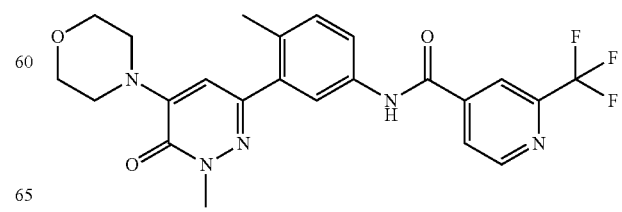

1H NMR (400 MHz, <dmso>) δ ppm 2.29 (s, 3H) 3.43-3.52 (m, 8H) 3.67 (s, 3H) 3.68-3.76 (m, 4H) 6.59 (s, 1H) 7.31 (d, J=8.22 Hz, 1H) 7.69-7.79 (m, 2H) 8.18 (d, J=4.30 Hz, 1H) 8.36 (s, 1H) 8.98 (d, J=5.09 Hz, 1H) 10.69 (s, 1H). LCMS (m/z) (M+H)=474.2, Rt=0.94 min.

The compounds listed below were prepared using methods similar to those described in Method 1 using the appropriate starting materials and purified via preparative HPLC to yield the corresponding TFA salt upon lyophilization.

Example 169

N-(3-(4-ethyl-6-morpholino-5-oxo-4,5-dihydropyrazin-2-yl)-4-methylphenyl)-3-(trifluoromethyl)benzamide

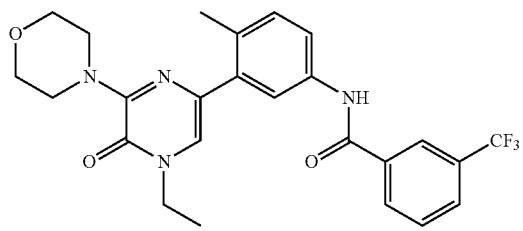 [SMILES: CCn1cc(-c2cc(NC(=O)c3cccc(C(F)(F)F)c3)ccc2C)nc(N2CCOCC2)c1=O]

Method 1 was followed using N-(4-methyl-3-(6-morpholino-5-oxo-4,5-dihydropyrazin-2-yl)phenyl)-3-(trifluoromethyl)benzamide (1.0 equiv.), iodoethane (1.2 equiv.) and potassium carbonate (2.0 equiv.) at room temperature. ¹H NMR (400 MHz, <cd3od>) δ ppm 1.38 (t, J=7.24 Hz, 3H) 2.39 (s, 3H) 3.80 (s, 8H) 4.02 (q, J=7.30 Hz, 2H) 7.02-7.31 (m, 2H) 7.57 (dd, J=8.22, 1.96 Hz, 1H) 7.65-7.81 (m, 2H) 7.89 (d, J=7.83 Hz, 1H) 8.13-8.38 (m, 1H). LCMS (m/z) (M+H)= 487.4, Rt=1.02 min.

Example 170

N-(3-(4-(2,2-difluoroethyl)-6-morpholino-5-oxo-4,5-dihydropyrazin-2-yl)-4-methylphenyl)-3-(trifluoromethyl)benzamide

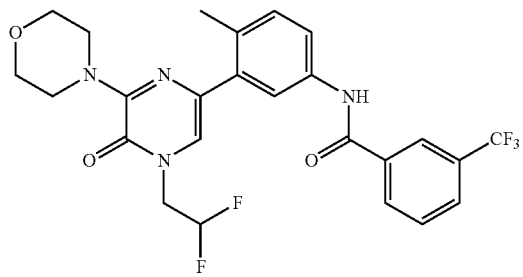 [SMILES: Cc1ccc(NC(=O)c2cccc(C(F)(F)F)c2)cc1-c1cn(CC(F)F)c(=O)c(N2CCOCC2)n1]

Method 1 was followed using N-(4-methyl-3-(6-morpholino-5-oxo-4,5-dihydropyrazin-2-yl)phenyl)-3-(trifluoromethyl)benzamide (1.0 equiv.), 1,1-difluoro-2-iodoethane (1.2 equiv.) and potassium carbonate (2.0 equiv.) at 60° C. ¹H NMR (400 MHz, <cd3od>) δ ppm 2.39 (s, 3H) 3.81 (d, J=5.09 Hz, 8H) 4.38 (td, J=14.09, 3.91 Hz, 2H) 6.02-6.44 (m, 1H) 7.14 (s, 1H) 7.26 (d, J=8.22 Hz, 1H) 7.59 (dd, J=8.22, 1.96 Hz, 1H) 7.67-7.79 (m, 2H) 7.89 (d, J=7.83 Hz, 1H) 8.16-8.34 (m, 1H). LCMS (m/z) (M+H)=523.3, Rt=1.05 min.

Synthesis of 5-(5-amino-2-methylphenyl)-1-methyl-3-morpholinopyridin-2(1H)-one

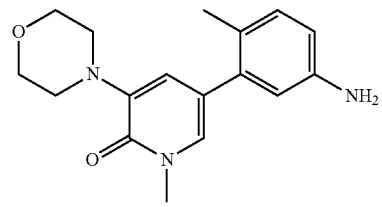 [SMILES: Cc1ccc(N)cc1-c1cc(N2CCOCC2)c(=O)n(C)c1]

To a solution of 5-bromo-1-methyl-3-morpholinopyridin-2(1H)-one (1.0 equiv.) and 4-methyl-3-(4,4,5,5-tetramethyl-1,3,2-dioxaborolan-2-yl)aniline (1.2 equiv.) in DME and 2M sodium carbonate (3:1, 0.14 M) was added PdCl₂(dppf)-DCM adduct (0.1 equiv.) in a microwave vial equipped with a stir bar. The reaction was heated to 120° C. for 15 min in the microwave. The solution was partitioned between water and ethyl acetate, the organic phase was dried with sodium sulfate, filtered and concentrated. The crude material was purified via silica gel column chromatography eluting with 100% ethyl acetate followed by 10% methanol in ethyl acetate. The pure fractions were concentrated and dried under vacuo to afford 5-(5-amino-2-methylphenyl)-1-methyl-3-morpholinopyridin-2(1H)-one in 31% yield. LCMS (m/z) (M+H)= 300.2, Rt=0.41 min.

Synthesis of 5'-amino-1,2'-dimethyl-5-morpholino-[3,3'-bipyridin]-6(1H)-one

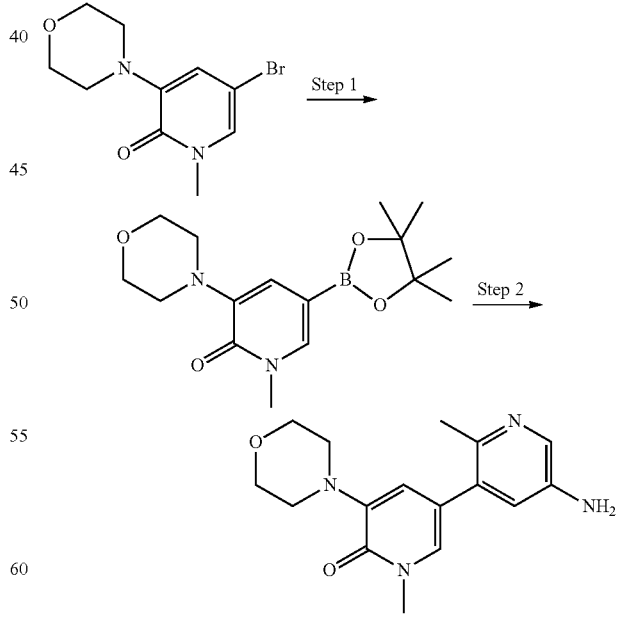

Step 1: To a 0.18 M solution of 5-bromo-1-methyl-3-morpholinopyridin-2(1H)-one (1.00 equiv.) in 1,4-dioxane was added bis(pinacolato)diboron (1.50 equiv.), potassium acetate (2.00 equiv.), and PdCl₂(dppf).CH₂Cl₂ adduct (0.10 equiv.). The reaction was irradiated at 120° C. for 20 min. The reaction was diluted with DCM (20 mL) and filtered. The filtrate was concentrated to give 5'-amino-1,2'-dimethyl-5-morpholino-[3,3'-bipyridin]-6(1H)-one as a mixture with the corresponding boronic acid as a dark brown tacky solid in quantitative yield. LCMS (m/z) (M+H)=321.0, Rt=0.65 min.

Step 2: To a 0.18 M solution of 5'-amino-1,2'-dimethyl-5-morpholino-[3,3'-bipyridin]-6(1H)-one (1.00 equiv.) in DME and 5-bromo-6-methylpyridin-3-amine (1.00 equiv.) was added PdCl$_2$(dppf).CH$_2$Cl$_2$ adduct (0.10 equiv.) and 2M aqueous sodium carbonate (3.00 equiv.). The reaction mixture was irradiated at 125° C. for 20 min. LC-MS showed primarily conversion to P. The cooled reaction mixture was diluted with 2:1 DCM:MeOH and filtered. The filtrate was concentrated and purified by flash chromatography over silica gel (ethyl acetate with a 0-15% methanol gradient) to give 5'-amino-1,2'-dimethyl-5-morpholino-[3,3'-bipyridin]-6(1H)-one as a brown solid. LCMS (m/z) (M+H)=301.0, Rt=0.33 min.

Synthesis of 6-(5-amino-2-methylphenyl)-2-methyl-4-morpholinopyridazin-3(2H)-one

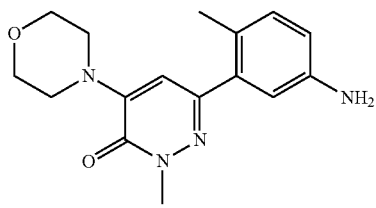 [SMILES: Cc1ccc(N)cc1-c1cc(N2CCOCC2)c(=O)n(C)n1]

To a solution of 6-chloro-2-methyl-4-morpholinopyridazin-3(2H)-one (1.0 equiv.) and 4-methyl-3-(4,4,5,5-tetramethyl-1,3,2-dioxaborolan-2-yl)aniline (1.1 equiv.) in DME and water (2:1, 0.2 M) was added PdCl$_2$(dppf).CH$_2$Cl$_2$ adduct (0.5 equiv.) and sodium carbonate (6.6 equiv.). The solution was heated in the microwave for 40 min at 120° C. Upon cooling to room temperature, the solution was diluted with ethyl acetate and water, the aqueous layer was extracted with ethyl acetate two more times, the organics were combined, dried over magnesium sulfate, filtered and concentrated to yield a brown solid. Isolated 6-(5-amino-2-methylphenyl)-2-methyl-4-morpholinopyridazin-3(2H)-one as the desired product. LCMS (m/z) (M+H)=301.1, Rt=0.49 min.

Method 3:
To a solution of the amine (1.0 equiv.) and the corresponding carboxylic acid (1.0-1.2 equiv.) in DMF (0.1 M) was added EDC (1.0-1.2 equiv.) and HOAt (1.0-1.2 equiv.) and the reaction was stirred at room temperature for 6-24 hours. Upon completion, the solution was filtered through a HPLC filter and purified via reverse phase preparative HPLC. Alternatively, the solution was partitioned between water and ethyl acetate, the organic phase was dried over sodium sulfate or magnesium sulfate, filtered and concentrated to yield a crude material that was further purified via reverse phase preparative HPLC. Upon lyophilization of the pure fractions, the desired product was isolated as the TFA salt.

Example 171

Synthesis of 3-(difluoromethyl)-N-(4-methyl-3-(1-methyl-5-morpholino-6-oxo-1,6-dihydropyridin-3-yl)phenyl)benzamide

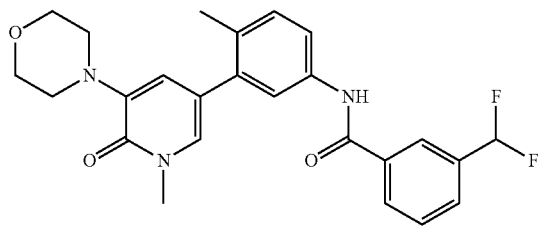 [SMILES: Cc1ccc(NC(=O)c2cccc(C(F)F)c2)cc1-c1cc(N2CCOCC2)c(=O)n(C)c1]

To a solution of 5-(5-amino-2-methylphenyl)-1-methyl-3-morpholinopyridin-2(1H)-one (1.0 equiv.) in DMF (0.07 M) was added 3-(difluoromethyl)benzoic acid (1.2 equiv.), EDC-HCl (1.2 equiv.) and HOAt (1.2 equiv.). The reaction was stirred at room temperature for 6 hours. Upon completion, the solution was filtered through a HPLC filter and purified via reverse phase preparative HPLC. Upon lyophilization of the pure fractions, 3-(difluoromethyl)-N-(4-methyl-3-(1-methyl-5-morpholino-6-oxo-1,6-dihydropyridin-3-yl)phenyl)benzamide was isolated as the TFA salt in 45% yield. LCMS (m/z) (M+H)=454.2, Rt=0.79 min. $^1$H NMR (400 MHz, <cd3od>) δ ppm 2.30 (s, 3H) 3.08-3.22 (m, 4H) 3.64 (s, 3H) 3.81-3.94 (m, 4H) 6.66-7.05 (m, 2H) 7.29 (d, J=8.61 Hz, 1H) 7.40 (d, J=2.35 Hz, 1H) 7.56 (dd, J=8.41, 2.15 Hz, 1H) 7.60-7.68 (m, 2H) 7.76 (d, J=7.43 Hz, 1H) 8.05-8.15 (m, 1H).

The compounds listed below were prepared using methods similar to those described for the preparation of Example # (Method 3) using the appropriate starting materials.

Example 172

3-(2-cyanopropan-2-yl)-N-(4-methyl-3-(1-methyl-5-morpholino-6-oxo-1,6-dihydropyridin-3-yl)phenyl)benzamide

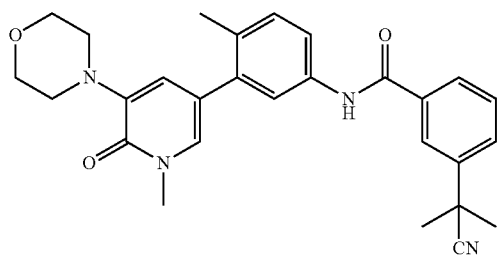 [SMILES: Cc1ccc(NC(=O)c2cccc(C(C)(C)C#N)c2)cc1-c1cc(N2CCOCC2)c(=O)n(C)c1]

$^1$H NMR (400 MHz, <cd3od>) δ ppm 1.78 (s, 6H) 2.30 (s, 3H) 3.08-3.25 (m, 4H) 3.64 (s, 3H) 3.82-3.95 (m, 4H) 7.03 (d, J=1.96 Hz, 1H) 7.29 (d, J=8.22 Hz, 1H) 7.41 (d, J=1.96 Hz, 1H) 7.51-7.66 (m, 3H) 7.76 (d, J=9.00 Hz, 1H) 7.90 (d, J=7.83 Hz, 1H) 8.08 (s, 1H). LCMS (m/z) (M+H)=471.3, Rt=0.80 min.

Example 173

3-((dimethylamino)methyl)-N-(4-methyl-3-(1-methyl-5-morpholino-6-oxo-1,6-dihydropyridin-3-yl)phenyl)-5-(trifluoromethyl)benzamide

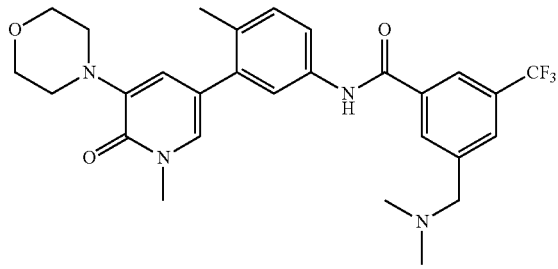 [SMILES: Cc1ccc(NC(=O)c2cc(CN(C)C)cc(C(F)(F)F)c2)cc1-c1cc(N2CCOCC2)c(=O)n(C)c1]

$^1$H NMR (400 MHz, <cd3od>) δ ppm 2.31 (s, 3H) 2.92 (s, 6H) 3.07-3.20 (m, 4H) 3.63 (s, 3H) 3.79-3.91 (m, 4H) 4.51 (s, 2H) 6.92 (d, J=1.96 Hz, 1H) 7.22-7.40 (m, 2H) 7.53-7.72 (m, 2H) 8.10 (s, 1H) 8.30-8.46 (m, 1H). LCMS (m/z) (M+H)=529.4, Rt=0.65 min.

Example 174

3-(4-ethylpiperazin-1-yl)-N-(4-methyl-3-(1-methyl-5-morpholino-6-oxo-1,6-dihydropyridin-3-yl)phenyl)-5-(trifluoromethyl)benzamide

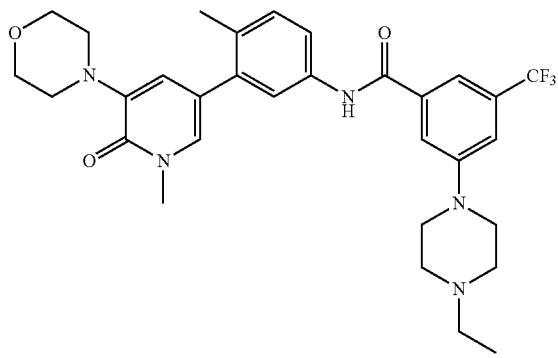 [SMILES: CCN1CCN(c2cc(C(=O)Nc3ccc(C)c(-c4cc(N5CCOCC5)c(=O)n(C)c4)c3)cc(C(F)(F)F)c2)CC1]

$^1$H NMR (400 MHz, <cd3od>) δ ppm 1.41 (t, J=7.24 Hz, 3H) 2.30 (s, 3H) 3.14 (d, J=4.30 Hz, 5H) 3.21 (d, J=18.00 Hz, 4H) 3.63 (s, 3H) 3.70 (br. s., 2H) 3.81-3.91 (m, 4H) 4.09 (d, J=12.13 Hz, 2H) 6.91 (d, J=1.96 Hz, 1H) 7.29 (d, J=7.83 Hz, 1H) 7.33 (d, J=1.96 Hz, 1H) 7.50 (s, 1H) 7.54-7.62 (m, 2H) 7.79 (d, J=4.70 Hz, 2H). LCMS (m/z) (M+H)=584.4, Rt=0.70 min.

Example 175

5-(dimethylamino)-N-(4-methyl-3-(1-methyl-5-morpholino-6-oxo-1,6-dihydropyridin-3-yl)phenyl)nicotinamide

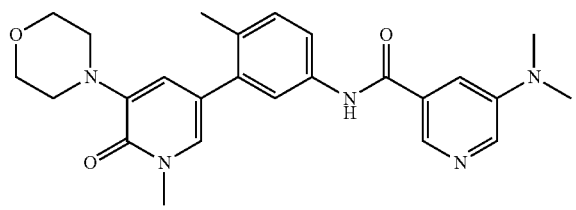 [SMILES: Cc1ccc(NC(=O)c2cncc(N(C)C)c2)cc1-c1cc(N2CCOCC2)c(=O)n(C)c1]

$^1$H NMR (400 MHz, <cd3od>) δ ppm 2.31 (s, 3H) 3.01-3.16 (m, 4H) 3.20 (s, 6H) 3.63 (s, 3H) 3.78-3.92 (m, 4H) 6.91 (d, J=2.35 Hz, 1H) 7.23-7.37 (m, 2H) 7.54-7.75 (m, 2H) 8.14-8.30 (m, 2H) 8.45 (s, 1H). LCMS (m/z) (M+H)=448.3, Rt=0.57 min.

Example 176

Synthesis of N-(4-methyl-3-(1-methyl-5-morpholino-6-oxo-1,6-dihydropyridin-3-yl)phenyl)-3-(methylsulfonyl)-5-(trifluoromethyl)benzamide

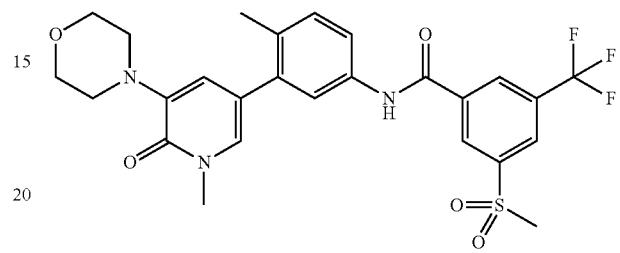

$^1$H NMR (400 MHz, <cd3od>) δ ppm 2.32 (s, 3H) 3.06-3.19 (m, 4H) 3.27 (s, 4H) 3.64 (s, 3H) 3.77-3.93 (m, 4H) 6.92 (d, J=1.96 Hz, 1H) 7.23-7.39 (m, 2H) 7.53-7.71 (m, 2H) 8.45 (s, 1H) 8.60 (s, 1H) 8.78 (s, 1H). LCMS (m/z) (M+H)=550.1, Rt=0.83.

Example 177

Synthesis of 3-(1,1-difluoroethyl)-N-(4-methyl-3-(1-methyl-5-morpholino-6-oxo-1,6-dihydropyridin-3-yl)phenyl)benzamide

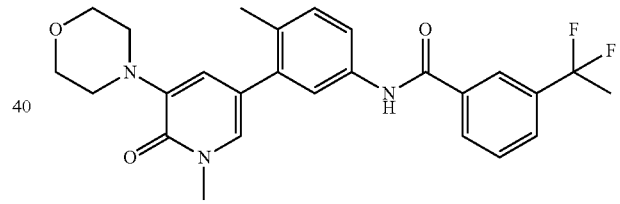

1H NMR (400 MHz, <cd3od>) δ ppm 1.98 (t, J=18.39 Hz, 3H) 2.31 (s, 3H) 3.13-3.23 (m, 4H) 3.65 (s, 3H) 3.82-3.93 (m, 4H) 7.01 (d, J=1.96 Hz, 1H) 7.29 (d, J=8.22 Hz, 1H) 7.40 (d, J=1.96 Hz, 1H) 7.53-7.67 (m, 3H) 7.76 (d, J=7.83 Hz, 1H) 8.03 (d, J=7.83 Hz, 1H) 8.11 (s, 1H). LCMS (m/z) (M+H)=468.1, Rt=0.85.

Example 178

2-(1,1-difluoroethyl)-N-(4-methyl-3-(1-methyl-5-morpholino-6-oxo-1,6-dihydropyridin-3-yl)phenyl)isonicotinamide

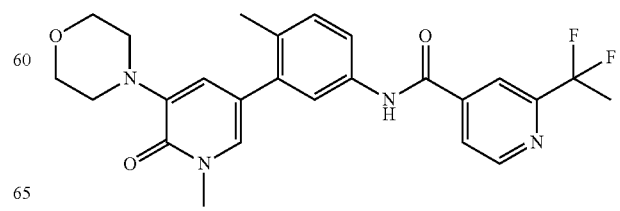

1H NMR (400 MHz, <cd3od>) δ ppm 2.04 (t, J=18.78 Hz, 3H) 2.31 (s, 3H) 3.10-3.23 (m, 4H) 3.65 (s, 3H) 3.81-3.93 (m, 4H) 7.00 (d, J=1.96 Hz, 1H) 7.31 (d, J=8.22 Hz, 1H) 7.39 (d, J=1.96 Hz, 1H) 7.55-7.68 (m, 2H) 7.96 (d, J=4.30 Hz, 1H) 8.17 (s, 1H) 8.81 (d, J=5.09 Hz, 1H). LCMS (m/z) (M+H)=469.1, Rt=0.78.

Example 179

N-(4-methyl-3-(1-methyl-5-morpholino-6-oxo-1,6-dihydropyridin-3-yl)phenyl)-2-(trifluoromethyl)isonicotinamide

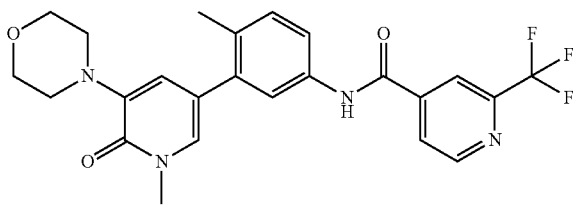

1H NMR (400 MHz, <cd3od>) δ ppm 2.31 (s, 3H) 3.10-3.22 (m, 4H) 3.65 (s, 3H) 3.80-3.93 (m, 4H) 6.98 (d, J=1.96 Hz, 1H) 7.31 (d, J=8.22 Hz, 1H) 7.38 (d, J=2.35 Hz, 1H) 7.60 (dd, J=8.22, 2.35 Hz, 1H) 7.65 (d, J=1.96 Hz, 1H) 8.12 (d, J=5.09 Hz, 1H) 8.30 (s, 1H) 8.91 (d, J=5.09 Hz, 1H). LCMS (m/z) (M+H)=473.1, Rt=0.83.

Example 181

N-(1',2-dimethyl-5'-morpholino-6'-oxo-1',6'-dihydro-[3,3'-bipyridin]-5-yl)-4-methoxy-3-(trifluoromethyl)benzamide

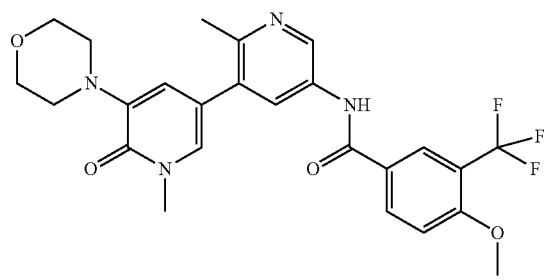 [SMILES: COc1ccc(C(=O)Nc2cnc(C)c(-c3cc(N4CCOCC4)c(=O)n(C)c3)c2)cc1C(F)(F)F]

1H NMR (400 MHz, <cd3od>) δ ppm 2.69 (s, 3H) 3.10-3.21 (m, 4H) 3.65 (s, 3H) 3.79-3.91 (m, 4H) 4.02 (s, 3H) 6.95 (d, J=1.96 Hz, 1H) 7.37 (d, J=8.61 Hz, 1H) 7.52 (d, J=1.96 Hz, 1H) 8.22-8.34 (m, 2H) 8.42 (d, J=2.35 Hz, 1H) 9.24 (d, J=2.35 Hz, 1H). LCMS (m/z) (M+H)=503.1, Rt=0.67 min.

Example 182

N-(1',2-dimethyl-5'-morpholino-6'-oxo-1',6'-dihydro-[3,3'-bipyridin]-5-yl)-4-fluoro-3-methoxybenzamide

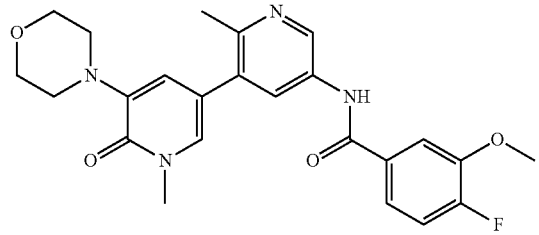 [SMILES: COc1cc(C(=O)Nc2cnc(C)c(-c3cc(N4CCOCC4)c(=O)n(C)c3)c2)ccc1F]

1H NMR (400 MHz, <cd3od>) δ ppm 2.70 (s, 3H) 3.12-3.20 (m, 4H) 3.65 (s, 3H) 3.80-3.89 (m, 4H) 3.97 (s, 3H) 6.95 (d, J=2.35 Hz, 1H) 7.27 (dd, J=10.96, 8.61 Hz, 1H) 7.53 (d, J=2.35 Hz, 1H) 7.62 (ddd, J=8.41, 4.11, 1.96 Hz, 1H) 7.75 (dd, J=8.22, 1.96 Hz, 1H) 8.43 (d, J=2.35 Hz, 1H) 9.25 (d, J=2.35 Hz, 1H). LCMS (m/z) (M+H)=453.0, Rt=0.58 min.

Example 183

N-(4-methyl-3-(1-methyl-5-morpholino-6-oxo-1,6-dihydropyridin-3-yl)phenyl)acetamide

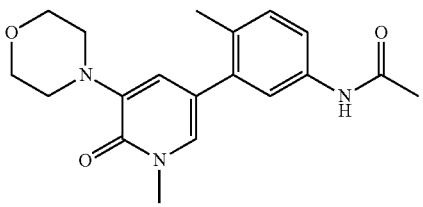 [SMILES: CC(=O)Nc1ccc(C)c(-c2cc(N3CCOCC3)c(=O)n(C)c2)c1]

1H NMR (400 MHz, <cd3od>) δ ppm 2.11 (s, 3H) 2.26 (s, 3H) 3.08-3.23 (m, 4H) 3.63 (s, 3H) 3.79-3.92 (m, 4H) 6.98 (d, J=1.96 Hz, 1H) 7.21 (d, J=8.22 Hz, 1H) 7.32-7.41 (m, 2H) 7.46 (d, J=1.96 Hz, 1H). LCMS (m/z) (M+H)=342.1, Rt=0.59.

Example 184

N-(4-methyl-3-(1-methyl-5-morpholino-6-oxo-1,6-dihydropyridin-3-yl)phenyl)-2-(methylsulfonyl)isonicotinamide

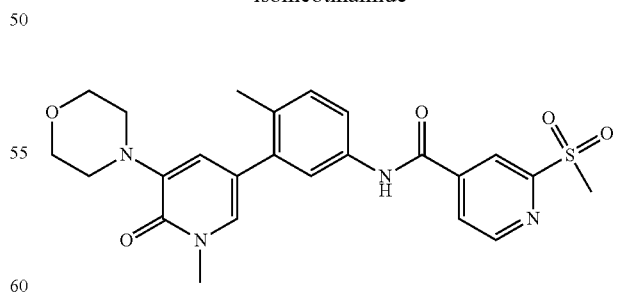

¹H NMR (400 MHz, <dmso>) δ ppm 2.27 (s, 3H) 3.11 (br. s., 4H) 3.35 (s, 5H) 3.50 (s, 5H) 3.72 (br. s., 4H) 6.70 (s, 1H) 7.30 (d, J=8.22 Hz, 1H) 7.41 (s, 1H) 7.64 (s, 1H) 7.69 (d, J=8.22 Hz, 1H) 8.22 (d, J=4.69 Hz, 1H) 8.53 (s, 1H) 9.00 (d, J=5.09 Hz, 1H) 10.76 (s, 1H). LCMS (m/z) (M+H)=483.3, Rt=0.65.

Example 185

N-(4-methyl-3-(1-methyl-5-morpholino-6-oxo-1,6-dihydropyridin-3-phenyl)-3-(methylsulfonyl)benzamide

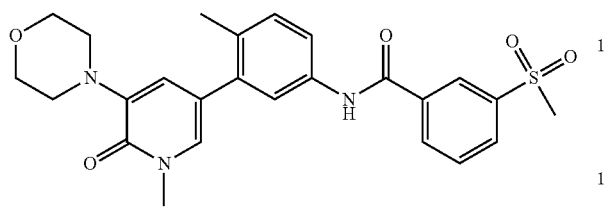

1H NMR (400 MHz, <dmso>) δ ppm 2.27 (s, 3H) 3.11 (br. s., 4H) 3.29 (s, 3H) 3.50 (s, 4H) 3.68-3.77 (m, 5H) 6.71 (d, J=1.96 Hz, 1H) 7.28 (d, J=8.22 Hz, 1H) 7.41 (d, J=1.96 Hz, 1H) 7.63 (d, J=1.96 Hz, 1H) 7.69 (dd, J=8.22, 1.96 Hz, 1H) 7.83 (t, J=7.83 Hz, 1H) 8.14 (d, J=7.83 Hz, 1H) 8.29 (d, J=8.22 Hz, 1H) 8.48 (s, 1H) 10.49 (s, 1H). LCMS (m/z) (M+H)=482.3, Rt=0.68.

Example 189

2-(difluoromethyl)-N-(4-methyl-3-(1-methyl-5-morpholino-6-oxo-1,6-dihydropyridazin-3-yl)phenyl)isonicotinamide

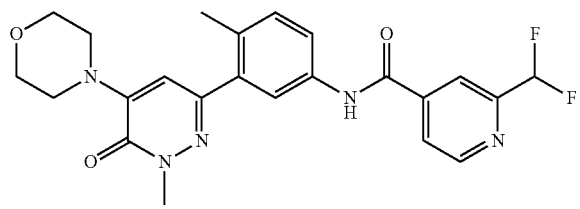 [SMILES: Cc1ccc(NC(=O)c2ccnc(C(F)F)c2)cc1-c1cc(N2CCOCC2)c(=O)n(C)n1]

1H NMR (400 MHz, <dmso>) δ ppm 2.31 (br. s., 1H) 3.42-3.49 (m, 5H) 3.67 (s, 3H) 3.68-3.74 (m, 4H) 6.59 (s, 1H) 7.07 (s, 1H) 7.30 (d, J=8.22 Hz, 1H) 7.74 (s, 2H) 8.05 (d, J=5.09 Hz, 1H) 8.17 (s, 1H) 8.89 (d, J=5.09 Hz, 1H) 10.65 (s, 1H), LCMS (m/z) (M+H)=456.0, Rt=0.76 min.

Example 190

3-(difluoromethyl)-N-(4-methyl-3-(1-methyl-5-morpholino-6-oxo-1,6-dihydropyridazin-3-yl)phenyl)benzamide

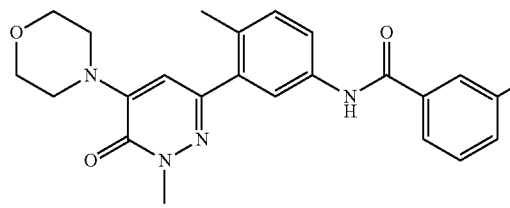

1H NMR (400 MHz, <dmso>) δ ppm 2.23-2.33 (m, 3H) 3.37-3.52 (m, 4H) 3.61-3.77 (m, 7H) 6.59 (s, 1H) 7.23-7.32 (m, 1H) 7.60-7.71 (m, 1H) 7.71-7.80 (m, 3H) 8.07-8.18 (m, 2H) 10.41 (s, 1H), LCMS (m/z) (M+H)=455.0, Rt=0.87 min.

Example 191

2-(2-cyanopropan-2-yl)-N-(4-methyl-3-(1-methyl-5-morpholino-6-oxo-1,6-dihydropyridazin-3-yl)phenyl)isonicotinamide

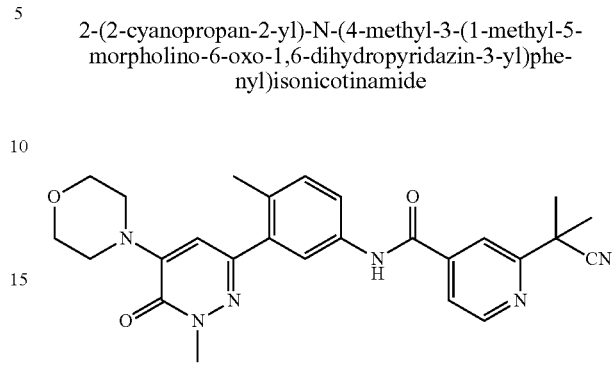

1H NMR (400 MHz, <dmso>) δ ppm 1.75 (s, 6H) 2.29 (s, 3H) 3.36-3.51 (m, 4H) 3.57-3.76 (m, 7H) 6.59 (s, 1H) 7.30 (d, J=8.22 Hz, 1H) 7.65-7.78 (m, 2H) 7.85 (d, J=3.91 Hz, 1H) 7.94-8.06 (m, 1H) 8.79 (d, J=5.09 Hz, 1H) 10.56 (s, 1H), LCMS (m/z) (M+H)=473.4, Rt=0.84 min.

Example 192

Synthesis of 4-(difluoromethyl)-3-(1-methyl-5-morpholino-6-oxo-1,6-dihydropyridin-3-yl)-N-(3-(trifluoromethyl)phenyl)benzamide

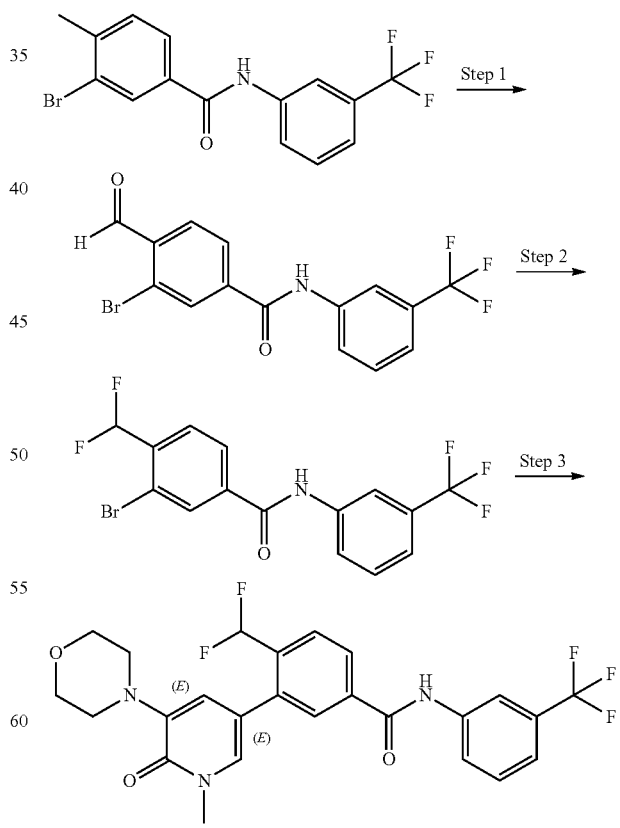

Step 1: MnO$_2$ (8.0 equiv.) was added into a solution of 3-bromo-4-(hydroxymethyl)-N-(3-(trifluoromethyl)phenyl)

benzamide (1.0 equiv.) in DCM (0.14 M). The suspension was stirred at rt for 1 hr. The mixture was filtered over celite and concentrated to yield 3-bromo-4-formyl-N-(3-(trifluoromethyl)phenyl)benzamide in 100% yield. LC/MS (m/z)=373.9 (MH+), R$_t$=0.0.94 min.

Step 2: To a cooled solution of 3-bromo-4-formyl-N-(3-(trifluoromethyl)phenyl)benzamide (1.0 equiv.) in dry CH$_2$Cl$_2$ (0.18 M), (diethylamino)sulfur trifluoride (3.5 equiv.) was added under vigorous stirring. The resulting reaction mixture was stirred at 0° C. for 2 hrs. Quenched the reaction with sat NaHCO$_3$ and extracted with DCM. The organic layer was washed with Brine, filtered over Na$_2$SO$_4$ and concentrated to yield 3-bromo-4-(difluoromethyl)-N-(3-(trifluoromethyl)phenyl)benzamide in 47% yield. LC/MS (m/z)=393.9 (MH+), R$_t$=1.11 min.

Step 3: Method 2 was followed using 1-methyl-3-morpholino-5-(4,4,5,5-tetramethyl-1,3,2-dioxaborolan-2-yl)pyridin-2(1H)-one and 3-bromo-4-(difluoromethyl)-N-(3-(trifluoromethyl)phenyl)benzamide to give 4-(difluoromethyl)-3-(1-methyl-5-morpholino-6-oxo-1,6-dihydropyridin-3-yl)-N-(3-(trifluoromethyl)phenyl)benzamid in 8% yield. LC/MS (m/z)=508.1 (MH+), Rt=0.98 min. $^1$H NMR (400 MHz, <cd3od>) δ ppm 3.12-3.21 (m, 4H), 3.64 (s, 3H), 3.80-3.90 (m, 4H), 6.96 (d, J=1.96 Hz, 2H), 7.41 (d, J=1.96 Hz, 2H), 7.52-7.62 (m, 1H), 7.84-7.92 (m, 1H), 7.97 (br. s., 2H), 8.05-8.12 (m, 1H), 8.14-8.20 (m, 1H).

Example 193

Synthesis of methyl (2-(2'-methyl-5-morpholino-6-oxo-5'-(3-trifluoromethyl)benzamido)-[3,3'-bipyridin]-1(6H)-yl)ethyl)carbamate

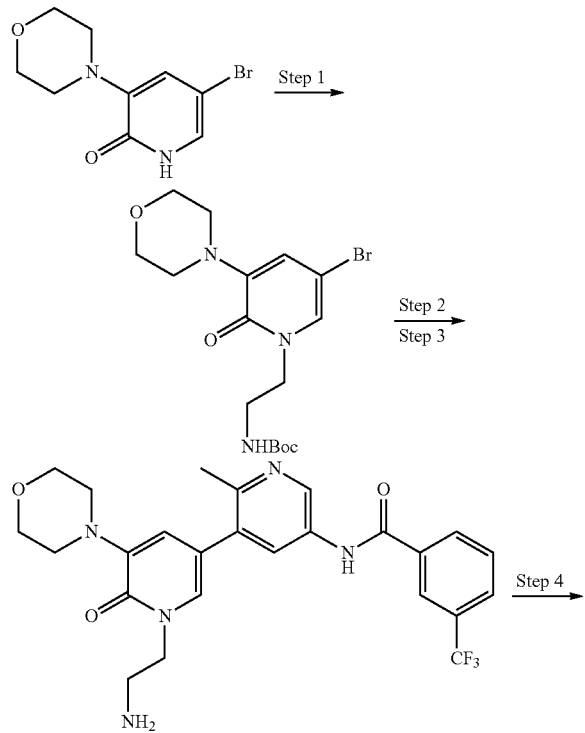

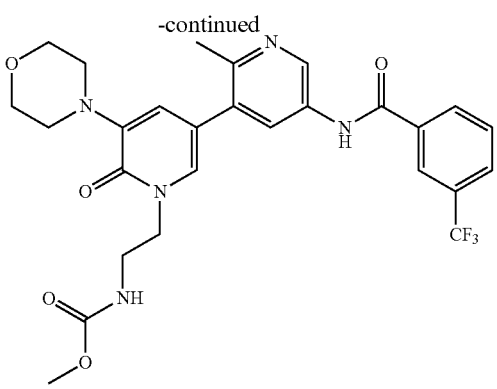

Step 1: A 0.3 M solution of 5-bromo-3-morpholinopyridin-2(1H)-one (1.00 equiv.) in DMF was treated with sodium hydride (1.20 equiv.). The mixture was stirred for 15 min at ambient temperature. Tert-butyl (2-bromoethyl)carbamate (1.20 equiv.) was added. The mixture was stirred at 60° C. for 3 hr. The cooled reaction mixture was diluted with water and extracted with ethyl acetate. The combined organics were washed with saturated aqueous sodium bicarbonate, dried over sodium sulfate, filtered, and concentrated to give tert-butyl (2-(5-bromo-3-morpholino-2-oxopyridin-1(2H)-yl)ethyl)carbamate. LCMS (m/z) (M+H)=402.1/404.1, Rt=0.78 min.

Step 2: Tert-butyl (2-(2'-methyl-5-morpholino-6-oxo-5'-(3-(trifluoromethyl)benzamido)-[3,3'-bipyridin]-1(6H)-yl)ethyl)carbamate was prepared using methods similar to those described for the preparation of Example # using the appropriate starting materials. LCMS (m/z) (M+H)=602.2, Rt=0.78 min.

Step 3: A 0.1 M solution of tert-butyl (2-(2'-methyl-5-morpholino-6-oxo-5'-(3-(trifluoromethyl)benzamido)-[3,3'-bipyridin]-1(6H)-yl)ethyl)carbamate (1.00 equiv.) in 1:1 DCM:TFA was stirred for 15 min at ambient temperature. The reaction mixture was concentrated. The residue was basified with aqueous sodium carbonate and extracted with DCM. The combined extracts were dried over sodium sulfate, filtered, and concentrated to give crude N-(1'-(2-aminoethyl)-2-methyl-5'-morpholino-6'-oxo-1',6'-dihydro-[3,3'-bipyridin]-5-yl)-3-(trifluoromethyl)benzamide which was used without further purification. LCMS (m/z) (M+H)=502.2, Rt=0.58 min.

Step 4: To a 0.2 M solution of N-(1'-(2-aminoethyl)-2-methyl-5'-morpholino-6'-oxo-1',6'-dihydro-[3,3-bipyridin]-5-yl)-3-(trifluoromethyl)benzamide (1.0 equiv.) in DCM was added and triethylamine (3.00 equiv.) and methyl chloroformate (1.10 equiv.). The reaction was stirred at ambient temperature for 20 min. The reaction was quenched by the addition of water and concentrated. The crude material was purified via preparative reverse phase HPLC. Upon lyophilization of the pure fractions, methyl (2-(2'-methyl-5-morpholino-6-oxo-5'-(3-(trifluoromethyl)benzamido)-[3,3'-bipyridin]-1(6H)-yl)ethyl)carbamate was isolated as the TFA salt in 7% yield. $^1$H NMR (400 MHz (400 MHz, <cd3od>) δ ppm 2.69 (s, 3H) 3.10-3.21 (m, 5H) 3.47-3.62 (m, 5H) 3.80-3.90 (m, 4H) 4.10-4.20 (m, 2H) 6.93 (d, J=2.05 Hz, 1H) 7.41 (d, J=2.10 Hz, 1H) 7.73-7.83 (m, 1H) 7.96 (dd, J=7.87, 0.68 Hz, 1H) 8.27 (d, J=7.87 Hz, 1H) 8.33 (s, 1H) 8.43 (d, J=2.20 Hz, 1H) 9.18 (d, J=2.15 Hz, 1H). LCMS (m/z) (M+H)=560.3, Rt=0.68 min.

The compound listed below was prepared using methods similar to those described for the preparation of Example 193 using the appropriate starting materials.

Example 194

Methyl (2-(5-(2-methyl-5-(3-(trifluoromethyl)benzamido)phenyl)-3-morpholino-2-oxopyridin-1(2H)-yl)ethyl)carbamate

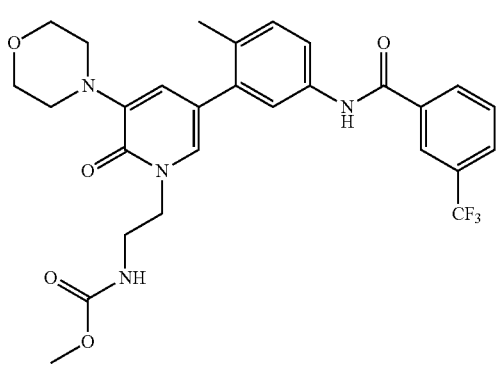 [SMILES: COC(=O)NCCn1cc(-c2cc(NC(=O)c3cccc(C(F)(F)F)c3)ccc2C)cc(N2CCOCC2)c1=O]

$^1$H NMR (400 MHz, <cd3od>) δ ppm 2.30 (s, 3H) 3.16 (br. s., 4H) 3.48-3.55 (m, 2H) 3.56 (s, 3H) 3.81-3.91 (m, 4H) 4.08-4.19 (m, 2H) 6.97 (d, J=1.57 Hz, 1H) 7.24 (d, J=1.56 Hz, 1H) 7.29 (d, J=8.22 Hz, 1H) 7.55 (d, J=8.22 Hz, 1H) 7.62 (s, 1H) 7.69-7.78 (m, 1H) 7.89 (d, J=7.83 Hz, 1H) 8.20 (d, J=7.83 Hz, 1H) 8.25 (s, 1H). LCMS (m/z) (M+H)=559.3, Rt=0.89 min.

Synthesis of 5-bromo-1-ethyl-3-(trifluoromethyl)pyridin-2(1H)-one

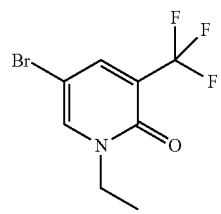

In a round bottom flask equipped with a stir bar and purged with nitrogen was added 5-bromo-3-(trifluoromethyl)pyridin-2-ol (1.0 equiv.), potassium carbonate (2.0 equiv.) and DMF (0.2 M). The mixture was stirred at room temperature and iodoethane (1.2 equiv.) was added via syringe. The mixture was warmed to 35° C. for 4 hours at which time LCMS indicated full conversion. The reaction was worked up by partitioning between water and ethyl acetate, the aqueous phase was extracted 3 more times with ethyl acetate, the organics were combined, washed with brine, dried with sodium sulfate, filtered and concentrated to yield 5-bromo-1-ethyl-3-(trifluoromethyl)pyridin-2(1H)-one (67%). $^1$H NMR (400 MHz, <cdcl3>) δ ppm 1.32-1.50 (m, 3H) 4.04 (q, J=7.17 Hz, 2H) 7.63 (br. s., 1H) 7.78 (br. s., 1H). LCMS (m/z) (M+H)=269.1/271.1, Rt=0.72 min

Example 196

N-(3-(4-methoxy-6-morpholinopyridin-2-yl)-4-methylphenyl)-3-(trifluoromethyl)benzamide

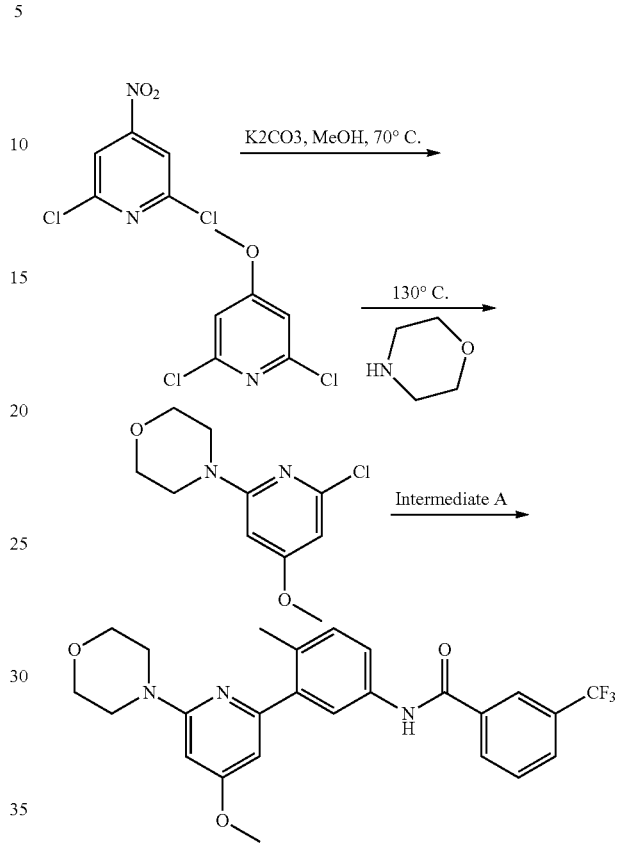

Step 1: A mixture of 2,6-dichloro-4-nitropyridine (1.0 equiv.), potassium carbonate (3 equiv.) and methanol (20 equiv.) were heated to 70° C. for 25 min in the microwave. The reaction mixture was diluted with methanol and was decanted from remaining solids. After concentration, the mixture was partitioned between water and EtOAc. The organic phase was washed with brine and dried over sodium sulfate. The solution was concentrated and dried under vacuo to give 2,6-dichloro-4-methoxypyridine in 88% yield. LCMS (m/z) (M+H)=177.9/179.9, Rt=0.72 min.

Step 2: A mixture of 2,6-dichloro-4-methoxypyridine (1.0 equiv.) and morpholine (20 equiv.) were heated to 130° C. for 40 min in the microwave. The reaction mixture was centrifuged and the soluble portion was removed from solids. Water was added to the soluble portion which resulted in precipitation of product. This mixture was centrifuged and the soluble portion was discarded. The remaining solids were partitioned between water and EtOAc. The organic phase was washed with brine and dried over sodium sulfate. The solution was concentrated and dried under vacuo to give 4-(6-chloro-4-methoxypyridin-2-yl)morpholine in 43% yield. LCMS (m/z) (M+H)=229.1, Rt=0.76 min.

Step 3: A mixture of 4-(6-chloro-4-methoxypyridin-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. After concentration, the crude material was purified via preparative reverse phase HPLC. Upon lyophilization of the pure fractions, N-(3-(4-methoxy-6-morpholinopyridin-2-yl)-4-methylphenyl)-3-(trifluoromethyl)benzamide was isolated as the TFA salt in 34% yield. LCMS (m/z) (M+H)=472.4, Rt=0.81 min.

Example 197

N-(4-methyl-3-(6-morpholino-4-oxo-1,4-dihydropyridin-2-yl)phenyl)-3-(trifluoromethyl)benzamide

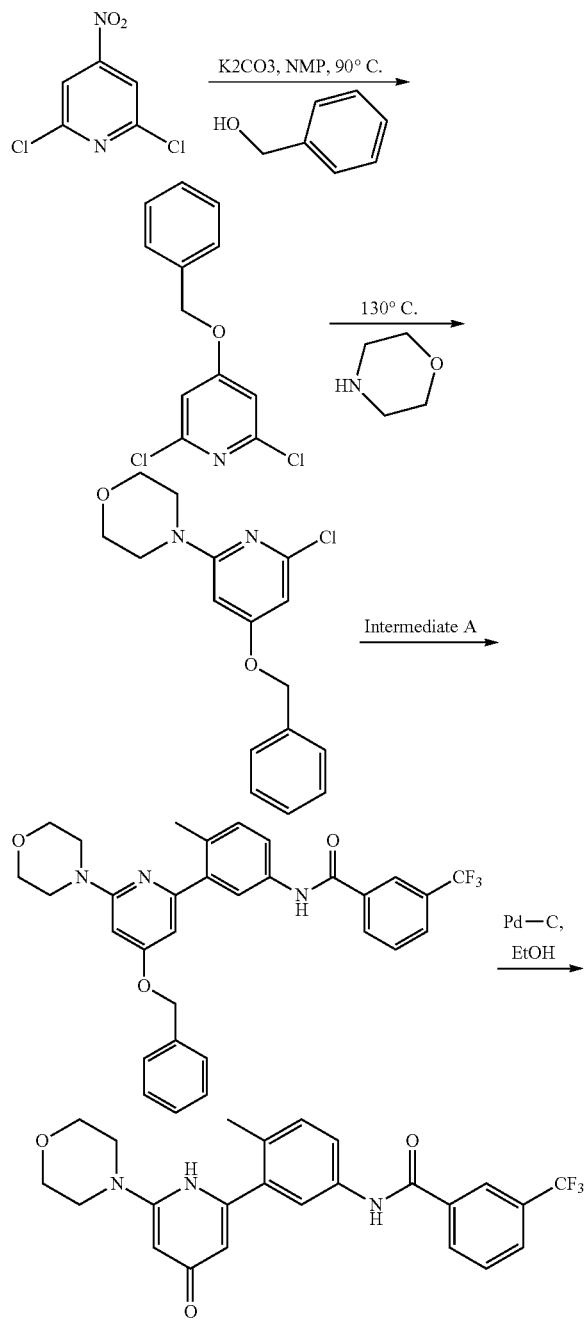

Step 1: A mixture of 2,6-dichloro-4-nitropyridine (1.0 equiv.), potassium carbonate (2 equiv.) and benzyl alcohol (2.4 equiv.) in NMP (4 M) were heated to 90° C. for 2 h in the microwave. The mixture was partitioned between water and EtOAc. The organic phase was washed with brine and dried over sodium sulfate. The solution was concentrated and dried under vacuo to give crude 4-(benzyloxy)-2,6-dichloropyridine and was used in the next step without further purification. LCMS (m/z) (M+H)=254.0/256.0, Rt=1.05 min.

Step 2: A mixture of 4-(benzyloxy)-2,6-dichloropyridine (1.0 equiv.) and morpholine (1.2 equiv.) in NMP (2 M) were heated to 130° C. for 1 h in the microwave. The reaction mixture was partitioned between water and EtOAc. The organic phase was washed with brine and dried over sodium sulfate. The solution was concentrated and dried under vacuo to give crude 4-(4-(benzyloxy)-6-chloropyridin-2-yl)morpholine and was used in the next step without further purification. LCMS (m/z) (M+H)=305.0, Rt=1.10 min.

Step 3: A mixture of 4-(4-(benzyloxy)-6-chloropyridin-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. The solution was concentrated and dried under vacuo to give crude N-(3-(4-(benzyloxy)-6-morpholinopyridin-2-yl)-4-methylphenyl)-3-(trifluoromethyl)benzamide and was used in the next step without further purification. LCMS (m/z) (M+H)=548.2, Rt=0.99 min.

Step 4: To N-(3-(4-(benzyloxy)-6-morpholinopyridin-2-yl)-4-methylphenyl)-3-(trifluoromethyl)benzamide (1.0 equiv.) in EtOH flushed with nitrogen was added Pd—C (0.2 equiv.). This mixture was then exposed to an atmosphere of hydrogen. After stirring for 4 h, the hydrogen atmosphere was replaced with nitrogen and the mixture was filtered over celite. After concentration, the crude material was purified via preparative reverse phase HPLC. Upon lyophilization of the pure fractions, N-(4-methyl-3-(6-morpholino-4-oxo-1,4-dihydropyridin-2-yl)phenyl)-3-(trifluoromethyl)benzamide was isolated as the TFA salt in 10% yield over four steps. $^1$H NMR (400 MHz, <dmso>) δ ppm 2.26 (s, 3H) 3.69 (br. s., 4H) 6.20-6.50 (m, 1H) 7.30 (br. s., 1H) 7.61-7.85 (m, 3H) 7.96 (d, J=7.83 Hz, 1H) 8.17-8.37 (m, 2H) 10.50 (br. s., 1H). LCMS (m/z) (M+H)=458.1, Rt=0.78 min.

Example 198

N-(4-methyl-3-(2-morpholinothiazol-5-yl)phenyl)-3-(trifluoromethyl)benzamide

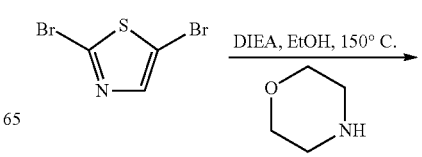

-continued

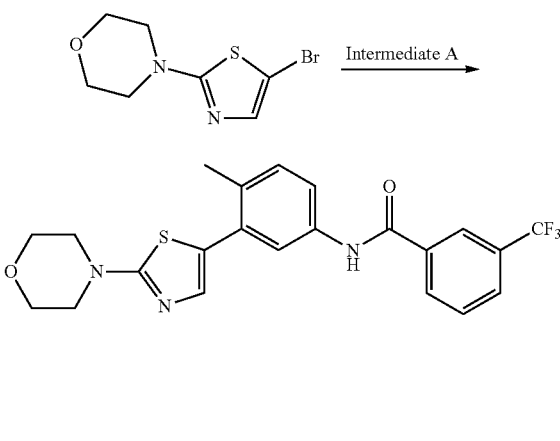

Step 1: A solution of 2,5-dibromothiazole (1.0 equiv.), morpholine (1.5 equiv.) and triethylamine (4 equiv.) were heated to 150° C. for 2 h in the microwave. After concentration, the mixture was partitioned between water and EtOAc. The organic phase was washed with brine and dried over sodium sulfate. The solution was concentrated and dried under vacuo to give crude N-(4-methyl-3-(2-morpholinothiazol-5-yl)phenyl)-3-(trifluoromethyl)benzamide and was used in the next step without further purification. LCMS (m/z) (M+H)=448.2, Rt=0.83 min.

Step 2: A mixture of 4-(5-bromothiazol-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. After concentration, the crude material was purified via preparative reverse phase HPLC. Upon lyophilization of the pure fractions, N-(4-methyl-3-(2-morpholinothiazol-5-yl)phenyl)-3-(trifluoromethyl)benzamide was isolated as the TFA salt in 15% yield. $^1$H NMR (400 MHz, <dmso>) δ ppm 2.36 (s, 3H) 3.40-3.43 (m, 4H) 3.70-3.74 (m, 4H) 7.22-7.33 (m, 2H) 7.63 (dd, J=8.22, 1.96 Hz, 1H) 7.72-7.84 (m, 2H) 7.95 (d, J=7.43 Hz, 1H) 8.19-8.33 (m, 2H) 10.45 (s, 1H). LCMS (m/z) (M+H)=448.2, Rt=0.83 min.

Example 199

N-(4-methyl-3-(2-morpholinothiazol-4-yl)phenyl)-3-(trifluoromethyl)benzamide

Starting with 2,4-dibromothiazole, the product was synthesized using the same procedure as for N-(4-methyl-3-(2-morpholinothiazol-5-yl)phenyl)-3-(trifluoromethyl)benzamide $^1$H NMR (400 MHz, <dmso>) δ ppm 2.39 (s, 3H) 3.68-3.77 (m, 4H) 6.94 (s, 1H) 7.17-7.27 (m, 1H) 7.68 (dd, J=8.41, 2.15 Hz, 1H) 7.77 (t, J=7.83 Hz, 1H) 7.89-8.00 (m, 2H) 8.19-8.34 (m, 2H) 10.43 (s, 1H). LCMS (m/z) (M+H)=448.2, Rt=0.85 min.

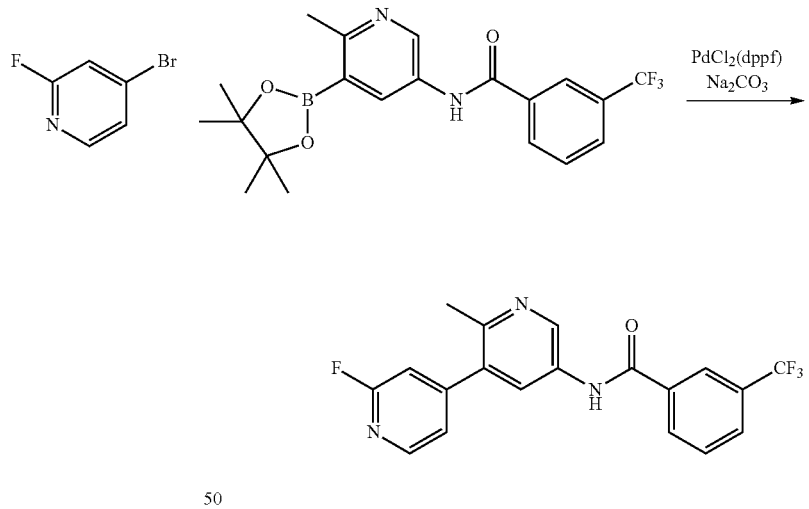

Synthesis of N-(2'-fluoro-2-methyl-[3,4'-bipyridin]-5-yl)-3-(trifluoromethyl)benzamide To a solution of 4-bromo-2-fluoropyridine (1.0 equiv.) and N-(6-methyl-5-(4,4,5,5-tetramethyl-1,3,2-dioxaborolan-2-yl)pyridin-3-yl)-3-(trifluoromethyl)benzamide (1.0 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 110° C. for 15 min in the microwave. The reaction was quenched with water and extracted with ethyl acetate. The combined organic phase was dried with sodium sulfate, filtered and concentrated. The crude material N-(4-methyl-3-(2-morpholinopyridin-4-yl)phenyl)-3-(trifluoromethyl)benzamide was isolated as a solid and used in the subsequent step without purification. LCMS (m/z) (M+H)=376.0, Rt=0.71 min.

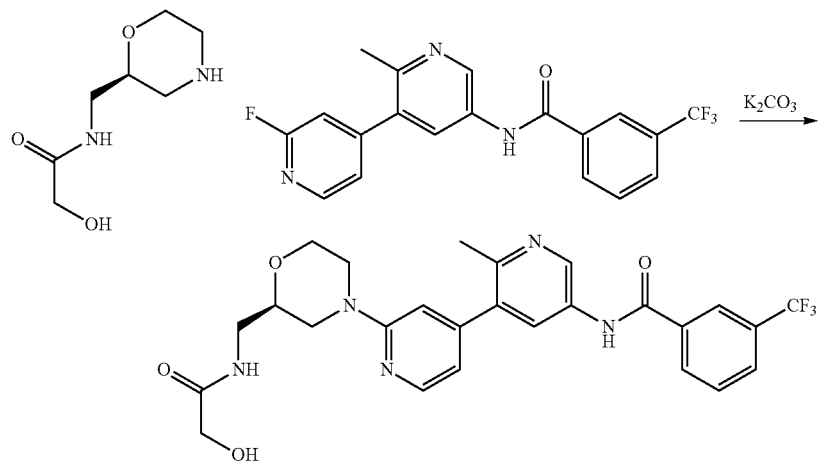

Example 215

2-(difluoromethyl)-N-(4-methyl-3-(1-methyl-5-morpholino-6-oxo-1,6-dihydropyridin-3-yl)phenyl)isonicotinamide

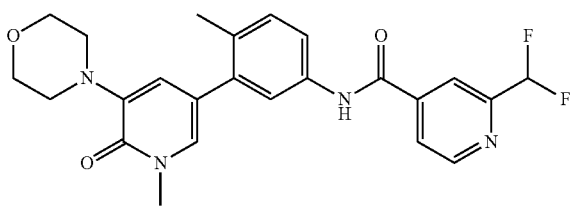 [SMILES: Cc1ccc(NC(=O)c2ccnc(C(F)F)c2)cc1-c1cc(N2CCOCC2)c(=O)n(C)c1]

1H NMR (400 MHz, <cd3od>) ppm 2.31 (s, 3H) 3.17-3.22 (m, 4H) 3.65 (s, 3H) 3.85-3.91 (m, 4H) 6.67-6.98 (m, 1H) 7.02 (d, J=1.96 Hz, 1H) 7.31 (d, J=8.22 Hz, 1H) 7.40 (d, J=1.96 Hz, 1H) 7.59 (dd, J=8.41, 2.15 Hz, 1H) 7.65 (d, J=1.96 Hz, 1H) 8.01 (d, J=5.09 Hz, 1H) 8.17 (s, 1H) 8.83 (d, J=5.09 Hz, 1H). LCMS (m/z) (M+H)=455.1, Rt=0.75 min.

The activity of a compound according to the present invention can be assessed by well-known in vitro & in vivo methods. Raf inhibition data provided herein was obtained using the following procedures.

Example 300

In Vitro Raf Activity Determination

The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf FL refers to the full-length protein described above; C-Raf TR refers to a truncated C-Raf protein, a Δ1-324 deletion mutant.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials
Assay buffer: Assay buffer: 50 mM Tris, pH 7.5, 50 mM NaCl, 10 mM MgCl$_2$, 0.05% Bovine Serum Albumin (BSA), 0.01% Tween-20 1 mM dithiothreitol (DTT)
Stop/Bead buffer: 25 mM ethylenediaminetetraacetic acid (EDTA), 50 mM Tris pH 7.5, 0.01% Tween® 20
Materials
b-Raf(V600E), active
Full-length C-Raf with activating mutations
C-Raf TR: Δ1-324 deletion mutant with activating mutations biotinylated Mek, kinase dead
Alpha Screen detection kit (available from PerkinElmer™, #6760617R)
Anti phospho-MEK1/2 (available from Cell Signaling Technology, Inc. #9121)
384 well low volume assay plates (White Greiner® plates)
Assay Conditions
b-Raf(V600E) approximately 4 pM
c-Raf 4 pM
biotinylated Mek, Kinase dead approximately 10 nM
ATP 10 μM for BRAF(V600E) and 3 uM for CRAF
Pre-incubation time with compounds 30 minutes at room temperature
Reaction time 2 hours at room temperature
Assay Protocol
Final assay conditions were 4 pM cRaf, 3 uM ATP, 10 nM biotin tagged MEK1 kinase dead protein substrate. Reactions were performed in Greiner384 well plates, catalog #784075. Reaction buffer was 50 mM Tris, pH 7.5, 50 mM NaCl, 10 mM MgCl2, 0.01% Tween-20, 0.05% BSA and 1 mM DTT. 5 ul of 2×cRaf plus MEK1 were dispensed into plates containing 0.25 ul of compound in 100% DMSO and incubated at room temperature for 30 minutes. Reactions were started by addition of 5 ul of 2×ATP. Reactions were run for two hours and terminated by addition of 10 ul of 2× antibody and Alphascreen bead mixture in Stop Buffer. Stop Buffer was 50 mM Tris, pH 7.5, 0.005% Tween-20, 25 mM EDTA. The antibody was catalog #9121B from Cell Signaling Corporation and the beads were the AlphaScreen IgG Detection kit catalog #676061R from Perkin Elmer. Plates were sealed and stored overnight in the dark at room temperature. Plates were counted in a Perkin Elmer Envision instrument. The concentration of each compound for 50% inhibition (IC50) was calculated by non-linear regression using XL Fit data analysis software.

Using the assays described above, compounds of the invention exhibit inhibition of Raf kinases as reported in Table 1.

TABLE 1

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 1 | 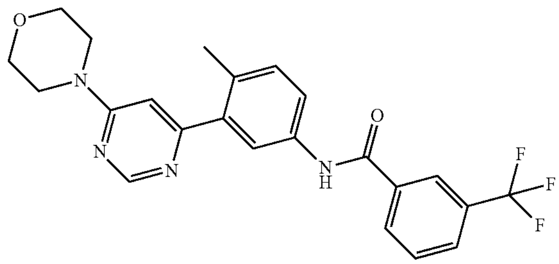 [SMILES: Cc1ccc(NC(=O)c2cccc(C(F)(F)F)c2)cc1-c1cc(N2CCOCC2)ncn1] | 0.000408 | 0.000145 | 0.000144 |
| 2 | 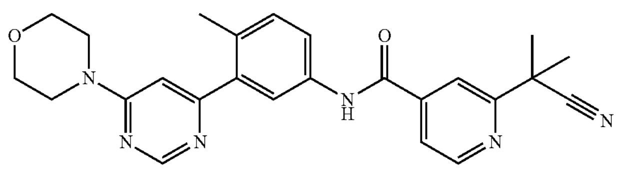 [SMILES: Cc1ccc(NC(=O)c2ccnc(C(C)(C)C#N)c2)cc1-c1cc(N2CCOCC2)ncn1] | 0.006271 | 0.001416 | 0.002953 |
| 3 | 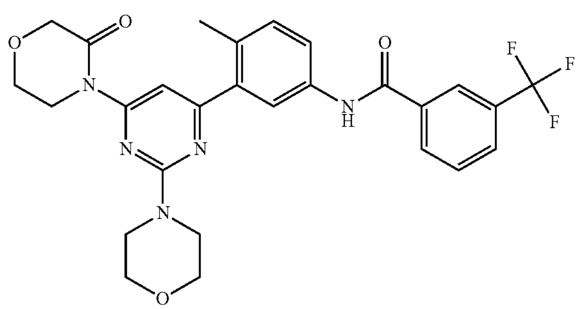 [SMILES: Cc1ccc(NC(=O)c2cccc(C(F)(F)F)c2)cc1-c1cc(N2CCOCC2=O)nc(N2CCOCC2)n1] | 0.00051 | 0000148 | |
| 4 | 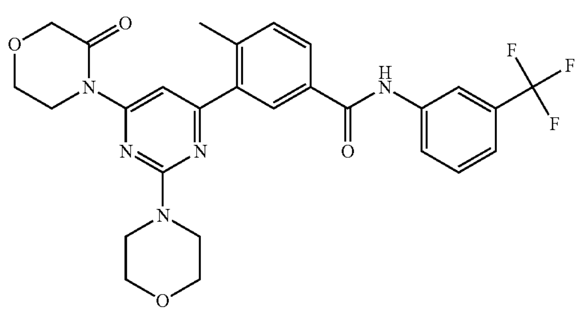 [SMILES: Cc1ccc(C(=O)Nc2cccc(C(F)(F)F)c2)cc1-c1cc(N2CCOCC2=O)nc(N2CCOCC2)n1] | 0.001332 | 0.000431 | |
| 5 | 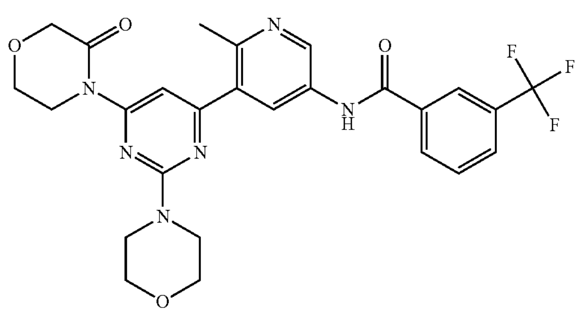 [SMILES: Cc1ncc(NC(=O)c2cccc(C(F)(F)F)c2)cc1-c1cc(N2CCOCC2=O)nc(N2CCOCC2)n1] | 0.002996 | 0.000713 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 6 | 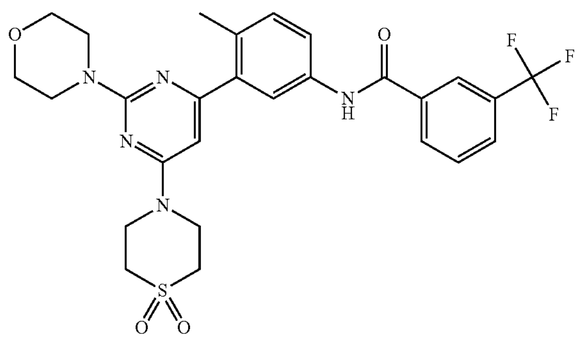 [SMILES: Cc1ccc(NC(=O)c2cccc(C(F)(F)F)c2)cc1-c1cc(N2CCS(=O)(=O)CC2)nc(N2CCOCC2)n1] | | | 0.000408 |
| 7 | 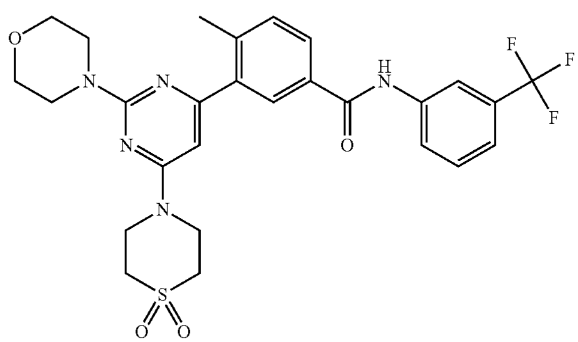 [SMILES: Cc1ccc(C(=O)Nc2cccc(C(F)(F)F)c2)cc1-c1cc(N2CCS(=O)(=O)CC2)nc(N2CCOCC2)n1] | 0.003146 | 0.001183 | 0.001114 |
| 8 | 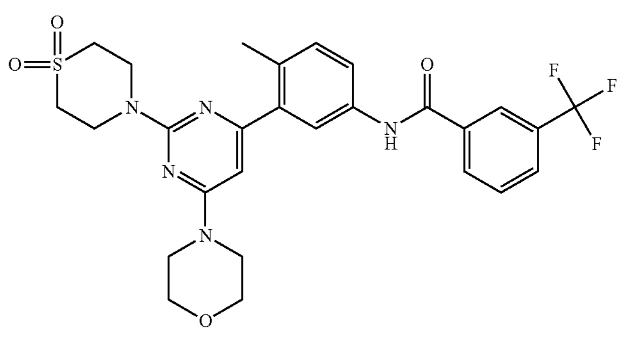 [SMILES: Cc1ccc(NC(=O)c2cccc(C(F)(F)F)c2)cc1-c1cc(N2CCOCC2)nc(N2CCS(=O)(=O)CC2)n1] | 0.000837 | 0.000389 | 0.000514 |
| 9 | 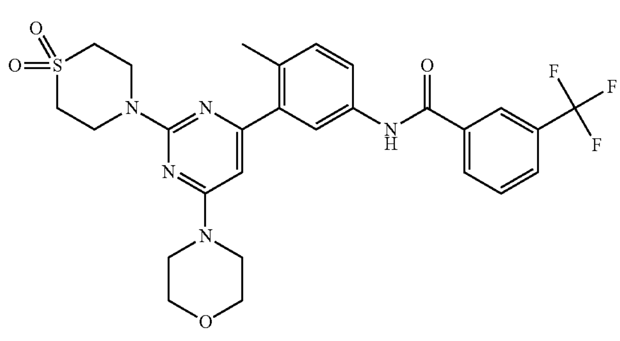 [SMILES: Cc1ccc(NC(=O)c2cccc(C(F)(F)F)c2)cc1-c1cc(N2CCOCC2)nc(N2CCS(=O)(=O)CC2)n1] | 0.001587 | 0.000949 | 0.000899 |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 10 | 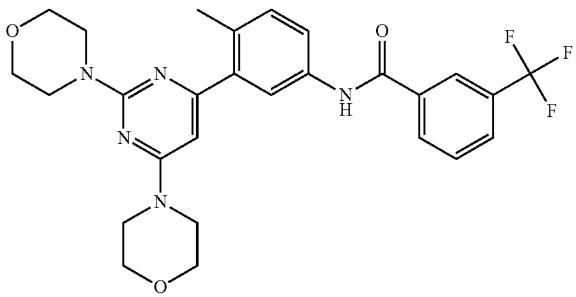 [SMILES: Cc1ccc(NC(=O)c2cccc(C(F)(F)F)c2)cc1-c1cc(N2CCOCC2)nc(N2CCOCC2)n1] | 0.00033 | 0.000103 | 0.000118 |
| 11 | 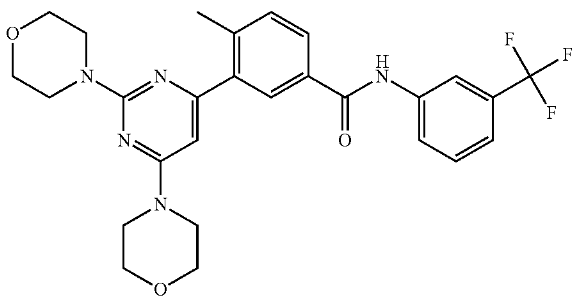 [SMILES: Cc1ccc(C(=O)Nc2cccc(C(F)(F)F)c2)cc1-c1cc(N2CCOCC2)nc(N2CCOCC2)n1] | 0.001481 | 0.000542 | 0.00058 |
| 12 | 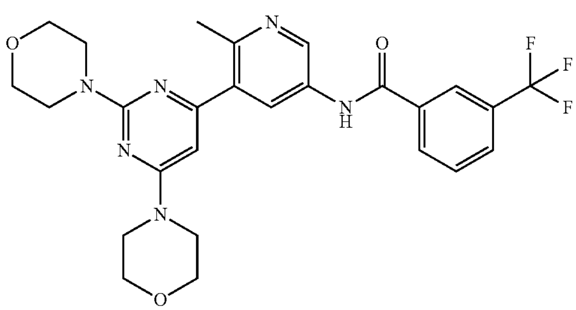 [SMILES: Cc1ncc(NC(=O)c2cccc(C(F)(F)F)c2)cc1-c1cc(N2CCOCC2)nc(N2CCOCC2)n1] | 0.00182 | 0.000353 | |
| 13 | 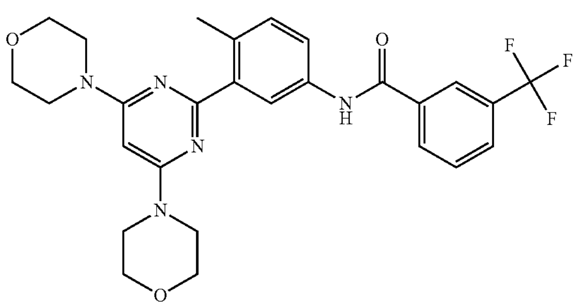 | 0.002168 | 0.000474 | 0.000533 |
| 14 | 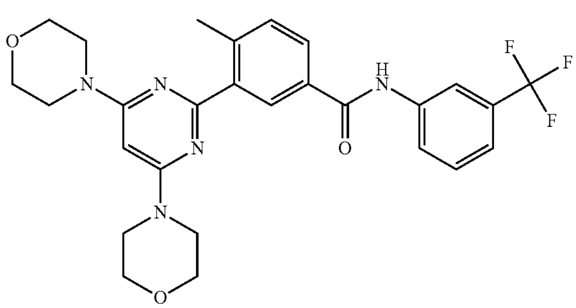 [SMILES: Cc1ccc(C(=O)Nc2cccc(C(F)(F)F)c2)cc1-c1nc(N2CCOCC2)cc(N2CCOCC2)n1] | 0.002007 | 0.000616 | 0.000803 |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 15 | 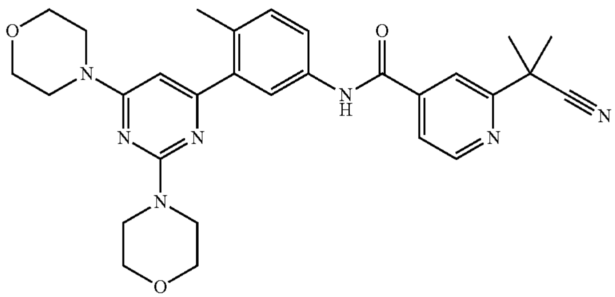 | 0.002224 | 0.00065 | |
| 16 | 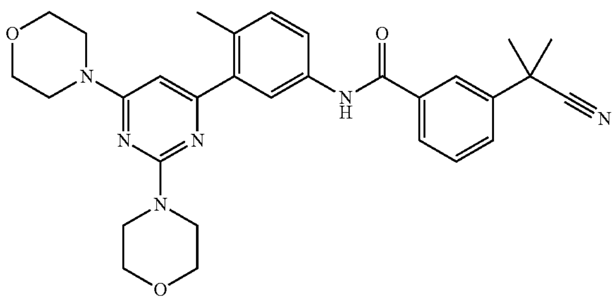 [SMILES: Cc1ccc(NC(=O)c2ccnc(C(C)(C)C#N)c2)cc1-c1cc(N2CCOCC2)nc(N2CCOCC2)n1] | 0.001521 | 0.000299 | |
| 17 | 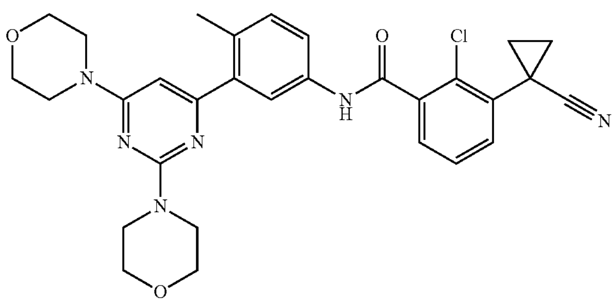 [SMILES: Cc1ccc(NC(=O)c2cccc(C3(C#N)CC3)c2Cl)cc1-c1cc(N2CCOCC2)nc(N2CCOCC2)n1] | 0.00305 | 0.000785 | |
| 18 | 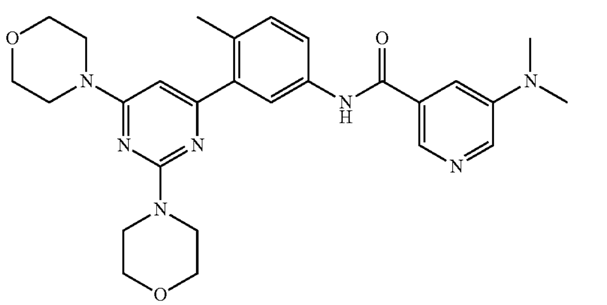 [SMILES: Cc1ccc(NC(=O)c2cncc(N(C)C)c2)cc1-c1cc(N2CCOCC2)nc(N2CCOCC2)n1] | 0.000456 | 0.000137 | |
| 19 | 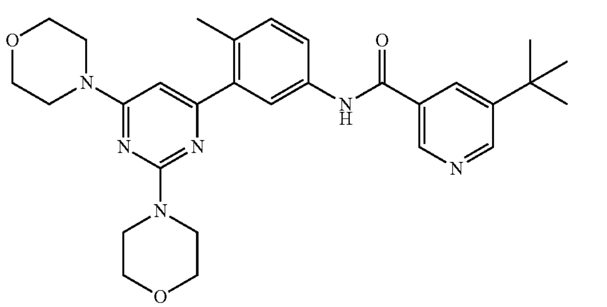 [SMILES: Cc1ccc(NC(=O)c2cncc(C(C)(C)C)c2)cc1-c1cc(N2CCOCC2)nc(N2CCOCC2)n1] | 0.001851 | 0.000562 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 20 | 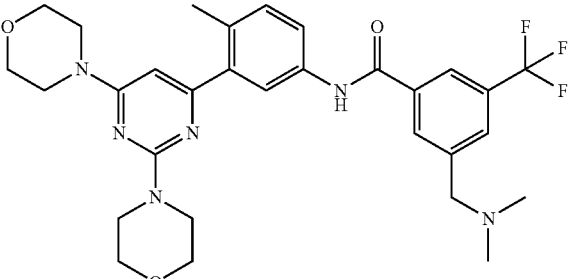 | 0.001967 | 0.000516 | |
| 21 | 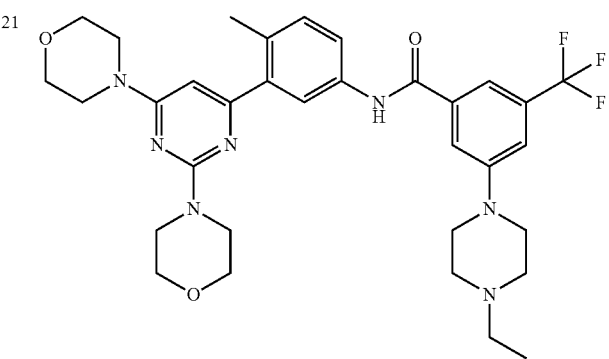 | 0.003433 | 0.000905 | |
| 22 | 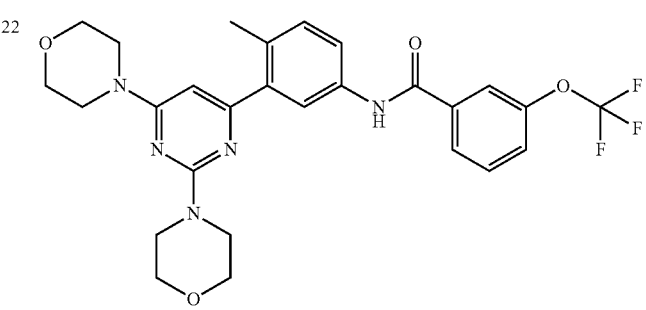 | 0.000652 | 0.000202 | |
| 23 | 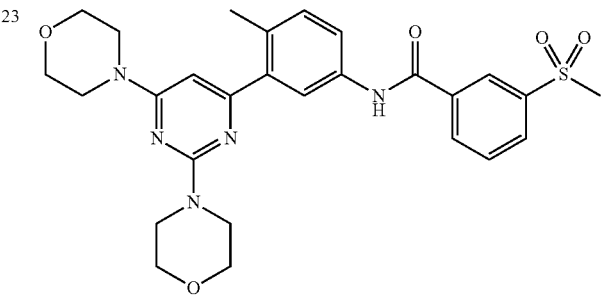 | 0.002416 | 0.00086 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 24 | 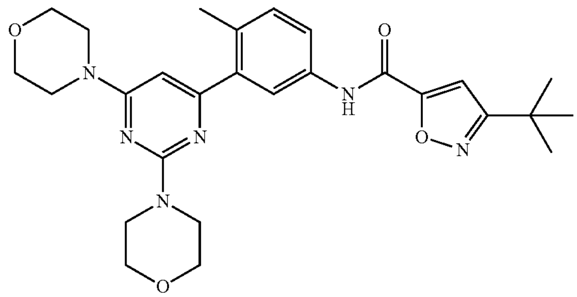 [SMILES: Cc1ccc(NC(=O)c2cc(C(C)(C)C)no2)cc1-c1cc(N2CCOCC2)nc(N2CCOCC2)n1] | 0.001356 | 0.000328 | |
| 25 | 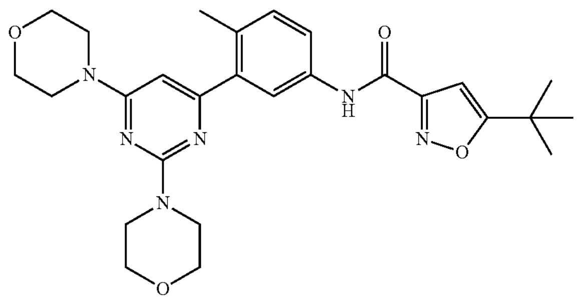 [SMILES: Cc1ccc(NC(=O)c2cc(C(C)(C)C)on2)cc1-c1cc(N2CCOCC2)nc(N2CCOCC2)n1] | 0.001197 | 0.000352 | |
| 26 | 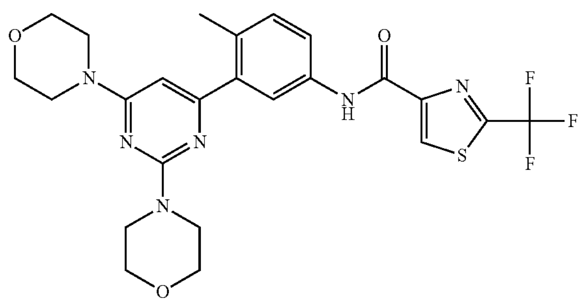 [SMILES: Cc1ccc(NC(=O)c2csc(C(F)(F)F)n2)cc1-c1cc(N2CCOCC2)nc(N2CCOCC2)n1] | 0.002177 | 0.000514 | |
| 27 | 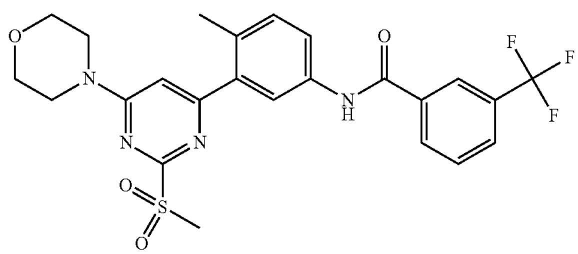 [SMILES: Cc1ccc(NC(=O)c2cccc(C(F)(F)F)c2)cc1-c1cc(N2CCOCC2)nc(S(C)(=O)=O)n1] | 0.00086 | 0.00011 | |
| 28 | 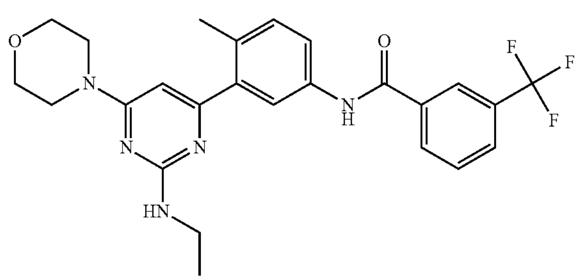 [SMILES: CCNc1nc(-c2cc(NC(=O)c3cccc(C(F)(F)F)c3)ccc2C)cc(N2CCOCC2)n1] | 0.000585 | 0.000214 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 29 | 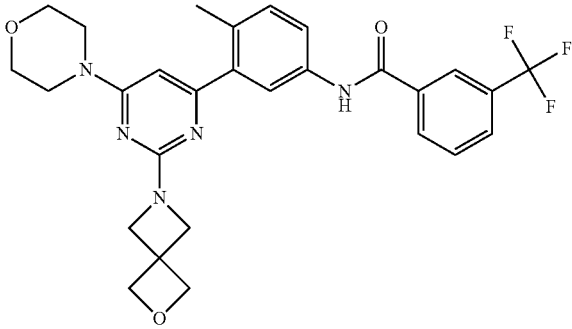 [SMILES: Cc1ccc(NC(=O)c2cccc(C(F)(F)F)c2)cc1-c1cc(N2CCOCC2)nc(N2CC3(COC3)C2)n1] | 0.001306 | 0.000421 | |
| 30 | 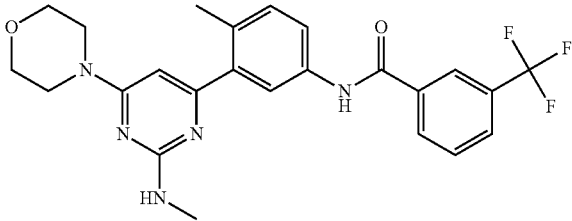 [SMILES: CNc1nc(-c2cc(NC(=O)c3cccc(C(F)(F)F)c3)ccc2C)cc(N2CCOCC2)n1] | 0.00083 | 0.000322 | |
| 31 | 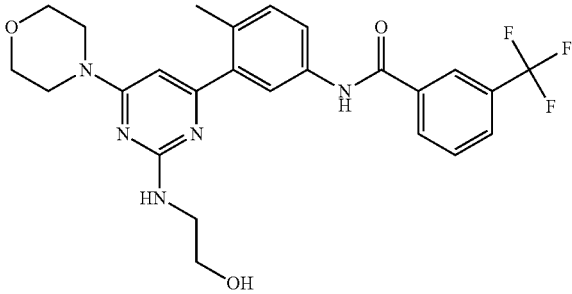 [SMILES: Cc1ccc(NC(=O)c2cccc(C(F)(F)F)c2)cc1-c1cc(N2CCOCC2)nc(NCCO)n1] | 0.000737 | 0.00021 | |
| 32 | 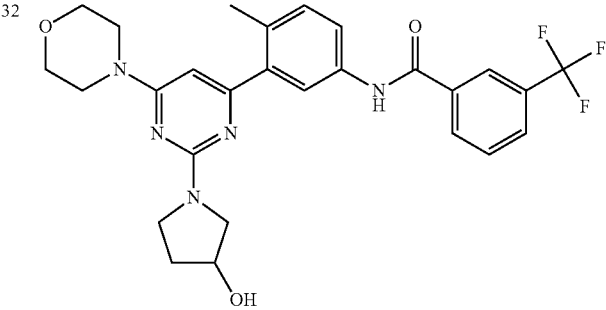 | 0.001695 | 0.00051 | |
| 33 | 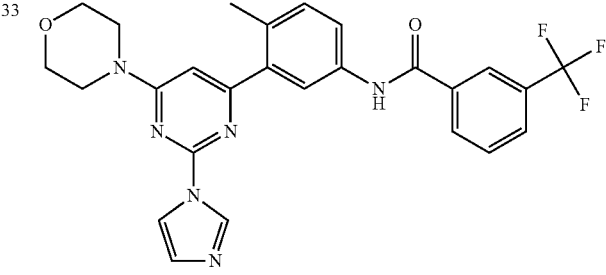 | 0.000455 | 0.000134 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 34 | 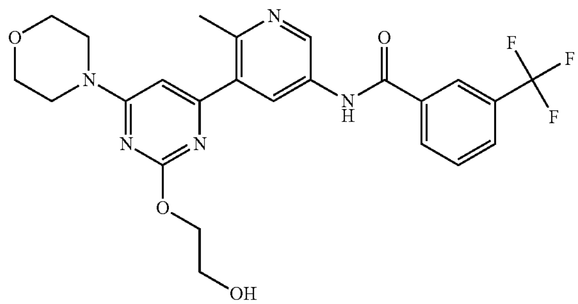 [SMILES: Cc1ncc(NC(=O)c2cccc(C(F)(F)F)c2)cc1-c1cc(N2CCOCC2)nc(OCCO)n1] | 0.001853 | 0.000304 | |
| 35 | 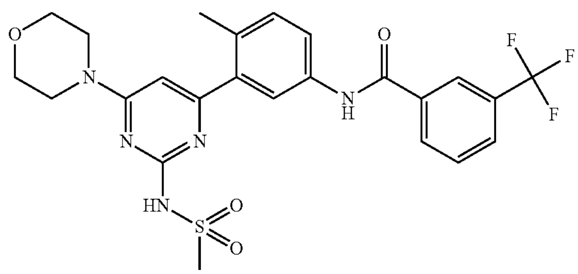 [SMILES: Cc1ccc(NC(=O)c2cccc(C(F)(F)F)c2)cc1-c1cc(N2CCOCC2)nc(NS(C)(=O)=O)n1] | 0.003454 | 0.000634 | |
| 36 | 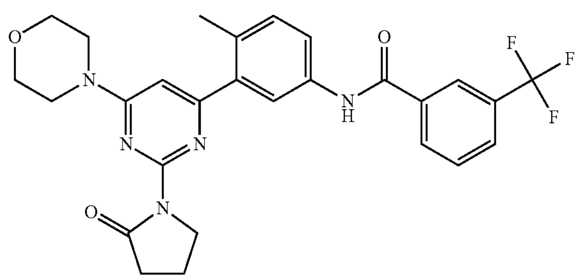 [SMILES: Cc1ccc(NC(=O)c2cccc(C(F)(F)F)c2)cc1-c1cc(N2CCOCC2)nc(N2CCCC2=O)n1] | 0.001277 | 0.000456 | |
| 37 | 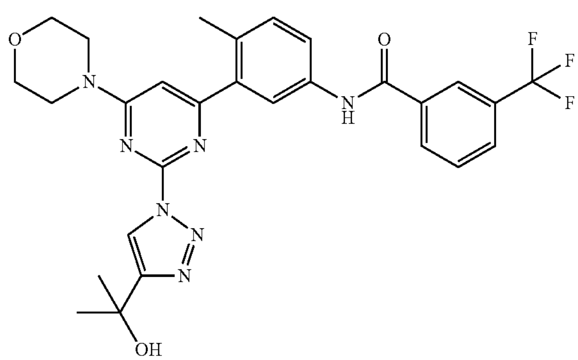 [SMILES: Cc1ccc(NC(=O)c2cccc(C(F)(F)F)c2)cc1-c1cc(N2CCOCC2)nc(-n2cc(C(C)(C)O)nn2)n1] | 0.000773 | 0.000198 | |
| 38 | 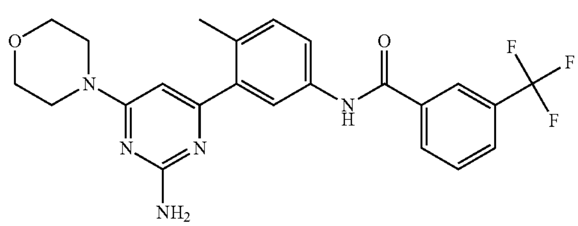 [SMILES: Cc1ccc(NC(=O)c2cccc(C(F)(F)F)c2)cc1-c1cc(N2CCOCC2)nc(N)n1] | 0.001429 | 0.000344 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 39 | 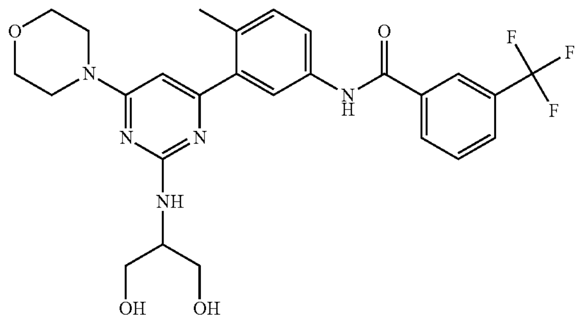 [SMILES: Cc1ccc(NC(=O)c2cccc(C(F)(F)F)c2)cc1-c1cc(N2CCOCC2)nc(NC(CO)CO)n1] | 0.000816 | 0.000322 | |
| 40 | 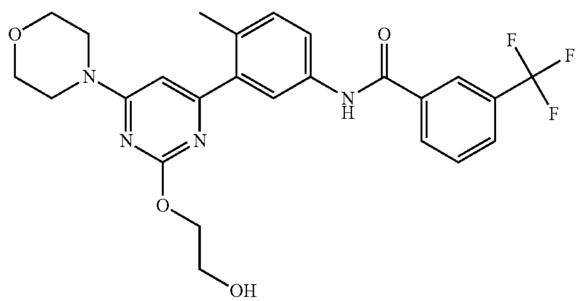 [SMILES: Cc1ccc(NC(=O)c2cccc(C(F)(F)F)c2)cc1-c1cc(N2CCOCC2)nc(OCCO)n1] | 0.000601 | 0.000132 | |
| 42 | 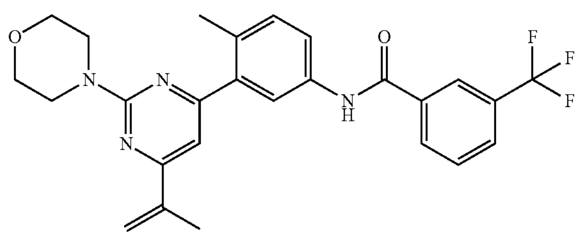 | 0.000422 | 0.00009 | 0.000137 |
| 43 | 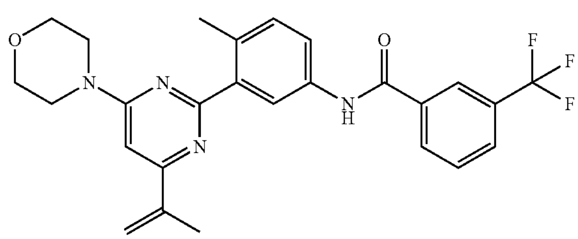 [SMILES: C=C(C)c1cc(N2CCOCC2)nc(-c2cc(NC(=O)c3cccc(C(F)(F)F)c3)ccc2C)n1] | 0.001648 | 0.000388 | 0.000376 |
| 44 | 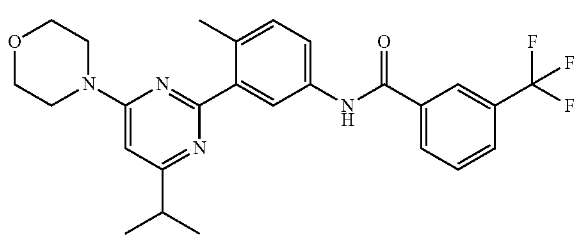 [SMILES: Cc1ccc(NC(=O)c2cccc(C(F)(F)F)c2)cc1-c1nc(C(C)C)cc(N2CCOCC2)n1] | 0.002875 | 0.000637 | 0.000714 |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 45 | 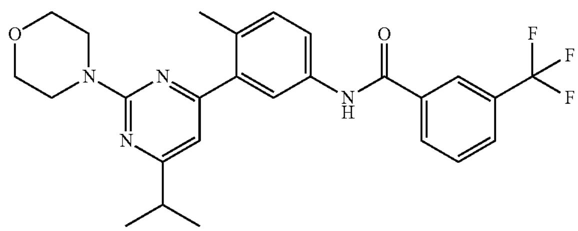 [SMILES: Cc1ccc(NC(=O)c2cccc(C(F)(F)F)c2)cc1-c1cc(C(C)C)nc(N2CCOCC2)n1] | 0.005678 | 0.001392 | 0.001018 |
| 46 | 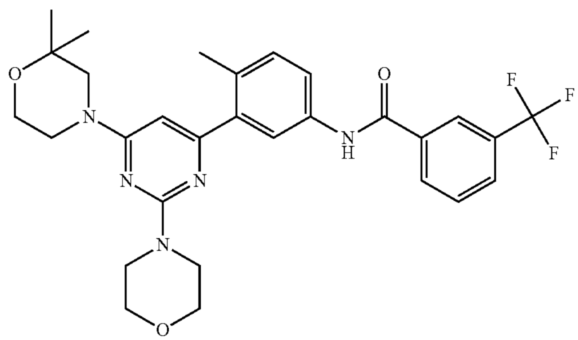 [SMILES: Cc1ccc(NC(=O)c2cccc(C(F)(F)F)c2)cc1-c1cc(N2CCOC(C)(C)C2)nc(N2CCOCC2)n1] | 0.002118 | 0.000433 | |
| 47 | 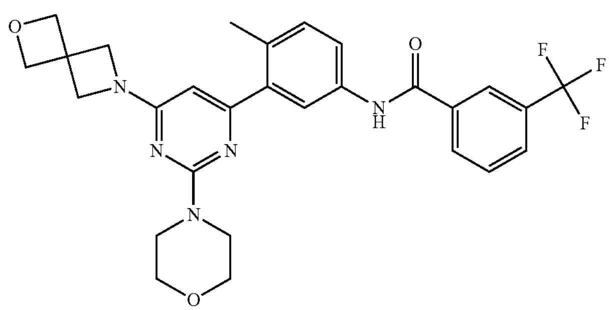 [SMILES: Cc1ccc(NC(=O)c2cccc(C(F)(F)F)c2)cc1-c1cc(N2CC3(COC3)C2)nc(N2CCOCC2)n1] | 0.002454 | 0.000356 | |
| 48 | 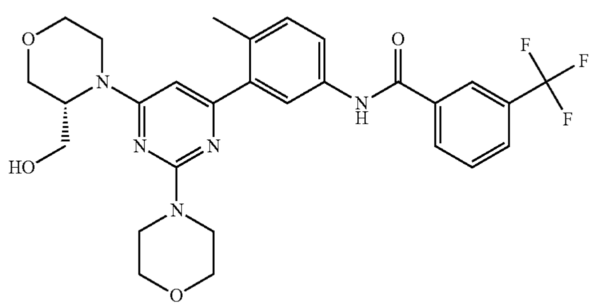 [SMILES: Cc1ccc(NC(=O)c2cccc(C(F)(F)F)c2)cc1-c1cc(N2CCOC[C@H]2CO)nc(N2CCOCC2)n1] | 0.00143 | 0.000347 | |
| 49 | 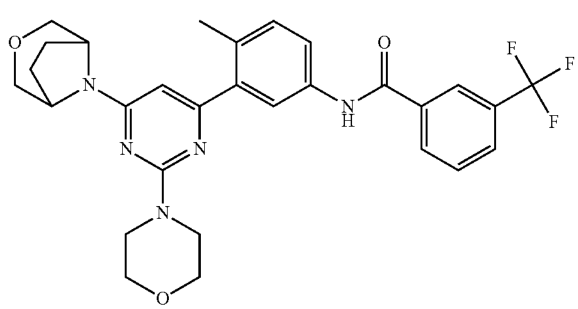 [SMILES: Cc1ccc(NC(=O)c2cccc(C(F)(F)F)c2)cc1-c1cc(N2C3CCC2COC3)nc(N2CCOCC2)n1] | 0.001495 | 0.000376 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 50 | 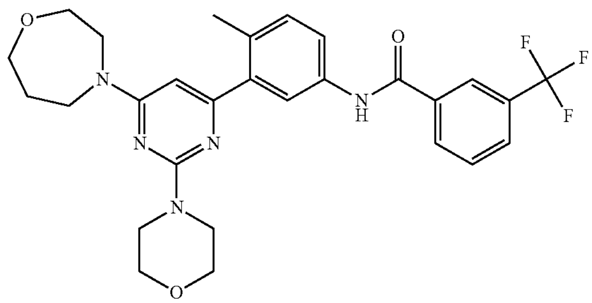 [SMILES: Cc1ccc(NC(=O)c2cccc(C(F)(F)F)c2)cc1-c1cc(N2CCCOCC2)nc(N2CCOCC2)n1] | 0.001131 | 0.00025 | |
| 51 | 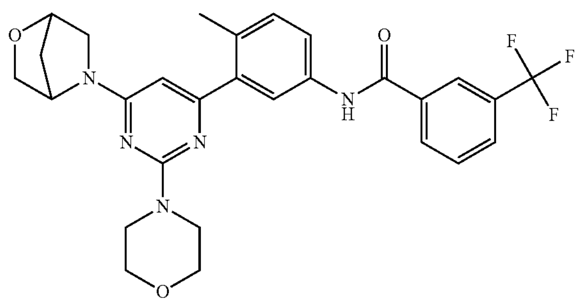 [SMILES: Cc1ccc(NC(=O)c2cccc(C(F)(F)F)c2)cc1-c1cc(N2CC3CC2CO3)nc(N2CCOCC2)n1] | 0.003162 | 0.000661 | |
| 52 | 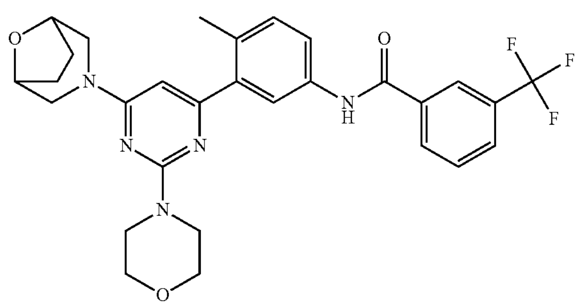 [SMILES: Cc1ccc(NC(=O)c2cccc(C(F)(F)F)c2)cc1-c1cc(N2CC3CCC(C2)O3)nc(N2CCOCC2)n1] | 0.000884 | 0.000282 | |
| 53 | 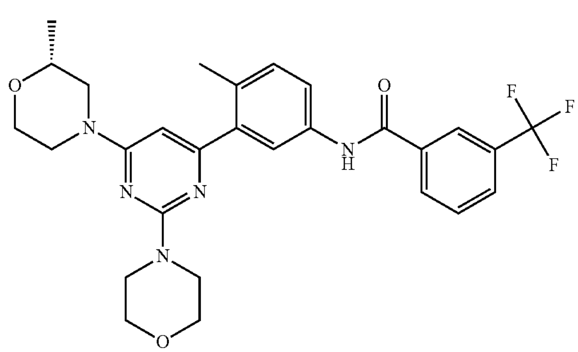 [SMILES: Cc1ccc(NC(=O)c2cccc(C(F)(F)F)c2)cc1-c1cc(N2CCO[C@H](C)C2)nc(N2CCOCC2)n1] | 0.002499 | 0.000651 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 54 | 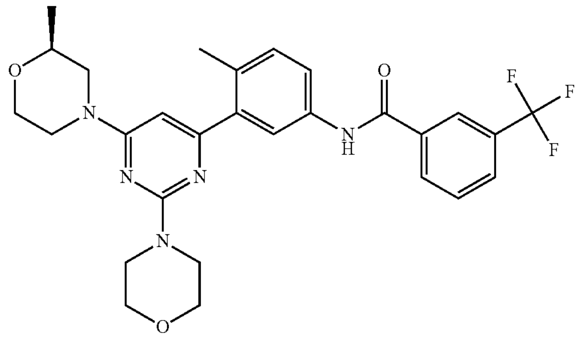 [SMILES: Cc1ccc(NC(=O)c2cccc(C(F)(F)F)c2)cc1-c1cc(N2CCO[C@@H](C)C2)nc(N2CCOCC2)n1] | 0.00314 | 0.000625 | |
| 55 | 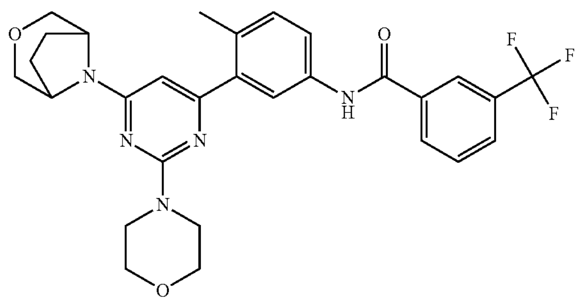 [SMILES: Cc1ccc(NC(=O)c2cccc(C(F)(F)F)c2)cc1-c1cc(N2C3CCC2COC3)nc(N2CCOCC2)n1] | | | |
| 56 | 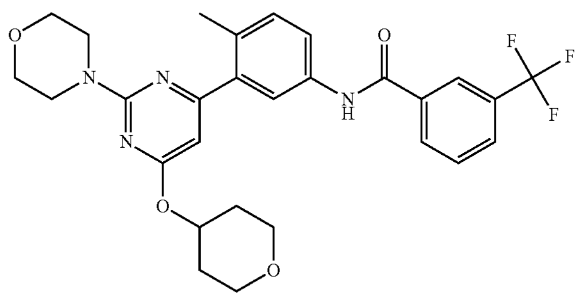 [SMILES: Cc1ccc(NC(=O)c2cccc(C(F)(F)F)c2)cc1-c1cc(OC2CCOCC2)nc(N2CCOCC2)n1] | 0.001001 | 0.000191 | |
| 57 | 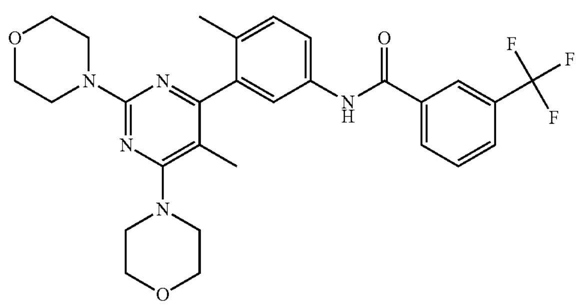 [SMILES: Cc1ccc(NC(=O)c2cccc(C(F)(F)F)c2)cc1-c1nc(N2CCOCC2)nc(N2CCOCC2)c1C] | 0.000994 | 0.000179 | |
| 58 | 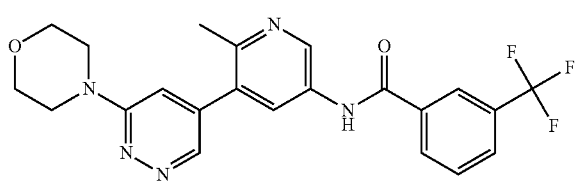 [SMILES: Cc1ncc(NC(=O)c2cccc(C(F)(F)F)c2)cc1-c1cnnc(N2CCOCC2)c1] | 0.008715 | 0.00103 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 59 | 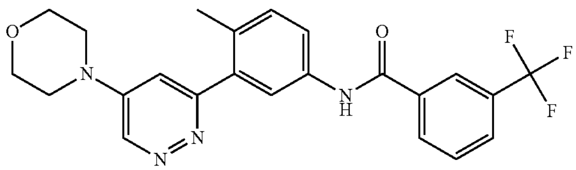 [SMILES: Cc1ccc(NC(=O)c2cccc(C(F)(F)F)c2)cc1-c1cc(N2CCOCC2)cnn1] | 0.002655 | 0.000432 | |
| 60 | 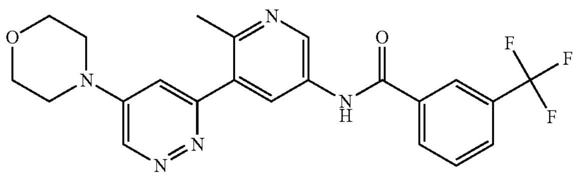 [SMILES: Cc1ncc(NC(=O)c2cccc(C(F)(F)F)c2)cc1-c1cc(N2CCOCC2)cnn1] | 0.006966 | 0.001007 | |
| 61 | 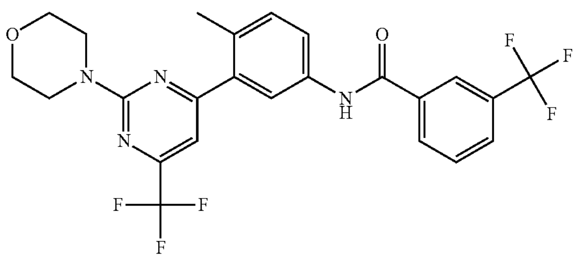 [SMILES: Cc1ccc(NC(=O)c2cccc(C(F)(F)F)c2)cc1-c1cc(C(F)(F)F)nc(N2CCOCC2)n1] | 0.002273 | 0.000314 | |
| 62 | 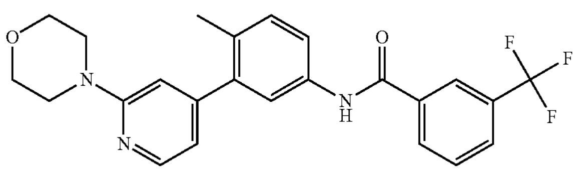 [SMILES: Cc1ccc(NC(=O)c2cccc(C(F)(F)F)c2)cc1-c1ccnc(N2CCOCC2)c1] | 0.00108 | 0.000161 | |
| 63 | 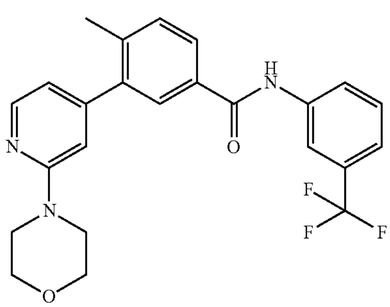 [SMILES: Cc1ccc(C(=O)Nc2cccc(C(F)(F)F)c2)cc1-c1ccnc(N2CCOCC2)c1] | 0.002553 | 0.000436 | 0.000508 |
| 64 | 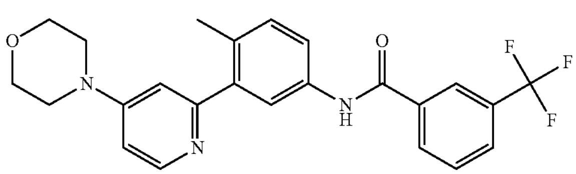 [SMILES: Cc1ccc(NC(=O)c2cccc(C(F)(F)F)c2)cc1-c1cc(N2CCOCC2)ccn1] | | | 0.000847 |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 65 | 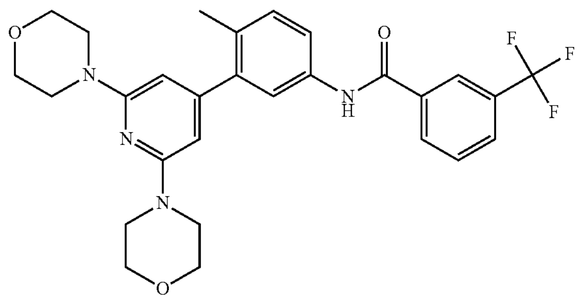 [SMILES: Cc1ccc(NC(=O)c2cccc(C(F)(F)F)c2)cc1-c1cc(N2CCOCC2)nc(N2CCOCC2)c1] | 0.001142 | 0.000187 | |
| 66 | 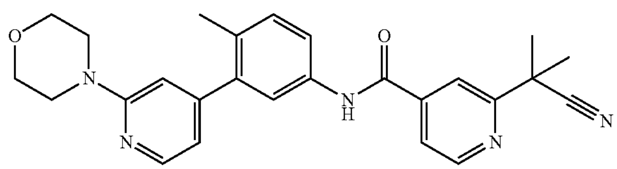 [SMILES: Cc1ccc(NC(=O)c2ccnc(C(C)(C)C#N)c2)cc1-c1ccnc(N2CCOCC2)c1] | 0.003002 | 0.000711 | |
| 67 | 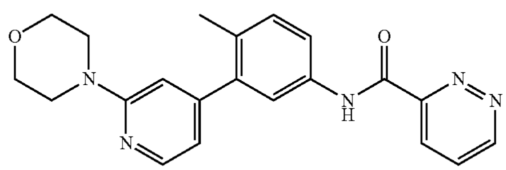 [SMILES: Cc1ccc(NC(=O)c2cccnn2)cc1-c1ccnc(N2CCOCC2)c1] | 0.458152 | 0.077922 | |
| 68 | 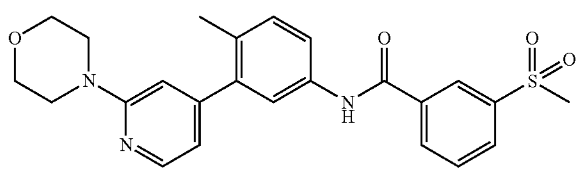 | 0.00064 | 0.000124 | |
| 69 | 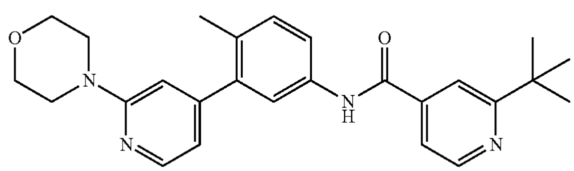 [SMILES: Cc1ccc(NC(=O)c2ccnc(C(C)(C)C)c2)cc1-c1ccnc(N2CCOCC2)c1] | 0.002054 | 0.000396 | |
| 70 | 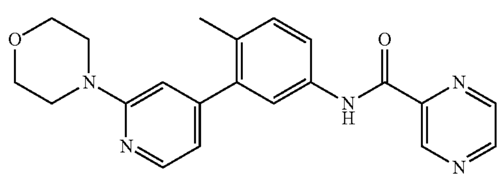 [SMILES: Cc1ccc(NC(=O)c2cnccn2)cc1-c1ccnc(N2CCOCC2)c1] | 0.157 | 0.024002 | |
| 71 | 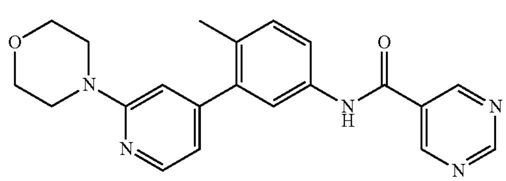 [SMILES: Cc1ccc(NC(=O)c2cncnc2)cc1-c1ccnc(N2CCOCC2)c1] | 0.599193 | 0.083265 | |
| 72 | 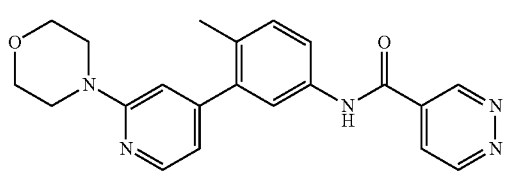 [SMILES: Cc1ccc(NC(=O)c2ccnnc2)cc1-c1ccnc(N2CCOCC2)c1] | 0.639127 | 0.078004 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 73 | 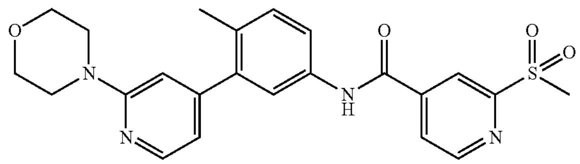 [SMILES: Cc1ccc(NC(=O)c2ccnc(S(C)(=O)=O)c2)cc1-c1ccnc(N2CCOCC2)c1] | 0.001499 | 0.00025 | |
| 74 | 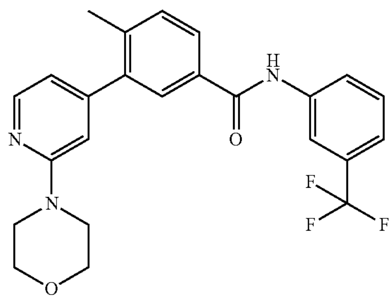 [SMILES: Cc1ccc(C(=O)Nc2cccc(C(F)(F)F)c2)cc1-c1ccnc(N2CCOCC2)c1] | | | |
| 75 | 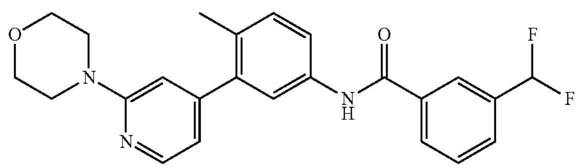 [SMILES: Cc1ccc(NC(=O)c2cccc(C(F)F)c2)cc1-c1ccnc(N2CCOCC2)c1] | 0.000385 | 0.000056 | |
| 76 | 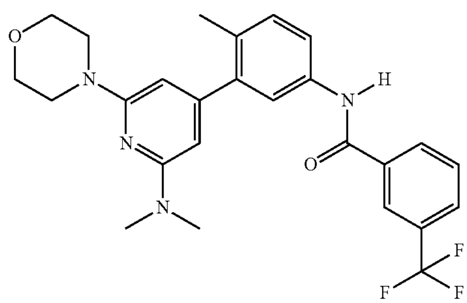 [SMILES: Cc1ccc(NC(=O)c2cccc(C(F)(F)F)c2)cc1-c1cc(N(C)C)nc(N2CCOCC2)c1] | 0.003222 | 0.000765 | |
| 77 | 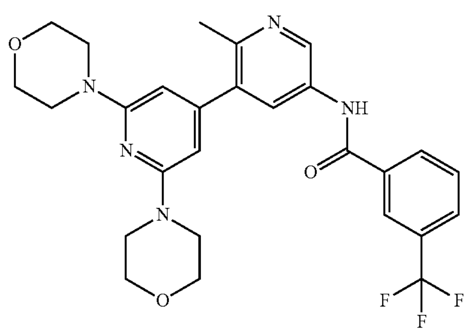 [SMILES: Cc1ncc(NC(=O)c2cccc(C(F)(F)F)c2)cc1-c1cc(N2CCOCC2)nc(N2CCOCC2)c1] | 0.000632 | 0.00013 | |
| 78 | 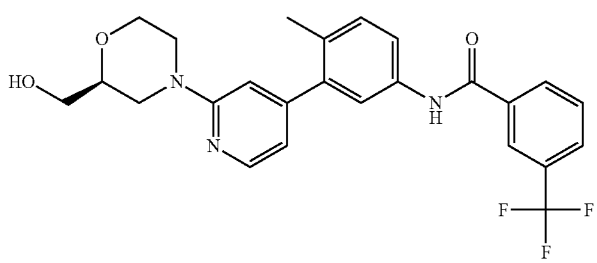 [SMILES: Cc1ccc(NC(=O)c2cccc(C(F)(F)F)c2)cc1-c1ccnc(N2CCO[C@H](CO)C2)c1] | 0.00149 | 0.000199 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 79 | 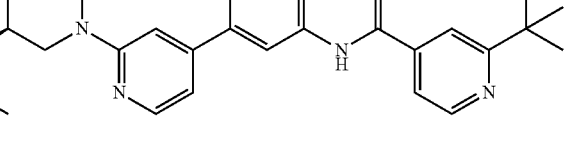 | 0.101957 | 0.028001 | |
| 80 | 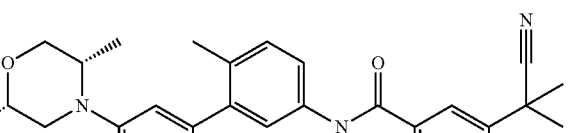 | 0.030653 | 0.010123 | |
| 81 | 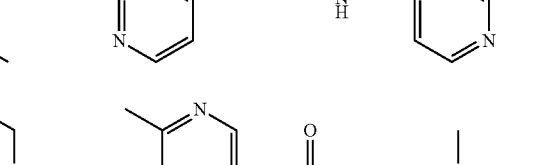 | 0.014017 | 0.001449 | |
| 82 | 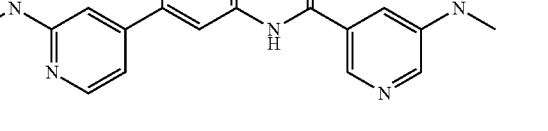 | 0.014469 | 0.001768 | |
| 83 | 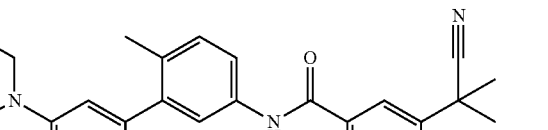 | 0.002533 | 0.00029 | |
| 84 | 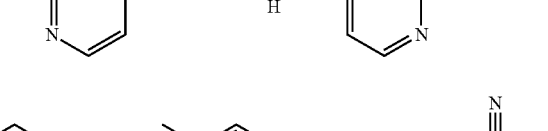 | 0.002927 | 0.001218 | |
| 85 | 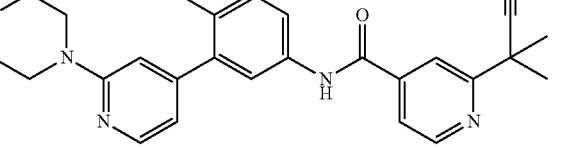 | 0.010918 | 0.001343 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 86 | 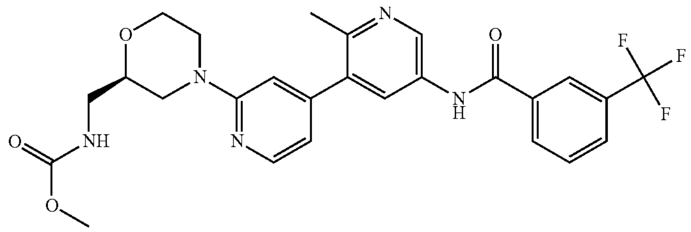 [SMILES: COC(=O)NC[C@@H]1CN(c2cc(-c3cc(NC(=O)c4cccc(C(F)(F)F)c4)cnc3C)ccn2)CCO1] | 0.00843 | 0.001099 | |
| 87 | 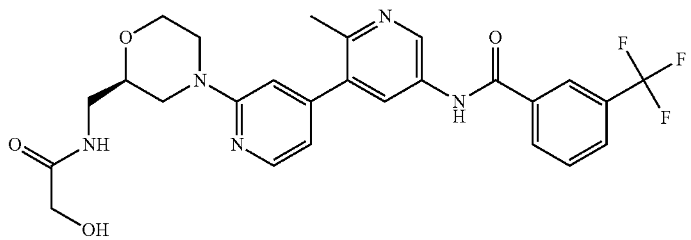 [SMILES: Cc1ncc(NC(=O)c2cccc(C(F)(F)F)c2)cc1-c1ccnc(N2CCO[C@H](CNC(=O)CO)C2)c1] | 0.012091 | 0.001495 | |
| 88 | 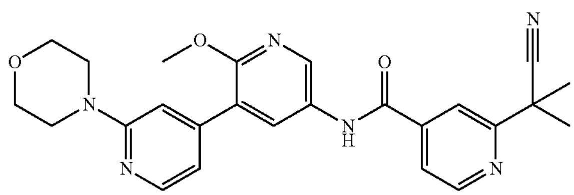 [SMILES: COc1ncc(NC(=O)c2ccnc(C(C)(C)C#N)c2)cc1-c1ccnc(N2CCOCC2)c1] | 0.037439 | 0.003837 | |
| 89 | 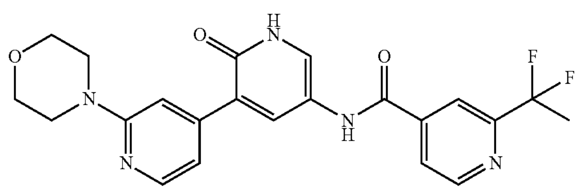 [SMILES: CC(F)(F)c1cc(C(=O)Nc2c[nH]c(=O)c(-c3ccnc(N4CCOCC4)c3)c2)ccn1] | >25.000340 | 7.685426 | |
| 90 | 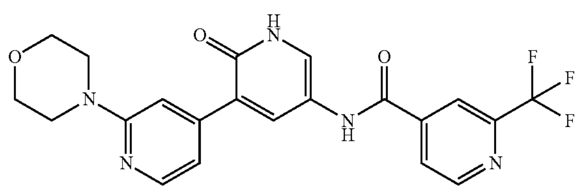 [SMILES: O=C(Nc1c[nH]c(=O)c(-c2ccnc(N3CCOCC3)c2)c1)c1ccnc(C(F)(F)F)c1] | >25.000340 | >25.000340 | |
| 91 | 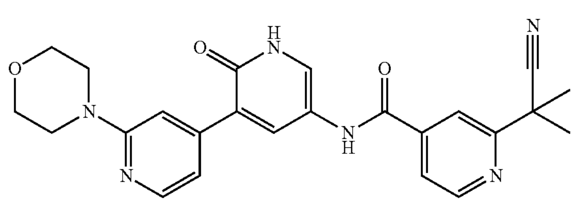 [SMILES: CC(C)(C#N)c1cc(C(=O)Nc2c[nH]c(=O)c(-c3ccnc(N4CCOCC4)c3)c2)ccn1] | 18.594788 | 1.925371 | |
| 92 | 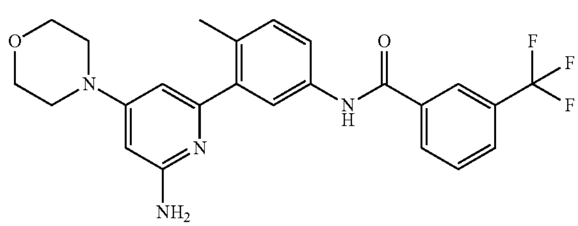 [SMILES: Cc1ccc(NC(=O)c2cccc(C(F)(F)F)c2)cc1-c1cc(N2CCOCC2)cc(N)n1] | | | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 93 | 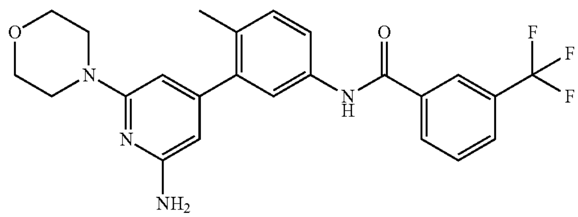 [SMILES: Cc1ccc(NC(=O)c2cccc(C(F)(F)F)c2)cc1-c1cc(N)nc(N2CCOCC2)c1] | 0.000802 | 0.000117 | |
| 94 | 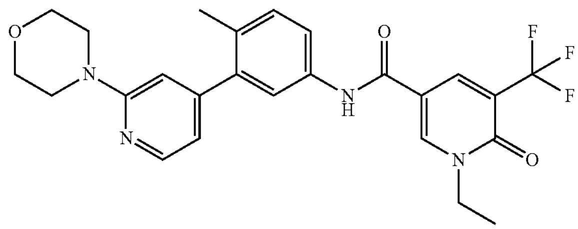 [SMILES: CCn1cc(C(=O)Nc2ccc(C)c(-c3ccnc(N4CCOCC4)c3)c2)cc(C(F)(F)F)c1=O] | 0.005788 | 0.000489 | |
| 95 | 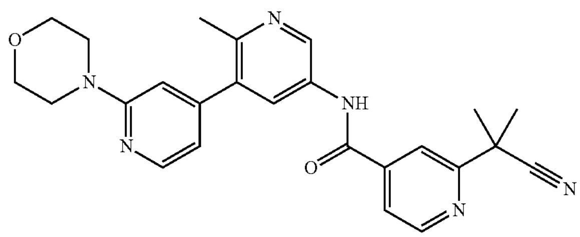 [SMILES: Cc1ncc(NC(=O)c2ccnc(C(C)(C)C#N)c2)cc1-c1ccnc(N2CCOCC2)c1] | 0.013459 | 0.001829 | |
| 96 | 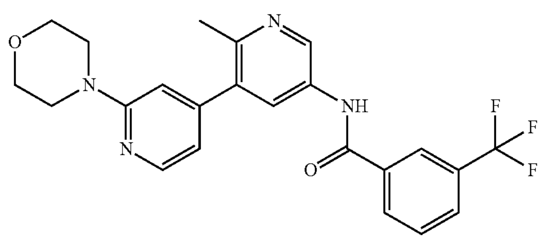 [SMILES: Cc1ncc(NC(=O)c2cccc(C(F)(F)F)c2)cc1-c1ccnc(N2CCOCC2)c1] | 0.001241 | 0.000182 | |
| 97 | 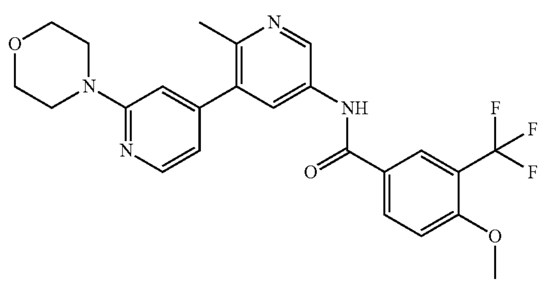 [SMILES: COc1ccc(C(=O)Nc2cnc(C)c(-c3ccnc(N4CCOCC4)c3)c2)cc1C(F)(F)F] | 0.009087 | 0.000998 | |
| 98 | 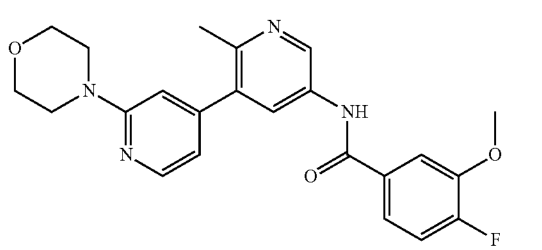 [SMILES: COc1cc(C(=O)Nc2cnc(C)c(-c3ccnc(N4CCOCC4)c3)c2)ccc1F] | 0.025693 | 0.001993 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 99 | 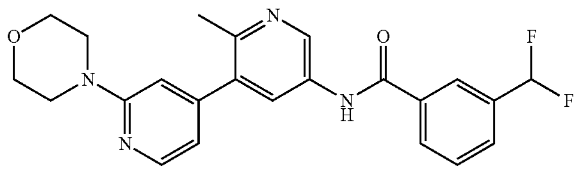 [SMILES: Cc1ncc(NC(=O)c2cccc(C(F)F)c2)cc1-c1ccnc(N2CCOCC2)c1] | 0.00117 | 0.00016 | |
| 100 | 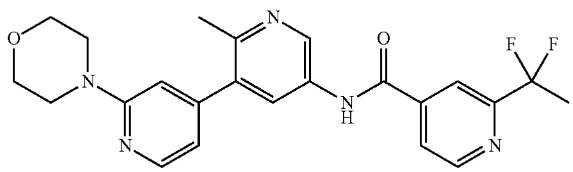 [SMILES: Cc1ncc(NC(=O)c2ccnc(C(C)(F)F)c2)cc1-c1ccnc(N2CCOCC2)c1] | 0.004089 | 0.000522 | |
| 101 | 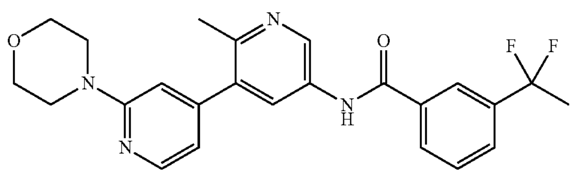 [SMILES: Cc1ncc(NC(=O)c2cccc(C(C)(F)F)c2)cc1-c1ccnc(N2CCOCC2)c1] | 0.002183 | 0.000253 | |
| 102 | 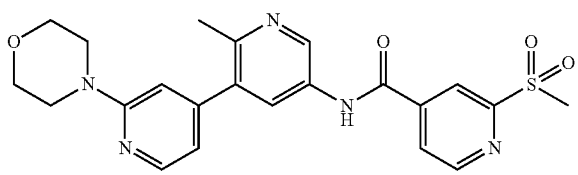 | 0.028046 | 0.003089 | |
| 103 | 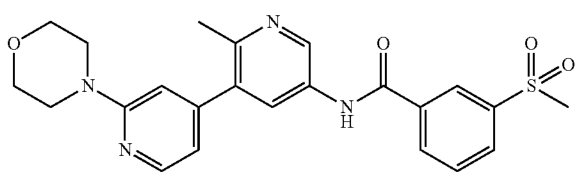 [SMILES: Cc1ncc(NC(=O)c2cccc(S(C)(=O)=O)c2)cc1-c1ccnc(N2CCOCC2)c1] | 0.018432 | 0.001947 | |
| 104 | 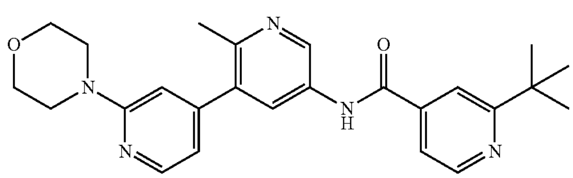 [SMILES: Cc1ncc(NC(=O)c2ccnc(C(C)(C)C)c2)cc1-c1ccnc(N2CCOCC2)c1] | 0.038535 | 0.005505 | |
| 106 | 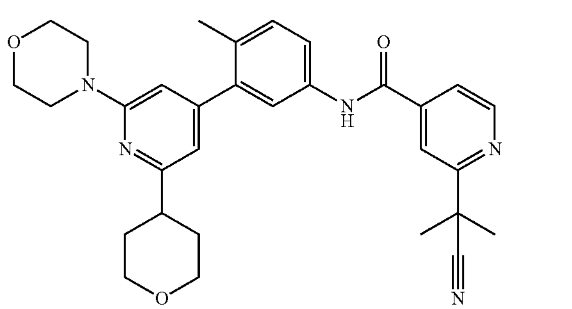 [SMILES: Cc1ccc(NC(=O)c2ccnc(C(C)(C)C#N)c2)cc1-c1cc(C2CCOCC2)nc(N2CCOCC2)c1] | 0.001708 | 0.000359 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 107 | 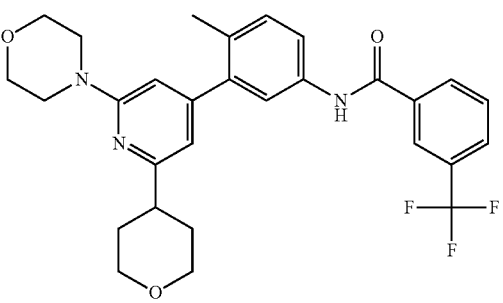 [SMILES: Cc1ccc(NC(=O)c2cccc(C(F)(F)F)c2)cc1-c1cc(C2CCOCC2)nc(N2CCOCC2)c1] | 0.001688 | 0.000363 | |
| 108 | 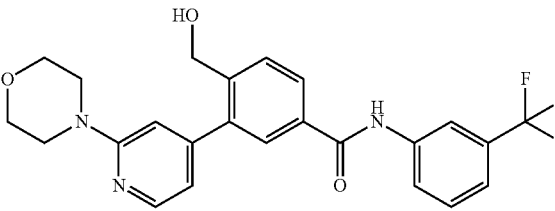 | 0.006113 | 0.000778 | |
| 109 | 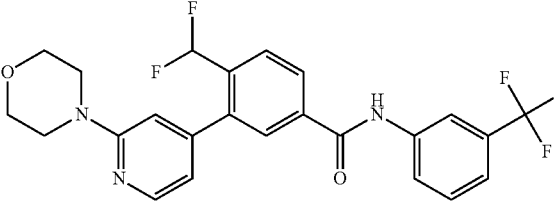 | 0.005035 | 0.000719 | |
| 110 | 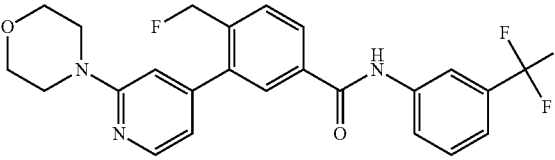 | 0.002185 | 0.000332 | |
| 111 | 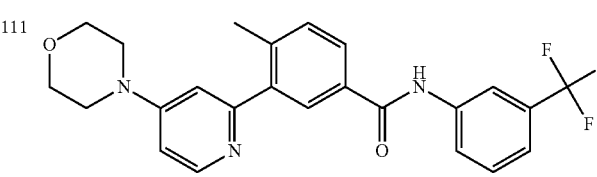 | | | 0.000403 |
| 112 | 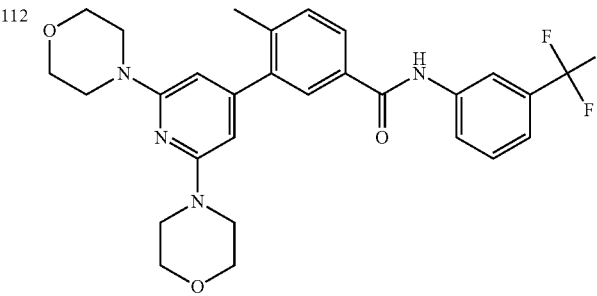 | 0.002384 | 0.0005 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 113 | 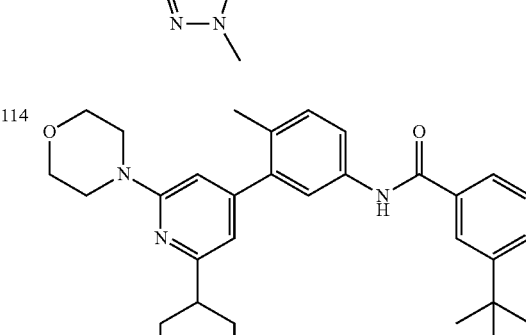 | 0.001137 | 0.000465 | |
| 114 | 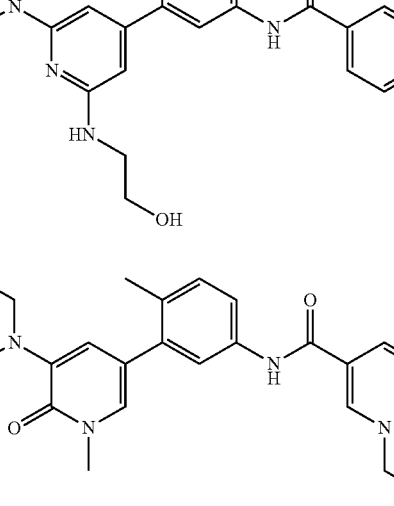 | 0.001626 | 0.000285 | |
| 115 | 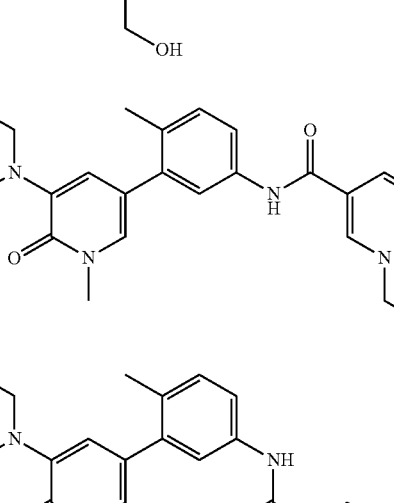 | 0.012797 | 0.000872 | |
| 116 | 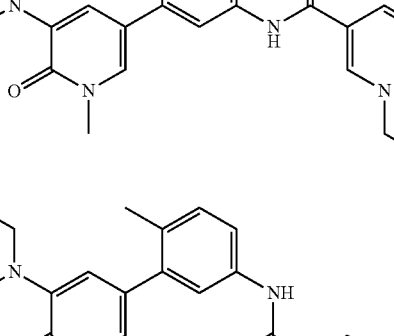 | 0.010923 | 0.000735 | |
| 117 | 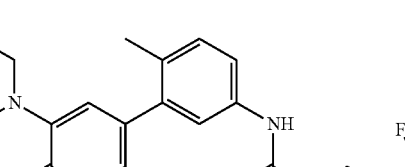 | 0.002035 | 0.000265 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 118 | 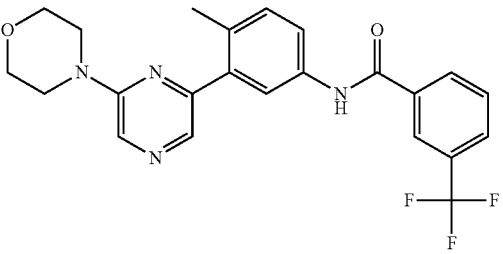 [SMILES: Cc1ccc(NC(=O)c2cccc(C(F)(F)F)c2)cc1-c1cncc(N2CCOCC2)n1] | 0.001003 | 0.000156 | 0.000308 |
| 119 | 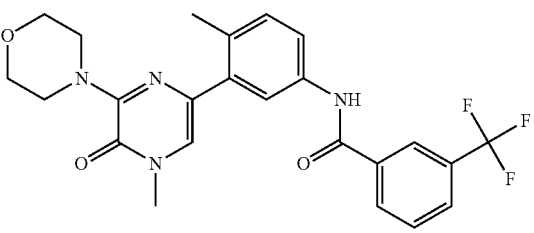 [SMILES: Cc1ccc(NC(=O)c2cccc(C(F)(F)F)c2)cc1-c1cn(C)c(=O)c(N2CCOCC2)n1] | | | 0.00027 |
| 120 | 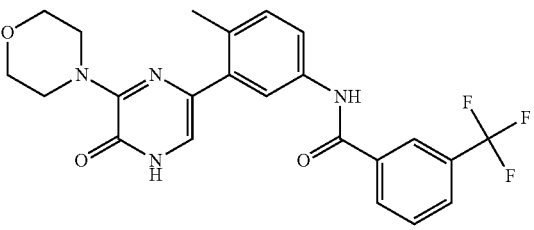 [SMILES: Cc1ccc(NC(=O)c2cccc(C(F)(F)F)c2)cc1-c1c[nH]c(=O)c(N2CCOCC2)n1] | 0.001214 | 0.000187 | |
| 121 | 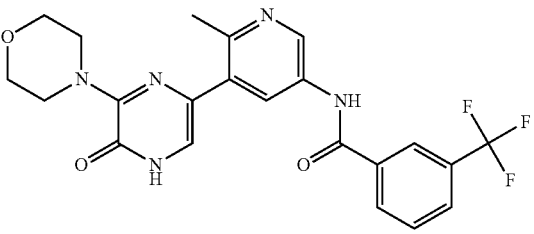 [SMILES: Cc1ncc(NC(=O)c2cccc(C(F)(F)F)c2)cc1-c1c[nH]c(=O)c(N2CCOCC2)n1] | 0.004451 | 0.000599 | |
| 122 | 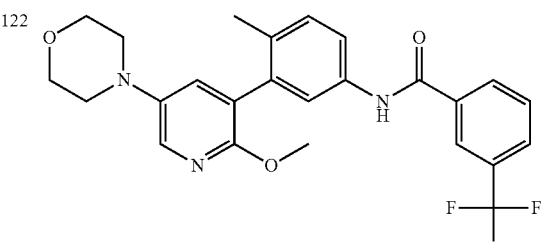 | 0.003877 | 0.000606 | |
| 123 | 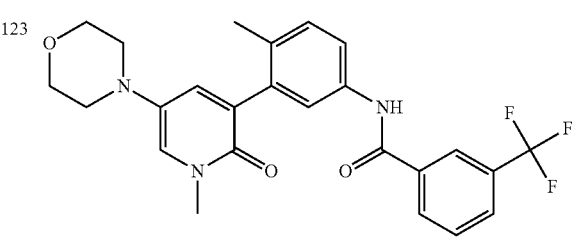 | 0.023164 | 0.004813 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 124 | 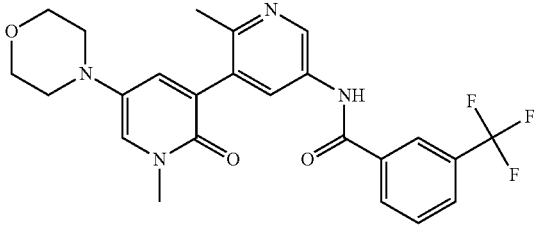 [SMILES: Cc1ncc(NC(=O)c2cccc(C(F)(F)F)c2)cc1-c1cc(N2CCOCC2)cn(C)c1=O] | 0.082672 | 0.017977 | |
| 125 | 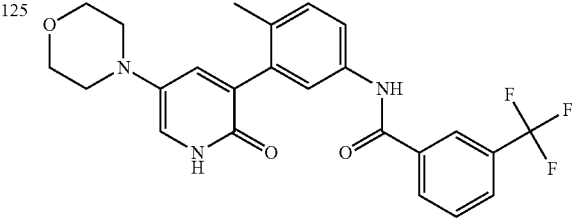 | 0.022327 | 0.006383 | |
| 126 | 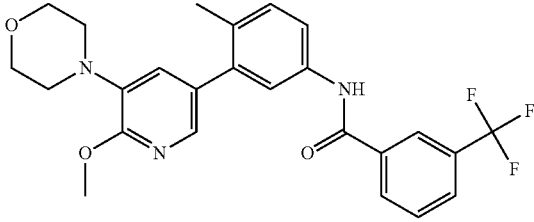 [SMILES: COc1ncc(-c2cc(NC(=O)c3cccc(C(F)(F)F)c3)ccc2C)cc1N1CCOCC1] | 0.00107 | 0.000299 | |
| 127 | 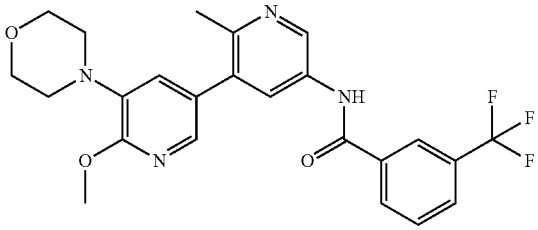 [SMILES: COc1ncc(-c2cc(NC(=O)c3cccc(C(F)(F)F)c3)cnc2C)cc1N1CCOCC1] | 0.001667 | 0.00031 | |
| 128 | 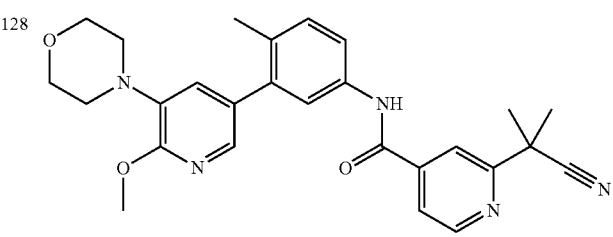 | 0.003782 | 0.000873 | |
| 129 | 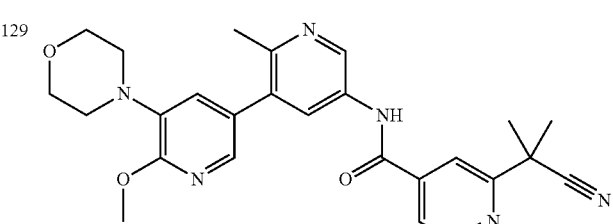 | 0.013441 | 0.002331 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 130 | 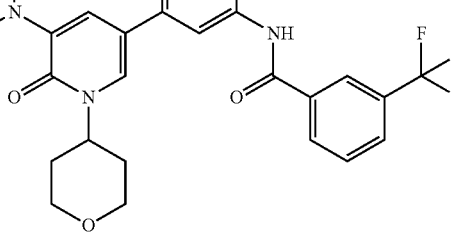 | 0.00577 | 0.001005 | |
| 131 | 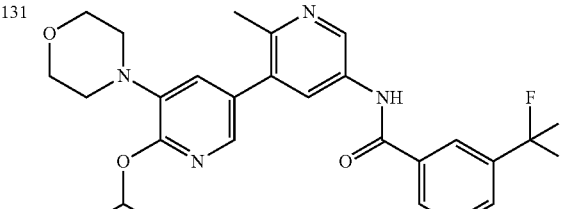 | 0.000483 | 0.000119 | |
| 132 | 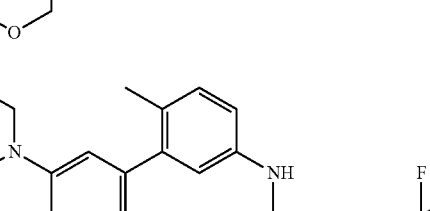 | 0.002708 | 0.000457 | |
| 133 | 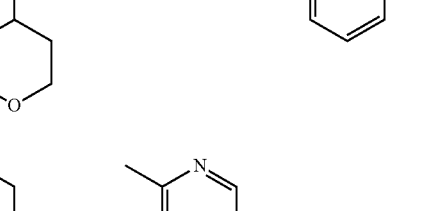 | 0.028875 | 0.001937 | |
| 134 | 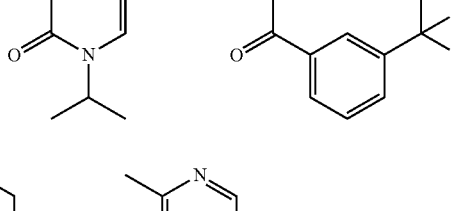 | 0.00364 | 0.000471 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 135 | 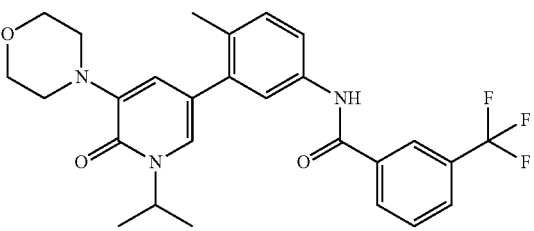 [SMILES: Cc1ccc(NC(=O)c2cccc(C(F)(F)F)c2)cc1-c1cc(N2CCOCC2)c(=O)n(C(C)C)c1] | 0.003957 | 0.000322 | |
| 136 | 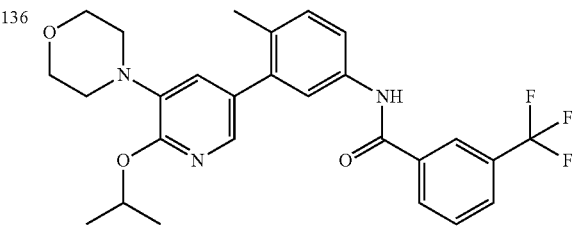 | 0.004173 | 0.000503 | |
| 137 | 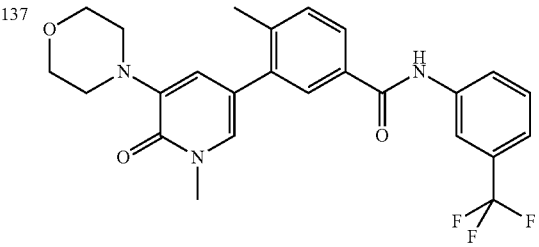 | 0.003792 | 0.000527 | |
| 138 | 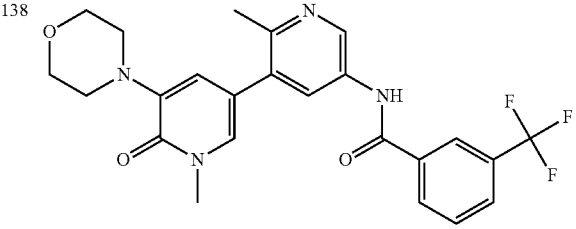 | 0.003112 | 0.000652 | |
| 139 | 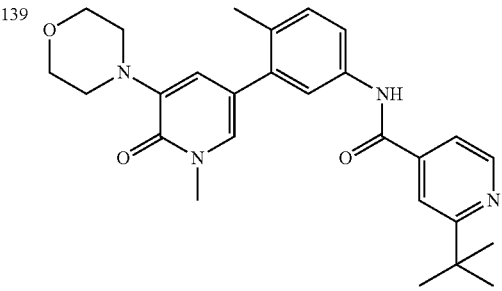 | 0.002454 | 0.000491 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 140 | 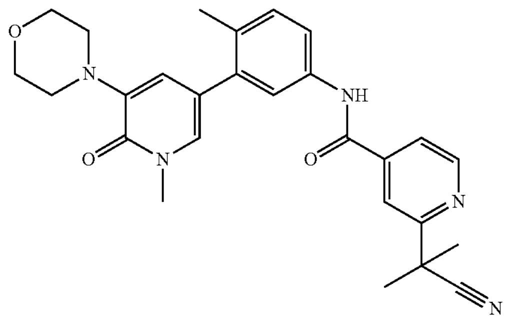 [SMILES: Cc1ccc(NC(=O)c2ccnc(C(C)(C)C#N)c2)cc1-c1cc(N2CCOCC2)c(=O)n(C)c1] | 0.0025 | 0.000483 | |
| 141 | 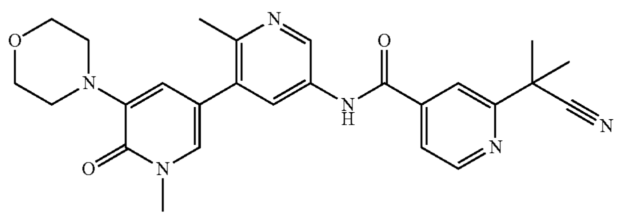 [SMILES: Cc1ncc(NC(=O)c2ccnc(C(C)(C)C#N)c2)cc1-c1cc(N2CCOCC2)c(=O)n(C)c1] | 0.034633 | 0.005762 | |
| 142 | 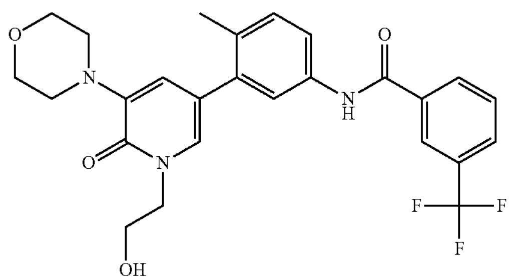 [SMILES: Cc1ccc(NC(=O)c2cccc(C(F)(F)F)c2)cc1-c1cc(N2CCOCC2)c(=O)n(CCO)c1] | 0.00223 | 0.000341 | |
| 143 | 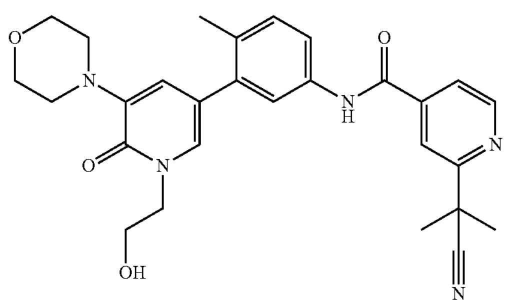 [SMILES: Cc1ccc(NC(=O)c2ccnc(C(C)(C)C#N)c2)cc1-c1cc(N2CCOCC2)c(=O)n(CCO)c1] | 0.00998 | 0.002261 | |
| 144 | 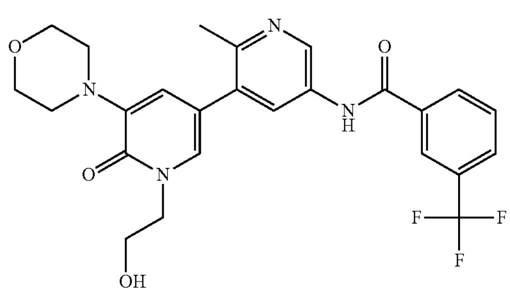 [SMILES: Cc1ncc(NC(=O)c2cccc(C(F)(F)F)c2)cc1-c1cc(N2CCOCC2)c(=O)n(CCO)c1] | 0.013851 | 0.002686 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 145 | 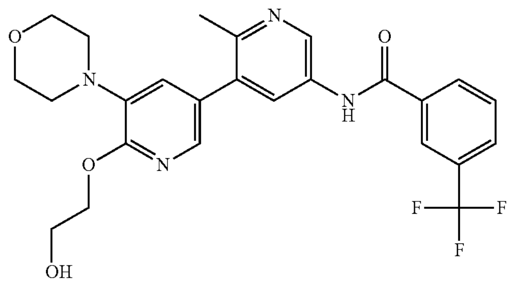 [SMILES: Cc1ncc(NC(=O)c2cccc(C(F)(F)F)c2)cc1-c1cnc(OCCO)c(N2CCOCC2)c1] | 0.003786 | 0.000676 | |
| 146 | 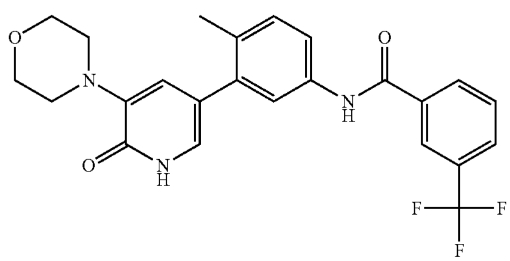 [SMILES: Cc1ccc(NC(=O)c2cccc(C(F)(F)F)c2)cc1-c1c[nH]c(=O)c(N2CCOCC2)c1] | 0.001918 | 0.000219 | |
| 147 | 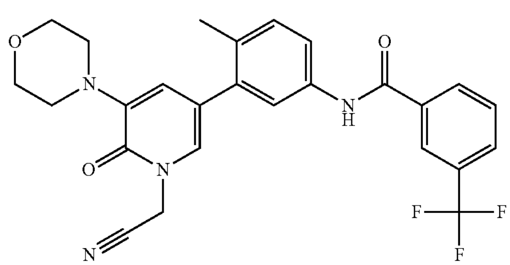 [SMILES: Cc1ccc(NC(=O)c2cccc(C(F)(F)F)c2)cc1-c1cc(N2CCOCC2)c(=O)n(CC#N)c1] | 0.000756 | 0.000103 | |
| 148 | 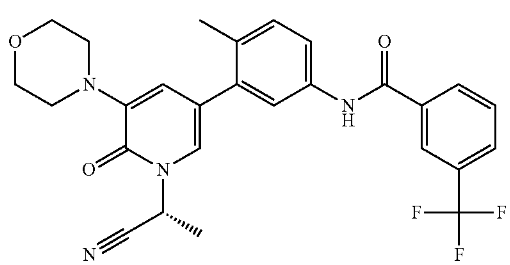 [SMILES: Cc1ccc(NC(=O)c2cccc(C(F)(F)F)c2)cc1-c1cc(N2CCOCC2)c(=O)n([C@H](C)C#N)c1] | 0.001889 | 0.000285 | |
| 149 | 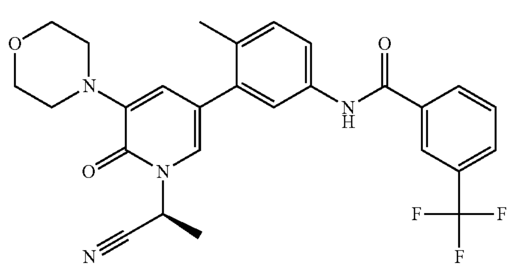 [SMILES: Cc1ccc(NC(=O)c2cccc(C(F)(F)F)c2)cc1-c1cc(N2CCOCC2)c(=O)n([C@@H](C)C#N)c1] | 0.002181 | 0.000273 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 150 | 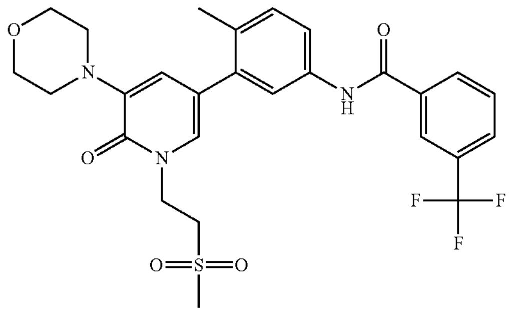 [SMILES: Cc1ccc(NC(=O)c2cccc(C(F)(F)F)c2)cc1-c1cc(N2CCOCC2)c(=O)n(CCS(C)(=O)=O)c1] | 0.003933 | 0.000562 | |
| 151 | 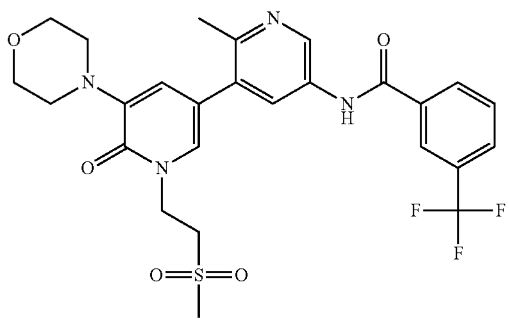 [SMILES: Cc1ncc(NC(=O)c2cccc(C(F)(F)F)c2)cc1-c1cc(N2CCOCC2)c(=O)n(CCS(C)(=O)=O)c1] | 0.019733 | 0.002897 | |
| 152 | 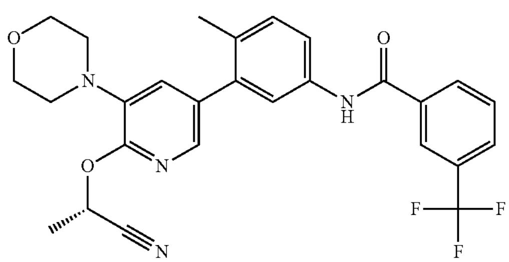 [SMILES: Cc1ccc(NC(=O)c2cccc(C(F)(F)F)c2)cc1-c1cnc(O[C@@H](C)C#N)c(N2CCOCC2)c1] | 0.003295 | 0.000474 | |
| 153 | 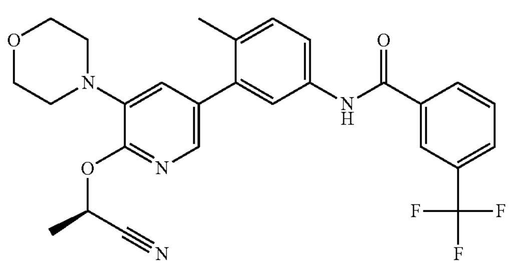 [SMILES: Cc1ccc(NC(=O)c2cccc(C(F)(F)F)c2)cc1-c1cnc(O[C@H](C)C#N)c(N2CCOCC2)c1] | 0.001023 | 0.000196 | |
| 154 | 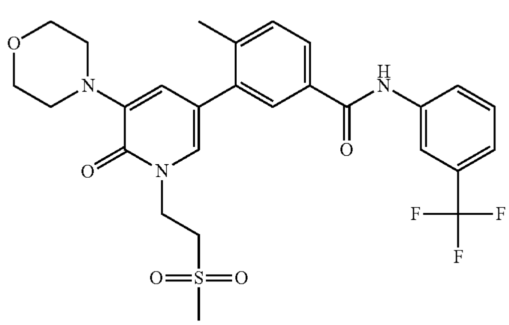 [SMILES: Cc1ccc(C(=O)Nc2cccc(C(F)(F)F)c2)cc1-c1cc(N2CCOCC2)c(=O)n(CCS(C)(=O)=O)c1] | 0.007186 | 0.001095 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 155 | 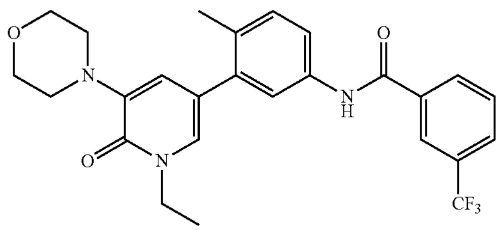 [SMILES: CCn1cc(-c2cc(NC(=O)c3cccc(C(F)(F)F)c3)ccc2C)cc(N2CCOCC2)c1=O] | 0.003831 | 0.000361 | |
| 156 | 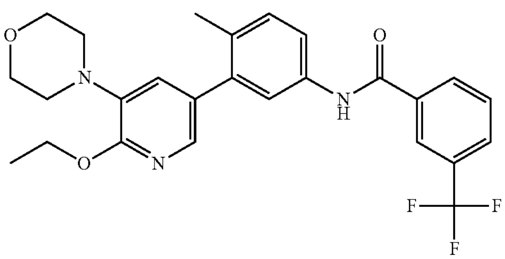 | 0.002484 | 0.000415 | |
| 157 | 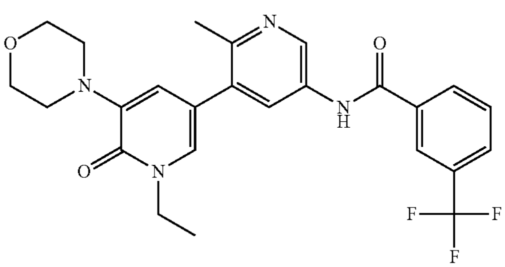 [SMILES: CCn1cc(-c2cc(NC(=O)c3cccc(C(F)(F)F)c3)cnc2C)cc(N2CCOCC2)c1=O] | 0.015761 | 0.002134 | |
| 158 | 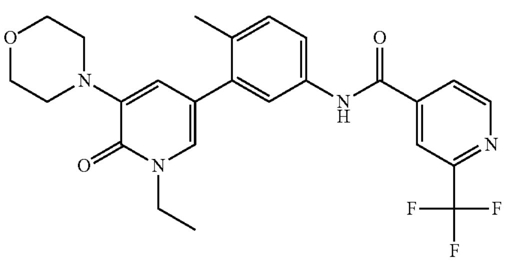 [SMILES: CCn1cc(-c2cc(NC(=O)c3ccnc(C(F)(F)F)c3)ccc2C)cc(N2CCOCC2)c1=O] | 0.008383 | 0.000835 | |
| 159 | 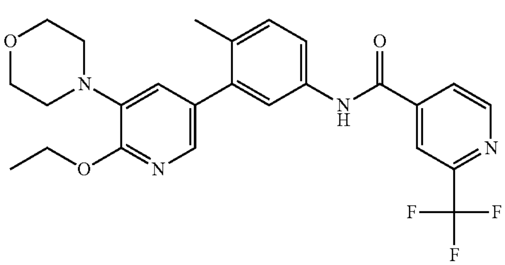 [SMILES: CCOc1ncc(-c2cc(NC(=O)c3ccnc(C(F)(F)F)c3)ccc2C)cc1N1CCOCC1] | 0.002618 | 0.000366 | |
| 160 | 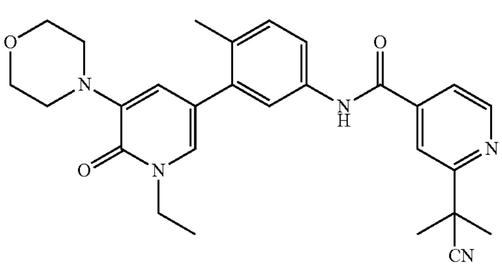 [SMILES: CCn1cc(-c2cc(NC(=O)c3ccnc(C(C)(C)C#N)c3)ccc2C)cc(N2CCOCC2)c1=O] | 0.009738 | 0.00089 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 161 | 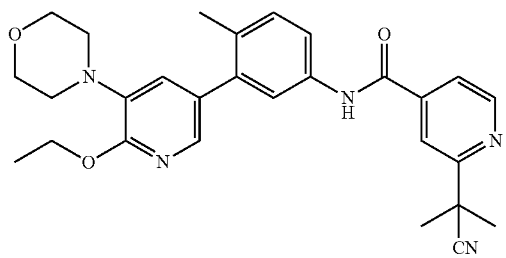 [SMILES: CCOc1ncc(-c2cc(NC(=O)c3ccnc(C(C)(C)C#N)c3)ccc2C)cc1N1CCOCC1] | 0.002648 | 0.000393 | |
| 162 | 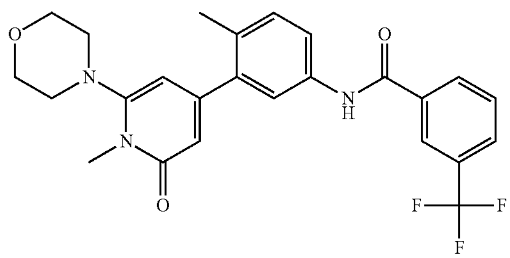 [SMILES: Cc1ccc(NC(=O)c2cccc(C(F)(F)F)c2)cc1-c1cc(N2CCOCC2)n(C)c(=O)c1] | 0.001835 | 0.000215 | |
| 163 | 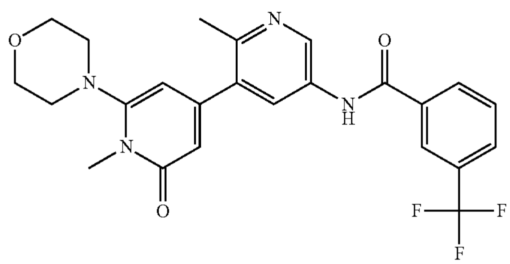 [SMILES: Cc1ncc(NC(=O)c2cccc(C(F)(F)F)c2)cc1-c1cc(N2CCOCC2)n(C)c(=O)c1] | 0.00769 | 0.000818 | |
| 164 | 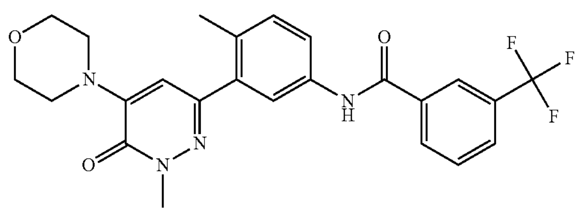 [SMILES: Cc1ccc(NC(=O)c2cccc(C(F)(F)F)c2)cc1-c1cc(N2CCOCC2)c(=O)n(C)n1] | 0.001575 | 0.000255 | |
| 165 | 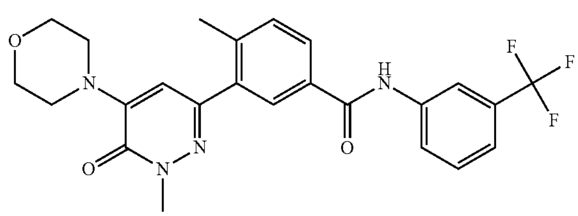 [SMILES: Cc1ccc(C(=O)Nc2cccc(C(F)(F)F)c2)cc1-c1cc(N2CCOCC2)c(=O)n(C)n1] | 0.003127 | 0.000416 | |
| 166 | 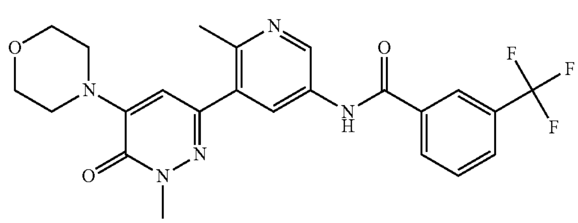 [SMILES: Cc1ncc(NC(=O)c2cccc(C(F)(F)F)c2)cc1-c1cc(N2CCOCC2)c(=O)n(C)n1] | 0.006933 | 0.000665 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 167 | 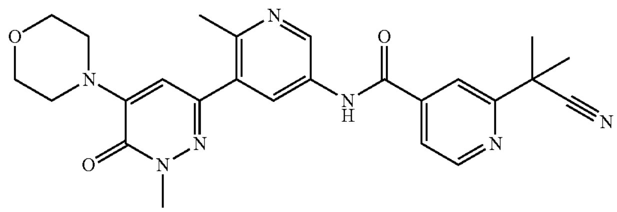 [SMILES: Cc1ncc(NC(=O)c2ccnc(C(C)(C)C#N)c2)cc1-c1cc(N2CCOCC2)c(=O)n(C)n1] | 0.106629 | 0.007674 | |
| 168 | 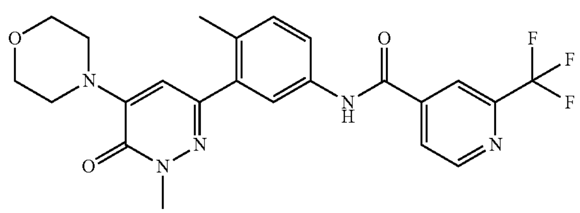 [SMILES: Cc1ccc(NC(=O)c2ccnc(C(F)(F)F)c2)cc1-c1cc(N2CCOCC2)c(=O)n(C)n1] | 0.003139 | 0.000245 | |
| 169 | 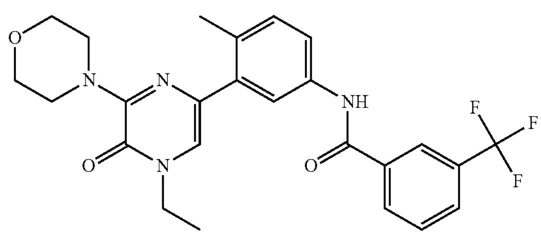 [SMILES: CCn1cc(-c2cc(NC(=O)c3cccc(C(F)(F)F)c3)ccc2C)nc(N2CCOCC2)c1=O] | 0.000775 | 0.00018 | |
| 170 | 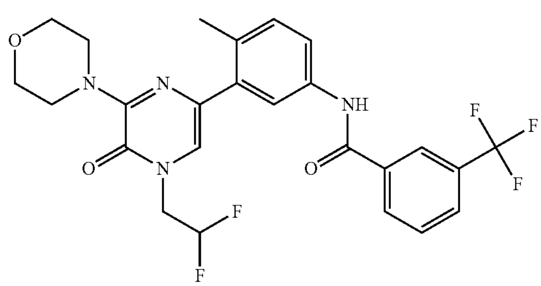 [SMILES: Cc1ccc(NC(=O)c2cccc(C(F)(F)F)c2)cc1-c1cn(CC(F)F)c(=O)c(N2CCOCC2)n1] | 0.001278 | 0.000263 | |
| 171 | 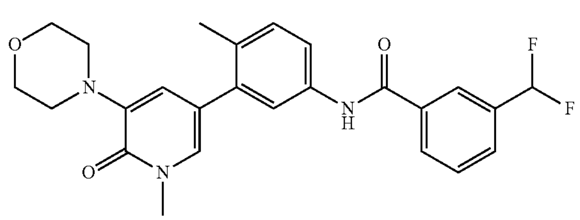 [SMILES: Cc1ccc(NC(=O)c2cccc(C(F)F)c2)cc1-c1cc(N2CCOCC2)c(=O)n(C)c1] | 0.001254 | 0.000213 | |
| 172 | 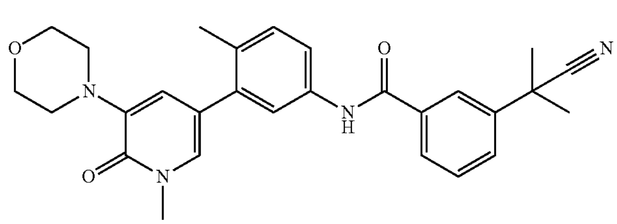 [SMILES: Cc1ccc(NC(=O)c2cccc(C(C)(C)C#N)c2)cc1-c1cc(N2CCOCC2)c(=O)n(C)c1] | 0.002908 | 0.000386 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 173 | 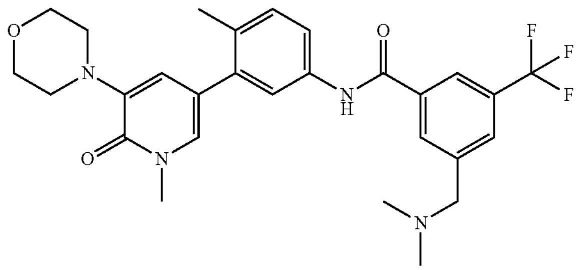 [SMILES: Cc1ccc(NC(=O)c2cc(CN(C)C)cc(C(F)(F)F)c2)cc1-c1cc(N2CCOCC2)c(=O)n(C)c1] | 0.0118 | 0.000853 | |
| 174 | 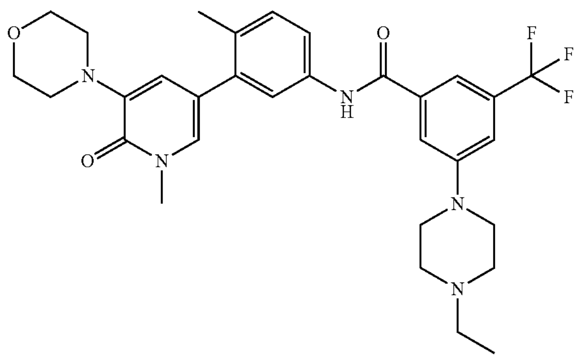 [SMILES: CCN1CCN(c2cc(C(=O)Nc3ccc(C)c(-c4cc(N5CCOCC5)c(=O)n(C)c4)c3)cc(C(F)(F)F)c2)CC1] | 0.010049 | 0.002238 | |
| 175 | 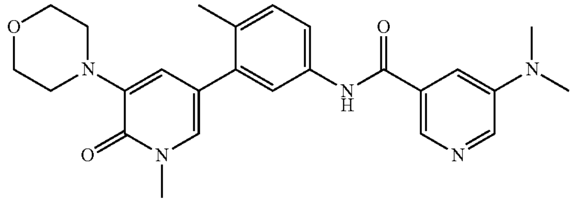 [SMILES: Cc1ccc(NC(=O)c2cncc(N(C)C)c2)cc1-c1cc(N2CCOCC2)c(=O)n(C)c1] | 0.001542 | 0.00023 | |
| 176 | 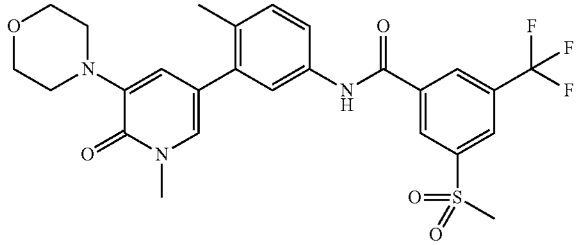 [SMILES: Cc1ccc(NC(=O)c2cc(C(F)(F)F)cc(S(C)(=O)=O)c2)cc1-c1cc(N2CCOCC2)c(=O)n(C)c1] | 0.002474 | 0.000398 | |
| 177 | 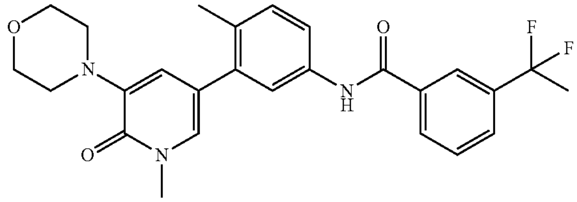 [SMILES: Cc1ccc(NC(=O)c2cccc(C(C)(F)F)c2)cc1-c1cc(N2CCOCC2)c(=O)n(C)c1] | 0.000706 | 0.000122 | |
| 178 | 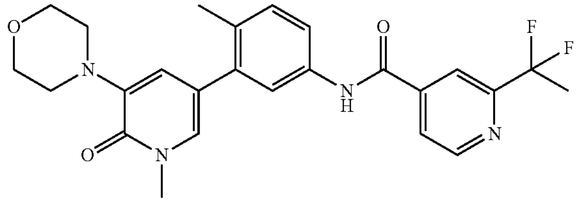 [SMILES: Cc1ccc(NC(=O)c2ccnc(C(C)(F)F)c2)cc1-c1cc(N2CCOCC2)c(=O)n(C)c1] | 0.000862 | 0.000172 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 179 | 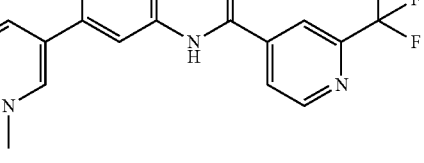 | 0.000905 | 0.00016 | |
| 181 | 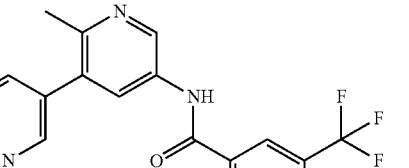 | 0.002664 | 0.000493 | |
| 182 | 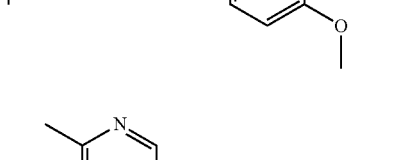 | 0.021222 | 0.002263 | |
| 184 | 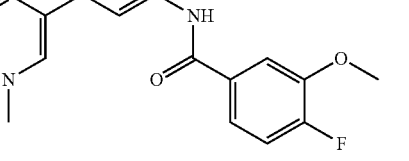 | 0.002202 | 0.000479 | |
| 185 | 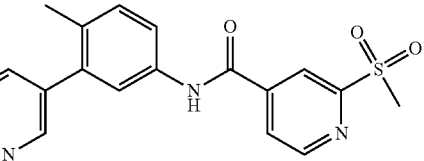 | 0.001819 | 0.000269 | |
| 186 | 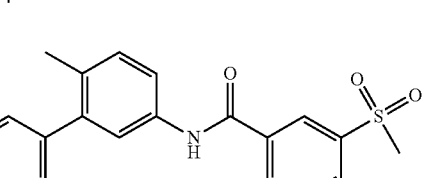 | 0.002242 | 0.000278 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 189 | 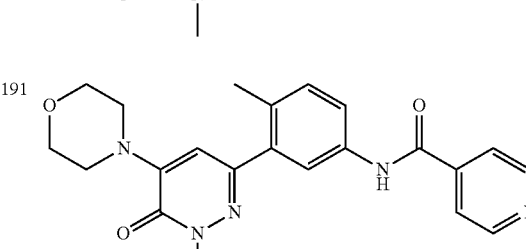 | 0.004735 | 0.000678 | |
| 191 | 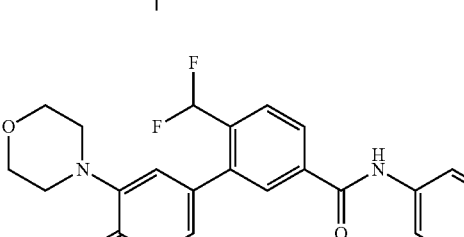 | 0.009525 | 0.001426 | |
| 192 | 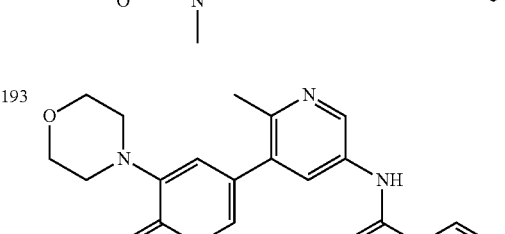 | 0.033857 | 0.002507 | |
| 193 | 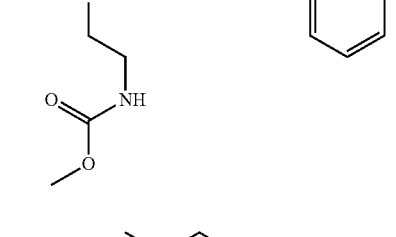 | 0.105813 | 0.011051 | |
| 194 | 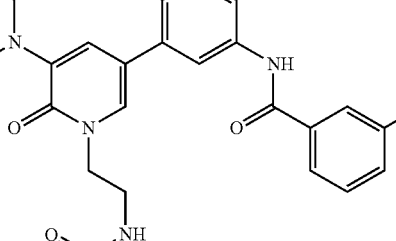 | 0.012407 | 0.002225 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 196 | 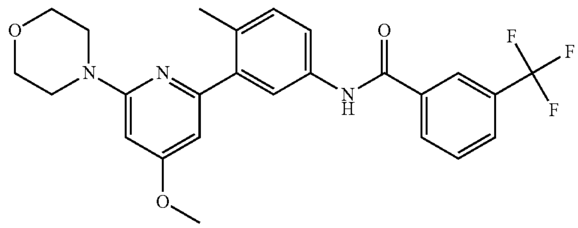 [SMILES: COc1cc(-c2cc(NC(=O)c3cccc(C(F)(F)F)c3)ccc2C)nc(N2CCOCC2)c1] | 0.002191 | 0.000403 | 0.000621 |
| 197 | 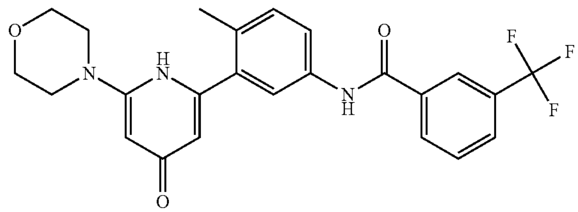 [SMILES: Cc1ccc(NC(=O)c2cccc(C(F)(F)F)c2)cc1-c1cc(=O)cc(N2CCOCC2)[nH]1] | 0.006733 | 0.001062 | |
| 198 | 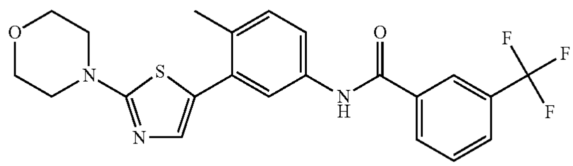 [SMILES: Cc1ccc(NC(=O)c2cccc(C(F)(F)F)c2)cc1-c1cnc(N2CCOCC2)s1] | | | 0.000455 |
| 199 | 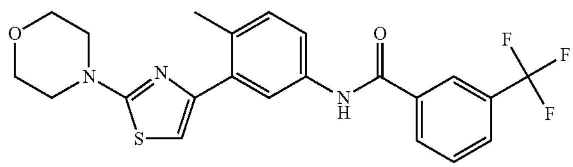 [SMILES: Cc1ccc(NC(=O)c2cccc(C(F)(F)F)c2)cc1-c1csc(N2CCOCC2)n1] | | | 0.001292 |
| 200 | 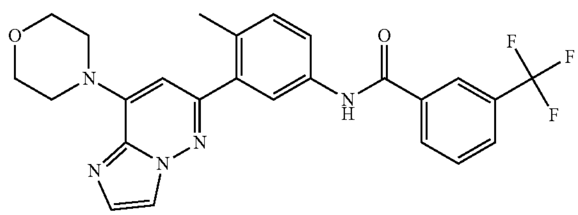 [SMILES: Cc1ccc(NC(=O)c2cccc(C(F)(F)F)c2)cc1-c1cc(N2CCOCC2)c2nccn2n1] | 0.001538 | 0.000205 | |
| 201 | 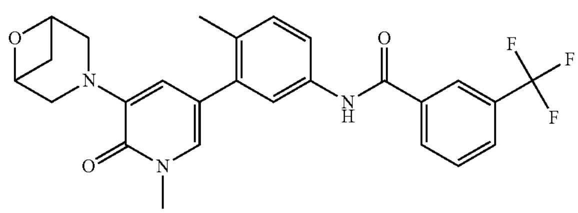 [SMILES: Cc1ccc(NC(=O)c2cccc(C(F)(F)F)c2)cc1-c1cc(N2CC3CC(C2)O3)c(=O)n(C)c1] | 0.014467 | 0.001991 | |
| 202 | 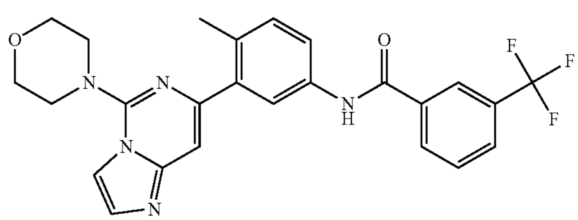 [SMILES: Cc1ccc(NC(=O)c2cccc(C(F)(F)F)c2)cc1-c1cc2nccn2c(N2CCOCC2)n1] | 0.000941 | 0.000155 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 203 | 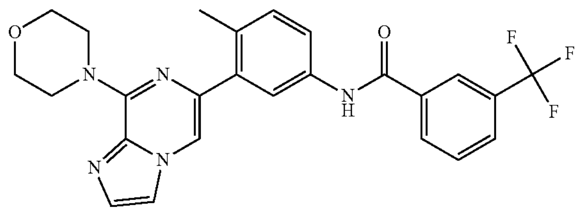 [SMILES: Cc1ccc(NC(=O)c2cccc(C(F)(F)F)c2)cc1-c1cn2ccnc2c(N2CCOCC2)n1] | 0.000389 | 0.000065 | |
| 204 | 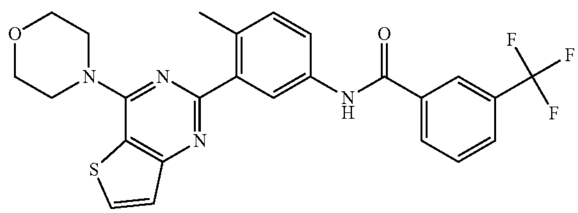 [SMILES: Cc1ccc(NC(=O)c2cccc(C(F)(F)F)c2)cc1-c1nc(N2CCOCC2)c2sccc2n1] | 0.000152 | 0.000039 | |
| 205 | 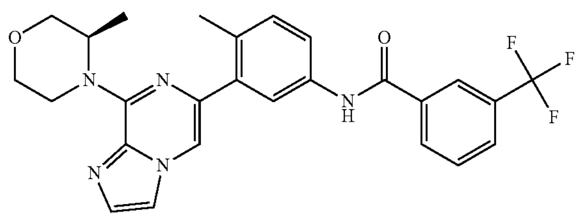 [SMILES: Cc1ccc(NC(=O)c2cccc(C(F)(F)F)c2)cc1-c1cn2ccnc2c(N2CCOC[C@H]2C)n1] | 0.001286 | 0.000185 | |
| 206 | 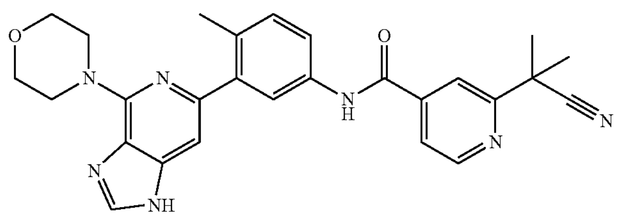 [SMILES: Cc1ccc(NC(=O)c2ccnc(C(C)(C)C#N)c2)cc1-c1cc2[nH]cnc2c(N2CCOCC2)n1] | 0.009218 | 0.001619 | |
| 207 | 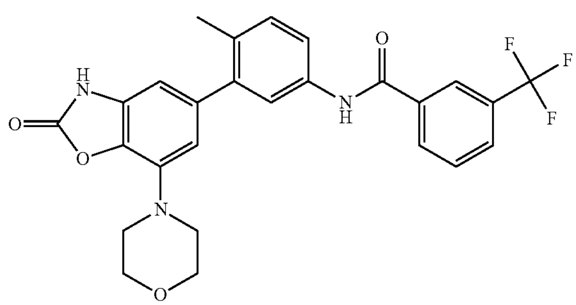 [SMILES: Cc1ccc(NC(=O)c2cccc(C(F)(F)F)c2)cc1-c1cc(N2CCOCC2)c2oc(=O)[nH]c2c1] | 0.001399 | 0.000225 | |
| 208 | 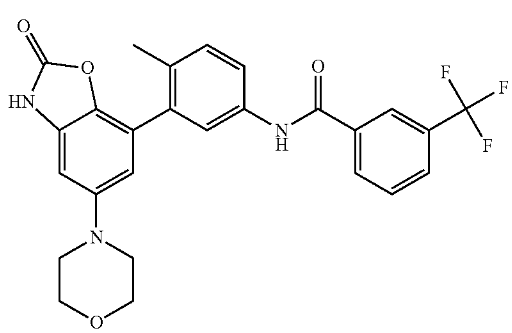 [SMILES: Cc1ccc(NC(=O)c2cccc(C(F)(F)F)c2)cc1-c1cc(N2CCOCC2)cc2[nH]c(=O)oc12] | 0.005048 | 0.001099 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 209 | 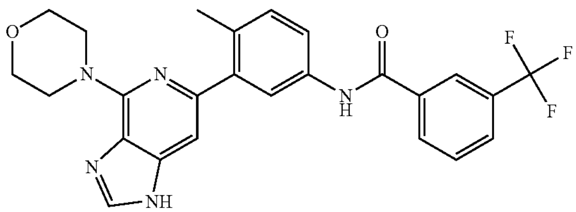 [SMILES: Cc1ccc(NC(=O)c2cccc(C(F)(F)F)c2)cc1-c1cc2[nH]cnc2c(N2CCOCC2)n1] | 0.001067 | 0.000171 | |
| 210 | 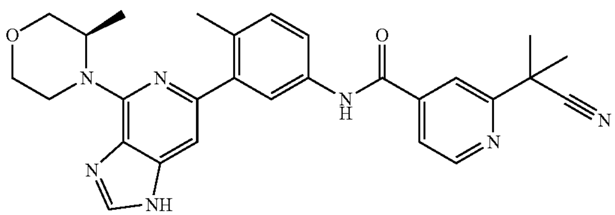 [SMILES: Cc1ccc(NC(=O)c2ccnc(C(C)(C)C#N)c2)cc1-c1cc2[nH]cnc2c(N2CCOC[C@H]2C)n1] | 0.022094 | 0.002729 | |
| 211 | 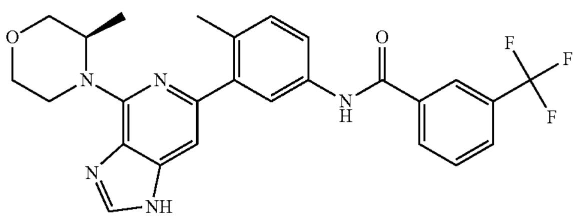 [SMILES: Cc1ccc(NC(=O)c2cccc(C(F)(F)F)c2)cc1-c1cc2[nH]cnc2c(N2CCOC[C@H]2C)n1] | 0.006261 | 0.000873 | |
| 212 | 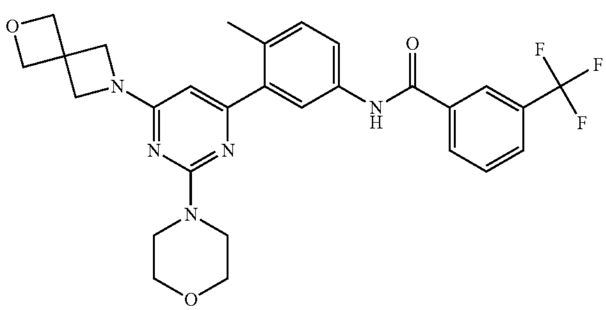 [SMILES: Cc1ccc(NC(=O)c2cccc(C(F)(F)F)c2)cc1-c1cc(N2CC3(COC3)C2)nc(N2CCOCC2)n1] | | | |
| 214 | 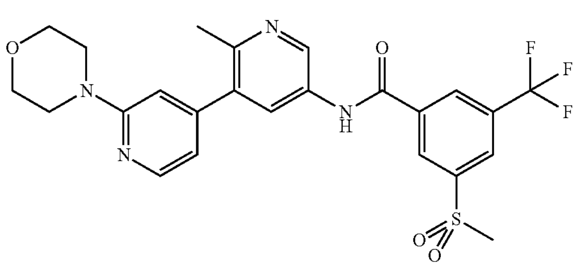 [SMILES: Cc1ncc(NC(=O)c2cc(C(F)(F)F)cc(S(C)(=O)=O)c2)cc1-c1ccnc(N2CCOCC2)c1] | 0.00483 | 0.000547 | |
| 215 | 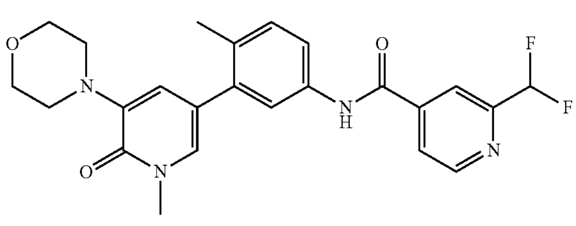 | 0.007267 | 0.000785 | |

TABLE 1-continued
Selected compound structures and Raf inhibition data (IC-50's are micromolar).
| Ex. No. | Structure | B-Raf IC50 | C-Raf FL IC50 | C-Raf TR IC50 |
|---|---|---|---|---|
| 216 | 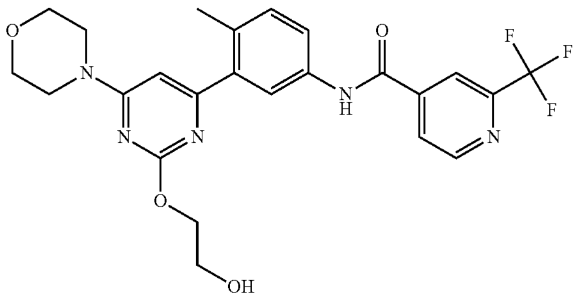 [SMILES: Cc1ccc(NC(=O)c2ccnc(C(F)(F)F)c2)cc1-c1cc(N2CCOCC2)nc(OCCO)n1] | | | |
| 217 | 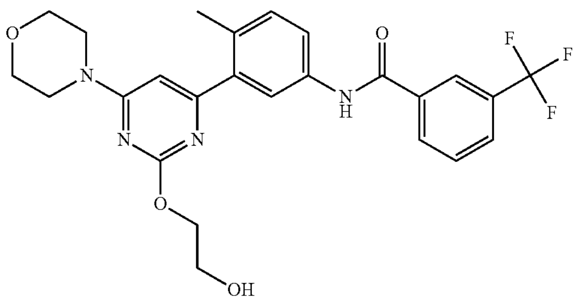 [SMILES: Cc1ccc(NC(=O)c2cccc(C(F)(F)F)c2)cc1-c1cc(N2CCOCC2)nc(OCCO)n1] | | | |
| 218 | 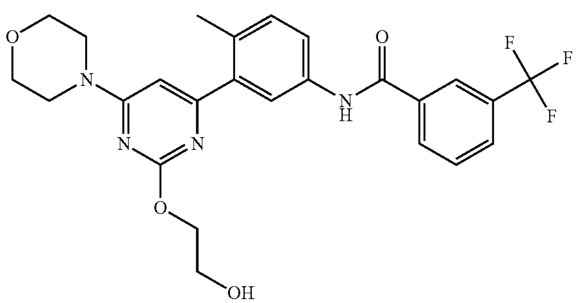 [SMILES: Cc1ccc(NC(=O)c2cccc(C(F)(F)F)c2)cc1-c1cc(N2CCOCC2)nc(OCCO)n1] | | | |
| 219 | 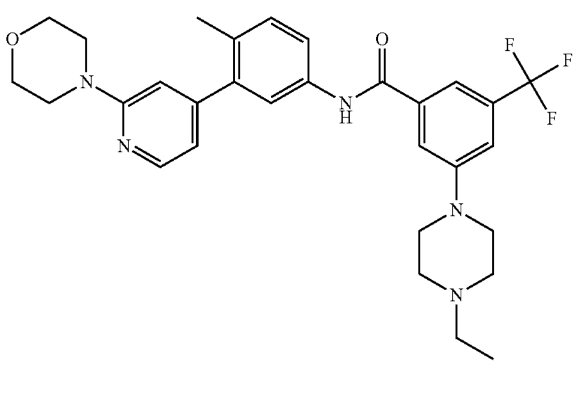 [SMILES: CCN1CCN(c2cc(C(=O)Nc3ccc(C)c(-c4ccnc(N5CCOCC5)c4)c3)cc(C(F)(F)F)c2)CC1] | 0.002834 | 0.000362 | |

TABLE 1-continued

Selected compound structures and Raf inhibition data (IC-50's are micromolar).

| Ex. No. | Structure | B-Raf IC50 | C-Raf FL IC50 | C-Raf TR IC50 |
|---|---|---|---|---|
| 220 | 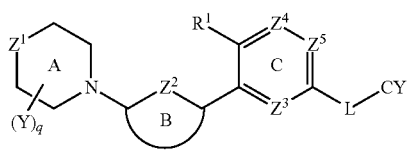 | | | |

The invention claimed is:

1. A compound of formula (I):

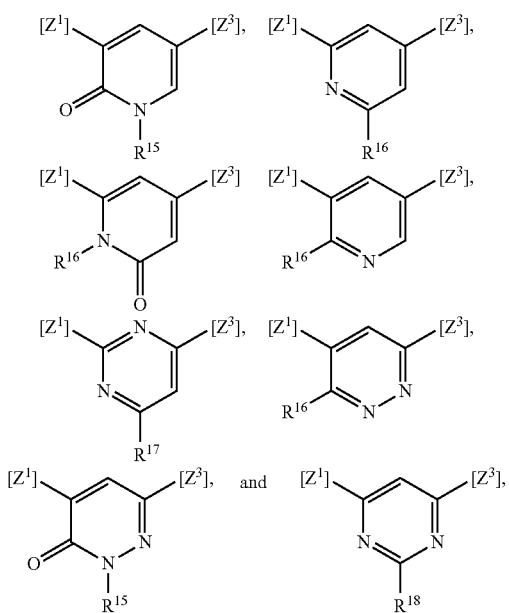

or a pharmaceutically acceptable salt thereof, wherein:

$Z^1$ is O, S, S(=O) or $SO_2$;

$Z^2$ is N or $CR^a$, where $R^a$ is H;

$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;

Ring B is selected from wherein [$Z^1$] indicates where the ring containing $Z^1$ is attached to ring B, and [$Z^3$] indicates where the ring containing $Z^3$ is attached to ring B, and $R^{15}$, $R^{16}$, $R^{17}$ and $R^{18}$ are each selected from $R^{20}$, CN, halo, $-N(R^{20})_2$, $-OR^{20}$, and $C_{4-8}$ heterocycloalkyl optionally substituted with up to two groups selected from hydroxyl, $C_{1-4}$ alkyl, oxo, and halo; where each $R^{20}$ is independently H or $C_{1-4}$ alkyl optionally substituted with up to three groups independently selected from halo, oxo, $C_{1-4}$ alkoxy, hydroxyl, amino, and CN;

each Y is independently selected from $C_{1-4}$ alkyl, $C_{1-4}$ alkoxy, CN, halo, oxo, $-(CH_2)_pOR^4$, $-(CH_2)_p N(R^4)_2$, $-(CH_2)_pNHC(O)R^4$, $-(CH_2)_pNHCOO(C_{1-4}$ alkyl), or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, $-(CH_2)_p OR^4$, $-(CH_2)_p N(R^4)_2$, $-(CH_2)_pNHC(O)R^4$, and $-(CH_2)_pNHCOO(C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N;

L is $-C(=O)-NH-[CY]$ or $-NH-C(=O)-[CY]$, where [CY] indicates which atom of L is attached to CY; and CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, OH, $NH_2$, $NHR^5$, and $-N(R^5)_2$;

wherein each $R^5$ is independently $C_{1-4}$ alkyl, $C_{4-6}$ heterocyclyl, or $C_{3-8}$ cycloalkyl, and $R^5$ is optionally substituted with up to three groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, $NHC(=O)R^6$, $-CH_2OR^7$, $-CH_2N(R^7)_2$, wherein each $R^6$ is independently $C_{1-4}$ alkyl, and each $R^7$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$ alkoxy.

2. A compound according to claim 1 or a pharmaceutically acceptable salt thereof, wherein $Z^1$ is O.

3. A compound according to claim 1 or a pharmaceutically acceptable salt thereof, wherein $Z^2$ is CH.

4. A compound of claim 1 or a pharmaceutically acceptable salt thereof, wherein CY is selected from phenyl, pyridine, pyrimidine, pyrazine, pyridazine, pyridone, thiazole, and oxazole.

5. A compound according to any of the preceding claims or a pharmaceutically acceptable salt thereof, wherein $R^1$ is methyl or $CF_3$.

6. A compound of claim 1, or a pharmaceutically thereof, wherein Ring B is pyridine or pyrimidine or pyridone.

7. A compound of claim 1, or a pharmaceutically acceptable salt thereof, wherein CY is substituted phenyl or substituted pyridin-4-yl.

8. A compound of claim 1, or a pharmaceutically acceptable salt thereof, wherein CY is substituted with at least one group selected from $CF_3$, $OCF_3$, t-butyl, —$C(Me)_2CN$, and —$SO_2Me$.

9. A compound of claim 1, or a pharmaceutically acceptable salt thereof, wherein $Z^4$ is CH.

10. A compound of claim 1, or a pharmaceutically acceptable salt thereof, wherein $Z^4$ is N.

11. A compound of claim 1, or a pharmaceutically acceptable salt thereof, wherein L is —C(=O)—NH—[CY], where [CY] indicates which atom of L is attached to ring CY.

12. A compound of claim 1, or a pharmaceutically acceptable salt thereof, wherein L is —NH—C(=O)—[CY], where [CY] indicates which atom of L is attached to ring CY.

13. A compound of claim 1, or a pharmaceutically acceptable salt thereof, wherein $Z^3$ is N.

14. A compound of claim 1, or a pharmaceutically acceptable salt thereof, selected from:

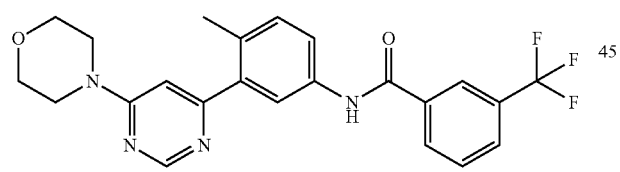

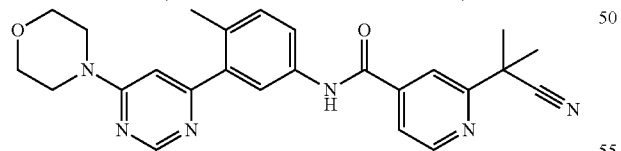

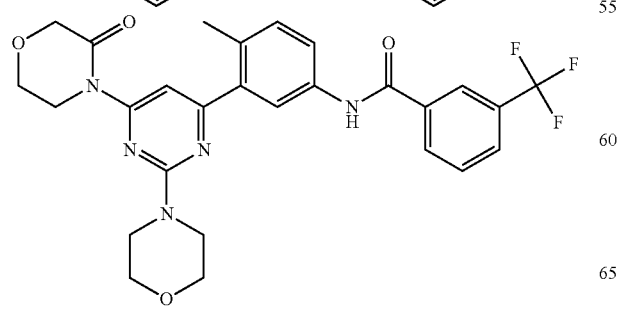

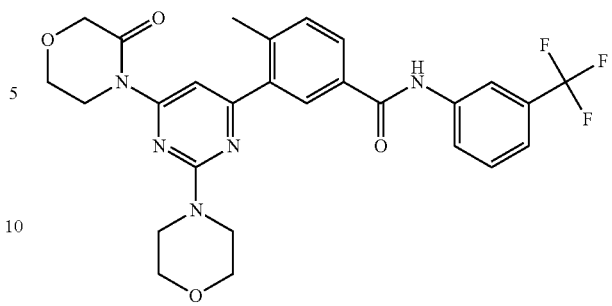

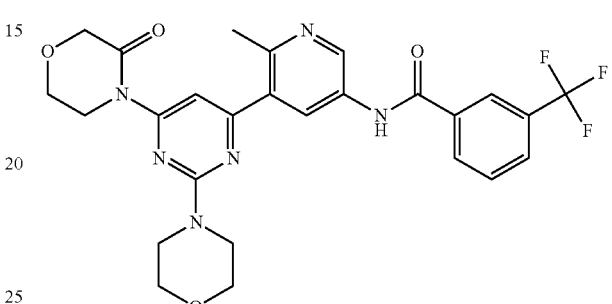

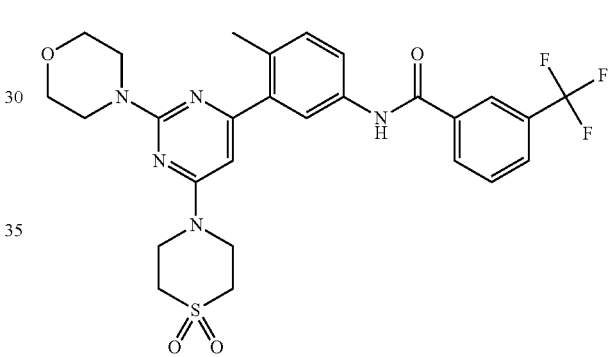

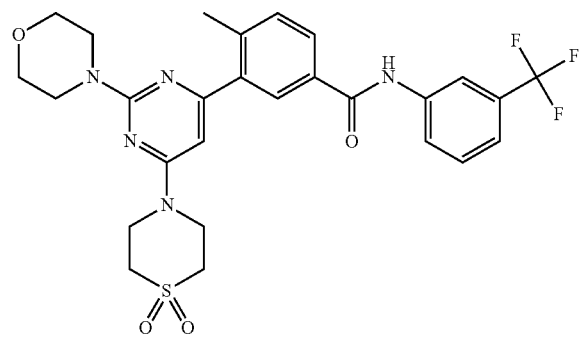

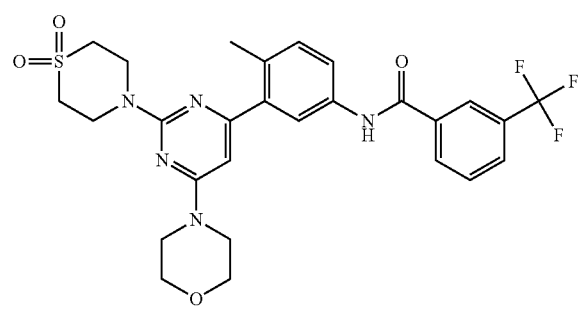

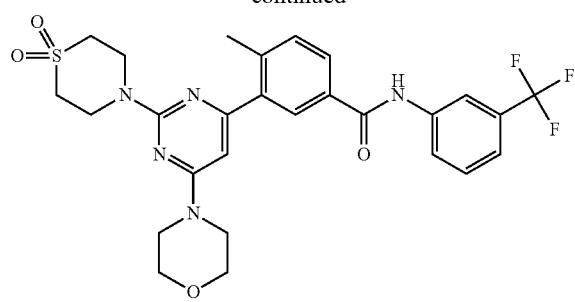
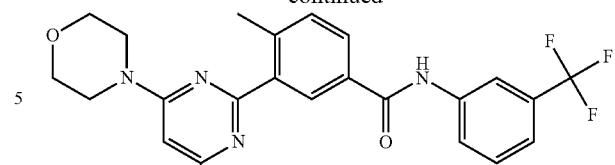
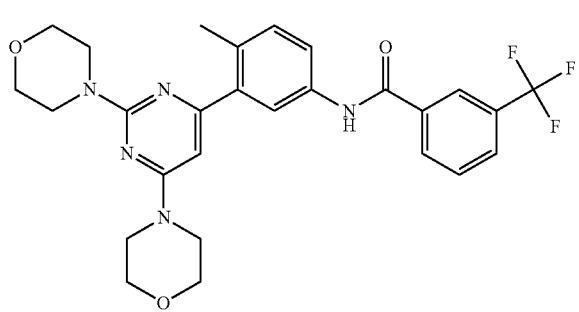 [SMILES: Cc1ccc(NC(=O)c2cccc(C(F)(F)F)c2)cc1-c1cc(N2CCOCC2)nc(N2CCOCC2)n1]
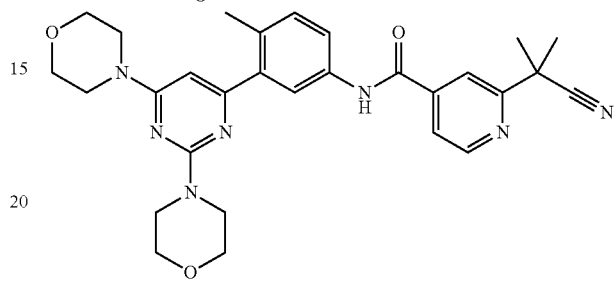
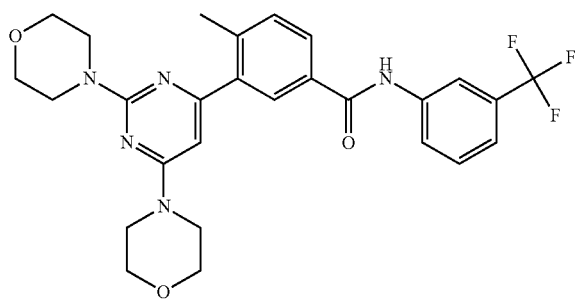
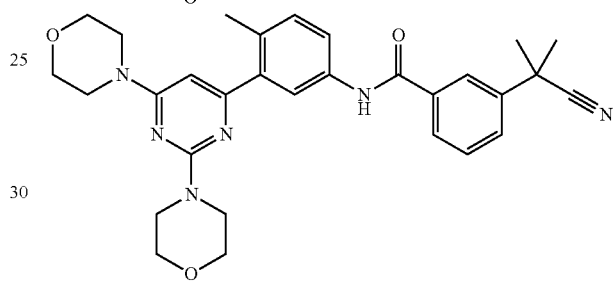
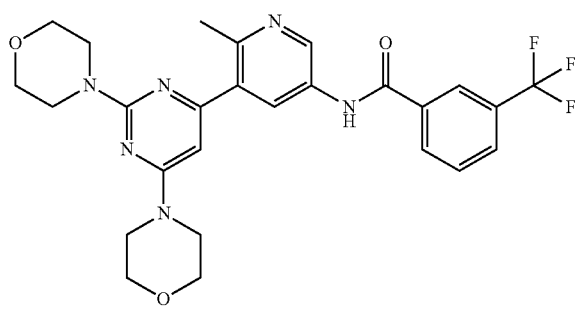
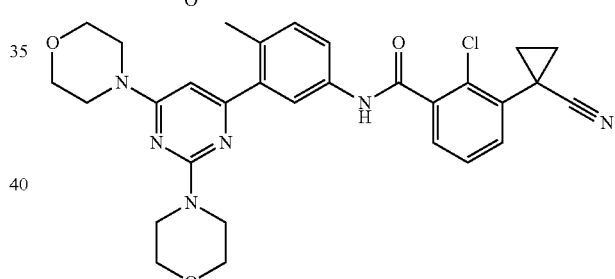
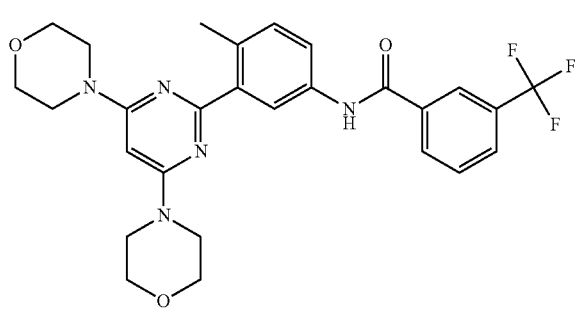
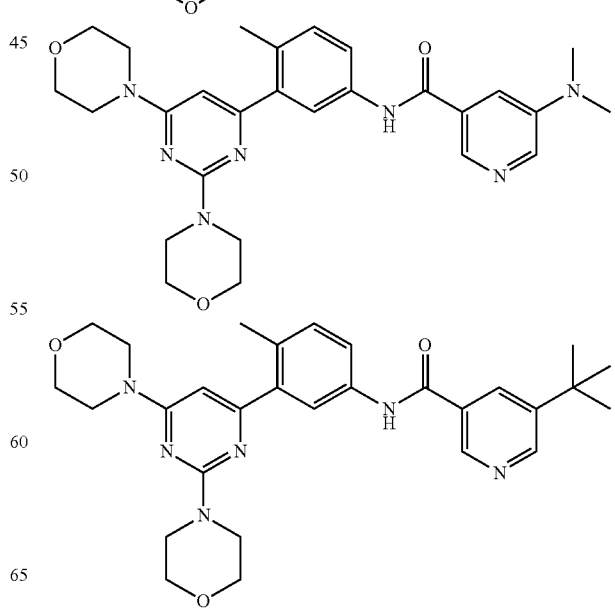

243
-continued
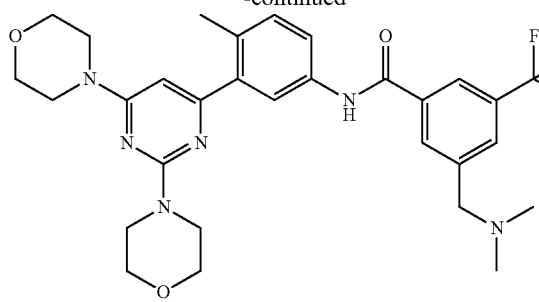
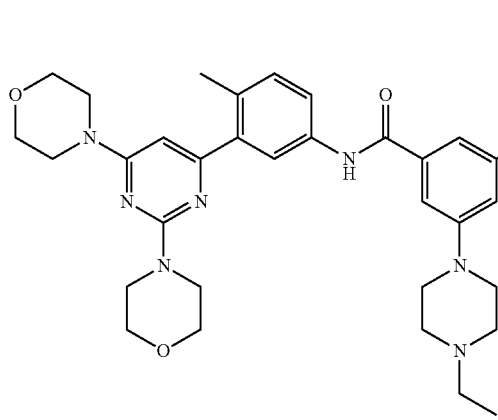
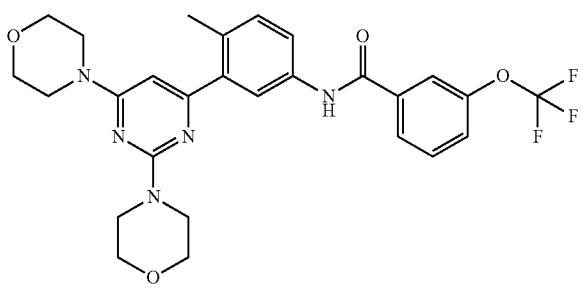
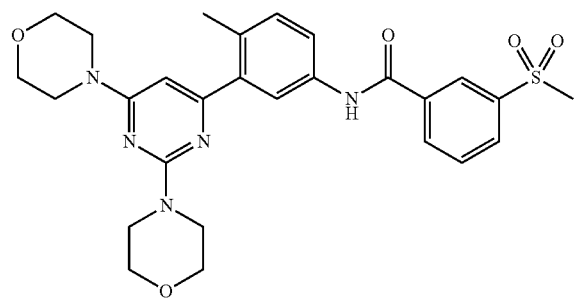
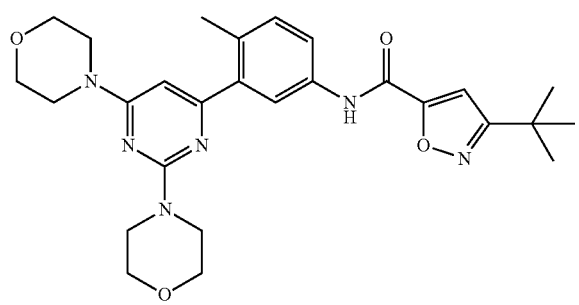
244
-continued
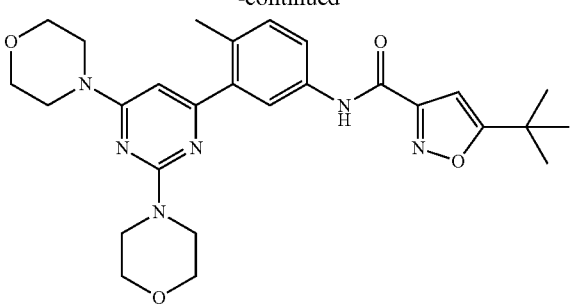
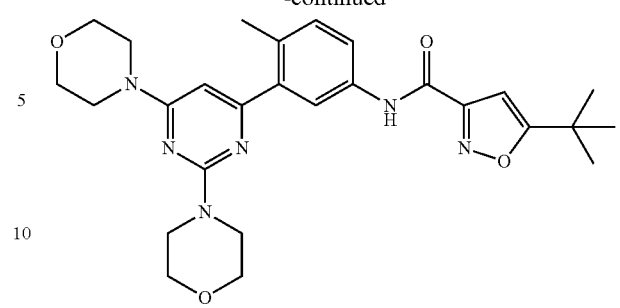

245
-continued
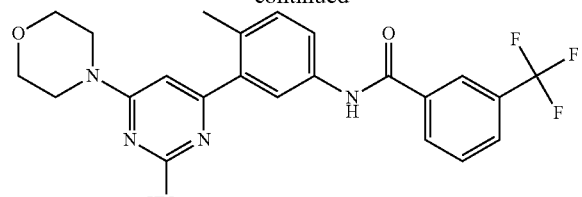
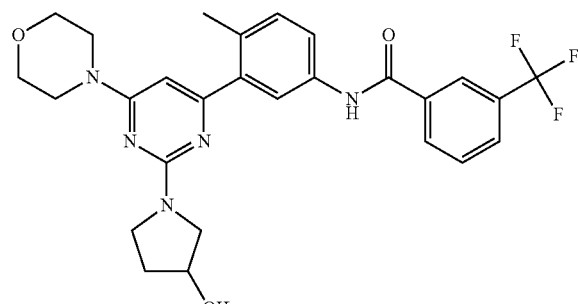
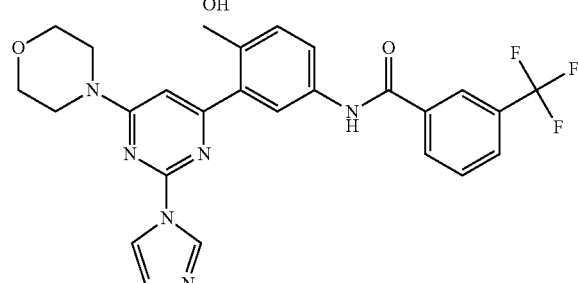
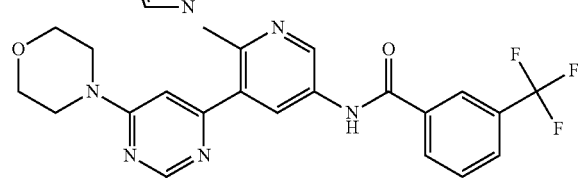
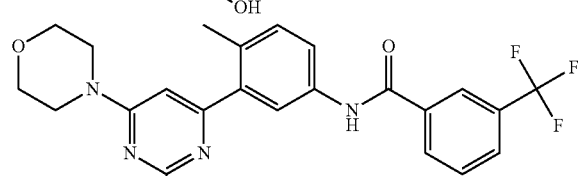
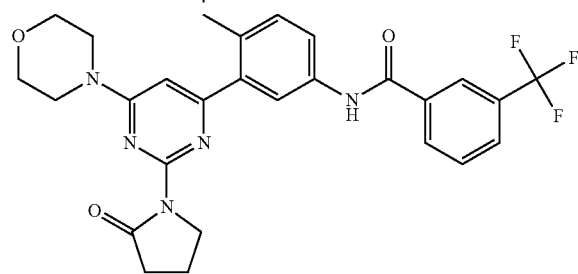
246
-continued
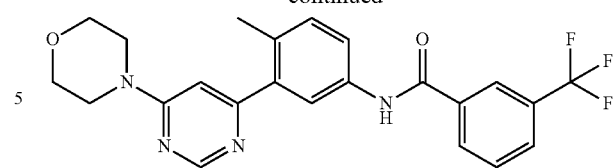
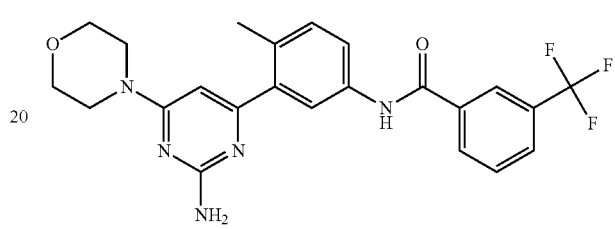
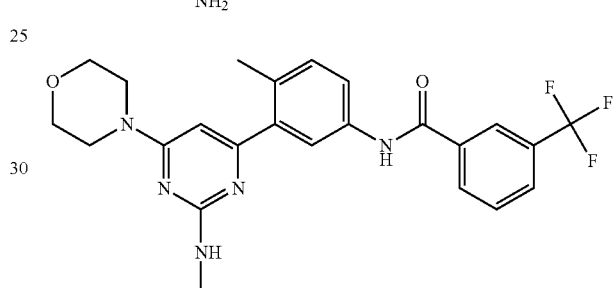
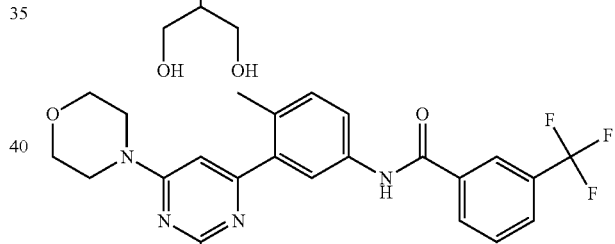
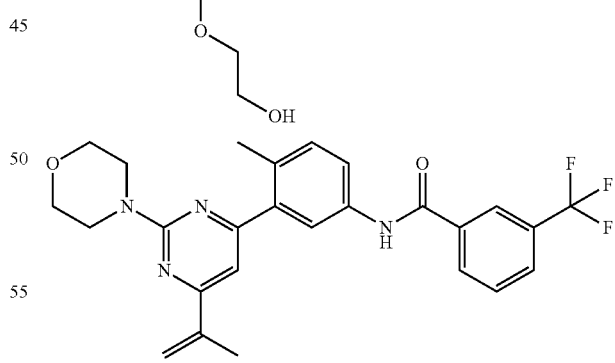
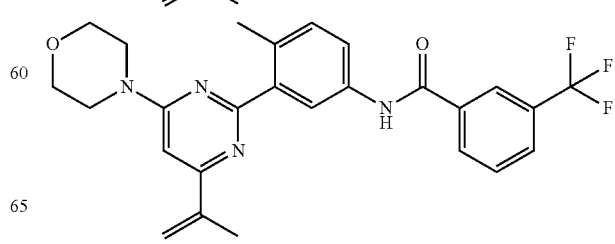

247
-continued
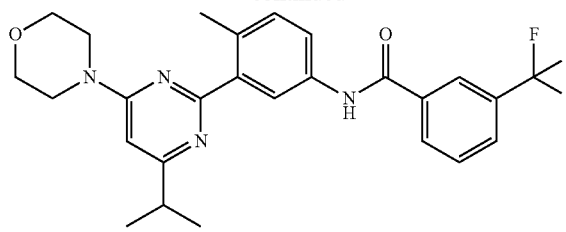
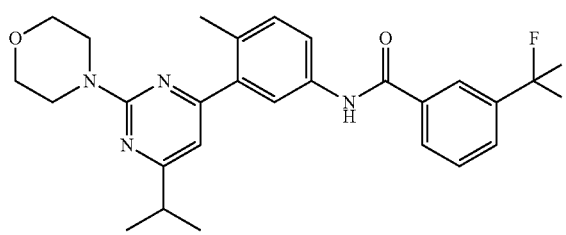
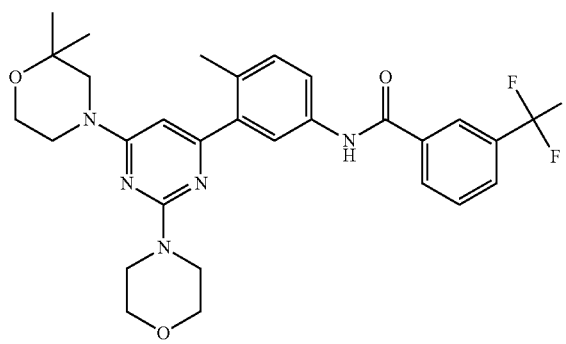
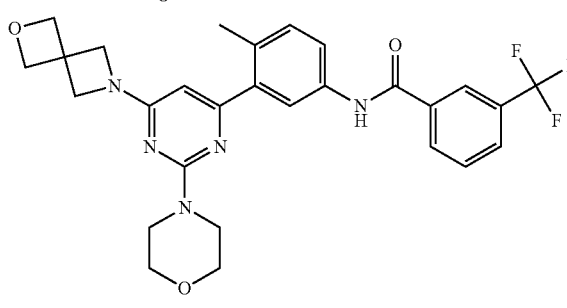
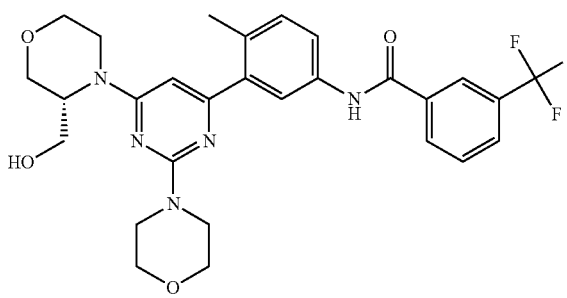
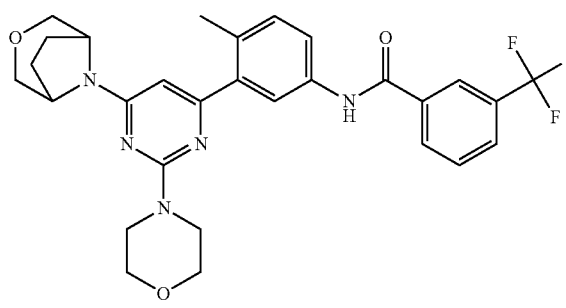
248
-continued
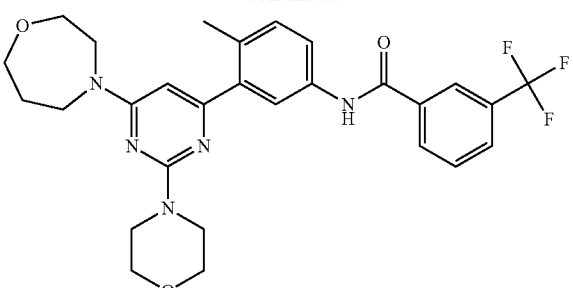
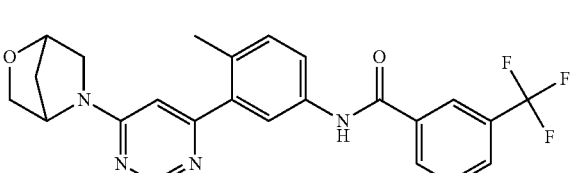
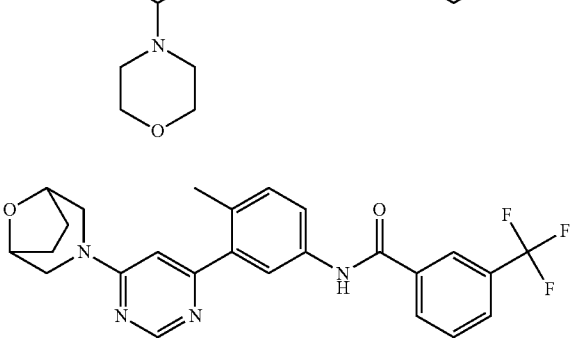
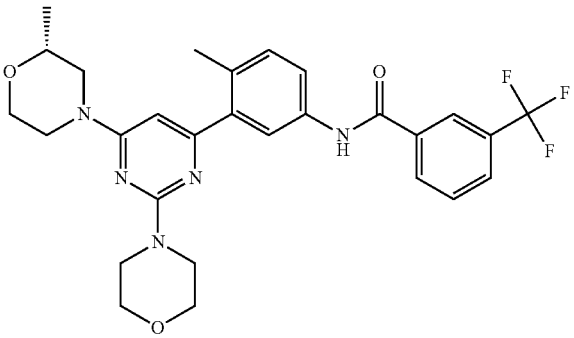
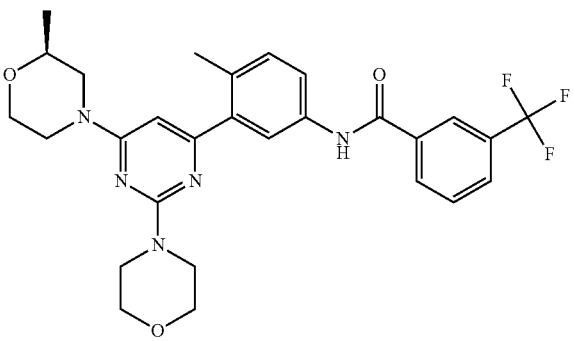

249
-continued
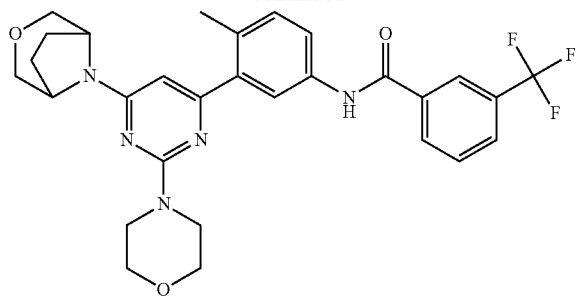
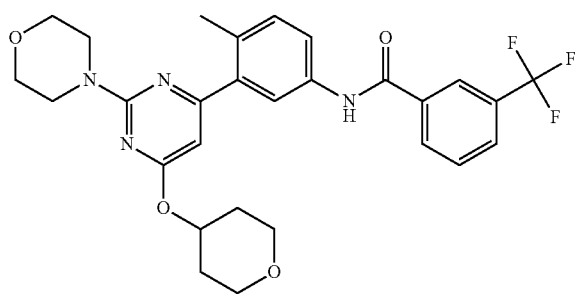
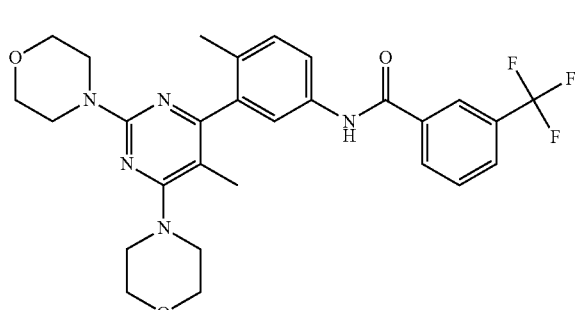
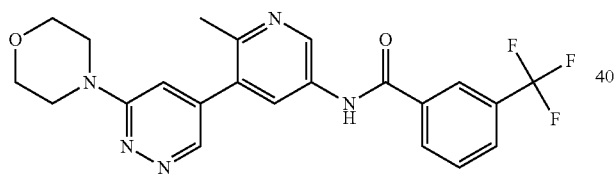
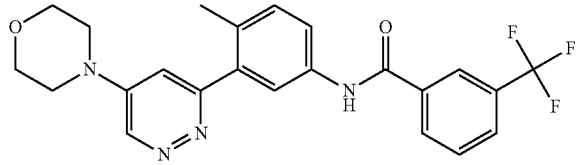
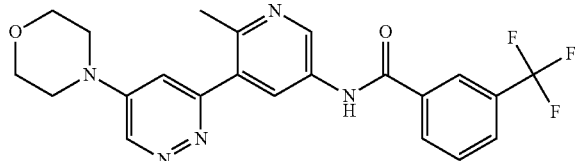
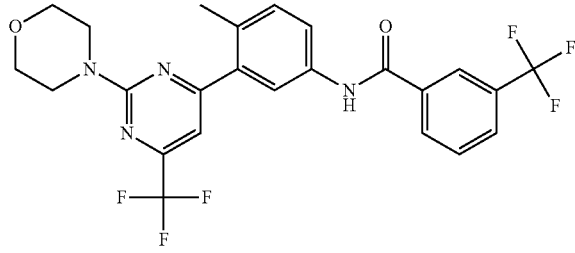
250
-continued
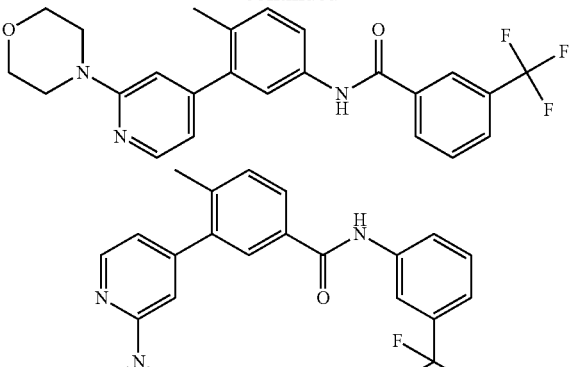
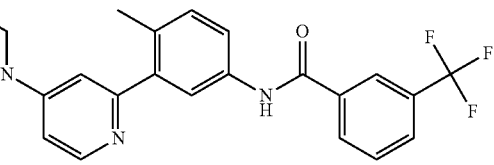
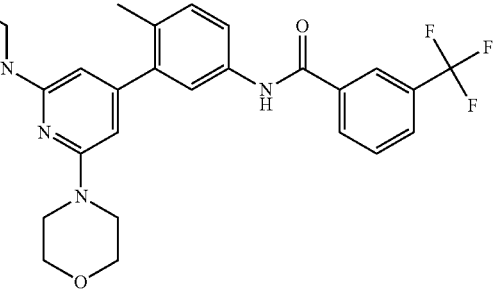
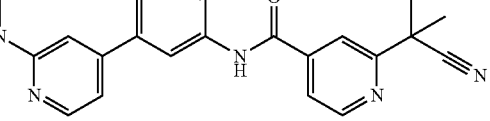
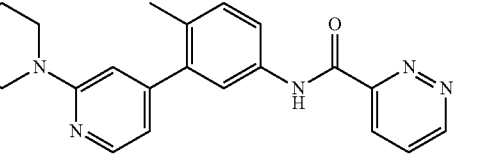
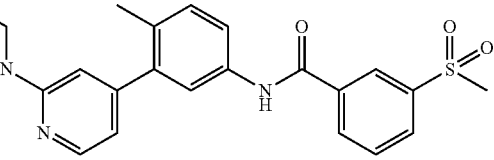
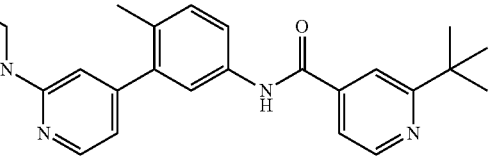
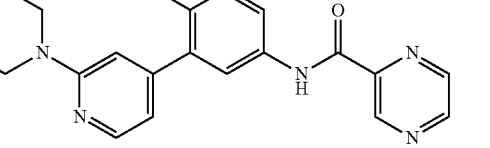

251
-continued
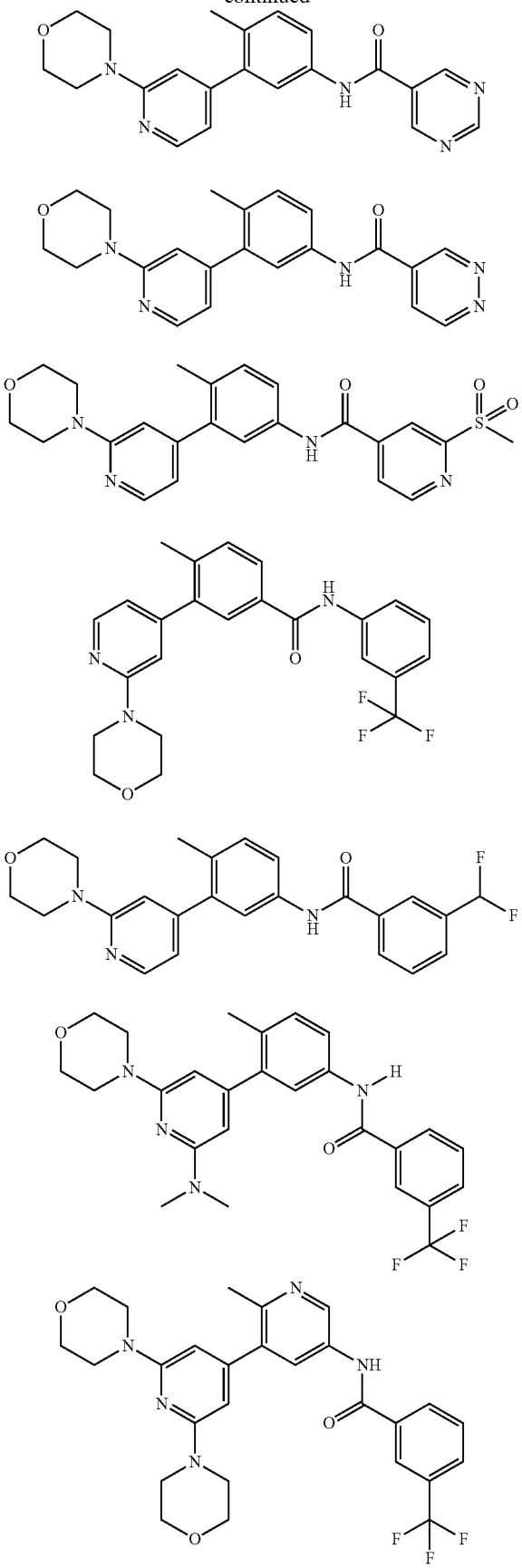
252
-continued
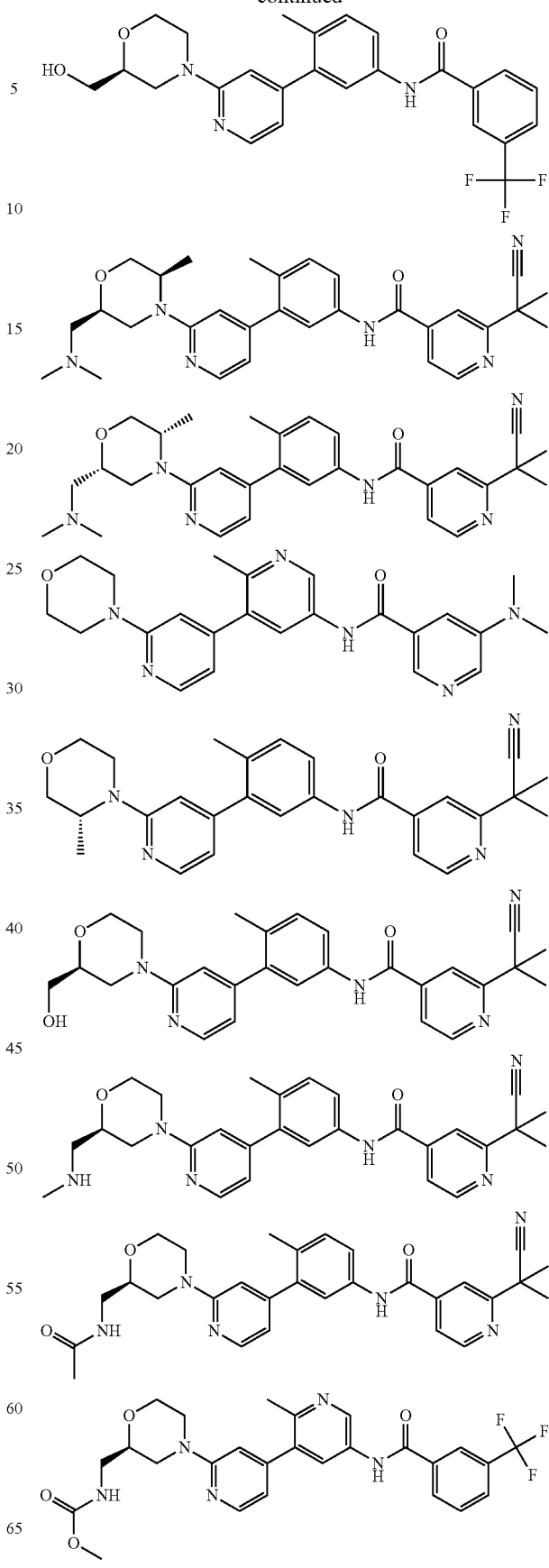

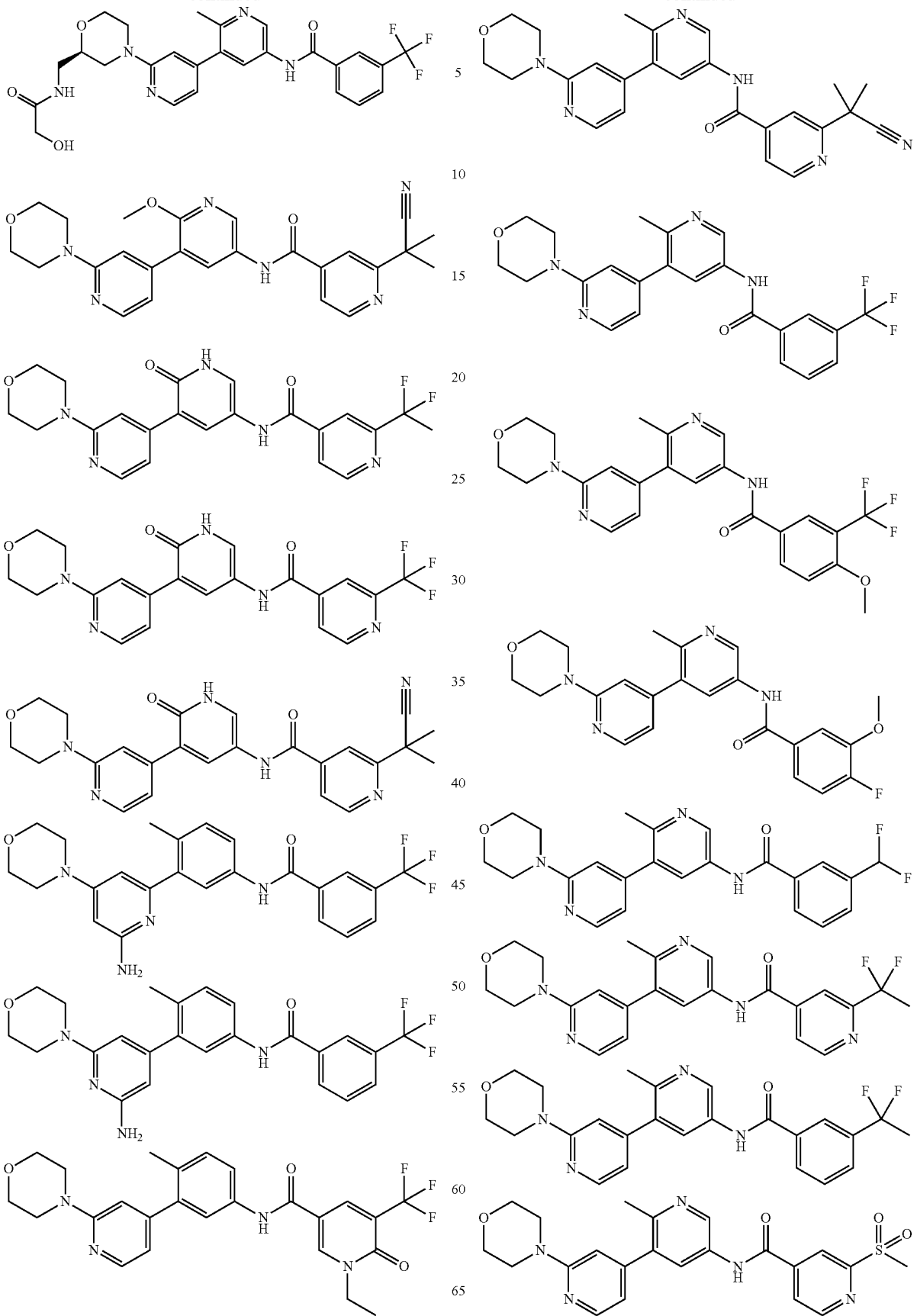

255
-continued
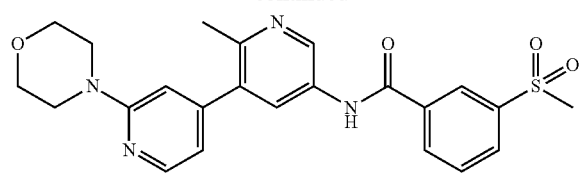
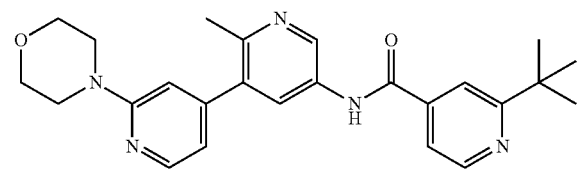
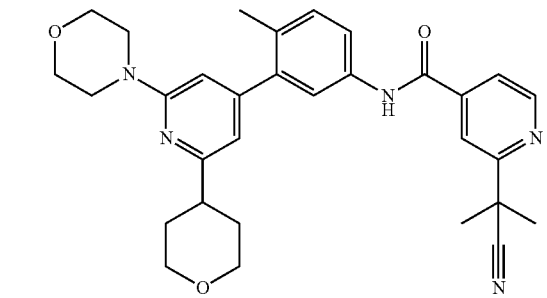
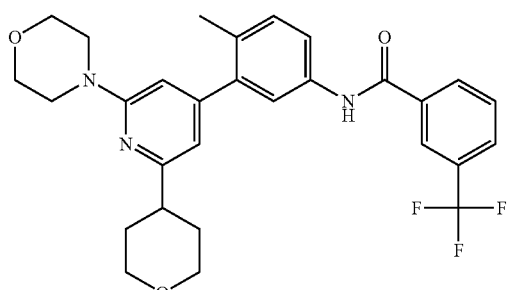
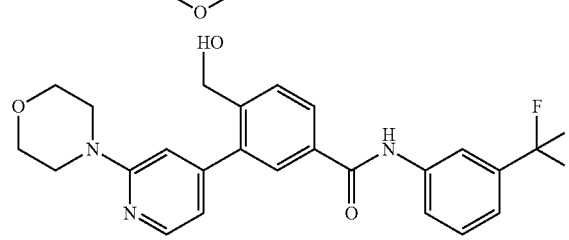
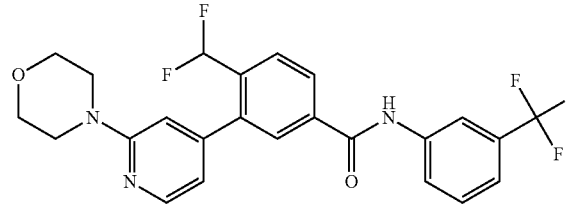
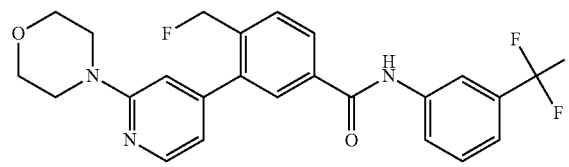
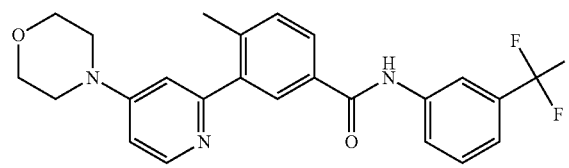
256
-continued
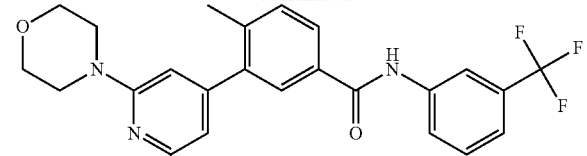
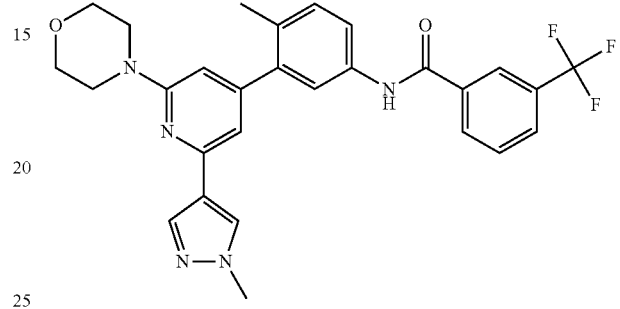
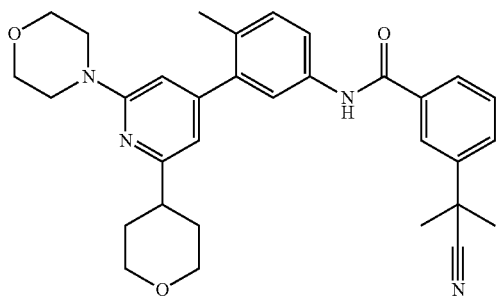
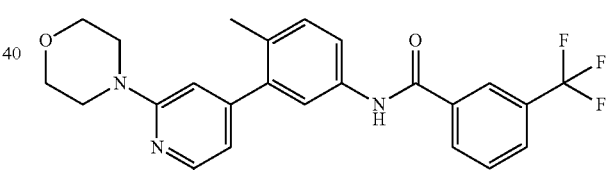
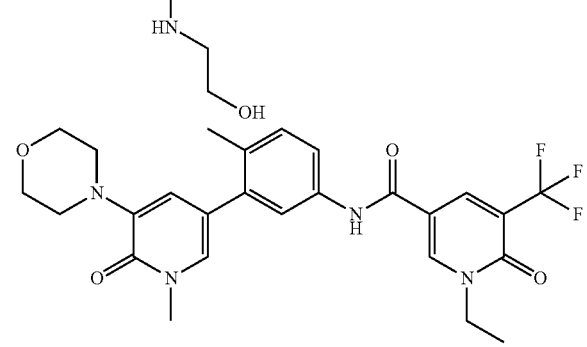
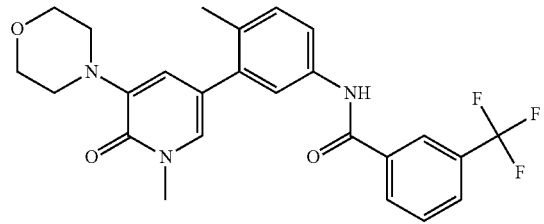

257
-continued
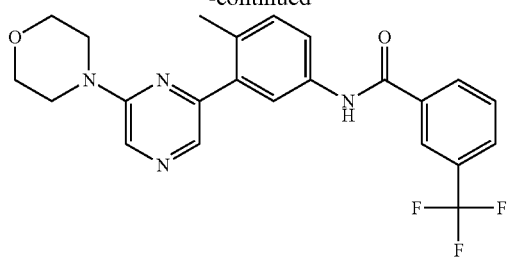
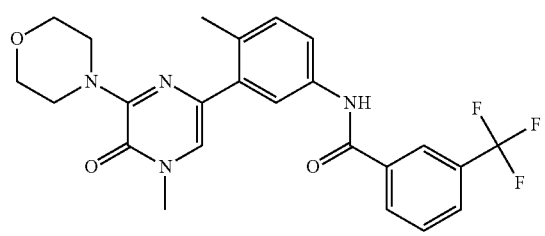
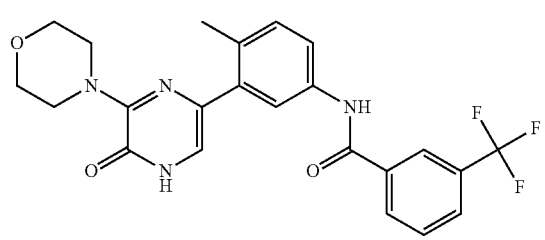
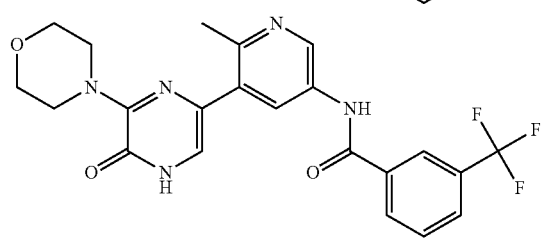
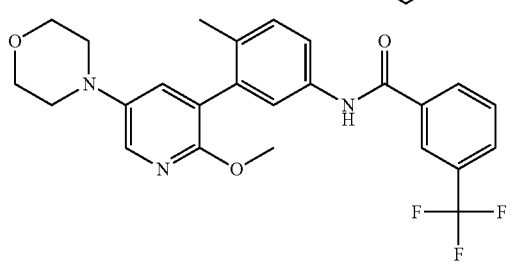
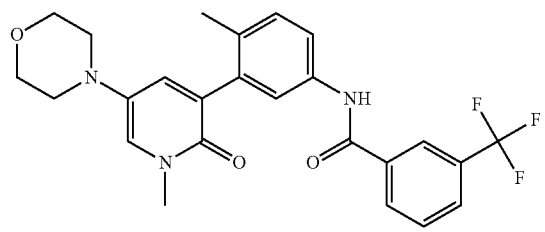
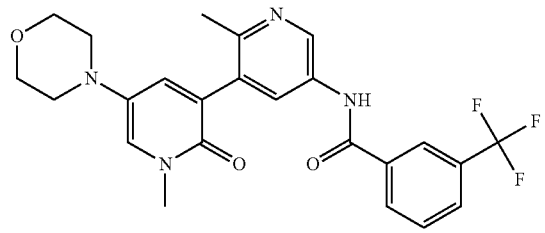
258
-continued
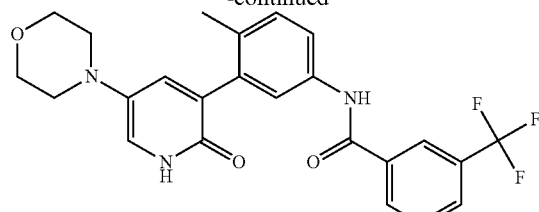
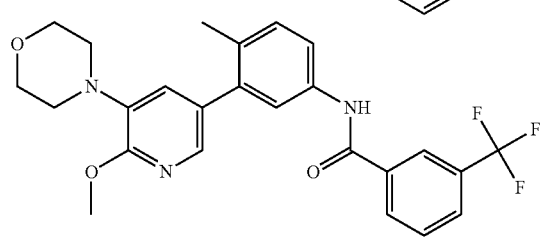
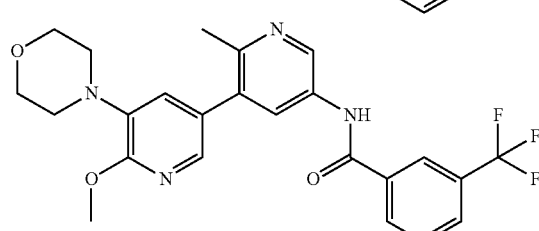
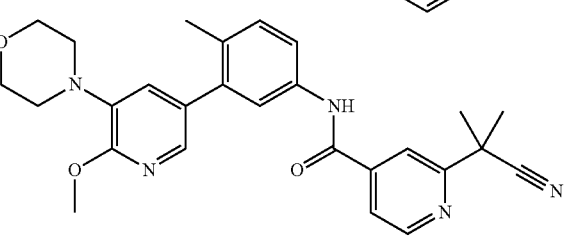
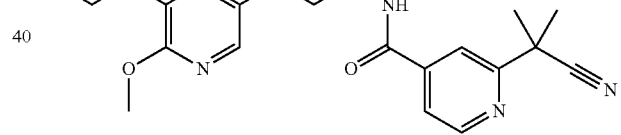
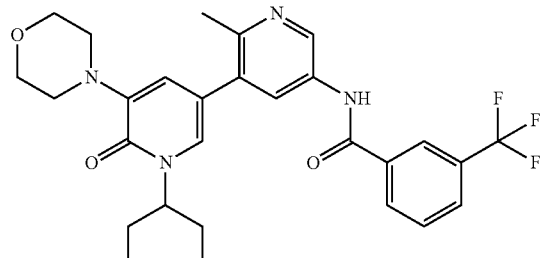
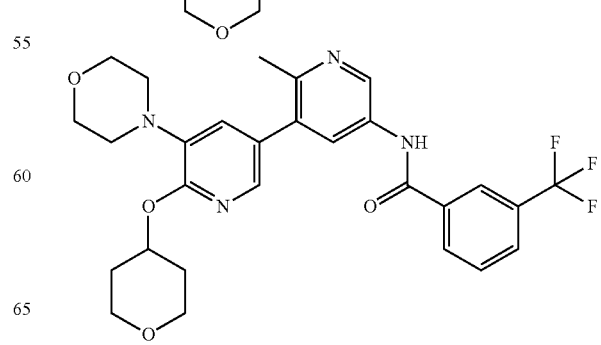

259
-continued
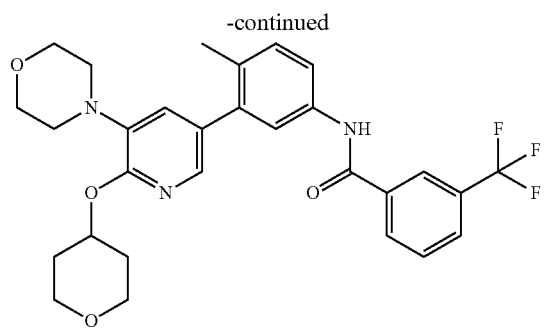
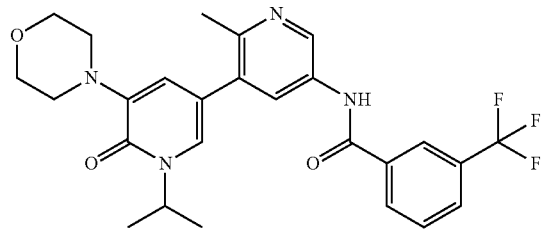
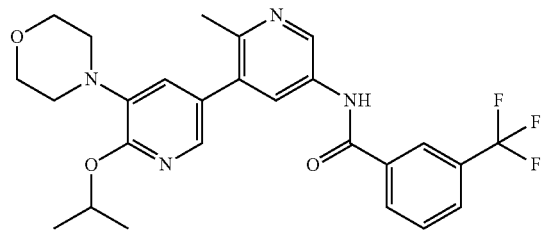
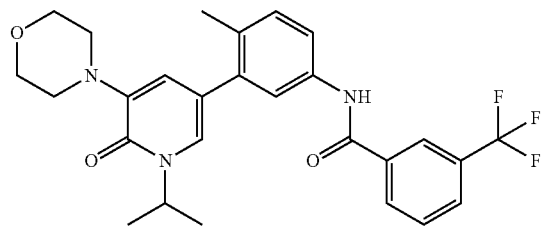
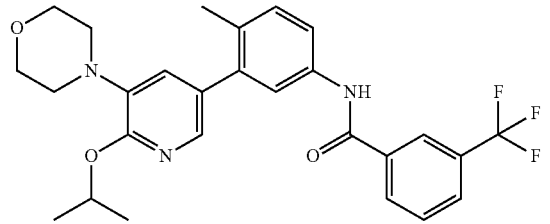
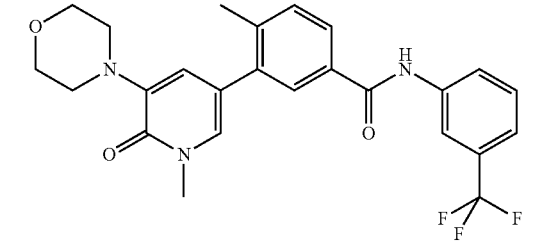
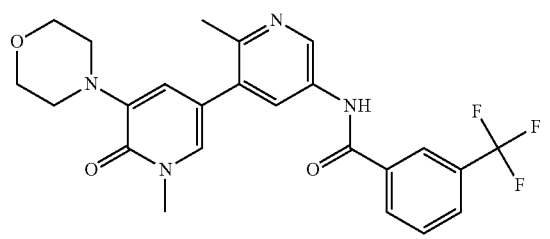
260
-continued
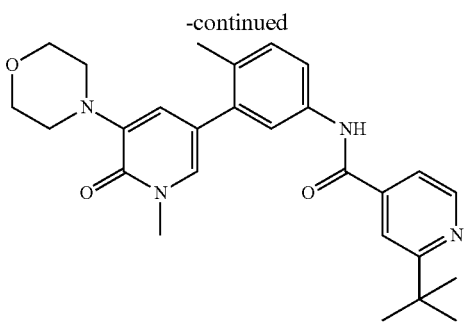
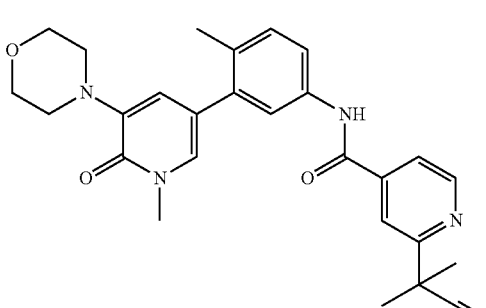
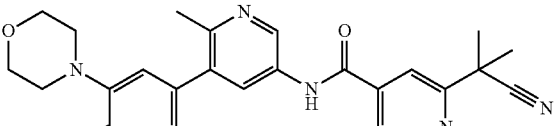
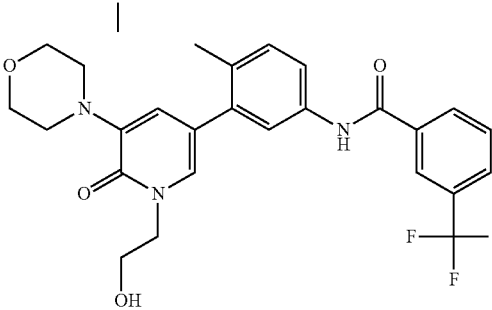
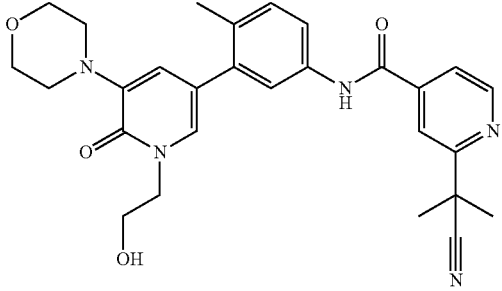
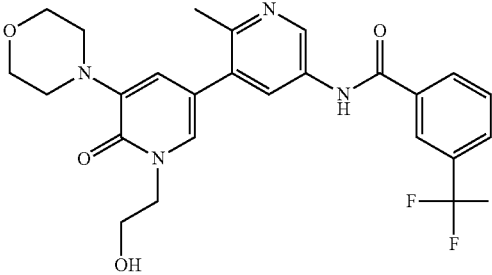

261
-continued
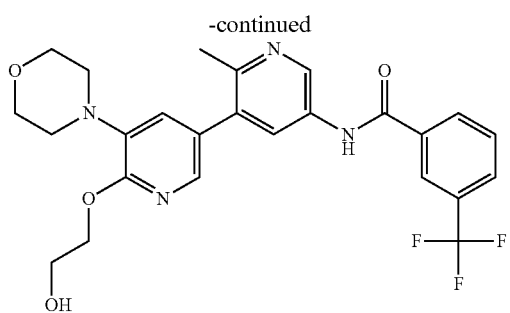
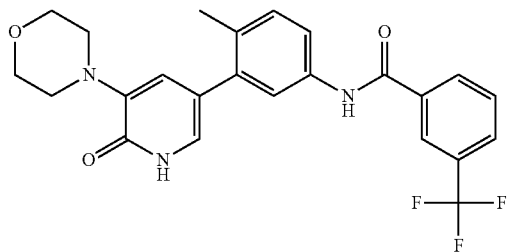
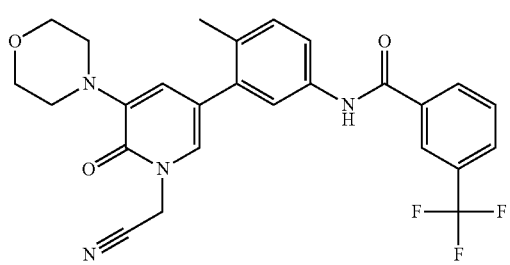
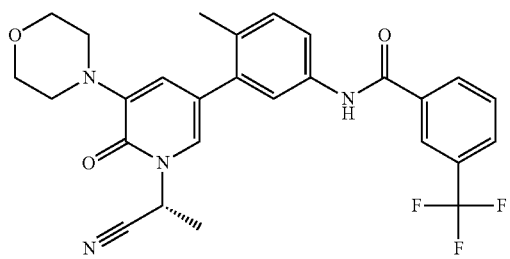
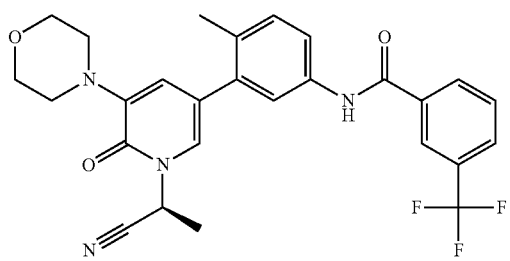
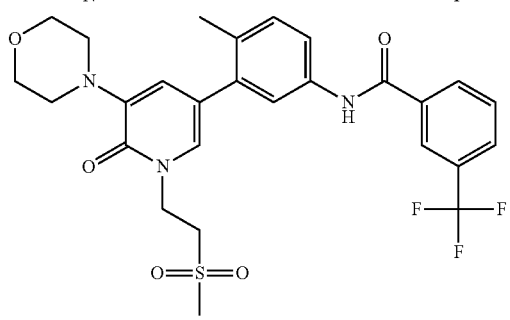
262
-continued
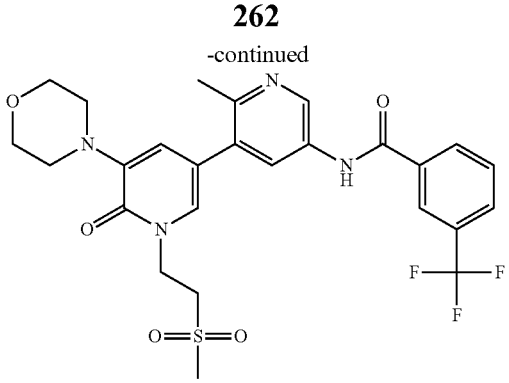
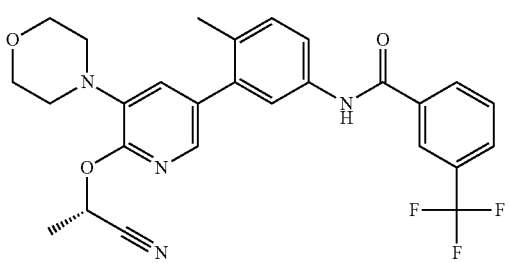
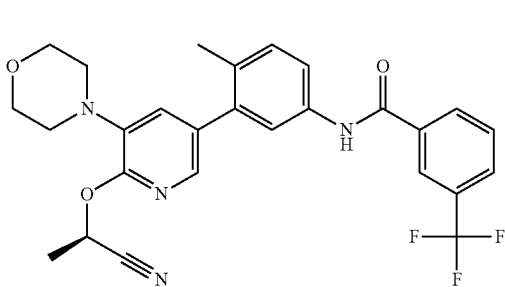
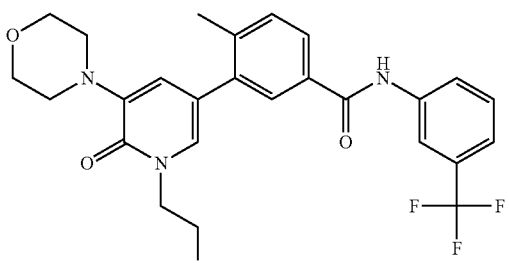
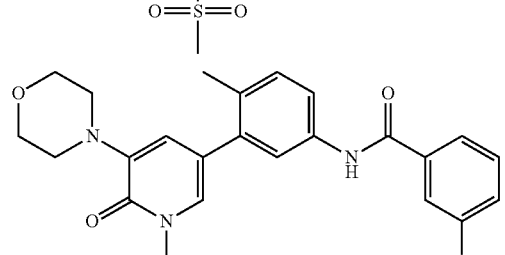
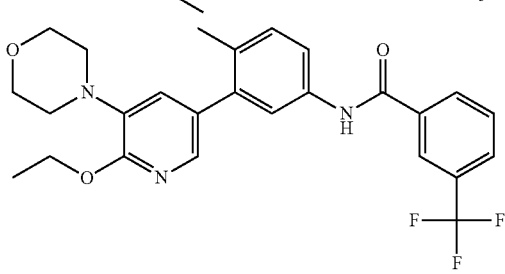

263
-continued
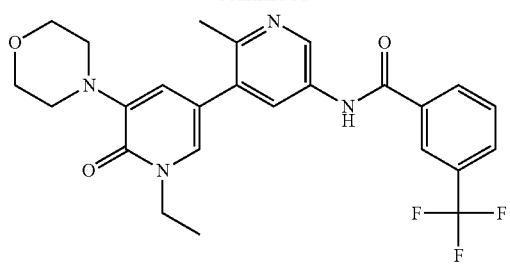
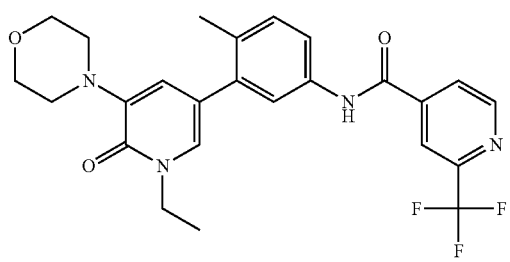
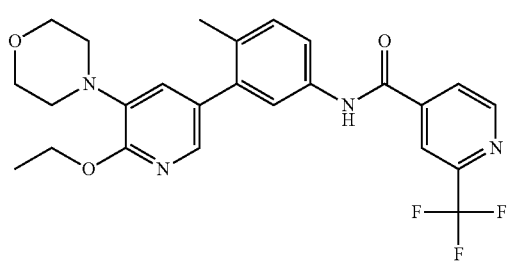
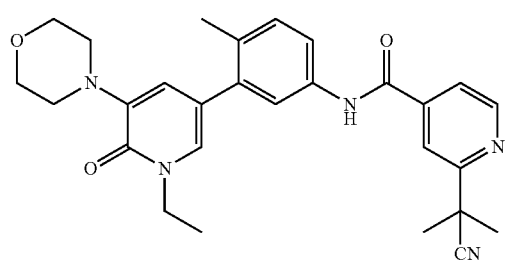
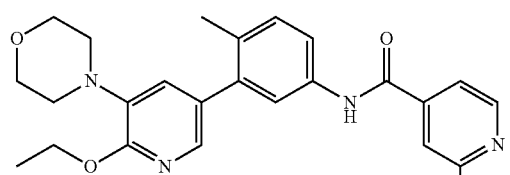
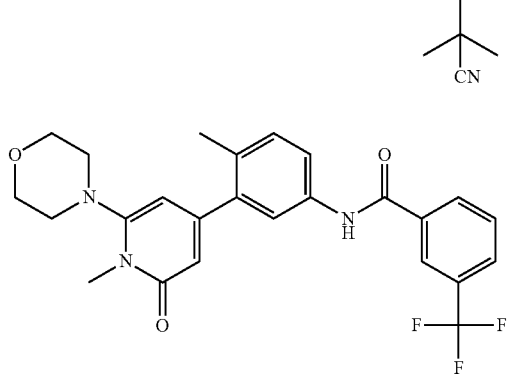
264
-continued
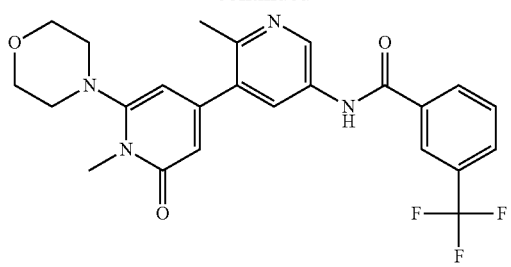
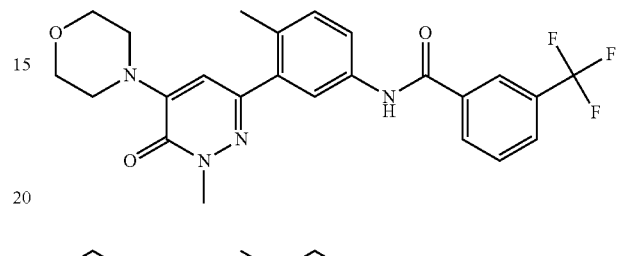
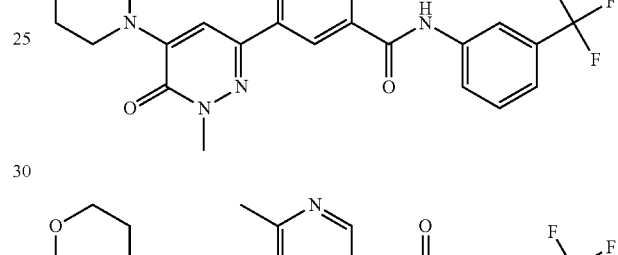
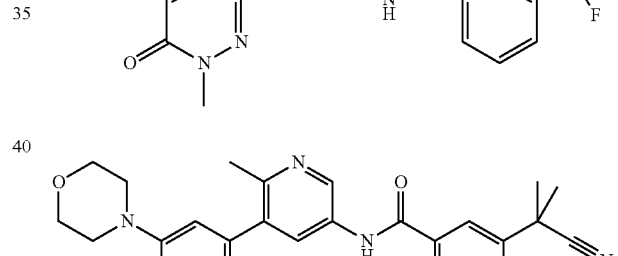
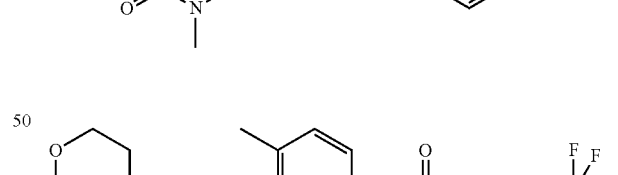
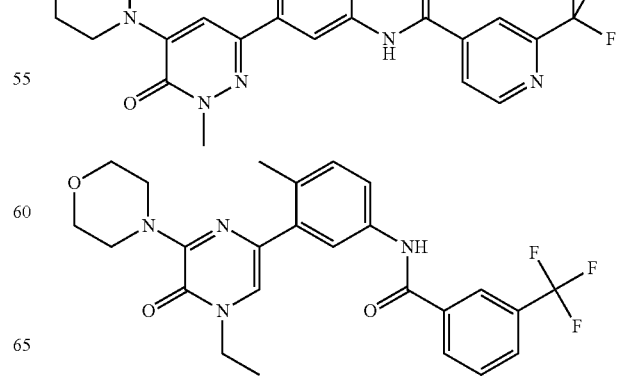

265 -continued
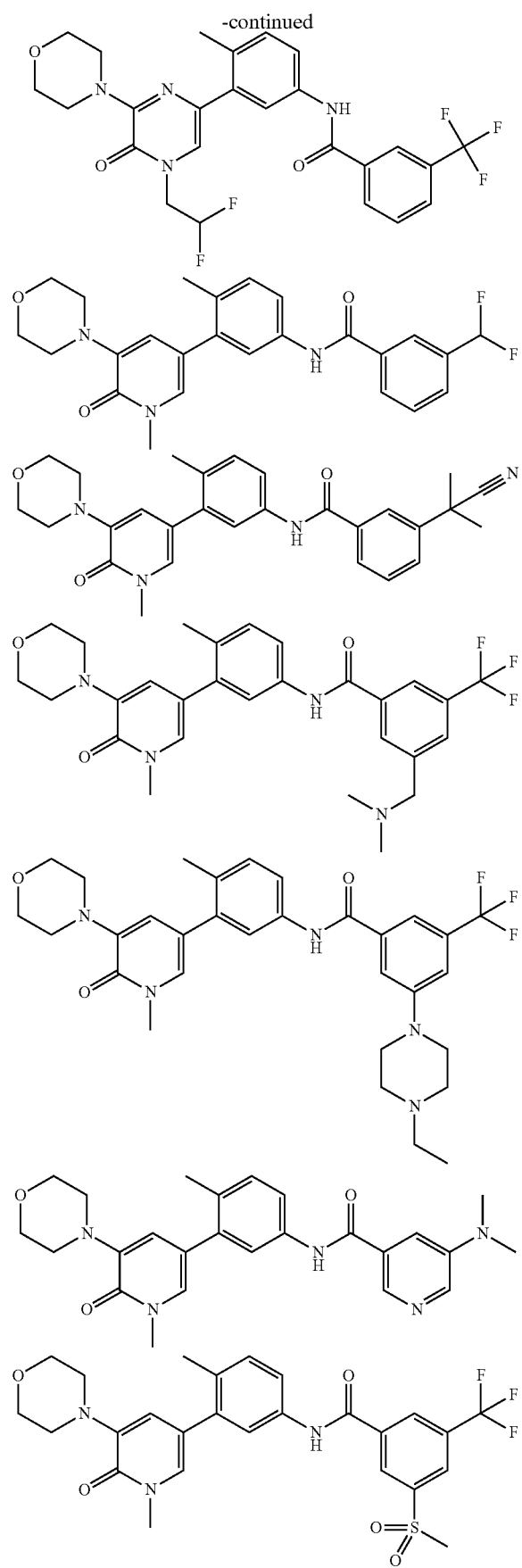
266 -continued
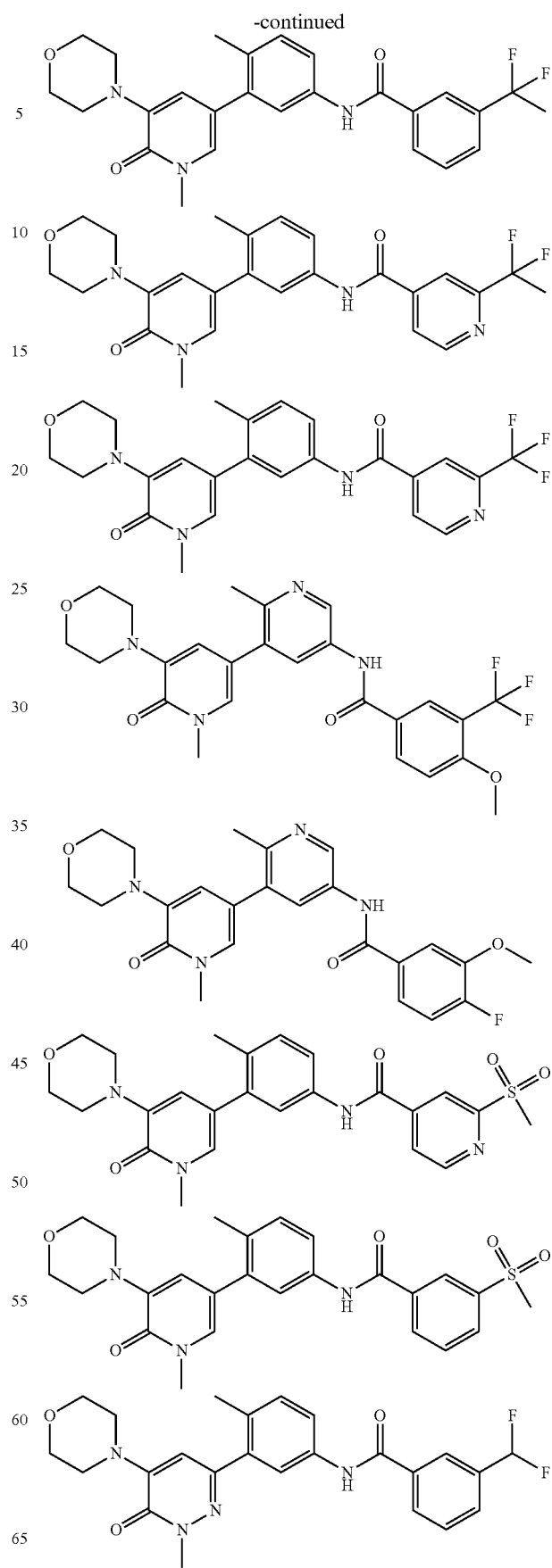

267
-continued

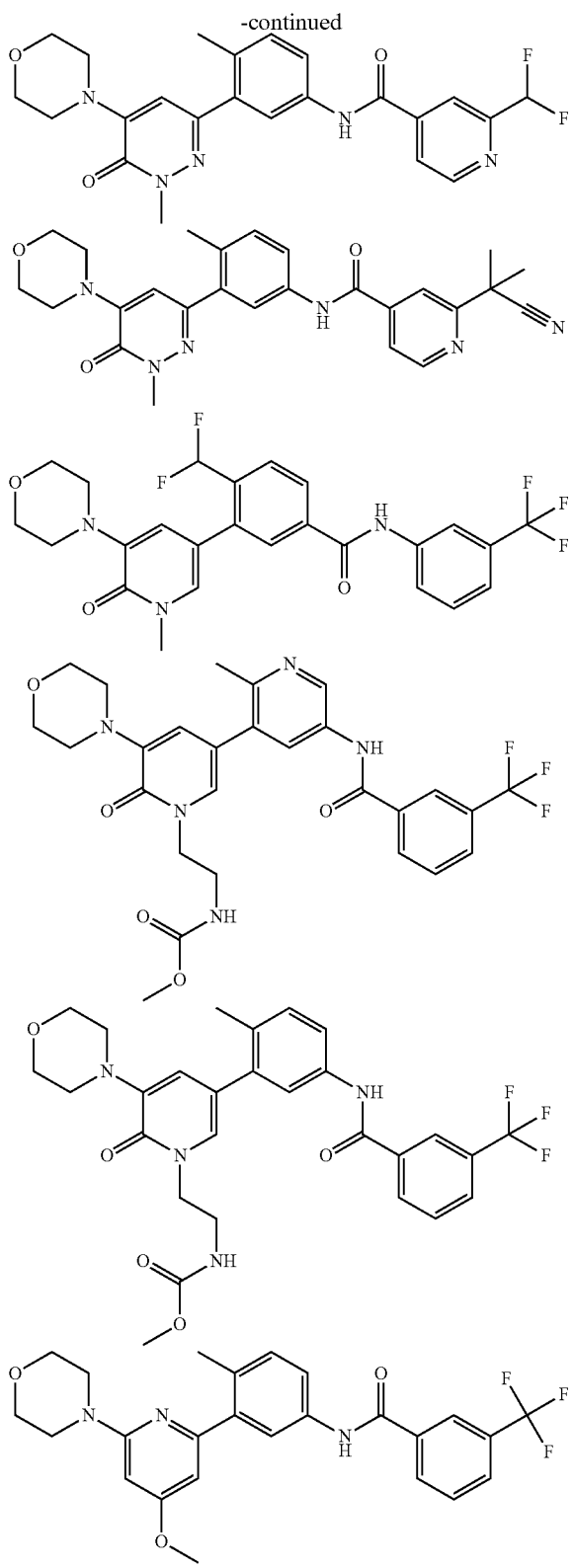

268
-continued

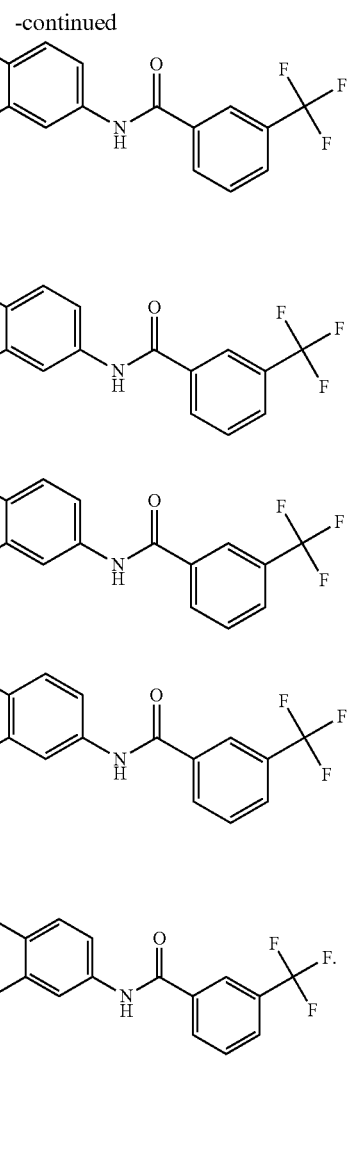

15. A pharmaceutical composition comprising a compound of claim 1, or a pharmaceutically acceptable salt thereof and one or more pharmaceutically acceptable carriers.

16. A combination comprising a therapeutically effective amount of a compound of claim 1, or a pharmaceutically acceptable salt thereof and one or more therapeutically active co-agents.

17. A method of treating melanoma, comprising administering to a subject in need thereof a therapeutically effective amount of a compound of claim 1, or a pharmaceutically acceptable salt thereof.

* * * * *